(12) United States Patent
Qian et al.

(10) Patent No.: US 8,043,620 B2
(45) Date of Patent: Oct. 25, 2011

(54) WISE BINDING AGENTS AND EPITOPES

(75) Inventors: Xueming Qian, Oak Park, CA (US); Kevin Graham, Thousand Oaks, CA (US); Grant Shimamoto, Newbury Park, CA (US); Barbara S. Tipton, Thousand Oaks, CA (US); Mei-Mei Tsai, Thousand Oaks, CA (US); Aaron George Winters, Ventura, CA (US); Li Zhang, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 346 days.

(21) Appl. No.: 12/275,850

(22) Filed: Nov. 21, 2008

(65) Prior Publication Data

US 2009/0130114 A1 May 21, 2009

Related U.S. Application Data

(60) Provisional application No. 61/004,037, filed on Nov. 21, 2007.

(51) Int. Cl.
*A61K 39/395* (2006.01)
*C07K 16/22* (2006.01)
*C07K 16/46* (2006.01)

(52) U.S. Cl. ............... 424/158.1; 424/142.1; 424/182.1; 530/388.15; 530/388.24

(58) Field of Classification Search ........................ None
See application file for complete search history.

(56) References Cited

U.S. PATENT DOCUMENTS

2008/0160060 A1* 7/2008 Ellies ........................... 424/422

FOREIGN PATENT DOCUMENTS

WO 02/08284 A2 1/2002

OTHER PUBLICATIONS

Clackson et al. Making antibody fragments using phage display libraries. Nature. Aug. 15, 1991;352(6336):624-8.*
Portolano et al. Lack of promiscuity in autoantigen-specific H and L chain combinations as revealed by human H and L chain "roulette". J Immunol. Feb. 1, 1993;150(3):880-7.*
Abstract "Human angiogenesis related protein PRO532 Seq Id No. 70" (Jul. 19, 2002).
Yanagita, et al., "Uterine sensitization-associated gene-1 (USAG-1), a novel BMP antagonist expressed in the kidney, accelerates tubular injury" J of Clinical Investigation (Jan. 1, 2006) pp. 70-79 vol. 116, 3.
Yanagita, et al., "Balance Between Bone Morphogenetic Proteins and Their Antagonist in Kidney Injury" J of the International Society for Apheresis; (Oct. 1, 2007) pp. 538-543 vol. 11, 1.
Yanagita, et al., "USAG-1:a bone morphogenetic protein antagonist abundantly expressed in the kidney" Biochemical & Biophysical Research Communications (Apr. 2, 2004) pp. 490-500 vol. 316, 2.

* cited by examiner

*Primary Examiner* — David Romeo
(74) *Attorney, Agent, or Firm* — Randolph M. Mohr

(57) ABSTRACT

The present invention relates to binding agents for WISE, and includes for their manufacture and use.

5 Claims, 40 Drawing Sheets

Figure 9A
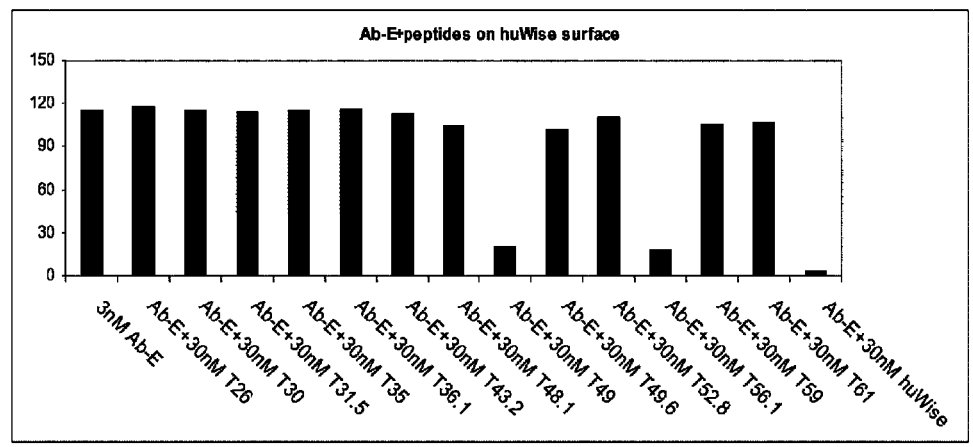
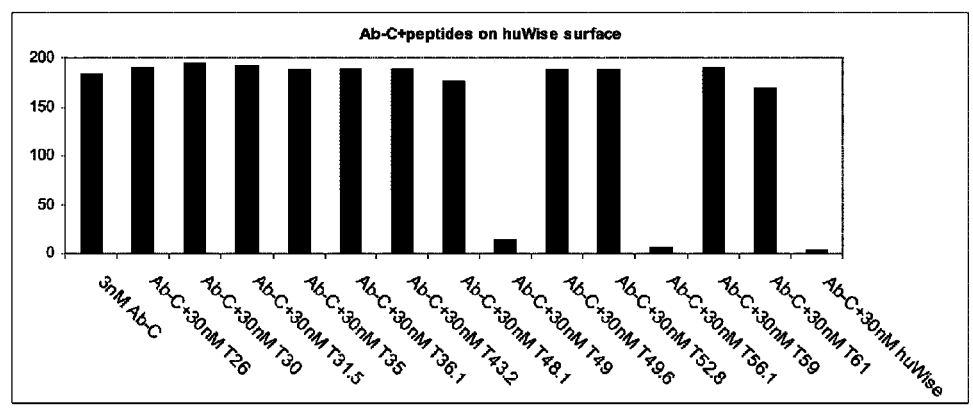
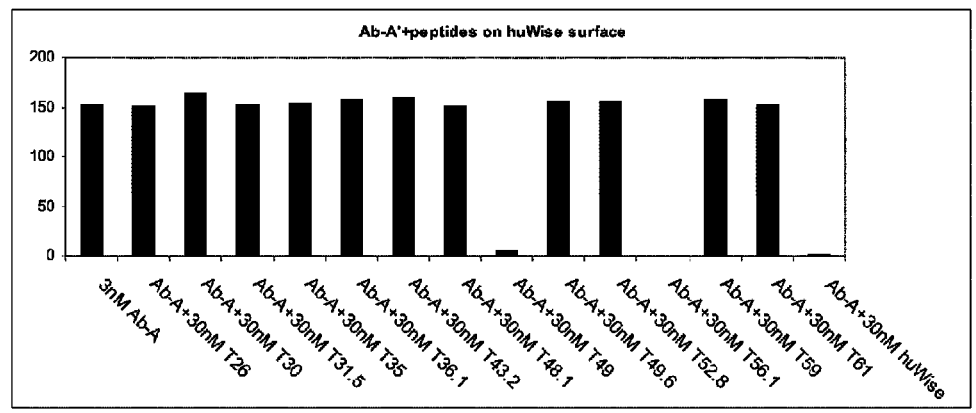

WISE BINDING AGENTS AND EPITOPES

This application claims the benefit of U.S. Provisional Application No. 61/004,037, filed Nov. 21, 2007, which is hereby incorporated by reference.

BACKGROUND OF THE INVENTION

Fibrosis is generally defined as the development of extra connective tissue as part of the healing process and includes a diverse set of symptoms. Excessive fibrosis is a grievous problem that has few therapeutic options.

Cystine knot-containing proteins are typically important regulators of key functions and affect diverse cell types. Wise (USAG-1, SOSTDC1) is a secreted, cystine knot-containing protein and is expressed primarily in the kidney, lungs and epithelial cells. WISE KO mice are fertile and their kidneys have normal function. However when challenged to develop kidney injury either by unilateral ureteral obstruction (UUO) or injection of chemotoxic agent Cisplatin, the WISE KO mice are protected (Yanagita et al., J. Clin Invest. Jan. 4, 2006; 116(1): 70-79). In the UUO model, there is much less fibrosis in the affected kidney in WISE KO mice and expressed much less aSMA, a marker of myofibroblast activation, and preserved the expression of epithelial cell marker E-cadherin. In a Cisplatin model for kidney injury, WISE deletion protected the animal from tubular injury and reduced mortality (Tanaka et al., Kidney International advance online publication 17 Oct. 2007). In addition, when WISE KO mice (aka USAG-1 KO mice) were breed with Col4a3 KO mice, the double knockout mice had significantly less proteinuria and developed less end stage renal disease relative to the Col4a3 KO mice with WT WISE gene. At 4 weeks of age, USAG-1+/+, 3(IV)-/- mice already showed severe proteinuria with extensive splitting of glomerular basement membrane (GBM), while double KO mice showed normal structure of GBM. At 10 weeks of age, USAG-1+/+, 3(IV)-/- mice developed end-stage renal disease, while double KO mice showed significantly preserved renal function with less renal histological changes. (Abstract TH-FC059 2008 ASN meeting).

These data suggest that WISE could be a regulator of adult kidney function. However these studies were limited to knock out mice lacking WISE for their entire development cycle, accordingly it was unpredictable whether acute inhibition of WISE activity using an inhibitor such as an antibody could provide therapeutic benefit to preserve kidney function under pathological conditions associated with various fibrotic diseases.

The present inventors demonstrate it is possible to treat lung and kidney disorders associated with damage and repair including fibrosis and organ dysfunction using binding agents that target WISE.

BRIEF SUMMARY OF THE INVENTION

Disclosed herein are compositions and methods that can be used to prevent or treat kidney and lung fibrosis as well as prevent or treat lung and kidney damage, disease and/or injury, and may be used to treat a wide variety of diseases and disorders described herein.

The invention further relates to regions of human WISE recognized by the binding agents disclosed herein, methods of using these regions, and methods of making such regions.

The invention also relates to epitopes specific to the region of WISE identified as the cystine knot domain, and binding agents which specifically bind to that region.

The invention relates to binding agents, such as antibodies, that specifically bind to WISE. The binding agents can be characterized by their ability to cross-block the binding of at least one antibody disclosed herein to WISE and/or to be cross-blocked from binding WISE by at least one of said antibodies. The antibodies and other binding agents of the invention can also be characterized by their binding pattern to human WISE peptides in a human WISE peptide epitope competition binding assay as disclosed herein.

In certain embodiments, the invention relates to binding agents such as antibodies that inhibit WISE activity and that can decrease tissue injury and associated fibrosis in tissues such as the kidneys, lungs, skin, eye, liver and heart. In addition, the invention relates to binding agents that inhibit proteinuria which is associated with various immunological and non-immune mediated renal diseases such as in patients with diabetic nephropathy, glomerolonephritis, membrane nephropathy, lupus, transplantation and other renal diseases involving manifestation of increased proteinuria. Furthermore the invention relates to binding agents that improve the function of organs or delay the loss of function in organs mentioned above that are impacted due to either fibrosis and/or proteinuria including but not limited to diseases such as chronic kidney diseases, chronic allograft nephropathy, idiopathic pulmonary fibrosis, cardiomyopathy, glaucoma (lens cell fibrosis) and scleroderma (skin fibrosis). In addition, as tumor metastasis also using similar mechanisms to those used in tissue fibrosis, WISE binding agent may also have utility in delaying tumor metastasis and/or cancer progression.

In other embodiments, the invention relates to binding agents, such as antibodies, that can block the inhibitory effect of WISE in a cell based assay.

The invention further relates in part to polypeptide constructs comprising two, three, or four polypeptide fragments linked by at least one disulfide bond, representing a core region of the cystine-knot of WISE, and antibodies capable of specifically binding thereto.

In one embodiment, the invention relates to methods of obtaining epitopes suitable for use as immunogens for generating, in mammals, binding agents, such as antibodies capable of binding specifically to WISE; in certain embodiments the binding agents generated are capable of neutralizing WISE activity in vitro and/or in vivo.

In another embodiment, the invention relates to a composition for eliciting an antibody specific for WISE when the composition is administered to an animal, the composition comprising a polypeptide having the amino acid sequence selected from the group consisting of SEQ ID NO: 2, 4, 6, and 8.

In other embodiments, the invention also relates to a composition for eliciting an antibody specific for WISE when the composition is administered to an animal, the composition comprising at least one polypeptide consisting essentially of the amino acid sequence of human, mouse, rat or cynomolgus WISE (SEQ ID NOs: 2, 4, 6, or 8).

In a specific embodiment, the invention also relates to polypeptide consisting essentially of a multiply truncated human WISE protein of SEQ ID NO: 2, wherein amino acids 1 to 70, 113 to 126, and 171 to 206 of SEQ ID NO: 2 are absent from the polypeptide; this polypeptide may be obtained by recombinant expression of fragments of the protein, tryptic digestion of human WISE, and the protein may be isolated by HPLC fractionation among other methods.

In another specific embodiment, the invention further relates to an immunogenic portion of the cystine knot of human WISE comprising amino acids 71 to 112 and 127 to 170 of SEQ ID NO:2, wherein the immunogenic portion comprises at least one of:
(a) a disulfide bond between amino acids C1 and C5;
(b) a disulfide bond between amino acids C2 and C6; and
(c) a disulfide bond between amino acids C3 and C7;
the immunogenic portion may have at least two of these disulfide bonds; and the immunogenic portion may have all three disulfide bonds.

In one embodiment, the invention relates to a method of generating an antibody capable of specifically binding to WISE, comprising: (a) immunizing an animal with a composition comprising a polypeptide having amino acids 24-206 of SEQ ID NO: 2, a polypeptide having amino acids 24-206 of SEQ ID NO: 4, a polypeptide having amino acids 24-206 of SEQ ID NO: 6, and a polypeptide having amino acids 24-206 of SEQ ID NO: 8; (b) collecting sera from the animal; and (c) isolating from the sera an antibody capable of specifically binding to and inhibiting the biological activity of WISE.

In additional embodiments, the invention also relates to a method of generating an antibody capable of specifically binding to WISE, the method comprising: (a) immunizing an animal with a composition comprising a cystine knot-containing fragment of WISE or a derivative thereof, (b) collecting sera from the animal; and (c) isolating from the sera an antibody capable of specifically binding to and inhibiting the biological activity of WISE.

In further embodiments, the invention further relates to a method of detecting an anti-WISE antibody in a biological sample, comprising the steps of (a) contacting the biological sample with a polypeptide consisting essentially of a polypeptide having amino acids 24 to 206 of SEQ ID NO: 2, a polypeptide having amino acids 24 to 206 of SEQ ID NO: 4, a polypeptide having amino acids 24 to 206 of SEQ ID NO: 6, and a polypeptide having amino acids 24 to 206 of SEQ ID NO: 8 under conditions allowing a complex to form between the antibody and the polypeptide; and (b) detecting the presence or absence of the complex, wherein the presence of the complex indicates that the biological sample contains an anti-WISE antibody.

In other embodiments, the invention comprises a method of detecting an anti-WISE antibody in a biological sample, comprising the steps of (a) contacting the biological sample with a composition comprising a cystine knot-containing fragment of WISE under conditions allowing a complex to form between the antibody and the polypeptide; and (b) detecting the presence or absence of the complex, wherein the presence of the complex indicates that the biological sample contains an anti-WISE antibody.

In certain embodiments, the invention relates to a WISE binding agent, such as an antibody that cross-blocks the binding of at least one of antibodies Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, and Ab-X to a WISE protein. In other embodiments, the invention relates to a WISE binding agent, such as an antibody that cross-blocks the binding of at least one of antibodies Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9 to a WISE protein.

The WISE binding agent may also be cross-blocked from binding to WISE by at least one of antibodies Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, and Ab-X. The WISE binding agent may also be cross-blocked from binding to WISE by at least one of antibodies Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9.

In these embodiments, the invention further relates to a WISE binding agent, such as an antibody, that is cross-blocked from binding to WISE by at least one of antibodies Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, and Ab-X. In these embodiments, the invention further relates to a WISE binding agent, such as an antibody, that is cross-blocked from binding to WISE by at least one of antibodies Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9.

In yet other embodiments, the invention relates to a binding agent, such as an isolated antibody that exhibits a similar binding pattern to human WISE peptides in a "human WISE peptide epitope competition binding assay" as that exhibited by at least one of the antibodies Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, Ab-X, Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9; the isolated antibody, or an antigen-binding fragment thereof, may be a polyclonal antibody, a monoclonal antibody, a humanized antibody, a human antibody, or a chimeric antibody.

The invention still further relates to a method for treating a renal and/or lung fibrotic disease or disorder in a mammalian subject which comprises providing to a subject in need of such treatment an amount of an anti-WISE binding agent sufficient to decrease symptoms associated with the disorder, wherein the anti-WISE binding agent comprises an antibody, or WISE-binding fragment thereof.

Provided herein are antibodies that specifically bind to human WISE. The antibodies of the invention are characterized by their ability to cross-block the binding of at least one antibody disclosed herein to human WISE and/or to be cross-blocked from binding human WISE by at least one antibody disclosed herein. The invention also provides is an isolated antibody, or an antigen-binding fragment thereof, that can block the effect of WISE in a cell based assay.

Also provided is a binding agent, such as an antibody, that specifically binds to WISE and comprises at least one CDR sequence selected from SEQ ID NOs: 123, 124, 125, 127, 128, 129, 131, 132, 133, 135, 136, 137, 139, 140, 141, 143, 144, 145, 147, 148, 149, 151, 152, 153, 155, 156, 157, 158, 159, 160, 164, 167, 168, 170, 171, 173, 174, 175, 177, 178, 179, 181, 182, 183, 184, 185, 186, 187, 189, 190, 191, 193, 194, 195, 197, 198, 199, 201, 202, 203, 205, 206, 207, 209, 210, 211, 213, 214, 215, 217, 218, 219, 221, 222, 223, 225, 226, 227, 229, 230, 231, 233, 234, 235, 237, 238, 239, 241, 242, 243, 245, 246, 247, 249, 250, 251, 253, 254, 255, 257, 258, 259, 261, 262, 263, 273, 274, 275, 277, 278 and 279, and variants thereof.

In another embodiment the invention contemplates a binding agent comprising three CDR sequences selected from the groups consisting of: CDR sequences of SEQ ID NOs: 123, 124, and 125; CDR sequences of SEQ ID NOs: 127, 128, and 129; CDR sequences of SEQ ID NOs: 131, 132, and 133; CDR sequences of SEQ ID NOs: 135, 136, and 137; CDR sequences of SEQ ID NOs: 139, 140, and 141; CDR sequences of SEQ ID NOs: 143, 144, and 145; CDR sequences of SEQ ID NOs: 147, 148, and 149; CDR sequences of SEQ ID NOs: 151, 152, and 153; CDR sequences of SEQ ID NOs: 155, 156, and 157; CDR sequences of SEQ ID NOs: 158, 159, and 160; CDR sequences of SEQ ID NOs: 161, 162, and 163; CDR sequences of SEQ ID NOs: 164, 165, and 166; CDR sequences of SEQ ID NOs: 167, 168, and 169; CDR sequences of SEQ ID NOs: 170, 171, and 172; CDR sequences of SEQ ID NOs: 173, 174, and 175; CDR sequences of SEQ ID NOs: 177, 178, and 179; CDR sequences of SEQ ID NOs: 181, 182, and 183; CDR sequences of SEQ ID NOs: 185, 186 and 187; CDR sequences of SEQ ID NOs: 189, 190, and 191; CDR sequences of SEQ ID NOs: 193, 194, and 195; CDR sequences of SEQ ID NOs: 197, 198, and 199; CDR sequences of SEQ ID NOs: 201, 202, and 203; CDR sequences of SEQ ID NOs: 205, 206 and 207; CDR sequences of SEQ ID NOs: 209, 210, and 211; CDR sequences of SEQ ID NOs: 213, 214, and 215; CDR sequences of SEQ ID NOs: 217, 218, and 219; CDR sequences of SEQ ID NOs: 221, 222, and 223; CDR sequences of SEQ ID NOs: 225, 226, and 227; CDR sequences of SEQ ID NOs: 229, 230, and 231; CDR sequences of SEQ ID NOs: 233, 234, and 235; CDR sequences of SEQ ID NOs: 237, 238, and 239; CDR sequences of SEQ ID NOs: 241, 242, and 243; CDR sequences of SEQ ID NOs: 245, 246, and 247; CDR sequences of SEQ ID NOs: 249, 250, and 251; CDR sequences of SEQ ID NOs: 253, 254, and 255; CDR sequences of SEQ ID NOs: 257, 258, and 259; CDR sequences of SEQ ID NOs: 261, 262 and 263; CDR sequences of SEQ ID NOs: 273, 274 and 275; or CDR sequences of SEQ ID NOs: 277, 278 and 279.

In one embodiment the invention contemplates a binding agent comprising six CDR sequences selected from the groups consisting of: SEQ ID NOs: 123, 124, and 125 and CDR sequences of SEQ ID NOs: 127, 128, and 129; CDR sequences of SEQ ID NOs: 131, 132, and 133 and CDR sequences of SEQ ID NOs: 135, 136, and 137; CDR sequences of SEQ ID NOs: 139, 140, and 141 and CDR sequences of SEQ ID NOs: 143, 144, and 145; CDR sequences of SEQ ID NOs: 147, 148, and 149 and CDR sequences of SEQ ID NOs: 151, 152, and 153; CDR sequences of SEQ ID NOs: 155, 156, and 157 and CDR sequences of SEQ ID NOs: 158, 159, and 160; CDR sequences of SEQ ID NOs: 161, 162, and 163 and CDR sequences of SEQ ID NOs: 164, 165, and 166; CDR sequences of SEQ ID NOs: 167, 168, and 169 and CDR sequences of SEQ ID NOs: 170, 171, and 172; CDR sequences of SEQ ID NOs: 135, 136 and 137 and CDR sequences of SEQ ID NOs: 173, 174, and 175; CDR sequences of SEQ ID NOs: 135, 136 and 137 and CDR sequences of SEQ ID NOs: 177, 178, and 179; CDR sequences of SEQ ID NOs: 135, 136 and 137 and CDR sequences of SEQ ID NOs: 181, 182, and 183; CDR sequences of SEQ ID NOs: 135, 136 and 137 and CDR sequences of SEQ ID NOs: 185, 186 and 187; CDR sequences of SEQ ID NOs: 135, 136 and 137 and CDR sequences of SEQ ID NOs: 189, 190, and 191; CDR sequences of SEQ ID NOs: 135, 136 and 137 and CDR sequences of SEQ ID NOs: 193, 194, and 195; CDR sequences of SEQ ID NOs: 135, 136 and 137 and CDR sequences of SEQ ID NOs: 197, 198, and 199; CDR sequences of SEQ ID NOs: 135, 136 and 137 and CDR sequences of SEQ ID NOs: 201, 202, and 203; CDR sequences of SEQ ID NOs: 135, 136 and 137 and CDR sequences of SEQ ID NOs: 205, 206 and 207; CDR sequences of SEQ ID NOs: 135, 136 and 137 and CDR sequences of SEQ ID NOs: 209, 210, and 211; CDR sequences of SEQ ID NOs: 135, 136 and 137 and CDR sequences of SEQ ID NOs: 213, 214, and 215; CDR sequences of SEQ ID NOs: 135, 136 and 137 and CDR sequences of SEQ ID NOs: 217, 218, and 219; CDR sequences of SEQ ID NOs: 135, 136 and 137 and CDR sequences of SEQ ID NOs: 221, 222, and 223; CDR sequences of SEQ ID NOs: 135, 136 and 137 and CDR sequences of SEQ ID NOs: 225, 226, and 227; CDR sequences of SEQ ID NOs: 135, 136 and 137 and CDR sequences of SEQ ID NOs: 229, 230, and 231; CDR sequences of SEQ ID NOs: 135, 136 and 137 and CDR sequences of SEQ ID NOs: 233, 234, and 235; CDR sequences of SEQ ID NOs: 135, 136 and 137 and CDR sequences of SEQ ID NOs: 237, 238, and 239; CDR sequences of SEQ ID NOs: 135, 136 and 137 and CDR sequences of SEQ ID NOs: 241, 242, and 243; CDR sequences of SEQ ID NOs: 135, 136 and 137 and CDR sequences of SEQ ID NOs: 245, 246, and 247; CDR sequences of SEQ ID NOs: 135, 136 and 137 and CDR sequences of SEQ ID NOs: 249, 250, and 251; CDR sequences of SEQ ID NOs: 135, 136 and 137 and CDR sequences of SEQ ID NOs: 253, 254, and 255; CDR sequences of SEQ ID NOs: 135, 136 and 137 and CDR sequences of SEQ ID NOs: 257, 258, and 259; CDR sequences of SEQ ID NOs: 135, 136 and 137 and CDR sequences of SEQ ID NOs: 261, 262 and 263; or CDR sequences of SEQ ID NOs: 273, 274 and 275 and CDR sequences of SEQ ID NOs: 277, 278 and 279.

Also provided is a binding agent, such as an antibody, that specifically binds to WISE and has at least one CDR sequence derived from SEQ ID NOs: 10, 12, 14, 16, 18, 20, 22, 24, 26, 28, 30, 32, 34, 36, 38, 40, 42, 44, 46, 48, 50, 60, 62, 64, 66, 68, 70, 72, 74, 266 and 268 and variants thereof, wherein the antibody or antigen-binding fragment thereof neutralizes WISE in vitro and/or in vivo.

Also provided is an antibody that specifically binds to WISE where the heavy chain is selected from Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, and Ab-X and the light chain has been identified via screening, such as use of phage display. Examples of such light chain sequences are depicted in SEQ ID NOs: 78, 80, 82, 84, 86, 88, 90, 92, 94, 96, 98, 100, 102, 104, 106, 108, 110, 112, 114, 116, 118 and 120.

These and other aspects of the present invention will become apparent upon reference to the following detailed description and attached drawings. All references disclosed herein are hereby incorporated by reference in their entireties as if each was incorporated individually.

BRIEF DESCRIPTION OF THE DRAWINGS

FIG. 9A: Competition assay showing binding of digested human WISE peptides to mature antibodies Ab-A, Ab-C, and Ab-E.

DETAILED DESCRIPTION

Figure 1:
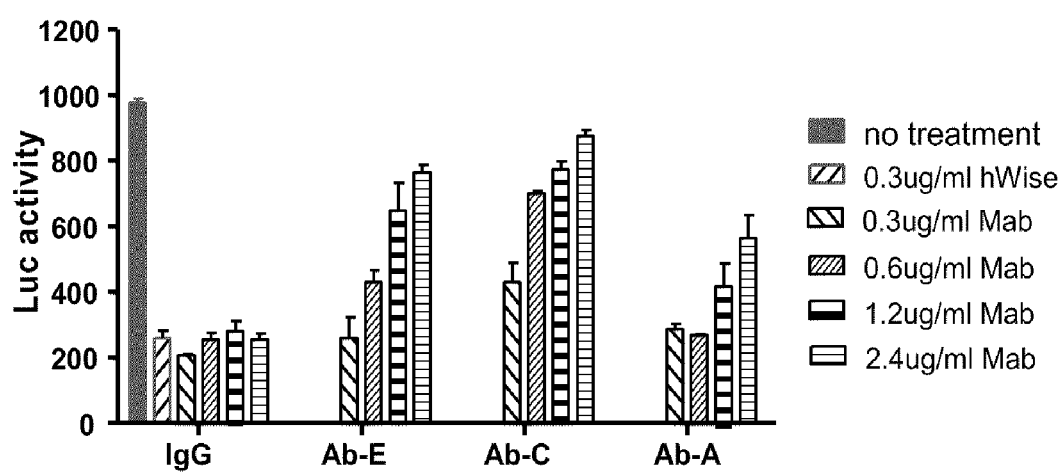
FIG. 1: Bioactivity of antibodies in neutralizing WISE activity in MC3T3-E1 SuperTopFlash (STF) cells. For each set of columns, the first column shows no treatment, the second is human WISE with no antibody, and for each of the four antibodies 0.3 ug/ml of human WISE is mixed with the antibody before being added to the testing well.

The present invention relates in part to regions of the WISE protein that contain epitopes recognized by antibodies that also bind to full-length WISE, and methods of making and using these epitopes. The invention also provides binding agents (such as antibodies) that specifically bind to WISE or portions of WISE, and methods for using such binding agents. The binding agents are useful to block or impair the binding of human WISE to one or more ligand(s) and its biological activity.

As used herein, the term human WISE is intended to include the protein of SEQ ID NO: 2 and allelic variants thereof. Orthologs of WISE are also described and include mouse, rat and cynomolgus (SEQ ID NOs: 4, 6, and 8, respectively). WISE can be purified from host cells that have been transfected by a gene encoding WISE by elution of filtered supernatant of host cell culture fluid. The preparation and further purification are described in the Examples. Human WISE is described in U.S. Pat. No. 5,780,263.

It will be understood by one of skill in the art that there is a high degree of sequence identity between the orthologs of WISE. Accordingly, binding agents to human WISE will be expected to bind to the mouse, rat or cynomolgus WISE in cases where the recognition site of the binding agent, e.g., an antibody binding site such as an epitope, is highly conserved and in particular nearly or completely identical to the human sequence. Thus, when the term "specific binding to WISE" is used, it is understood to include binding to multiple species of WISE where the sequences between species are conserved.

Examples of binding agents according to the invention include the following antibodies: Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, Ab-X, Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9.

As used herein, Ab-A is comprised of the polypeptides expressed by the nucleotides shown in SEQ ID NOs: 9 and 11. Ab-B is comprised of the polypeptides expressed by the nucleotides shown in SEQ ID NOs: 13 and 15. Ab-C is comprised of the polypeptides expressed by the nucleotides shown in SEQ ID NOs: 17 and 19. Ab-D is comprised of the polypeptides expressed by the nucleotides shown in SEQ ID NOs: 21 and 23. Ab-E is comprised of the polypeptides expressed by the nucleotides shown in SEQ ID NOs: 25 and 27. Ab-F is comprised of the polypeptides expressed by the nucleotides shown in SEQ ID NOs: 29 and 31. Ab-G is comprised of the polypeptides expressed by the nucleotides shown in SEQ ID NOs: 13 and 33. Ab-H is comprised of the polypeptides expressed by the nucleotides shown in SEQ ID NOs: 21 and 35. Ab-I is comprised of the polypeptides expressed by the nucleotides shown in SEQ ID NOs: 37 and 39. Ab-J is comprised of the polypeptides expressed by the nucleotides shown in SEQ ID NOs: 41 and 43. Ab-K is comprised of the polypeptides expressed by the nucleotides shown in SEQ ID NOs: 45 and 23. Ab-L is comprised of the polypeptides expressed by the nucleotides shown in SEQ ID NOs: 45 and 35. Ab-M is comprised of the mature polypeptides of SEQ ID NOs: 271 and 272. Ab-N is comprised of the polypeptides expressed by the nucleotides shown in SEQ ID NOs: 121 and 23. Ab-O is comprised of the polypeptides expressed by the nucleotides shown in SEQ ID NOs: 41 and 23. Ab-P is comprised of the polypeptides expressed by the nucleotides shown in SEQ ID NOs: 49 and 47. Ab-Q is comprised of the polypeptides expressed by the nucleotides shown in SEQ ID NOs: 55 and 57. Ab-R is comprised of the polypeptides expressed by the nucleotides shown in SEQ ID NOs: 53 and 51. Ab-S is comprised of the polypeptides expressed by the nucleotides shown in SEQ ID NOs: 61 and 59. Ab-T is comprised of the polypeptides expressed by the nucleotides shown in SEQ ID NOs: 265 and 267. Ab-U is comprised of the polypeptides expressed by the nucleotides shown in SEQ ID NOs: 65 and 63. Ab-V is comprised of the polypeptides expressed by the nucleotides shown in SEQ ID NOs: 69 and 67. Ab-W is comprised of the polypeptides expressed by the nucleotides shown in SEQ ID NOs: 73 and 71. Ab-X is comprised of the mature polypeptides of SEQ ID NOs: 269 and 270.

Ab-1 is comprised of the polypeptides expressed by the nucleotides shown in SEQ ID NOs: 75 and 23. Ab-13 is comprised of the polypeptides expressed by the nucleotides shown in SEQ ID NOs: 77 and 23. Ab-16 is comprised of the polypeptides expressed by the nucleotides shown in SEQ ID NOs: 79 and 23. Ab-18 is comprised of the polypeptides expressed by the nucleotides shown in SEQ ID NOs: 81 and 23. Ab-23 is comprised of the polypeptides expressed by the nucleotides shown in SEQ ID NOs: 83 and 23. Ab-24 is comprised of the polypeptides expressed by the nucleotides shown in SEQ ID NOs: 85 and 23. Ab-28 is comprised of the polypeptides expressed by the nucleotides shown in SEQ ID NOs: 87 and 23. Ab-29 is comprised of the polypeptides expressed by the nucleotides shown in SEQ ID NOs: 89 and 23. Ab-48 is comprised of the polypeptides expressed by the nucleotides shown in SEQ ID NOs: 91 and 23. Ab-60 is comprised of the polypeptides expressed by the nucleotides shown in SEQ ID NOs: 93 and 23. Ab-62 is comprised of the polypeptides expressed by the nucleotides shown in SEQ ID NOs: 95 and 23. Ab-63 is comprised of the polypeptides expressed by the nucleotides shown in SEQ ID NOs: 97 and 23. Ab-65 is comprised of the polypeptides expressed by the nucleotides shown in SEQ ID NOs: 99 and 23. Ab-66 is comprised of the polypeptides expressed by the nucleotides shown in SEQ ID NOs: 101 and 23. Ab-67 is comprised of the polypeptides expressed by the nucleotides shown in SEQ ID NOs: 103 and 23. Ab-69 is comprised of the polypeptides expressed by the nucleotides shown in SEQ ID NOs: 105 and 23. Ab-7 is comprised of the polypeptides expressed by the nucleotides shown in SEQ ID NOs: 107 and 23. Ab-70 is comprised of the polypeptides expressed by the nucleotides shown in SEQ ID NOs: 109 and 23. Ab-72 is comprised of the polypeptides expressed by the nucleotides shown in SEQ ID NOs: 111 and 23. Ab-74 is comprised of the polypeptides expressed by the nucleotides shown in SEQ ID NOs: 113 and 23. Ab-75 is comprised of the polypeptides expressed by the nucleotides shown in SEQ ID NOs: 115 and 23. Ab-76 is comprised of the polypeptides expressed by the nucleotides shown in SEQ ID NOs: 117 and 23. Ab-9 is comprised of the polypeptides expressed by the nucleotides shown in SEQ ID NOs: 119 and 23.

Binding agents of the invention are typically antibodies or fragments thereof, as defined herein. The term "antibody" refers to an intact antibody, or a binding fragment thereof. An antibody may comprise a complete antibody molecule (including polyclonal, monoclonal, chimeric, humanized, or human versions having full length heavy and/or light chains), or comprise an antigen binding fragment thereof. Antibody fragments include F(ab')2, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (See e.g., Hollinger and Hudson, 2005, Nature Biotechnology, 23, 9, 1126-1136). Antibody polypeptides are also disclosed in U.S. Pat. No. 6,703,199, including fibronectin polypeptide monobodies. Other antibody polypeptides are disclosed in U.S. patent Publication 2005/0238646, which are single-chain polypeptides. As used herein, the isolated antibody or an antigen-binding fragment thereof may be a polyclonal antibody, a monoclonal antibody, a humanized antibody, a human antibody, a chimeric antibody or the like.

Antigen binding fragments derived from an antibody can be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5S fragment termed F(ab')2. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., Arch. Biochem. Biophys. 89:230, 1960; Porter, Biochem. J. 73:119, 1959; Edelman et al., in Methods in Enzymology 1:422 (Academic Press 1967); and by Andrews, S. M. and Titus, J. A. in Current Protocols in Immunology (Coligan J. E., et al., eds), John Wiley & Sons, New York (2003). pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody fragment may also be any synthetic or genetically engineered protein. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker (scFv proteins).

Another form of an antibody fragment is a peptide comprising one or more complementarity determining regions (CDRs) of an antibody. CDRs (also termed "minimal recognition units", or "hypervariable region") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., Methods: A Companion to Methods in Enzymology 2:106, 1991; Courtenay-Luck, "Genetic Manipulation of Monoclonal Antibodies," in Monoclonal Antibodies. Production, Engineering and Clinical Application, Ritter et al. (eds.), page 166 (Cambridge University Press 1995); and Ward et al., "Genetic Manipulation and Expression of Antibodies," in Monoclonal Antibodies: Principles and Applications, Birch et al., (eds.), page 137 (Wiley-Liss, Inc. 1995)).

Thus, in one embodiment, the binding agent comprises at least one CDR as described herein. The binding agent may comprise at least two, three, four, five or six CDR's as described herein. The binding agent further may comprise at least one variable region domain of an antibody described herein. The variable region domain may be of any size or amino acid composition and will generally comprise at least one CDR sequence responsible for binding to human WISE, for example CDR-H1, CDR-H2, CDR-H3 and/or the light chain CDRs specifically described herein and which is adjacent to or in frame with one or more framework sequences. In general terms, the variable (V) region domain may be any suitable arrangement of immunoglobulin heavy (VH) and/or light (VL) chain variable domains. Thus, for example, the V region domain may be monomeric and be a VH or VL domain, which is capable of independently binding human WISE with an affinity at least equal to $1 \times 10^{-7}$ M or less as described below. Alternatively, the V region domain may be dimeric and contain VH-VH, VH-VL, or VL-VL, dimers. The V region dimer comprises at least one VH and at least one VL chain that may be non-covalently associated (hereinafter referred to as FV). If desired, the chains may be covalently coupled either directly, for example via a disulfide bond between the two variable domains, or through a linker, for example a peptide linker, to form a single chain Fv (scFV).

The variable region domain may be any naturally occurring variable domain or an engineered version thereof By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly a VL domain may be linked to a CK domain or a fragment thereof. In this way, for example, the antibody may be a Fab fragment wherein the antigen binding domain contains associated VH and VL domains covalently linked at their C-termini to a CHI and CK domain, respectively. The CH1 domain may be extended with further amino acids, for example to provide a hinge region or a portion of a hinge region domain as found in a Fab' fragment, or to provide further domains, such as antibody CH2 and CH3 domains.

As described herein, binding agents comprise at least one of these CDRs. For example, one or more CDR may be incorporated into known antibody framework regions (IgG1, IgG2, etc.), or conjugated to a suitable vehicle to enhance the half-life thereof. Suitable vehicles include, but are not limited to Fc, polyethylene glycol (PEG), albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent.

In certain embodiments, a binding agent comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative binding agent comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated by one of skill in the art that a binding agent of the present invention may have at least one amino acid substitution, providing that the binding agent retains binding specificity. Therefore, modifications to the binding agent structures are encompassed within the scope of the invention. These may include amino acid substitutions, which may be conservative or non-conservative and that do not destroy the WISE binding capability of a binding agent. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position.

Non-conservative substitutions may involve the exchange of a member of one class of amino acids or amino acid mimetics for a member from another class with different physical properties (e.g. size, polarity, hydrophobicity, charge). Such substituted residues may be introduced into regions of the human antibody that are homologous with non-human antibodies, or into the non-homologous regions of the molecule.

Moreover, one skilled in the art may generate test variants containing a single amino acid substitution at each desired amino acid residue. Such testing can be done on the target of the binding agent as described below in the examples or on the therapeutic binding agent of the invention. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol., 47: 45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3): 377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

In certain embodiments, variants of binding agents include glycosylation variants wherein the number and/or type of glycosylation site has been altered compared to the amino acid sequences of a parent polypeptide. In certain embodiments, variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to WISE, or to increase or decrease the affinity of the antibodies to WISE described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (5) confer or modify other physiochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

In certain embodiments, binding agents of the invention may be chemically bonded with polymers, lipids, or other moieties.

The binding agents may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LAC1-D1, Z domain and tendramisat domains may be used (See e.g., Nygren and Uhlen, 1997, Current Opinion in Structural Biology, 7, 463-469).

In preferred embodiments, it will be appreciated that the binding agents of the invention include the humanized antibodies described herein. Humanized antibodies such as those described herein can be produced using techniques known to those skilled in the art (Zhang, W., et al., Molecular Immunology. 42(12): 1445-1451, 2005; Hwang W. et al., Methods. 36(1):35-42, 2005; Dall'Acqua W F, et al., Methods 36(1): 43-60, 2005; and Clark, M., Immunology Today. 21(8):397-402, 2000).

Additionally, one skilled in the art will recognize that suitable binding agents include portions of these antibodies, such as one or more of CDR-H1, CDR-H2, CDR-H3, CDR-L1, CDR-L2 and CDR-L3 as specifically disclosed herein. At least one of the regions of CDR-H1, CDR-H2, CDR-H3, CDR-L1, CDR-L2 and CDR-L3 may have at least one amino acid substitution, provided that the binding agent retains the binding specificity of the non-substituted CDR. The non-CDR portion of the binding agent may be a non-protein molecule, wherein the binding agent cross-blocks the binding of an antibody disclosed herein to WISE and/or neutralizes WISE. The non-CDR portion of the binding agent may be a non-protein molecule in which the binding agent exhibits a similar binding pattern to human WISE peptides in a "human WISE peptide epitope competition binding assay" as that exhibited by at least one of antibodies Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, Ab-X, Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9 and/or neutralizes WISE. The non-CDR portion of the binding agent may be composed of amino acids, wherein the binding agent is a recombinant binding protein or a synthetic peptide, and the recombinant binding protein cross-blocks the binding of an antibody disclosed herein to WISE and/or neutralizes WISE. The non-CDR portion of the binding agent may be composed of amino acids, wherein the binding agent is a recombinant binding protein, and the recombinant binding protein exhibits a similar binding pattern to human WISE peptides in the human WISE peptide epitope competition binding assay (described hereinbelow) as that exhibited by at least one of the antibodies Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, Ab-X, Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9, and/or neutralizes WISE.

In one embodiment, it is contemplated that one can use the antibody heavy chain as 'bait' in a library screen where the library is composed of human antibody light chains, to identify complementing human light chains where the reconstituted antibody binds to WISE. In this embodiment, the heavy chain is from an antibody specific to WISE and is mouse, chimeric or humanized. Ab-K heavy chain was used for this type of screen and several human light chain partners were identified that restored affinity for WISE, and importantly also inhibitory activity that was found in the parent mouse antibody. Such light chains are found in the examples below where the heavy chain shown in SEQ ID NO: 24 was used as bait, and these light chains are shown in SEQ ID NOs: 76, 78, 80, 82, 84, 86, 88, 90, 92, 94, 96, 98, 100, 102, 104, 106, 108, 110, 112, 114, 116, 118, 120, and 122.

Where an antibody comprises one or more of CDR-H1, CDR-H2, CDR-H3, CDR-L1, CDR-L2 and CDR-L3 as described above, it may be obtained by expression from a host cell containing DNA coding for these sequences. A DNA coding for each CDR sequence may be determined on the basis of the amino acid sequence of the CDR and synthesized together with any desired antibody variable region framework and constant region DNA sequences using oligonucleotide synthesis techniques, site-directed mutagenesis and polymerase chain reaction (PCR) techniques as appropriate. DNA coding for variable region frameworks and constant regions is widely available to those skilled in the art from genetic sequences databases such as GenBank™. Each of the above-mentioned CDRs will be typically located in a variable region framework at positions 31-35 (CDR-H1), 50-65 (CDR-H2) and 95-102 (CDR-H3) of the heavy chain and positions 24-34 (CDR-L1), 50-56 (CDR-L2) and 89-97 (CDR-L3) of the light chain according to the Kabat numbering system (Kabat et al., 1987 in Sequences of proteins of Immunological Interest, U.S. Department of Health and Human Services, NIH, USA).

Once synthesized, the DNA encoding an antibody of the invention or fragment thereof may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 Methods Enzymol. 178:497-515). In certain other embodiments, expression of the antibody or a fragment thereof may be preferred in a eukaryotic host cell, including yeast (e.g., *Saccharomyces cerevisiae, Schizosaccharomyces pombe,* and *Pichia pastoris*), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells.

One or more replicable expression vectors containing DNA encoding an antibody variable and/or constant region may be prepared and used to transform an appropriate cell line, for example, a non-producing myeloma cell line, such as a mouse NSO line or a bacteria, such as *E. coli*, in which production of the antibody will occur. In order to obtain efficient transcription and translation, the DNA sequence in each vector should include appropriate regulatory sequences, particularly a promoter and leader sequence operatively linked to the variable domain sequence. Particular methods for producing antibodies in this way are generally well-known and routinely used. For example, basic molecular biology procedures are described by Maniatis et al. (Molecular Cloning, A Laboratory Manual, 2nd ed., Cold Spring Harbor Laboratory, New York, 1989; see also Maniatis et al, 3rd ed., Cold Spring Harbor Laboratory, New York, (2001)). DNA sequencing can be performed as described in Sanger et al. (PNAS 74:5463, (1977)) and the Amersham International plc sequencing handbook, and site directed mutagenesis can be carried out according to methods known in the art (Kramer et al., Nucleic Acids Res. 12:9441, (1984); Kunkel Proc. Natl. Acad. Sci. USA 82:488-92 (1985); Kunkel et al., Methods in Enzymol. 154:367-82 (1987); the Anglian Biotechnology Ltd handbook). Additionally, numerous publications describe techniques suitable for the preparation of antibodies by manipulation of DNA, creation of expression vectors, and transformation and culture of appropriate cells (Mountain A and Adair, J R in Biotechnology and Genetic Engineering Reviews (ed. Tombs, M P, 10, Chapter 1, 1992, Intercept, Andover, UK); "Current Protocols in Molecular Biology", 1999, F. M. Ausubel (ed.), Wiley Interscience, New York).

Where it is desired to improve the affinity of antibodies according to the invention containing one or more of the above-mentioned CDRs can be obtained by a number of affinity maturation protocols including maintaining the CDRs (Yang et al., J. Mol. Biol., 254, 392-403, 1995), chain shuffling (Marks et al., Bio/Technology, 10, 779-783, 1992), use of mutation strains of *E. coli*. (Low et al., J. Mol. Biol., 250, 350-368, 1996), DNA shuffling (Patten et al., Curr. Opin. Biotechnol., 8, 724-733, 1997), phage display (Thompson et al., J. Mol. Biol., 256, 7-88, 1996) and sexual PCR (Crameri, et al., Nature, 391, 288-291, 1998). All of these methods of affinity maturation are discussed by Vaughan et al. (Nature Biotechnology, 16, 535-539, 1998).

Other antibodies according to the invention may be obtained by conventional immunization and cell fusion procedures as described herein and known in the art. Monoclonal antibodies of the invention may be generated using a variety of known techniques. In general, monoclonal antibodies that bind to specific antigens may be obtained by methods known to those skilled in the art (see, for example, Kohler et al., Nature 256:495, 1975; Coligan et al. (eds.), Current Protocols in Immunology, 1:2.5.12.6.7 (John Wiley & Sons 1991); U.S. Pat. Nos. RE 32,011, 4,902,614, 4,543,439, and 4,411,993; Monoclonal Antibodies, Hybridomas: A New Dimension in Biological Analyses, Plenum Press, Kennett, McKearn, and Bechtol (eds.) (1980); and Antibodies: A Laboratory Manual, Harlow and Lane (eds.), Cold Spring Harbor Laboratory Press (1988); Picksley et al., "Production of monoclonal antibodies against proteins expressed in *E. coli*," in DNA Cloning 2: Expression Systems, 2nd Edition, Glover et al. (eds.), page 93 (Oxford University Press 1995)). Antibody fragments may be derived therefrom using any suitable standard technique such as proteolytic digestion, or optionally, by proteolytic digestion (for example, using papain or pepsin) followed by mild reduction of disulfide bonds and alkylation. Alternatively, such fragments may also be generated by recombinant genetic engineering techniques as described herein.

Monoclonal antibodies can be obtained by injecting an animal, for example, a rat, hamster, a rabbit, or preferably a mouse, including for example a transgenic or a knock-out, as known in the art, with an immunogen comprising human WISE of SEQ ID NO: 2, or a fragment thereof, according to methods known in the art and described herein. The presence of specific antibody production may be monitored after the initial injection and/or after a booster injection by obtaining a serum sample and detecting the presence of an antibody that binds to human WISE or peptide using any one of several immunodetection methods known in the art and described herein. From animals producing the desired antibodies, lymphoid cells, most commonly cells from the spleen or lymph node, are removed to obtain B-lymphocytes. The B lymphocytes are then fused with a drug-sensitized myeloma cell fusion partner, preferably one that is syngeneic with the immunized animal and that optionally has other desirable properties (e.g., inability to express endogenous Ig gene products, e.g., P3X63-Ag 8.653 (ATCC No. CRL 1580); NSO, SP20) to produce hybridomas, which are immortal eukaryotic cell lines. The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. A preferred selection media is HAT (hypoxanthine, aminopterin, thymidine). After a sufficient time, usually about one to two weeks, colonies of cells are observed. Single colonies are isolated, and antibodies produced by the cells may be tested for binding activity to human WISE, using any one of a variety of immunoassays known in the art and described herein. The hybridomas are cloned (e.g., by limited dilution cloning or by soft agar plaque isolation) and positive clones that produce an antibody specific to WISE are selected and cultured. The monoclonal antibodies from the hybridoma cultures may be isolated from the supernatants of hybridoma cultures. An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anticonstant region (light chain or heavy chain) antibody, an anti-idiotype antibody, and a TGF-beta binding protein, or fragment or variant thereof.

An antibody of the present invention may also be a human monoclonal antibody. Human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. For example, human monoclonal antibodies may be obtained from transgenic mice that have been engineered to produce specific human antibodies in response to antigenic challenge. Methods for obtaining human antibodies from transgenic mice are described, for example, by Green et al., Nature Genet. 7:13, 1994; Lonberg et al., Nature 368:856, 1994; Taylor et al., Int. Immun. 6:579, 1994; U.S. Pat. No. 5,877,397; Bruggemann et al., 1997 Curr. Opin. Biotechnol. 8:455-58; Jakobovits et al., 1995 Ann. N. Y Acad. Sci. 764: 525-35. In this technique, elements of the human heavy and light chain locus are introduced into strains of mice derived from embryonic stem cell lines that contain targeted disruptions of the endogenous heavy chain and light chain loci (see also Bruggemann et al., Curr. Opin. Biotechnol. 8:455-58 (1997)). For example, human immunoglobulin transgenes may be mini-gene constructs, or transloci on yeast artificial chromosomes, which undergo B cell-specific DNA rearrangement and hypermutation in the mouse lymphoid tissue. Human monoclonal antibodies may be obtained by immunizing the transgenic mice, which may then produce human antibodies specific for WISE. Lymphoid cells of the immunized transgenic mice can be used to produce human antibody-secreting hybridomas according to the methods described herein. Polyclonal sera containing human antibodies may also be obtained from the blood of the immunized animals.

Another method for generating human antibodies of the invention includes immortalizing human peripheral blood cells by EBV transformation. See, e.g., U.S. Pat. No. 4,464, 456. Such an immortalized B cell line (or lymphoblastoid cell line) producing a monoclonal antibody that specifically binds to WISE can be identified by immunodetection methods as provided herein, for example, an ELISA, and then isolated by standard cloning-techniques. The stability of the lymphoblastoid cell line producing an anti-WISE antibody may be improved by fusing the transformed cell line with a murine myeloma to produce a mouse-human hybrid cell line according to methods known in the art (see, e.g., Glasky et al., Hybridoma 8:377-89 (1989)). Still another method to generate human monoclonal antibodies is in vitro immunization, which includes priming human splenic B cells with human WISE, followed by fusion of primed B cells with a heterohybrid fusion partner. See, e.g., Boerner et al., 1991 J. Immunol. 147:86-95.

In certain embodiments, a B cell that is producing an anti-human WISE antibody is selected and the light chain and heavy chain variable regions are cloned from the B cell according to molecular biology techniques known in the art (WO 92/02551; U.S. Pat. No. 5,627,052; Babcook et al., Proc. Natl. Acad. Sci. USA 93:7843-48 (1996)) and described herein. B cells from an immunized animal may be isolated from the spleen, lymph node, or peripheral blood sample by selecting a cell that is producing an antibody that specifically binds to WISE. B cells may also be isolated from humans, for example, from a peripheral blood sample. Methods for detecting single B cells that are producing an antibody with the desired specificity are well known in the art, for example, by plaque formation, fluorescence-activated cell sorting, in vitro stimulation followed by detection of specific antibody, and the like. Methods for selection of specific antibody-producing B cells include, for example, preparing a single cell suspension of B cells in soft agar that contains human WISE. Binding of the specific antibody produced by the B cell to the antigen results in the formation of a complex, which may be visible as an immunoprecipitate. After the B cells producing the desired antibody are selected, the specific antibody genes may be cloned by isolating and amplifying DNA or mRNA according to methods known in the art and described herein.

An additional method for obtaining antibodies of the invention is by phage display. See, e.g., Winter et al., 1994 Annu. Rev. Immunol. 12:433-55; Burton et al., 1994 Adv. Immunol. 57:191-280. Human or murine immunoglobulin variable region gene combinatorial libraries may be created in phage vectors that can be screened to select Ig fragments (Fab, Fv, sFv, or multimers thereof) that bind specifically to TGF-beta binding protein or variant or fragment thereof. See, e.g., U.S. Pat. No. 5,223,409; Huse et al., 1989 Science 246: 1275-81; Sastry et al., Proc. Natl. Acad. Sci. USA 86:5728-32 (1989); Alting-Mees et al., Strategies in Molecular Biology 3:1-9 (1990); Kang et al., 1991 Proc. Natl. Acad. Sci. USA 88:4363-66; Hoogenboom et al., 1992 J. Molec. Biol. 227: 381-388; Schlebusch et al., 1997 Hybridoma 16:47-52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using lambda ImmunoZap™ (H) and lambda ImmunoZap™ (L) vectors (Stratagene, La Jolla, Calif.). Briefly, mRNA is isolated from a B cell population, and used to create heavy and light chain immunoglobulin cDNA expression libraries in the lambda ImmunoZap(H) and lambda ImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high level expression of monoclonal antibody fragments from *E. coli*.

In one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, Calif.), which sells primers for mouse and human variable regions including, among others, primers for VHa, VHb, VHc, VHd, CHI, VL and CL regions.) These primers may be used to amplify heavy or light chain variable regions, which may then be inserted into vectors such as ImmunoZAP™ H or ImmunoZAP™ (Stratagene), respectively. These vectors may then be introduced into *E. coli*, yeast, or mammalian-based systems for expression. Large amounts of a single-chain protein containing a fusion of the VH and VL domains may be produced using these methods (see Bird et al., Science 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

Preferably the binding agents specifically bind to WISE. As with all binding agents and binding assays, one of skill in this art recognizes that the various moieties to which a binding agent should not detectably bind in order to be therapeutically effective and suitable would be exhaustive and impractical to list. Therefore, for a binding agent disclosed herein, the term "specifically binds" refers to the ability of a binding agent to bind to WISE, preferably human WISE, with greater affinity than it binds to an unrelated control protein. Preferably the control protein is hen egg white lysozyme. Preferably the binding agents bind to WISE with an affinity that is at least, 50, 100, 250, 500, 1000, or 10,000 times greater than the affinity for a control protein. A binding agent may have a binding affinity for human WISE of less than or equal to $1 \times 10^{-7}$ M, less than or equal to $1 \times 10^{-8}$ M, less than or equal to $1 \times 10^{-9}$ M, less than or equal to $1 \times 10^{-10}$ M, less than or equal to $1 \times 10^{-11}$ M, or less than or equal to $1 \times 10^{-12}$ M.

Affinity may be determined by an affinity ELISA assay. In certain embodiments, affinity may be determined by a BIAcore assay. In certain embodiments, affinity may be determined by a kinetic method. In certain embodiments, affinity may be determined by an equilibrium/solution method. Such methods are described in further detail herein or known in the art.

WISE binding agents of the present invention preferably modulate WISE function in the cell-based assay described herein and/or the in vivo assay described herein and/or bind to one or more of the epitopes described herein and/or cross-block the binding of one of the antibodies described in this application and/or are cross-blocked from binding WISE by one of the antibodies described in this application. Accordingly such binding agents can be identified using the assays described herein.

In certain embodiments, binding agents are generated by first identifying antibodies that bind to one or more of the epitopes provided herein and/or neutralize in the cell-based and/or in vivo assays described herein and/or cross-block the antibodies described in this application and/or are cross-blocked from binding WISE by one of the antibodies described in this application. The CDR regions from these antibodies are then used to insert into appropriate biocompatible frameworks to generate WISE binding agents. The non-CDR portion of the binding agent may be composed of amino acids, or may be a non-protein molecule. The assays described herein allow the characterization of binding agents. Preferably the binding agents of the present invention are antibodies as defined herein.

It will be understood by one skilled in the art that some proteins, such as antibodies, may undergo a variety of post-translational modifications during expression and secretion from host cells. The type and extent of these modifications often depends on the host cell line used to express the protein as well as the culture conditions. Such modifications may include variations in glycosylation, methionine or tryptophan oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705:129-134, 1995). Once the proteins have been expressed and processed they are in a 'mature' form. Thus it is understood that the invention includes mature antibodies that result from expression of the DNAs of the invention.

Antibodies disclosed herein bind to regions of human WISE which are important for the in vivo activity of the protein thereby inhibiting the activity of WISE. Binding of an antibody to WISE can be correlated with changes in biomarkers associated with kidney function, for example urinary levels of albumin or 24 hours total urinary protein excretion. Methods of constructing and expressing antibodies and fragments thereof comprising CDR's of the present invention are known to those of skill in the art.

An oligopeptide or polypeptide is within the scope of the invention if it has an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to at least one of the CDR's depicted SEQ ID NOs: 123, 124, and 125; 127, 128, and 129; 131, 132, and 133; 135, 136, and 137; 139, 140, and 141; 143, 144, and 145; 147, 148, and 149; 151, 152, and 153; 155, 156, and 157; 158, 159, and 160; 161, 162, and 163; 164, 165, and 166; 167, 168, and 169; 170, 171, and 172; 173, 174, and 175; 177, 178, and 179; 181, 182, and 183; 185, 186 and 187; 189, 190, and 191; 193, 194, and 195; 197, 198, and 199; 201, 202, and 203; 205, 206 and 207; 209, 210, and 211; 213, 214, and 215; 217, 218, and 219; 221, 222, and 223; 225, 226, and 227; 229, 230, and 231; 233, 234, and 235; 237, 238, and 239; 241, 242, and 243; 245, 246, and 247; 249, 250, and 251; 253, 254, and 255; 257, 258, and 259; 261, 262 and 263; 273, 274 and 275; or 277, 278 and 279; and/or to a CDR of a WISE binding agent that cross-blocks the binding of at least one of antibodies Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, Ab-X, Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9 to WISE, and/or is cross-blocked from binding to WISE by at least one of antibodies Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, Ab-X, Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9; and/or to a CDR of a WISE binding agent wherein the binding agent can block the inhibitory effect of WISE in a cell based assay (i.e. a WISE neutralizing binding agent); and/or to a CDR of a WISE binding agent that binds to a cystine knot domain epitope.

WISE binding agent polypeptides and antibodies are within the scope of the invention if they have amino acid sequences that are at least 85%, 86%, 87%, 88%, 89%, 90%, 91%, 92%, 93%, 94%, 95%, 96%, 97%, 98% or 99% identical to a variable region of at least one of antibodies Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, Ab-X, Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9, and cross-block the binding of at least one of antibodies Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, Ab-X, Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9 to WISE, and/or are cross-blocked from binding to WISE by at least one of antibodies Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, Ab-X, Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9; and/or can block the inhibitory effect of WISE in a cell based assay (i.e. a WISE neutralizing binding agent); and/or bind to a cystine knot domain epitope.

Polynucleotides encoding WISE binding agents are within the scope of the invention if they have polynucleotide sequences that are at least 85%, 86%, 87%, 88%, 89%, 90%, 91%, 92%, 93%, 94%, 95%, 96%, 97%, 98% or 99% identical to a polynucleotide encoding a variable region of at least one of antibodies Ab-A, Ab-B, and Ab-C, and wherein the encoded WISE binding agents cross-block the binding of at least one of antibodies Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, Ab-X, Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9 to WISE, and/or are cross-blocked from binding to WISE by at least one of antibodies Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, Ab-X, Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9; and/or can block the inhibitory effect of WISE in a cell based assay (i.e. a WISE neutralizing binding agent); and/or bind to a cystine knot domain epitope.

The affinity of a binding agent such as an antibody or binding partner, as well as the extent to which a binding agent (such as an antibody) inhibits binding, can be determined by one of ordinary skill in the art using conventional techniques, for example those described by Scatchard et al. (Ann. N.Y. Acad. Sci. 51:660-672 (1949)) or by surface plasmon resonance (SPR; BIAcore, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., Cancer Res. 53:2560-65 (1993)).

An antibody according to the present invention may belong to any immunoglobin class, for example IgG, IgE, IgM, IgD, or IgA. It may be obtained from or derived from an animal, for example, fowl (e.g., chicken) and mammals, which includes but is not limited to a mouse, rat, hamster, rabbit, or other rodent, cow, horse, sheep, goat, camel, human, or other primate. The antibody may be an internalizing antibody. Production of antibodies is disclosed generally in U.S. patent Publication No. 2004/0146888 A1.

Characterization Assays

In the methods described herein to generate antibodies according to the invention, including the manipulation of the specific Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, Ab-X, Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9 CDRs into new frameworks and/or constant regions, appropriate assays are available to select the desired antibodies or binding agents (i.e. assays for determining binding affinity to WISE; cross-blocking assays; Biacore-based "human WISE peptide epitope competition binding assay;" MC3T3-E1 cell based assay; in vivo assays).

Epitope Binding Assays

The unprocessed human WISE is 206 amino acids with the signal peptide and the mature form of human WISE is a 183 amino acid glycoprotein containing a cystine-knot motif. Due to conservation of key amino acid residues, particularly the cysteines, it is believed that WISE has a structure similar to previously described cysteine knot proteins. This structure includes, in addition to the cystine-knot motif, three loops designated as Loop 1, Loop 2 and Loop 3. As used herein, the positions of the loops are defined as approximately at amino acids 75 to 104 of SEQ ID NO: 2 for Loop 1; Loop 2 is approximately at amino acids 105 to 132; and Loop 3 is approximately at amino acids 134 to 170 of SEQ ID NO:2. It is understood that approximate positions mean that the relative positions could be plus or minus 2 amino acids carboxy terminal or amino terminal of the stated positions.

Human WISE was subjected to proteolytic digestion to produce fragments. Briefly, using different proteases, including trypsin, aspN, and lysC, fragments with various cleavage sites and sizes were generated. The sequences and mass for various human WISE peptides were determined. Antibody protection was evaluated to determine the effect on accessibility for proteolysis, including clipped site masking and peptide shifting. Finally, a BIAcore-based "human WISE peptide epitope competition assay" was performed.

One such fragment called T49 consists essentially of a multiply truncated human WISE protein of SEQ ID NO:2, wherein amino acids 1 to 70, 113 to 126, and 171 to 206 of SEQ ID NO:2 are absent from the polypeptide; this polypeptide may be obtained by tryptic digestion of human WISE, and the protein may be isolated by HPLC fractionation. This fragment is an immunogenic portion of the cystine knot of human WISE comprising amino acids 71 to 112 and 127 to 170 of SEQ ID NO:2, wherein the immunogenic portion comprises at least one of: (a) a disulfide bond between amino acids C1 and C5; (b) a disulfide bond between amino acids C2 and C6; and (c) a disulfide bond between amino acids C3 and C7; the immunogenic portion may have at least two of these disulfide bonds; and the immunogenic portion may have all three disulfide bonds.

Another fragment called T56.1 consists essentially of a multiply truncated human WISE protein of SEQ ID NO: 2, wherein amino acids 1 to 70, 122 to 126, and 171 to 206 of SEQ ID NO: 2 are absent from the polypeptide; this polypeptide may be obtained by tryptic digestion of human WISE, and the protein may be isolated by HPLC fractionation. This fragment is an immunogenic portion of the cystine knot of human WISE comprising amino acids 71 to 121 and 127 to 170 of SEQ ID NO: 2, wherein the immunogenic portion comprises at least one of: (a) a disulfide bond between amino acids C1 and C5; (b) a disulfide bond between amino acids C2 and C6; and (c) a disulfide bond between amino acids C3 and C7; the immunogenic portion may have at least two of these disulfide bonds; and the immunogenic portion may have all three disulfide bonds.

One group of antibodies exhibits a specific pattern of binding to certain epitopes as evidenced by a Biacore-based "human WISE peptide epitope competition binding assay." Briefly, the antibody is preincubated with the epitope to be tested, at concentrations that will saturate the epitope-binding sites on the antibody. The antibody is then exposed to WISE bound to a chip surface. After the appropriate incubation and washing procedures, a pattern of competitive binding is established.

Cross-Blocking Assays

The terms "cross-block", "cross-blocked" and "cross-blocking" are used interchangeably herein to mean the ability of an antibody or other binding agent to interfere with the binding of other antibodies or binding agents to WISE.

The extent to which an antibody or other binding agent is able to interfere with the binding of another to WISE, and therefore whether it can be said to cross-block according to the invention, can be determined using competition binding assays. One particularly suitable quantitative assay uses a Biacore machine which can measure the extent of interactions using surface plasmon resonance technology. Another suitable quantitative cross-blocking assay uses an ELISA-based approach to measure competition between antibodies or other binding agents in terms of their binding to WISE.

Biacore Cross-Blocking Assay

The following generally describes a suitable Biacore assay for determining whether an antibody or other binding agent cross-blocks or is capable of cross-blocking according to the invention. For convenience reference is made to two antibodies, but it will be appreciated that the assay can be used with any of the WISE binding agents described herein. The Biacore machine (for example the Biacore 3000) is operated in line with the manufacturer's recommendations.

Thus in one cross-blocking assay, WISE is coupled to a CM5 Biacore chip using standard amine coupling chemistry to generate a WISE-coated surface. Typically 200-800 resonance units of WISE would be coupled to the chip (an amount that gives easily measurable levels of binding but that is readily saturable by the concentrations of test reagent being used).

The two antibodies (termed A* and B*) to be assessed for their ability to cross-block each other are mixed at a one to one molar ratio of binding sites in a suitable buffer to create the test mixture. When calculating the concentrations on a binding site basis the molecular weight of an antibody is assumed to be the total molecular weight of the antibody divided by the number of WISE binding sites on that antibody.

The concentration of each antibody in the test mix should be high enough to readily saturate the binding sites for that antibody on the WISE molecules captured on the Biacore chip. The antibodies in the mixture are at the same molar concentration (on a binding basis) and that concentration would typically be between 1.00 and 1.5 micromolar (on a binding site basis).

Separate solutions containing antibody A* alone and antibody B* alone are also prepared. Antibody A* and antibody B* in these solutions should be in the same buffer and at the same concentration as in the test mix.

The test mixture is passed over the WISE-coated Biacore chip and the total amount of binding recorded. The chip is then treated in such a way as to remove the bound antibodies without damaging the chip-bound WISE. Typically this is done by treating the chip with 30 mM HCl for 60 seconds.

The solution of antibody A* alone is then passed over the WISE-coated surface and the amount of binding recorded. The chip is again treated to remove all of the bound antibody without damaging the chip-bound WISE.

The solution of antibody B* alone is then passed over the WISE-coated surface and the amount of binding recorded.

The maximum theoretical binding of the mixture of antibody A* and antibody B* is next calculated, and is the sum of the binding of each antibody when passed over the WISE surface alone. If the actual recorded binding of the mixture is less than this theoretical maximum then the two antibodies are cross-blocking each other.

Thus, in general, a cross-blocking antibody or other binding agent according to the invention is one which will bind to WISE in the above Biacore cross-blocking assay such that during the assay and in the presence of a second antibody or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two antibodies or binding agents in combination.

The Biacore assay described above is an assay used to determine if antibodies or other binding agents cross-block each other according to the invention. On rare occasions particular antibodies or other binding agents may not bind to WISE coupled via amine chemistry to a CM5 Biacore chip (this usually occurs when the relevant binding site on WISE is masked or destroyed by the coupling to the chip). In such cases cross-blocking can be determined using a tagged version of WISE, for example N-terminal His-tagged WISE. In this particular format, an anti-His antibody would be coupled to the Biacore chip and then the His-tagged WISE would be passed over the surface of the chip and captured by the anti-His antibody. The cross blocking analysis would be carried out essentially as described above, except that after each chip regeneration cycle, new His-tagged WISE would be loaded back onto the anti-His antibody coated surface. In addition to the example given using N-terminal His-tagged WISE, C-terminal His-tagged WISE could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

Elisa-Based Cross-Blocking Assay

The following generally describes an ELISA assay for determining whether an anti-WISE antibody or other WISE binding agent cross-blocks or is capable of cross-blocking according to the invention. For convenience, reference is made to two antibodies, but it will be appreciated that the assay can be used with any of the WISE binding agents described herein.

The general principal of the assay is to have an anti-WISE antibody coated onto the wells of an ELISA plate. An excess amount of a second, potentially cross-blocking, anti-WISE antibody is added in solution (i.e. not bound to the ELISA plate). A limited amount of WISE is then added to the wells. The coated antibody and the antibody in solution compete for binding of the limited number of WISE molecules. The plate is washed to remove WISE that has not been bound by the coated antibody and to also remove the second, solution phase antibody as well as any complexes formed between the second, solution phase antibody and WISE. The amount of bound WISE is then measured using an appropriate WISE detection reagent. An antibody in solution that is able to cross-block the coated antibody will be able to cause a decrease in the number of WISE molecules that the coated antibody can bind relative to the number of WISE molecules that the coated antibody can bind in the absence of the second, solution phase, antibody.

This assay is described in more detail further below for Ab-A, Ab-C and Ab-E. In the instance where Ab-A is chosen to be the immobilized antibody, it is coated onto the wells of the ELISA plate, after which the plates are blocked with a suitable blocking solution to minimize non-specific binding of reagents that are subsequently added. An excess amount of Ab-C is then added to the ELISA plate such that the moles of Ab-C WISE binding sites per well are at least 10 fold higher than the moles of Ab-A WISE binding sites that were used, per well, during the coating of the ELISA plate.

WISE is then added such that the moles of WISE added per well are at least 25-fold lower than the moles of Ab-A WISE binding sites that were used for coating each well. Following a suitable incubation period the ELISA plate is washed and a WISE detection reagent is added to measure the amount of WISE specifically bound by the coated anti-WISE antibody (in this case Ab-A). The background signal for the assay is defined as the signal obtained in wells with the coated antibody (in this case Ab-A), second solution phase antibody (in this case Ab-B), WISE buffer only (i.e. no WISE) and WISE detection reagents. The positive control signal for the assay is defined as the signal obtained in wells with the coated antibody (in this case Ab-A), second solution phase antibody buffer only (i.e. no second solution phase antibody), WISE and WISE detection reagents. The ELISA assay needs to be run in such a manner so as to have the positive control signal at least 3 times the background signal.

To avoid any artifacts (e.g. significantly different affinities between Ab-A and Ab-B for WISE) resulting from the choice of which antibody to use as the coating antibody and which to use as the second (competitor) antibody, the cross-blocking assay needs to be run in two formats: 1) format 1 is where the first antibody is the antibody that is coated onto the ELISA plate and second antibody is the competitor antibody that is in solution and 2) format 2 is where the first and second antibody are reversed in coating and solution.

Cell Based Neutralization Assay

MC3T3-E1 SuperTopFlash (STF) reporter cells are used to determine whether WISE protein can modulate Wnt signaling. The activation of TCF-dependent signaling in MC3T3-E1 STF cells can be triggered using either endogenous Wnt signaling induced by switching culturing medium to differentiation medium or by adding exogenous Wnt such as Wnt3a. Recombinant WISE protein derived from either *E coli* or mammalian cell can dose-dependently inhibit Wnt signaling in MC3T3-EL STF cells.

Luciferase assay: a vial of MC3T3-E1/STF cells is plated into a culture flask in expansion medium. When the cells are confluent they are trypsinized and cells in expansion medium plated into each well in 96 well plate. Next day all expansion medium is removed and replaced with 100 ul of freshly prepared differentiation medium.

Half of the differentiation medium (50 ul) was replaced with freshly prepared differentiation medium every day for the next four days. After five days of differentiation, all medium is replaced with testing samples in the fresh differentiation medium in 100 ul volume. The plates are then allowed to incubate for 24 hours before luciferase signal are measured. Luciferase signal is measured upon removal of medium from testing plates and addition of 20 ul of 1× lysis buffer that has been equilibrated to room temperature. The plate is sealed and rocked for 30 minutes at room temperature and 100 ul of luciferase assay reagent was added to each well and the signal was captured using Luminometer (LMAX, Molecular Device) according to manufacturer's instruction.

In Vivo Neutralization Assay

Increases in various parameters associated with, or that result from, renal protection or pulmonary protection can be measured as an output from in vivo testing of WISE binding agents in order to identify those binding agents that are able to neutralize WISE and provide a therapeutic benefit. Such parameters include various renal/pulmonary markers and histomorphometric markers of renal/pulmonary health. A WISE neutralizing binding agent is defined as one capable of causing a statistically significant increase, as compared to vehicle treated animals, in any parameter associated with, or that results from, the stimulation of renal/pulmonary protection. Such in vivo testing can be performed in any suitable mammal (e.g. mouse, rat, monkey).

Formulation and Delivery of Therapeutics

Pharmaceutical compositions are provided, comprising one of the above-described binding agents such as at least one of antibody Ab-A, Ab-B, Ab-C, Ab-D, Ab-E, Ab-F, Ab-G, Ab-H, Ab-I, Ab-J, Ab-K, Ab-L, Ab-M, Ab-N, Ab-O, Ab-P, Ab-Q, Ab-R, Ab-S, Ab-T, Ab-U, Ab-V Ab-W, Ab-X, Ab-1, Ab-13, Ab-16, Ab-18, Ab-23, Ab-24, Ab-28, Ab-29, Ab-48, Ab-60, Ab-63, Ab-65, Ab-66, Ab-67, Ab-69, Ab-7, Ab-70, Ab-72, Ab-74, Ab-75, Ab-76, and Ab-9 to human WISE, along with a pharmaceutically or physiologically acceptable carrier, excipient, or diluent.

The development of suitable dosing and treatment regimens for using the particular compositions described herein in a variety of treatment regimens, including e.g., subcutaneous, oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein subcutaneously, parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, Remington's Pharmaceutical Sciences, 15th ed., pp. 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol. 16(7):307-21, 1998; Takakura, Nippon Rinsho 56(3):691-95, 1998; Chandran et al., Indian J. Exp. Biol. 35(8):801-09, 1997; Margalit, Crit. Rev. Ther. Drug Carrier Syst. 12(2-3):233-61, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety). The use of liposomes does not appear to be associated with autoimmune responses or unacceptable toxicity after systemic delivery. In certain embodiments, liposomes are formed from phospholipids that are dispersed in an aqueous medium and spontaneously form multilamellar concentric bilayer vesicles (also termed multilamellar vesicles (MLVs)).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev. Ind. Pharm. 24(12): 1113-28, 1998). To avoid side effects due to intracellular polymeric overloading, such ultrafine particles (sized around 0.1 um) may be designed using polymers able to be degraded in vivo. Such particles can be made as described, for example, by Couvreur et al., Crit. Rev. Ther. Drug Carrier Syst. 5(1):1-20, 1988; zur Muhlen et al., Eur. J. Pharm. Biopharm. 45(2):149-55, 1998; Zambaux et al., J Controlled Release 50(1-3):31-40, 1998; and U.S. Pat. No. 5,145,684.

In addition, pharmaceutical compositions of the present invention may be placed within containers, along with packaging material that provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) that may be necessary to reconstitute the pharmaceutical composition.

The dose administered may range from 0.01 mg/kg to 200 mg/kg of body weight. Typical dosages are between 30 mg/kg and 75 mg/kg. However, as will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

Method of Treatment Using WISE Binding Agents

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

As used in the context of treating renal disorders or diseases, the phrase "therapeutically effective amount" is meant to refer to an amount of therapeutic or prophylactic WISE antibody that provides a reduction in renal damage or deterioration, or that provides a reduction in the severity or progression of symptoms associated with renal disease, such as fibrosis and proteinuria (i.e. that provides "therapeutic efficacy"). As used in the context of treating fibrosis the phrase "therapeutically effective amount" is meant to refer to an amount of therapeutic or prophylactic WISE antibody that provides a reduction in fibroid elements or their precursors, and/or that provides a reduction in the severity or progression of symptoms associated with fibrotic disease (i.e. that provides "therapeutic efficacy"), e.g., proteinuric glomerula disease.

In one embodiment, the compositions of the invention are contemplated to be useful for treating, reducing and/or preventing renal dysfunction including those selected from the group consisting of proteinuric glomerula disease, end stage renal disease, chronic renal disease, IgA nephropathy, Bartter's syndrome, Gitelman syndrome, nephrolithiasis, renal amyloidosis, hypertension, primary aldosteronism, Addison's disease; renal failure; glomerulonephritis and chronic glomerulonephritis: tubulointerstitial nephritis; cystic disorders of the kidney and dysplastic malformations such as polycystic disease, renal dysplasias, and cortical or medullary cysts; inherited polycystic renal diseases (PRD), such as recessive and autosomal dominant PRD; medullary cystic disease; medullary sponge kidney and tubular dysplasia; Alport's syndrome; non-renal cancers which affect renal physiology, such as bronchogenic tumors of the lungs or tumors of the basal region of the brain; multiple myeloma; adenocarcinomas of the kidney; metastatic renal carcinoma; in addition, nephrotoxic disorders include any functional or morphologic change in the kidney produced by any pharmaceutical, chemical, or biological agent that is ingested, injected, inhaled, or absorbed. Some broad categories of common nephrotoxic agents include but are not limited to immune suppressants, such as calcineurin inhibitors, heavy metals, all classes of antibiotics, analgesics, solvents, oxalosis-inducing agents, anticancer drugs, herbicides and pesticides, botanicals and biologicals, and antiepileptics.

The phrase "fibrotic-reducing activity" is meant to refer to the ability to inhibit, fully or partially, fibroid formation or to remove or reduce existing fibrosis. Thus, in one embodiment the compositions of the present invention are contemplated to be useful for treat fibrotic diseases, including pathological fibrosis or scarring (including endocardial sclerosis), idiopathic interstitial fibrosis, interstitial pulmonary fibrosis, perimuscular fibrosis, Symmers' fibrosis, pericentral fibrosis, hepatitis, dermatofibroma, billary cirrhosis, alcoholic cirrhosis, acute pulmonary fibrosis, idiopathic pulmonary fibrosis, acute respiratory distress syndrome, kidney fibrosis/glomerulonephritis, kidney fibrosis/diabetic nephropathy, scleroderma/systemic, scleroderma/local, keloids, hypertrophic scars, severe joint adhesions/arthritis, myelofibrosis, corneal scarring, cystic fibrosis, muscular dystrophy (duchenne's), cardiac fibrosis, muscular fibrosis/retinal separation, esophageal stricture and payronles disease. Further fibrotic disorders may be induced or initiated by surgery, including scar revision/plastic surgeries, glaucoma, cataract fibrosis, corneal scarring, joint adhesions, graft vs. host disease (e.g., in transplant patients), tendon surgery, nerve entrapment, dupuytren's contracture, OB/GYN adhesions/fibrosis, pelvic adhesions, peridural fibrosis, restenosis. It is also contemplated that fibrotic conditions where deposition of fibronectin is a causative factor can be treated according to the invention. Idiopathic pulmonary fibrosis, bleomycin lung, cystic fibrosis, and glomerular nephropathy, including disease characterized by fibronectin deposits in the kidneys ultimately leading to renal failure are examples of conditions which can also be treated in accordance with the present invention.

The invention also contemplates an antibody that has an affinity of at less than $1 \times 10^{-7}$M to WISE and inhibits WISE activity for use in a method for treating a medical condition associated with fibrosis, wherein the fibrosis can be associated with a disease discussed above including lung disease or kidney disease. Furthermore, also contemplated is an antibody that has an affinity of at less than $1 \times 10^{-7}$M to WISE and inhibits WISE activity suitable for use in a method for treating a medical condition associated with proteinuria.

The invention also provides for combination therapies where the compositions of the invention are administered to a patient in need thereof with additional therapeutic agents that either treat the underlying disease or reduce symptoms associated with the disease being treated. These additional therapies can be administered simultaneously, before or after the administration of the composition of the present invention. Additional therapies for use in combination with the compositions of the present invention include ACE inhibitors, angiotensin receptor blockade (ARB), erythropoietin (e.g., Aranesp® (darbepoetin), Epogen® (erythropoietin alfa), calcineurin inhibitors, steroids, beta blockers and the like.

The invention also provides a diagnostic kit comprising at least one anti-WISE binding agent according to the present invention. The binding agent may be an antibody. In addition, such a kit may optionally comprise one or more of the following: (1) instructions for using the one or more binding agent(s) for screening, diagnosis, prognosis, therapeutic monitoring or any combination of these applications; (2) a labeled binding partner to the anti-WISE binding agent(s); (3) a solid phase (such as a reagent strip) upon which the anti-WISE binding agent(s) is immobilized; and (4) a label or insert indicating regulatory approval for screening, diagnostic, prognostic or therapeutic use or any combination thereof. If no labeled binding partner to the binding agent(s) is provided, the binding agent(s) itself can be labeled with one or more of a detectable marker(s), e.g. a chemiluminescent, enzymatic, fluorescent, or radioactive moiety.

The following examples are offered by way of illustration, and not by way of limitation.

EXAMPLES

A human WISE clone was used as template for PCR to generate huWise-MYC expression cassette by PCR. The resulting product was assembled into a vector after confirming the sequence, the fragment from clone was then cloned into a pCDNA3.1 vector. huWise-MYC/pCDNA3.1 was used as template to generate a huWise expression cassette using PCR. The PCR product sequence was confirmed, and subsequently cut and then sub-cloned into an expression vector. The DNA sequence of huWise is depicted in SEQ ID NO:1. The polypeptide sequence of human WISE is depicted in SEQ ID NO:2

Cloning of Mouse, Rat and Cynomolgus Wise

Mouse WISE was used as a template for PCR by using primers to generate a NSP-mWise expression construct (NSP—native signal peptide). The PCR product was cloning into vector for sequence confirming, the DNA fragment with right sequence was then cloned into a gene expression vector. The DNA sequence of mWISE is depicted in SEQ ID NO:3. The polypeptide sequence of mouse WISE/pTT5 is depicted in SEQ ID NO:4. Rat Wise was cloned using PCR, and cloned directly into a vector. DNA sequence of ratWise is depicted in SEQ ID NO:5. The polypeptide sequence of rat WISE is depicted in SEQ ID NO:6. Cynomolgous Wise was also cloned and inserted into an expression vector. The DNA sequence of cynoWise is depicted in SEQ ID NO:7. The polypeptide sequence of Cyno WISE is depicted in SEQ ID NO:8.

Expression and Purification of Mouse and Human WISE Protein in *E. coli*.

Cells that have been transformed with a WISE expression vector were grown to an optical density of 8 to 11 at 600 nm and then induced and harvested by centrifugation six hours later. Frozen cell paste was thawed and re-suspended into buffer with a homogenizer until the slurry was homogeneous. The cell slurry was then homogenized to break open the cells and release inclusion bodies. The resulting homogenate is then centrifuged at 5,000×g for an hour at 5 C to harvest the inclusion bodies as a pellet, leaving the cytoplasmic contaminants in the discarded supernatant. The residual cytoplasm is washed from the inclusion bodies by homogeneously re-suspending the pellet to the original homogenate volume using chilled water and a homogenizer at high speed followed by centrifugation as before. The resulting pellet, washed inclusion bodies (WIBS), is then frozen at −80 C.

A sufficient amount of WIBS and guanidine hydrochloride (GnHCl) are used in a reducing-solubilization to result in approximately 1 mg/ml reduced product and 0.18 M final concentrations. The solubilization was then added with stirring to refold solution. The refold was allowed to gently stir and air-oxidize for 72 hours at 6 C. Precipitation was removed by 0.45 um filtration leaving the filtrate (AP). The AP was then adjusted to 20 mM Tris, pH 8.5 using 1 M Tris HCl to generate a second slight precipitate that is removed by centrifugation at 5 K×g for 1 hour at 5 C.

For the purification of mouse WISE, a reverse phase HPLC column was equilibrated and loaded with the supernatant from the acid-base precipitation step followed by a wash with equilibration buffer until a baseline ultraviolet (UV) trace was achieved. Product was eluted and fractions were collected and subsequent pooling was determined by SDS-PAGE (sodium dodecyl sulfate-polyacrylamide electrophoresis) of the fractions.

Following protein folding human WISE was purified using column chromatography. Purification processes were carried out at room temperature. The purification scheme used cation exchange chromatography followed by reversed phase chromatography. The fractions were then assayed by Coomassie-stained SDS-PAGE to identify fractions containing a polypeptide that migrates at the predicted size of WISE. The appropriate fractions from the column were combined to make the SPHP pool. Following purification, the WISE was formulated in PBS by dialysis. Following formulation, the preparation was filtered through a sterile 0.2 μm filter and stored at 4° C. or frozen.

Expression and Purification of Mouse and Human WISE in Mammalian Cells

One vial of stock culture was inoculated into 10 ml culture medium in Shake Flask (125 ml, Plastic), the culture was continued for 2-3 days; then the culture was expanded from 10 mL into 100 mL shake flask and again from 100 ml into 500 ml volume culture. For transfection, were seeded into 1 liter culture medium and grown until appropriate cell density.

Transfection mix was prepared, the cells were transfected using standard techniques and 24 hours post-transfection a feed was added to the cells. The culture was then continued for another 48 hours and conditioned medium was harvested by spinning at 4000 rpm for 30 minutes and then filter through a 0.2 uM filter. A small sample (1 ml) was then taken for western and the rest was frozen down for purification. The host cell culture fluid (CCF) was centrifuged to remove cell debris. The CCF supernatant was then filtered.

A Heparin column was loaded with protein then washed with PBS until the absorbance at 280 nm of the flow-through returned to baseline. WISE protein was then eluted from the column using a linear gradient from 150 mM to 2 M sodium chloride in PBS and fractions collected. The fractions were then assayed by Coomassie-stained SDS-PAGE to identify fractions containing a polypeptide that migrates at the predicted size of WISE. The appropriate fractions from the column were combined to make the Heparin pool.

The WISE protein eluted from the Heparin column was further purified by reversed phase chromatography. The Heparin pool was made 22% ethanol and adjusted to pH 5.0 with acetic acid. The pool was filtered. The filtered Heparin pool was then loaded onto a equilibrated column. After loading, the column was washed until the absorbance at 280 nm of the flow-through returned to baseline. The WISE protein was then eluted from the column.

Following purification, the WISE was formulated in PBS by dialysis. Following formulation the WISE was filtered through a sterile 0.2 μm filter and stored at 4° C. or frozen.

In Vitro Bioactivity of Recombinant WISE Protein

Figure 2:
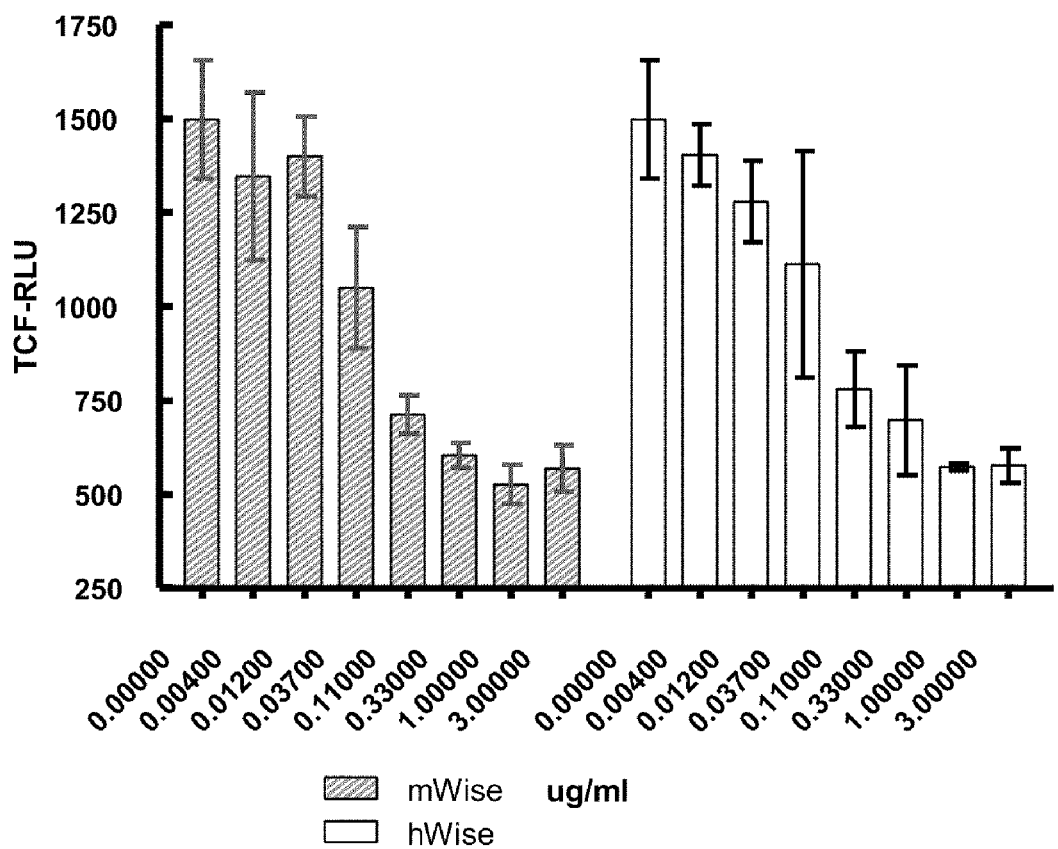
FIG. 2: WISE dose-dependently inhibited Wnt-induced luciferase expression in MC3T3-E1 STF cells.
Figure 3:
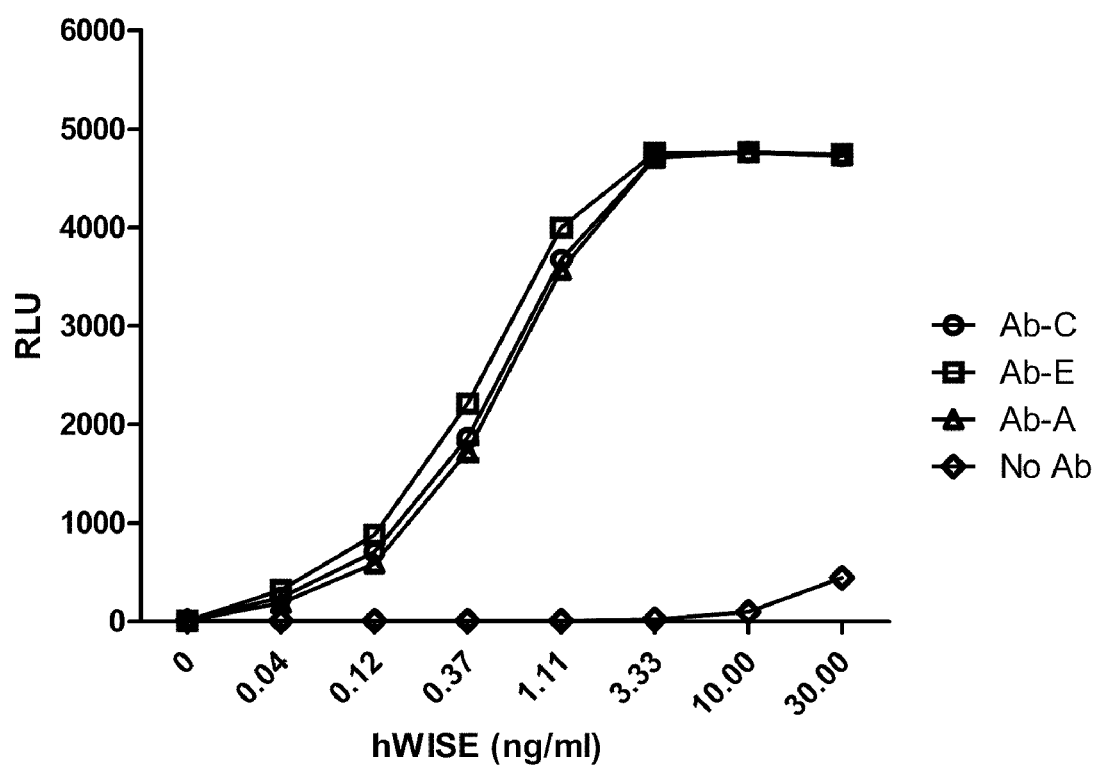
FIG. 3: Direct binding of anti-WISE Abs (Ab-C, Ab-E, Ab-A) to human WISE.
Figure 4:
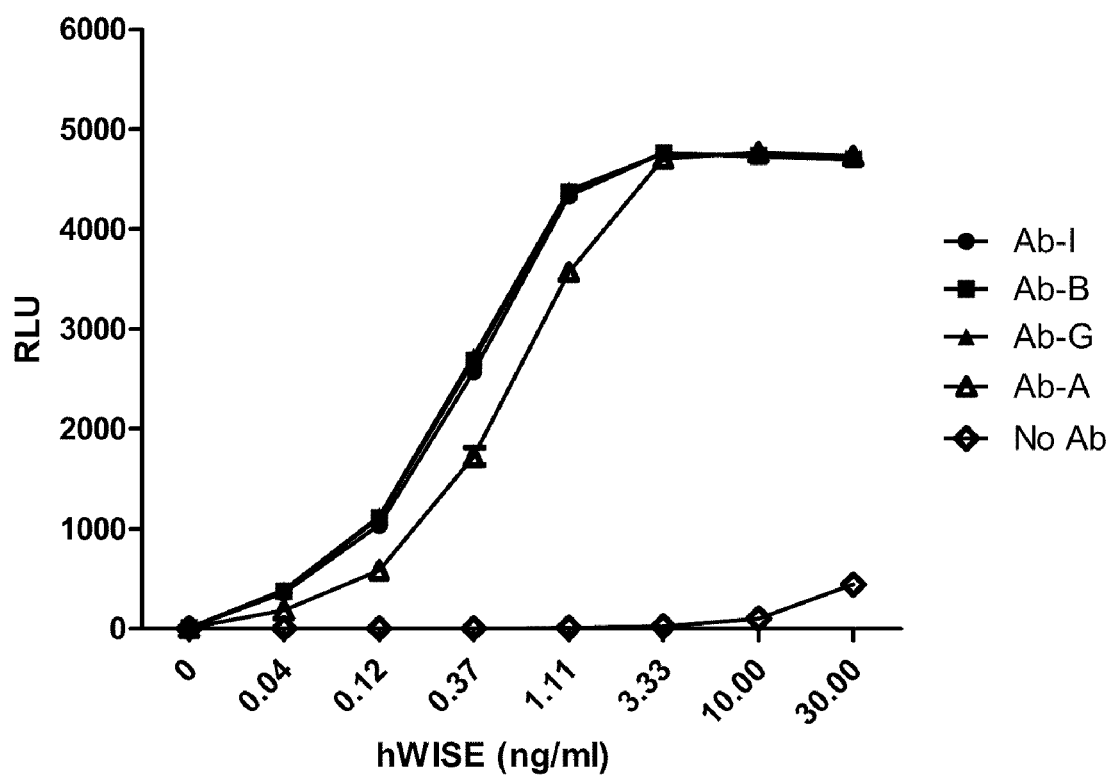
FIG. 4: Direct binding of anti-WISE Abs (Ab-A, Ab-B, Ab-G, Ab-I) to human WISE.
Figure 5:
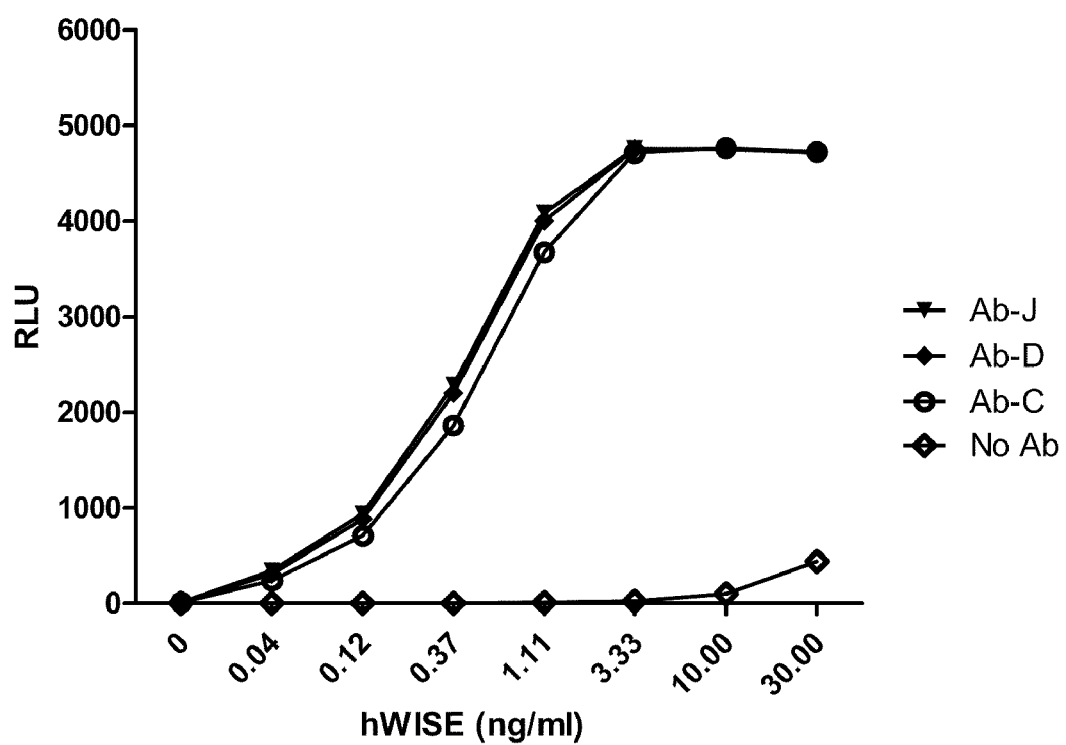
FIG. 5: Direct binding of anti-WISE Abs (Ab-C, Ab-D, Ab-J) to human WISE.
Figure 6:
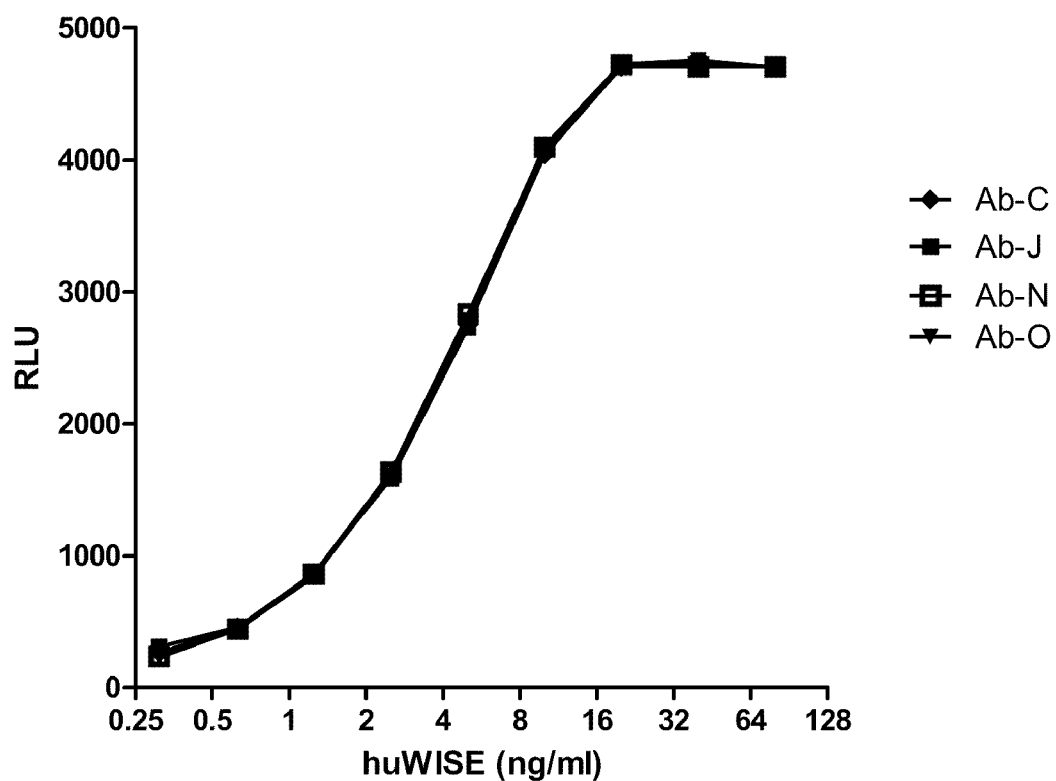
FIG. 6: Direct binding of anti-WISE Abs (Ab-C, Ab-J, Ab-N, Ab-O) to human WISE.

MC3T3-E1 STF reporter cells were used to determine whether WISE protein can modulate Wnt signaling. The activation of TCF-dependent signaling in MC3T3-E1 STF cells can be triggered using either endogenous Wnt signaling induced by switching culturing medium to differentiation medium or by adding exogenous Wnt such as Wnt3a. Recombinant WISE protein derived from either *E coli* or mammalian cell can dose-dependently inhibit Wnt signaling in MC3T3-E1 STF cells (FIG. 2).

Luciferase assay: a vial of MC3T3-E1/STF cells was plated into a culture flask in expansion medium. When the cells get confluent they were trypsinized and cells in 100 ul expansion medium were plated into each well in 96 well plate. Next day all expansion medium was removed and replaced with 100 ul of freshly prepared differentiation medium.

Half of the differentiation medium (50 ul) was replaced with freshly prepared differentiation medium every day for the next four days. After five days of differentiation, all medium was replaced with testing samples in the fresh differentiation medium in 100 ul total volume. The plates were then allowed to incubate for 24 hours before luciferase signal are measured. Luciferase signal was measured upon removal of medium from testing plates and addition of 20 ul of 1× lysis buffer that has been equilibrated to room temperature. The plate was sealed and rocked for 30 minutes at room temperature and 100 ul of luciferase assay reagent was added to each well and the signal was captured using Luminometer (LMAX, Molecular Device) according to manufacturer's instruction.

Generation and Characterization of Monoclonal Antibodies

Murine and human WISE protein from bacterial as well as mammalian sources was conjugated to a PADRE peptide.

Unreacted cross-linker was removed via dialysis followed by addition of the PADRE peptide in molar amounts equal to the amount of cross-linker added. This WISE-PADRE derivatized antigen was emulsified using various combinations of adjuvants then immunized sub-cutaneously and intraperitoneally into normal C57BL/6, BDF1, and 129× BL/6 F1 mice (Jackson Labs). In addition, Brown Norway rat was also used for immunization either with PADRE-WISE conjugates or native murine WISE protein. Immunization occurred at least every 2 weeks.

4 days prior to fusion, each mouse was boosted intraperitoneally with WISE-PADRE antigen in PBS. On the fusion day, the spleen was removed aseptically and the organ was processed into a single cell suspension. After washing, the cells were suspended in fusion buffer and this mixture was loaded into fusion chambers then subjected to electrofusion conditions.

The cell suspensions were removed from the chambers and suspended in cell growth media. 20 µl per well of this cell suspension was plated into 384 well cell culture plates and incubated overnight in an incubator. The following day, 20 µl of the above mentioned growth media containing 2× HAT (Sigma) was added to each well of the plates. The cultures were incubated for 7 days then the growth media was aspirated out of the wells and exchanged for fresh growth media. Screening of hybridoma supernatants commenced 2-3 days after the media change.

High-binding clear polystyrene 384 well plates were coated with 25 µl/well of a 1 ug/ml solution consisting of goat anti-mouse IgG, Fc specific pAb (Pierce) in PBS. The plates were incubated with coating solution overnight 4° c. then washed once on an automatic plate washer using PBS+0.05% Tween 20 (Sigma). Block solution was added to each well and incubated overnight at 4° c. 5 µl of hybridoma supernatant was transferred to each well of the ELISA plate and allowed to incubate for 60 min at room temp. The plates were then washed 2 times using the method described above. 20 µl/well of a 20 ng/ml solution of biotinylated WISE protein diluted in blocking solution that had been premixed with a 1:10,000 dilution of Nuetravidin-HRP (Pierce) was then added to each well of the plate.

After the addition of the WISE antigen, the ELISA plates were allowed to incubate for 60 min at RT. They were then washed. Finally, 20 µl/well of TMB (Pierce) was added to each well and the plates were read on an absorbance plate reader. Cells from the ELISA positive hybridoma wells were subsequently expanded in cell culture for further characterization studies.

Single cells from the ELISA positive hybridoma wells were isolated using FACS sorting and placed into 384-well plates (1 cell per well). These cells were allowed to grow for 3 days. Once the adequate cell mass was reached, supernatant from each well was collected and re-screened for antigen binding ability (see screening).

From each 384-well plate, two clones with highest antigen binding activity were identified and expanded further into 96-well plates (Falcon) with 150 ul of hybridoma growth medium per well. After 3 days, cells from 96-well plates were transferred to 24-well plates with medium and allowed to grow for 3 additional days. Once 24 well plates were confluent, cells were transferred to 6-well plates. After 5 days of incubation, a portion of the cells were frozen down. The remainder of the cells were transferred into a flask and allowed to expand. Once the flasks were confluent, half of cells were frozen down (3 vials per clone) in for additional backup. The other half was allowed to expand further in flasks with medium for antibody production.

Isotypes were determined using standard methodologies. WISE monoclonal antibodies (mAbs) were purified from hybridoma cell culture as follows. All purification processes were carried out at 4° C. One purification scheme was used to purify the various mAbs and used affinity chromatography.

The host cell culture fluid (CCF) was centrifuged to remove cell debris. The CCF supernatant was then filtered, diluted and then loaded onto Protein G chromatography media in the form of a column, Protein G High Performance (GE Healthcare) and equilibrated.

After loading, the Protein G column was washed until the absorbance at 280 nm of the flow-through returned to baseline. The WISE mAb was then eluted from the column using glycine, pH 2.5 and immediately neutralized by adding 50 µL of a stock solution of 1 M Tris Base per mL of elution volume. The absorbance at 280 nm of the eluate was monitored and fractions containing protein were collected to make the Protein G pool.

Following purification, the WISE mAbs were formulated in PBS by dialysis using 10,000 MWCO membranes (Pierce Slide-A-Lyzer or dialysis tubing). Following formulation the WISE mAbs were filtered.

Among the top 140 hybridoma CM tested, 40 showed good binding to recombinant muWISE protein. These hybridoma clones were selected for expansion and purification. To screen hybridoma clones that produce neutralizing antibody against mouse WISE, the ability of hybridoma CM to reverse the inhibition of TCF-luciferase signaling by 300 ng/ml recombinant WISE protein was tested.

Both mouse, rat, cyno and human WISE proteins inhibited Wnt-induced TCF-luciferase signal with similar potency (IC50~200 ng/ml). At 300 ng/ml muWISE consistently inhibits approximately 60% of the signal induced by differentiation. WISE protein alone or mWISE protein and hybridoma CM (1:1 dilution) pre-incubated mixture was added to the culture that have been differentiated for 5 days and then luciferase signal was measured at 24 hour post-treatment. Among the 40 top binding antibodies tested in cell-based assay, mature antibodies Ab-A, Ab-C and Ab-E showed potent neutralizing activities against mouse WISE.

The result was also confirmed using purified antibodies from CMs of the top hybridoma clones. In this case, Wise protein was either mixed with different amounts of purified antibodies or PBS for one hour at 37° C. before adding to the culture that have been differentiated for 5 days and luciferase signal was measured 24 hours later. These antibodies also neutralized the activity of human, rat and cynomolgus WISE in MC3T3-E1 STF-Luciferase assay and results for the human activity are shown in FIG. 1. Comparable results were seen in rat and cynomolgus assays.

Cross-Competition ELISA

Clear polystyrene plates (Corning #3708) were coated with 25 μl/well of a 2 ug/ml Mab solution in PBS consisting of one of the 40 mouse anti-WISE antibodies. The plates were incubated with coating solution overnight 4° c. then washed once on an automatic plate washer using PBS +0.05% Tween 20 (Sigma). 50 μl of block solution consisting of PBS +1% BSA +1% normal goat serum +0.5% Tween 20 (Sigma) was added to each well and incubated overnight at 4° c. 25 ul of competitive antibodies in blocking solution starting from 30 ug/ml and then 3 fold serial dilution were then added to each well of the plate followed by adding 25 μl/well of a 1 ng/ml solution of biotinylated WISE protein premixed with Nuetravidin-HRP (Pierce) in blocking solution.

After the addition of the antigen-antibody mix, the ELISA plates were allowed to incubate for reaching equilibrium for overnight at 4° C. They were then washed 4× with PBS+

0.05% Tween20. Finally, 25 µl/well of luminescent substrate (Pierce) was added to each well and the plates were read on a luminescence plate reader. Based on complete set of data, there are multiple antibody bins. Examples of the data are shown in FIGS. 20-26.

Epitope Mapping

To determine whether WISE antibodies bind to linear or conformational epitopes, the ability of select antibodies to bind to reduced or non-reduced antigen using western blot was tested. If the antibody binds to a linear epitope, it will bind to WISE protein whether or not it has been reduced or not. Otherwise, it is binding to a conformational epitope. Briefly, both human (1 ug/ul) and mouse (0.25 ug/ul) WISE proteins made in mammalian cells are denatured under either reduced or non-reduced conditions (65° C. for 10 minutes with or without b-ME respectively).

For each lane 100 ng of the denatured proteins in Laemmli sample buffer were loaded onto NuPAGE Bis-Tris 4-12% gel and subjected to SDS-polyacrylamide gel electrophoresis and western blotting using nitrocellulose membrane. Upon blocking, each testing antibody at 120 ng/ml was incubated in PBS and 0.05% Tween with the membrane for 1 hr at RT with gentle agitation.

The bound antibody was detected using HRP labeled secondary antibody against mouse IgG-Fc (Cat #31439, PIERCE) used at 1:10000 dilution for 1 hr at room temperature. The signal was detected using ECL substrates and exposed onto film. Among the antibodies tested, all antibodies are binding to conformational epitope.

To determine the epitope of the different antibodies, the tryptic peptide HPLC profile derived from trypsin digestion of WISE protein either in the presence or absence of individual antibodies was compared. Mammalian cell derived human recombinant Wise protein (10 ug) was mixed with individual antibody (32 ug) with a molar ratio of appr. 1:1 in 200 ul of 0.1M Tris-HCl buffer (pH 7.5). The mixture was incubated for 30 minutes at room temperature. Trypsin (Roche) (2 ug) was added and the digestion was allowed to proceed for 24 hours at 37 C. Under these conditions, the antibody against human Wise is comparatively stable against the proteolytic digestion, particularly the tryptic digestion. The trypsin-treated samples were directly subjected to reversed phase HPLC using the TFA-acetonitrile system. A reverse phase HPLC column was used for separation of the peptides. The peptides were eluted by a linear gradient from 2% solvent B to 35% solvent B for 30 min with a flow rate of 0.25 ml/min, monitoring at 215 nm absorbance. Using this approach it was found that several groups of antibodies that generated similar tryptic peptide profile including the mature forms of Ab-A, Ab-C and Ab-E.

To obtain sequence identity of individual peptides derived from tryptic digests, WISE protein (100 ug) was digested with trypsin (Roche) (2 ug) for 24 hours at 37 C and the digestion was allowed to proceed to further 24 hours after addition of 2 ug of trypsin in order to complete the proteolysis. The peptides were purified by reversed phase HPLC. Linear gradient conditions were used as follows: a column was equilibrated with 2% solvent B. After sample injection, a linear gradient from 2% solvent B to 35% solvent B for 60 min was performed with a flow rate of 0.25 ml/min. The HPLC peptide peaks were manually collected and dried. After reconstitution as described above, the samples (0.7-1 ul) were subjected to MALDI mass spectrometry (Micromass, Waters) and the remaining sample was kept for sequence analysis. One aliquot of the sample was loaded on stainless steel MALDI plate with a matrix, alpha-cyano 4-hydroxy cinnamic acid (4-HCCA). Peptide sequence was also determined.

Figure 9B:
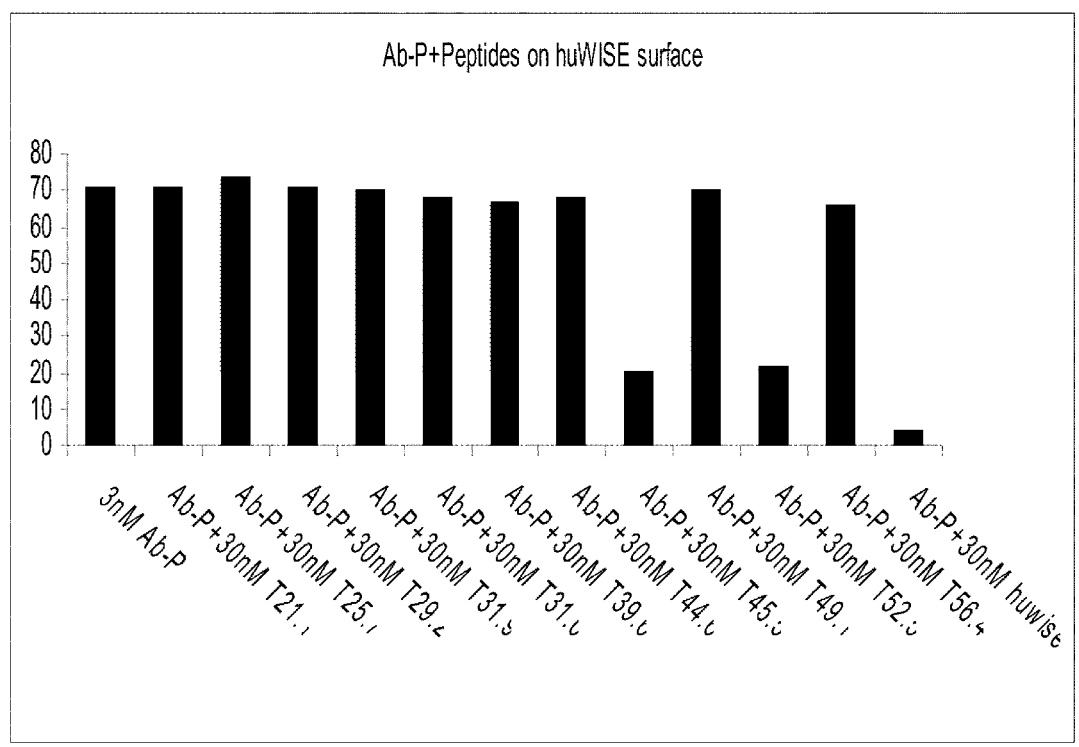
FIG. 9B: Competition assay showing binding of digested human WISE peptides to mature antibody Ab-P.
Figure 10:
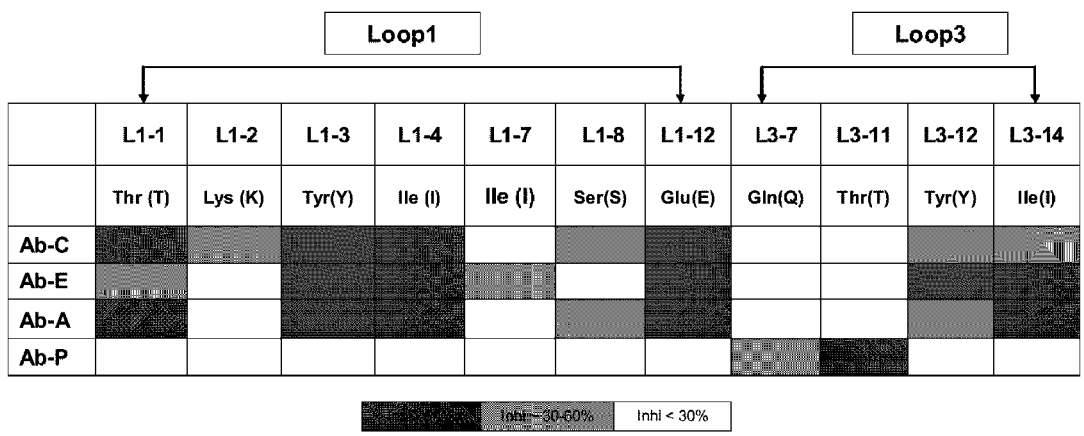
FIG. 10: Binding assay shows that the impact of specific mutation in the human WISE protein on the binding of four anti-WISE Abs (Ab-A, Ab-C, Ab-E and Ab-P) to wild type human WISE protein.
Figure 11:
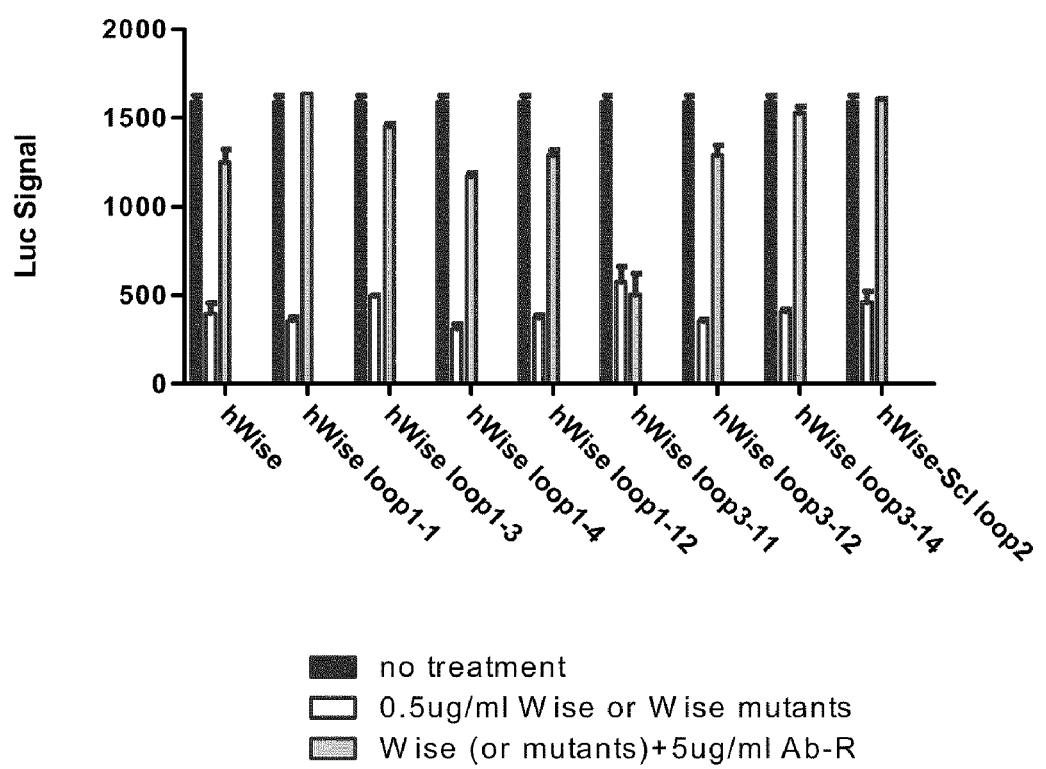
FIG. 11: Cell-based assay shows that the impact of change of individual amino acid to Ala at each of the designated position on the ability of Ab-R to neutralize mutant WISE protein activity in MC3T3-E1 SuperTopFlash (STF) cells. For each set of columns, the first column shows no treatment, the second is 0.5 ug/ml human WISE or WISE mutant with no antibody, and the third is 0.5 ug/ml of human WISE mixed with the antibody R (Ab-R) before being added to the testing well.
Figure 12:
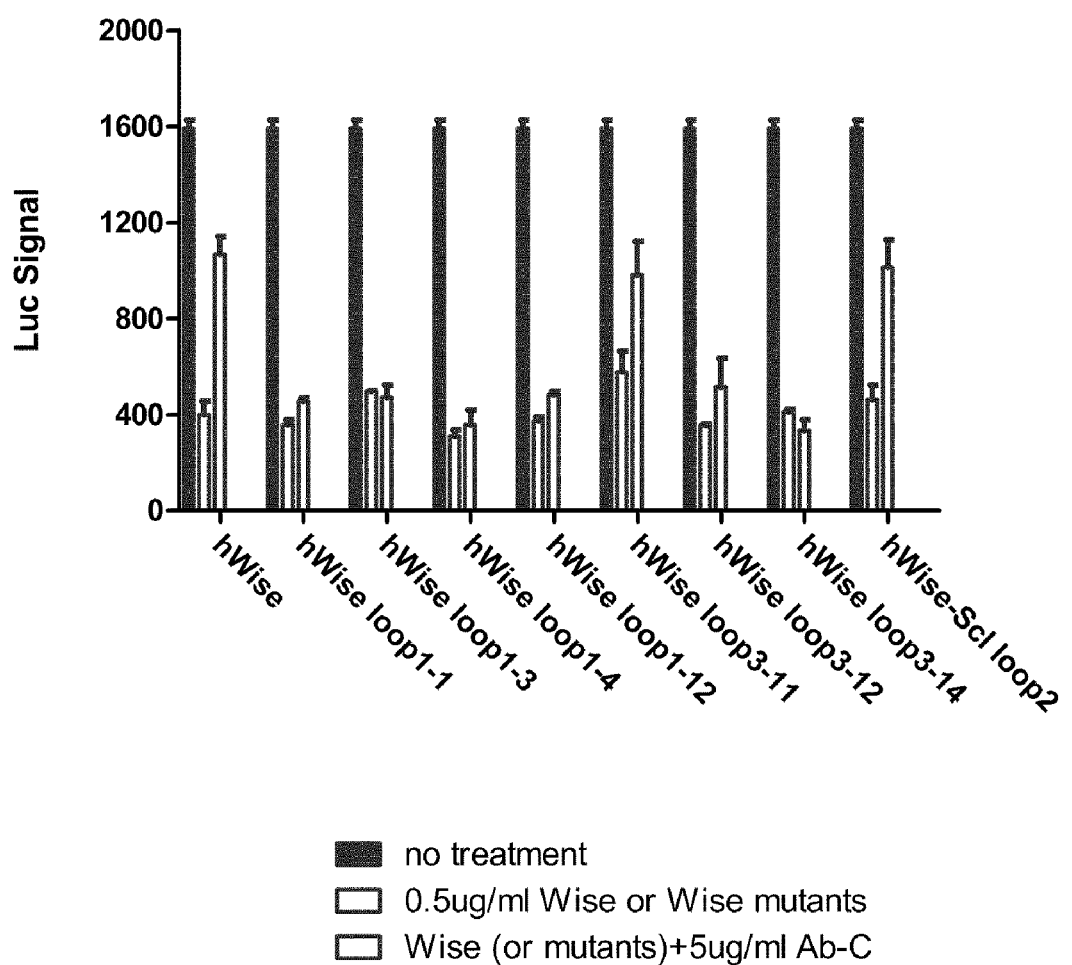
FIG. 12: Cell-based assay shows that the impact of change of individual amino acid to Ala at each of the designated position on the ability of Ab-C to neutralize mutant WISE protein activity in MC3T3-E1 SuperTopFlash (STF) cells. For each set of columns, the first column shows no treatment, the second is 0.5 ug/ml human WISE or WISE mutant with no antibody, and the third is 0.5 ug/ml of human WISE mixed with the antibody C (Ab-C) before being added to the testing well.
Figure 13:
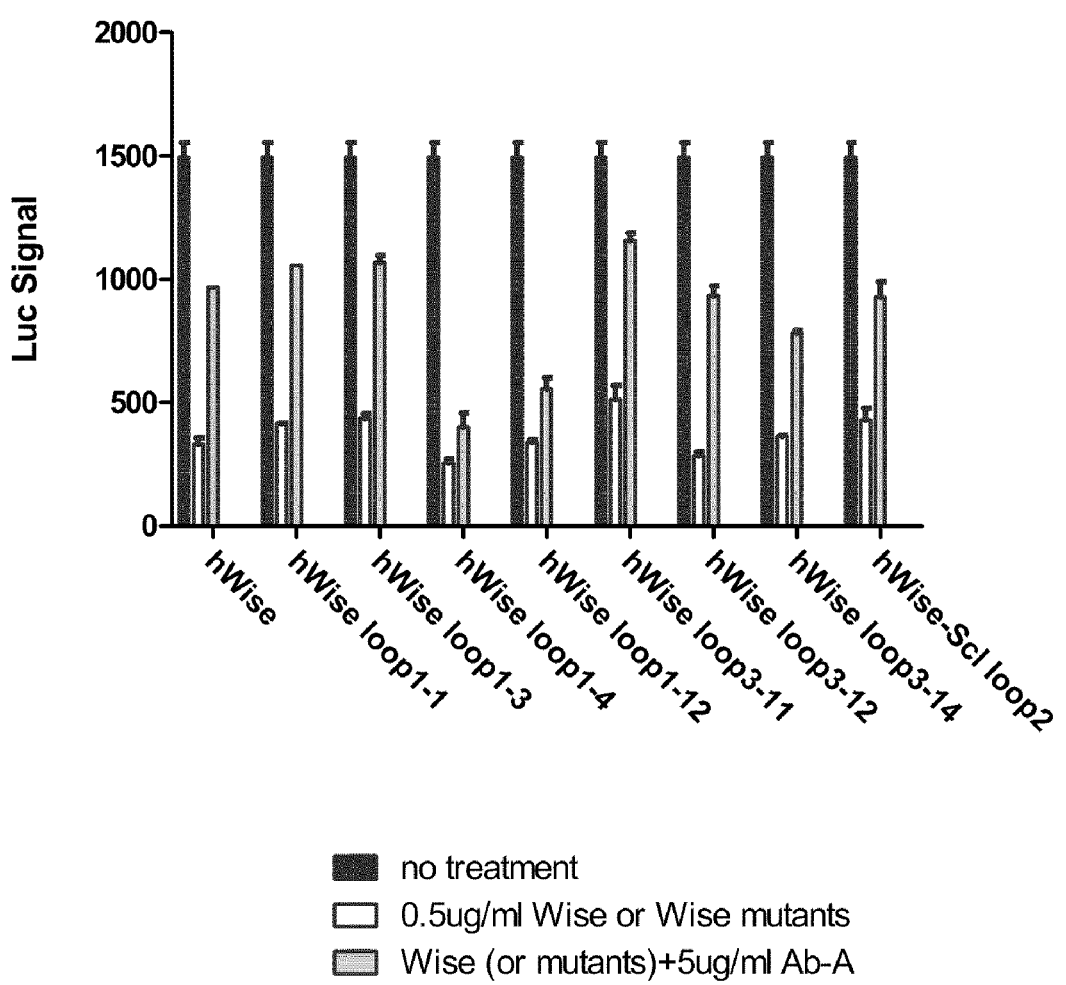
FIG. 13: Cell-based assay shows that the impact of change of individual amino acid to Ala at each of the designated position on the ability of Ab-A to neutralize mutant WISE protein activity in MC3T3-E1 SuperTopFlash (STF) cells. For each set of columns, the first column shows no treatment, the second is 0.5 ug/ml human WISE or WISE mutant with no antibody, and the third is 0.5 ug/ml of human WISE mixed with the antibody A (Ab-A) before being added to the testing well.
Figure 14:
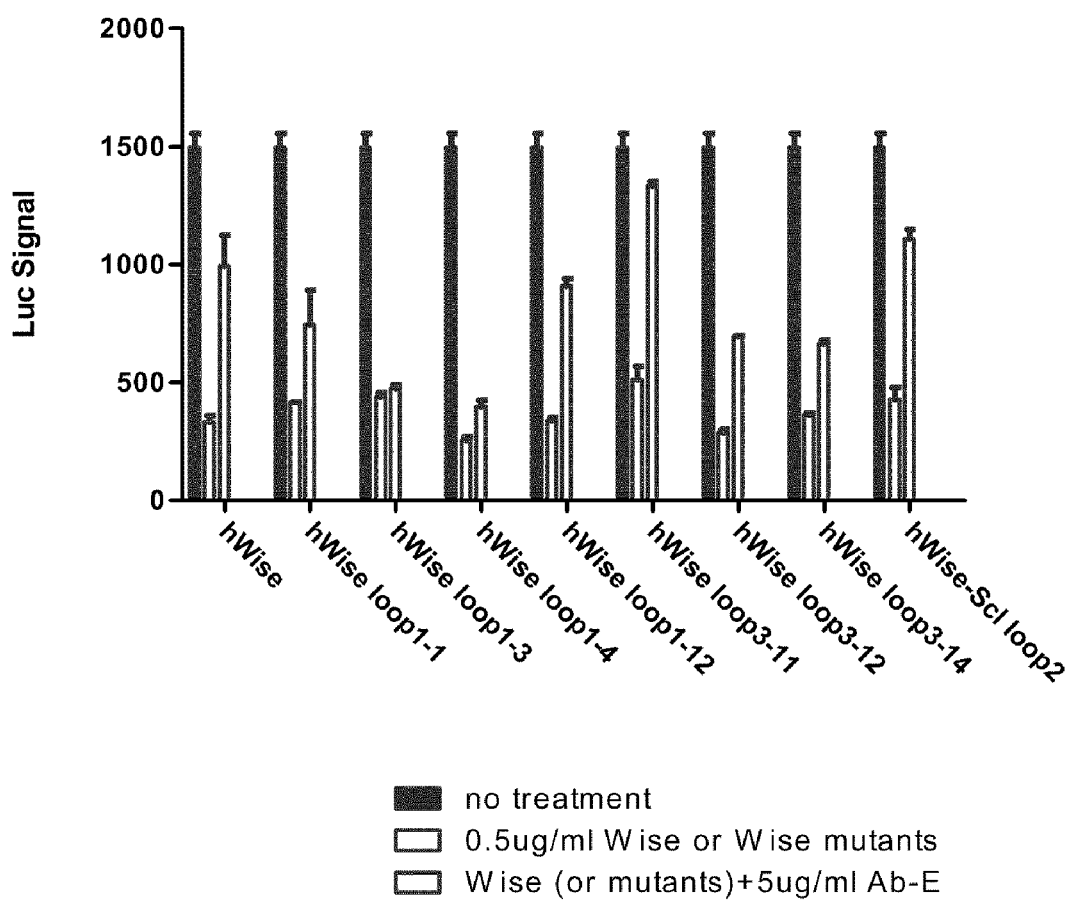
FIG. 14: Cell-based assay shows that the impact of change of individual amino acid to Ala at each of the designated position on the ability of Ab-E to neutralize mutant WISE protein activity in MC3T3-E1 SuperTopFlash (STF) cells. For each set of columns, the first column shows no treatment, the second is 0.5 ug/ml human WISE or WISE mutant with no antibody, and the third is 0.5 ug/ml of human WISE mixed with the antibody E (Ab-E) before being added to the testing well.
Figure 15:
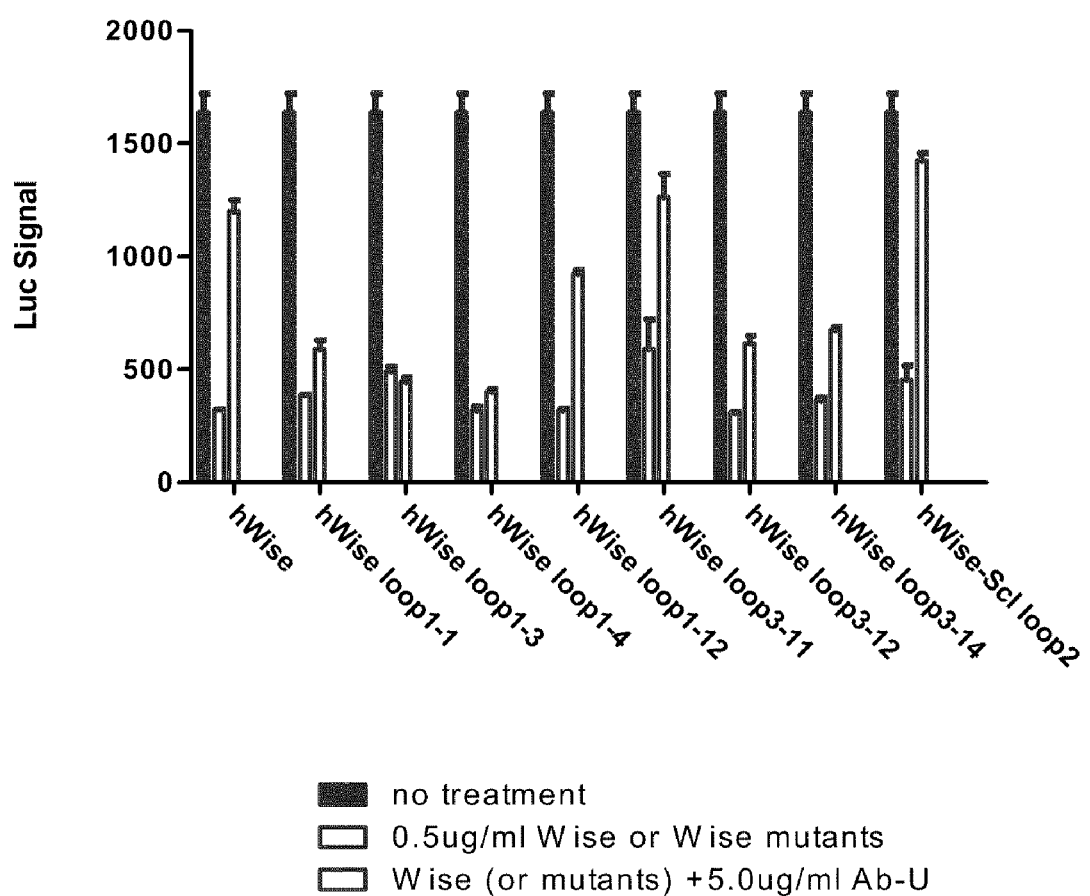
FIG. 15: Cell-based assay shows that the impact of change of individual amino acid to Ala at each of the designated position on the ability of Ab-U to neutralize mutant WISE protein activity in MC3T3-E1 SuperTopFlash (STF) cells. For each set of columns, the first column shows no treatment, the second is 0.5 ug/ml human WISE or WISE mutant with no antibody, and the third is 0.5 ug/ml of human WISE mixed with the antibody U (Ab-U) before being added to the testing well.
Figure 16:
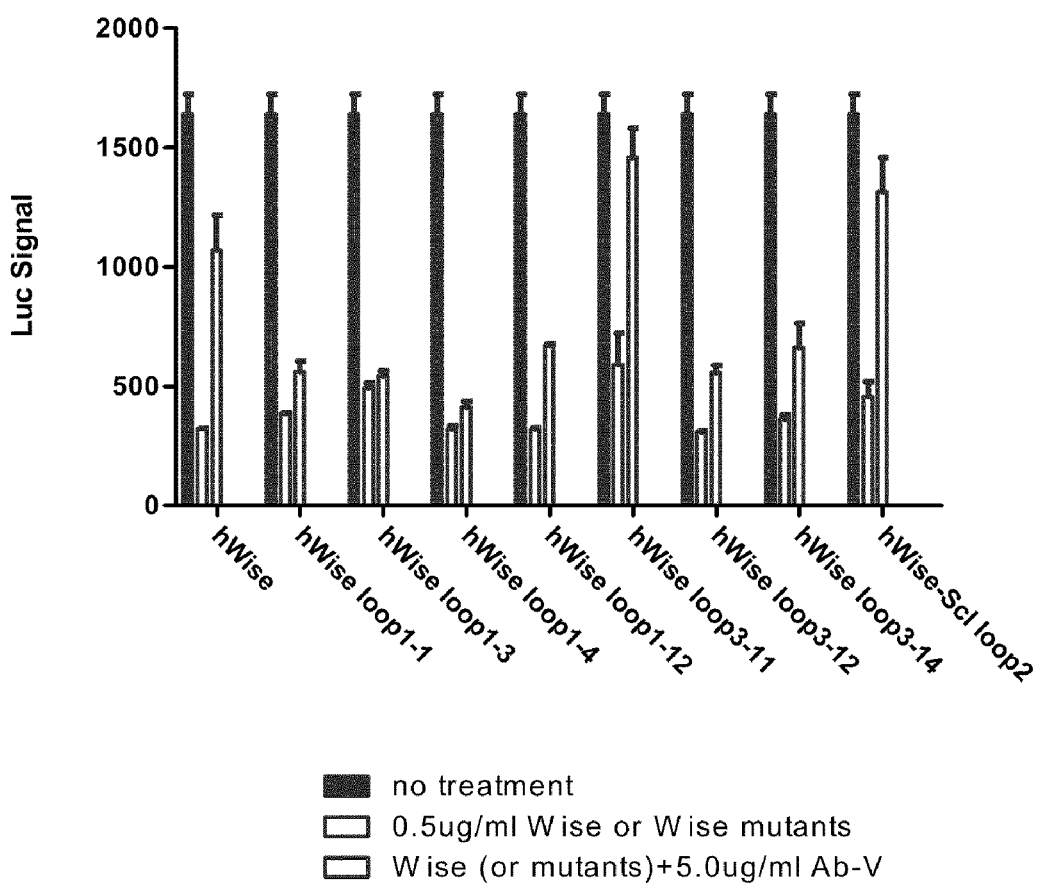
FIG. 16: Cell-based assay shows that the impact of change of individual amino acid to Ala at each of the designated position on the ability of Ab-V to neutralize mutant WISE protein activity in MC3T3-E1 SuperTopFlash (STF) cells. For each set of columns, the first column shows no treatment, the second is 0.5 ug/ml human WISE or WISE mutant with no antibody, and the third is 0.5 ug/ml of human WISE mixed with the antibody V (Ab-V) before being added to the testing well.
Figure 17:
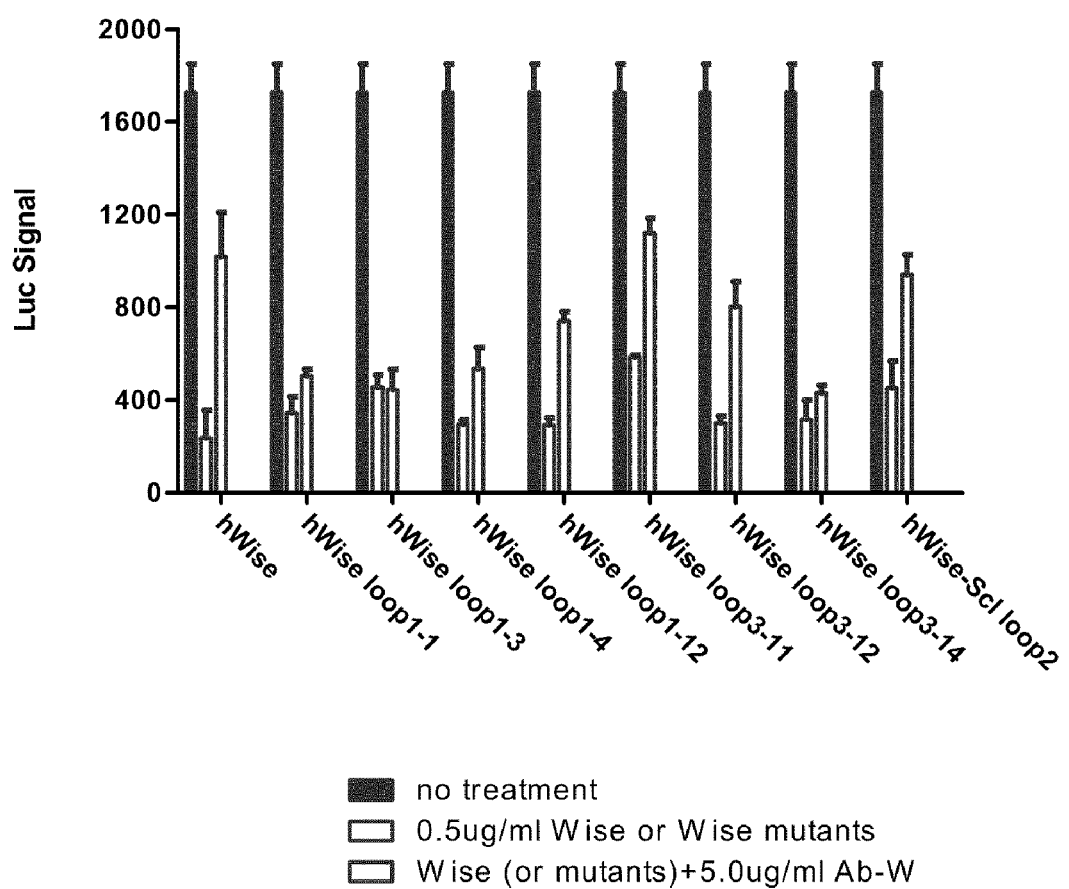
FIG. 17: Cell-based assay shows that the impact of change of individual amino acid to Ala at each of the designated position on the ability of Ab-W to neutralize mutant WISE protein activity in MC3T3-E1 SuperTopFlash (STF) cells. For each set of columns, the first column shows no treatment, the second is 0.5 ug/ml human WISE or WISE mutant with no antibody, and the third is 0.5 ug/ml of human WISE mixed with the antibody W (Ab-W) before being added to the testing well.
Figure 18:
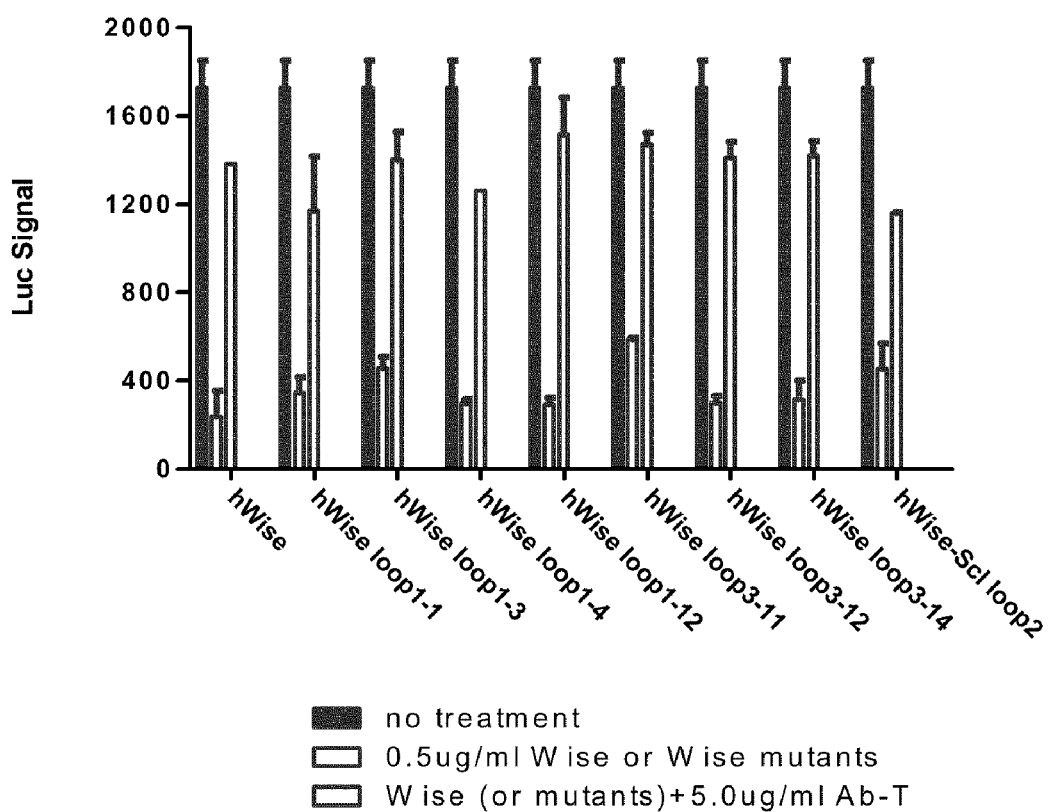
FIG. 18: Cell-based assay shows that the impact of change of individual amino acid to Ala at each of the designated position on the ability of Ab-T to neutralize mutant WISE protein activity in MC3T3-E1 SuperTopFlash (STF) cells. For each set of columns, the first column shows no treatment, the second is 0.5 ug/ml human WISE or WISE mutant with no antibody, and the third is 0.5 ug/ml of human WISE mixed with the antibody T (Ab-T) before being added to the testing well.
Figure 19:
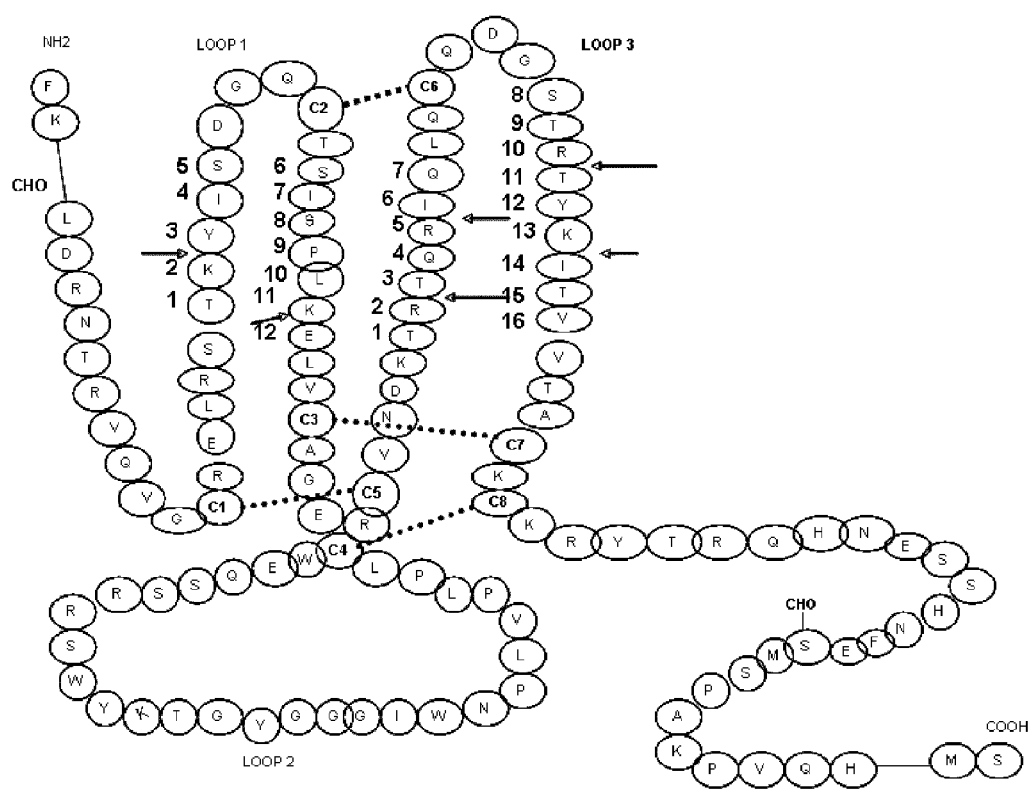
FIG. 19: Diagram showing that the position of each mutation in the loop1 or loop3 of human WISE protein.
Figure 20:
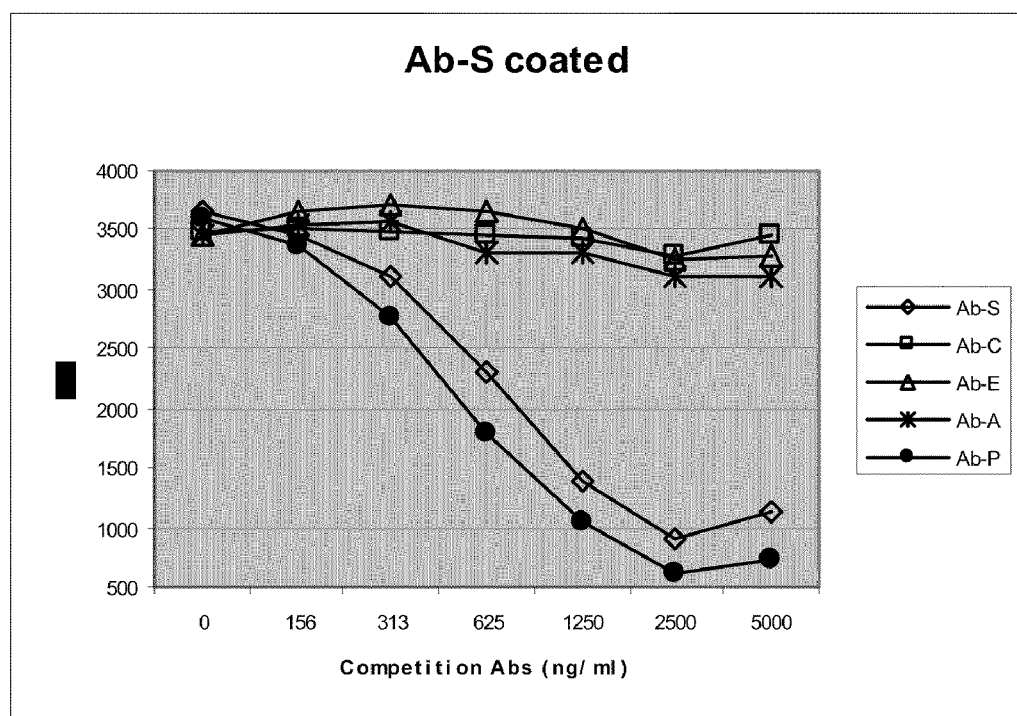
FIG. 20: Competition ELISA binding assay shows that the binding of Antibody S to human WISE can be cross-blocked by itself and Ab-P.
Figure 21:
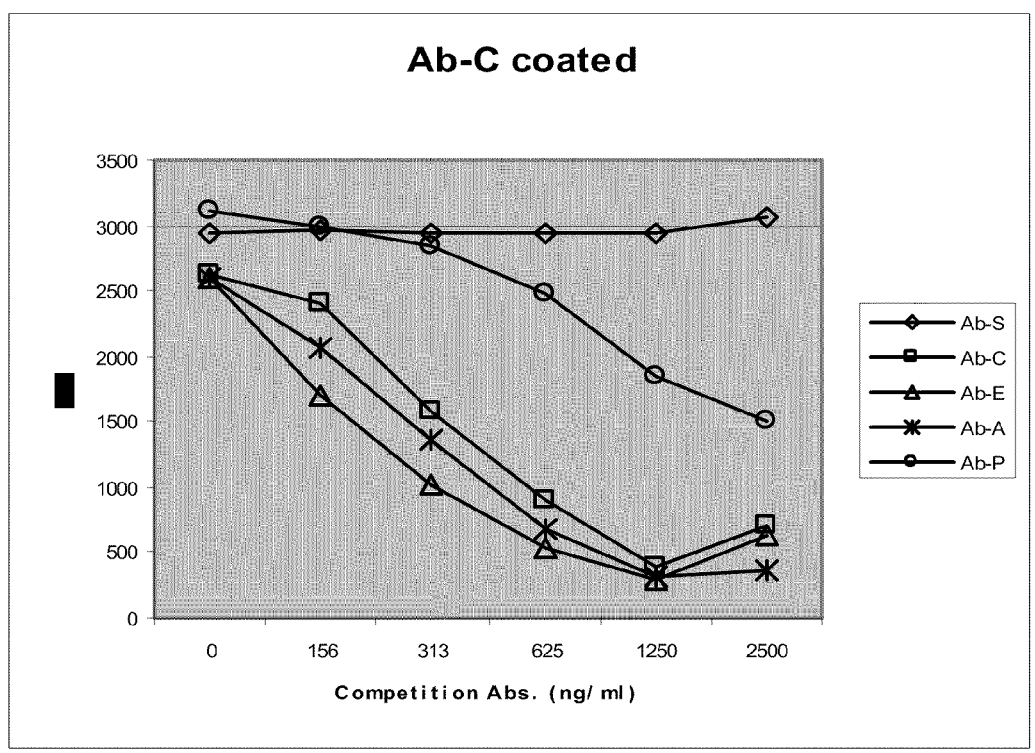
FIG. 21: Competition ELISA binding assay shows that the binding of Antibody C to human WISE can be cross-blocked completely by itself, Ab-A, Ab-E and partially by Ab-P.
Figure 22:
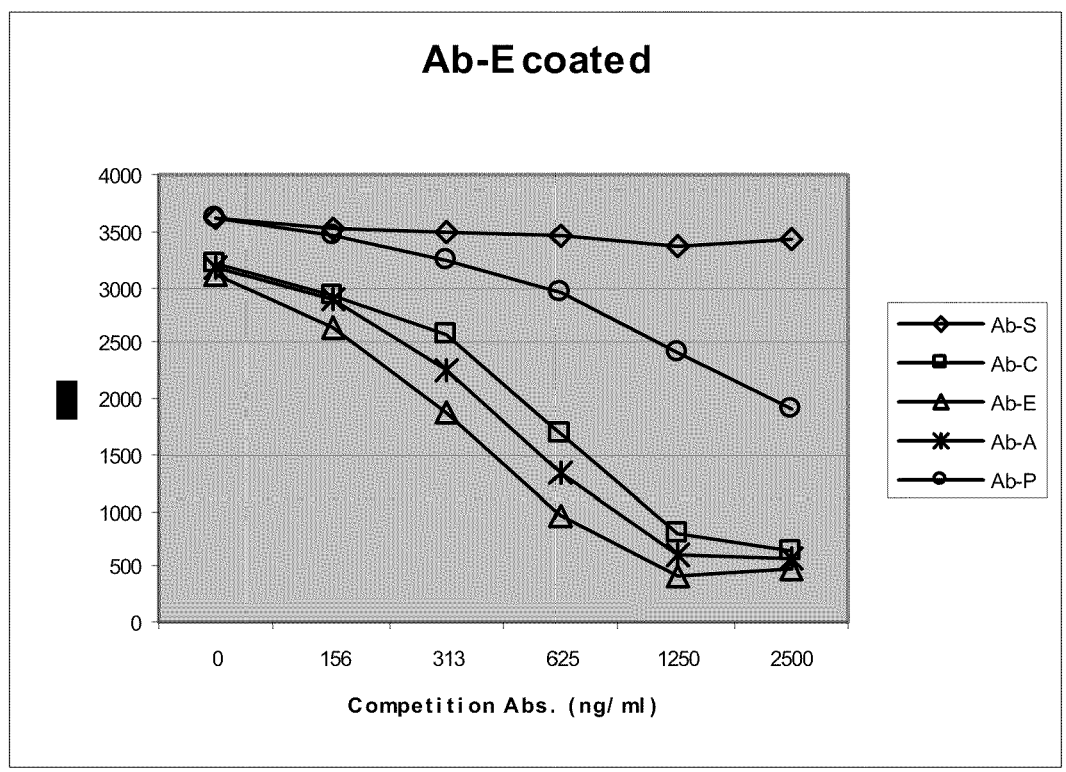
FIG. 22: Competition ELISA binding assay shows that the binding of Antibody E to human WISE can be cross-blocked completely by itself, Ab-A, Ab-C and partially by Ab-P.
Figure 23:
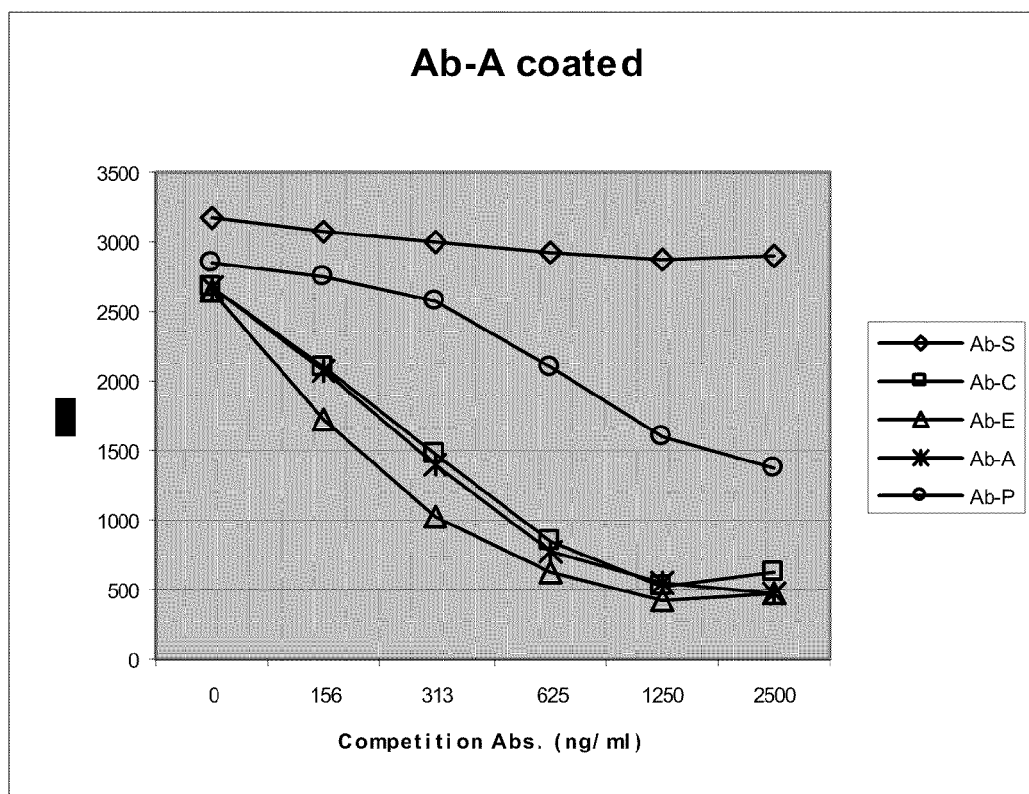
FIG. 23: Competition ELISA binding assay shows that the binding of Antibody A to human WISE can be cross-blocked completely by itself, Ab-C, Ab-E and partially by Ab-P.
Figure 24:
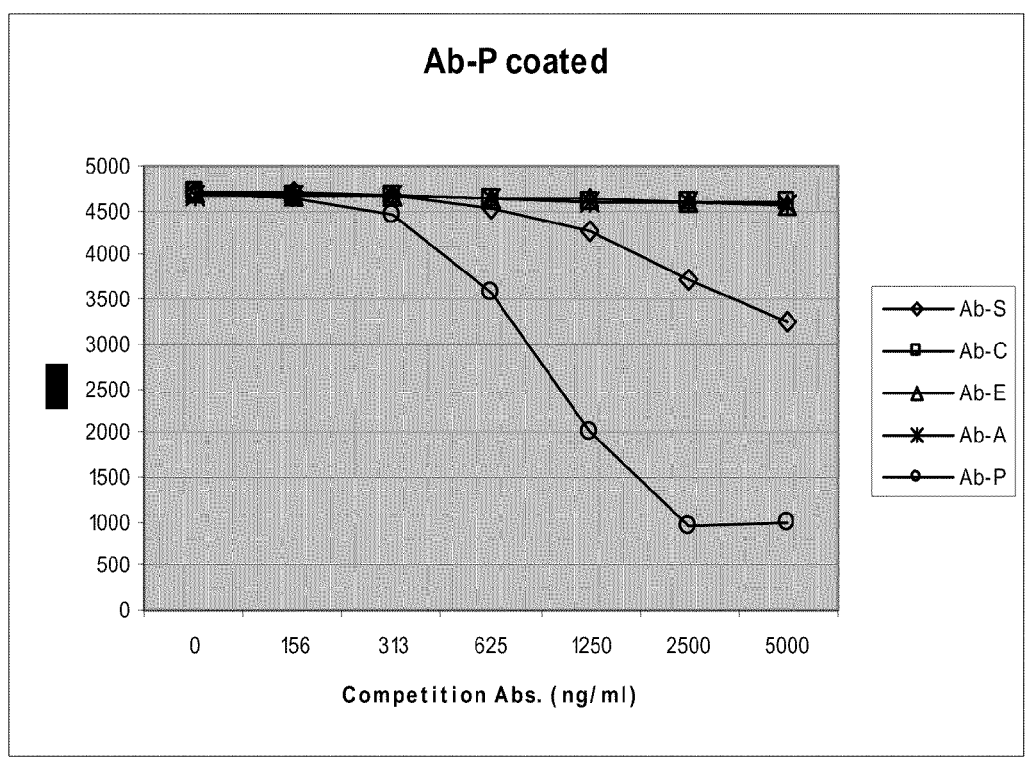
FIG. 24: Competition ELISA binding assay shows that the binding of Antibody P to human WISE can be cross-blocked completely only by itself and partially by Ab-S.
Figure 25:
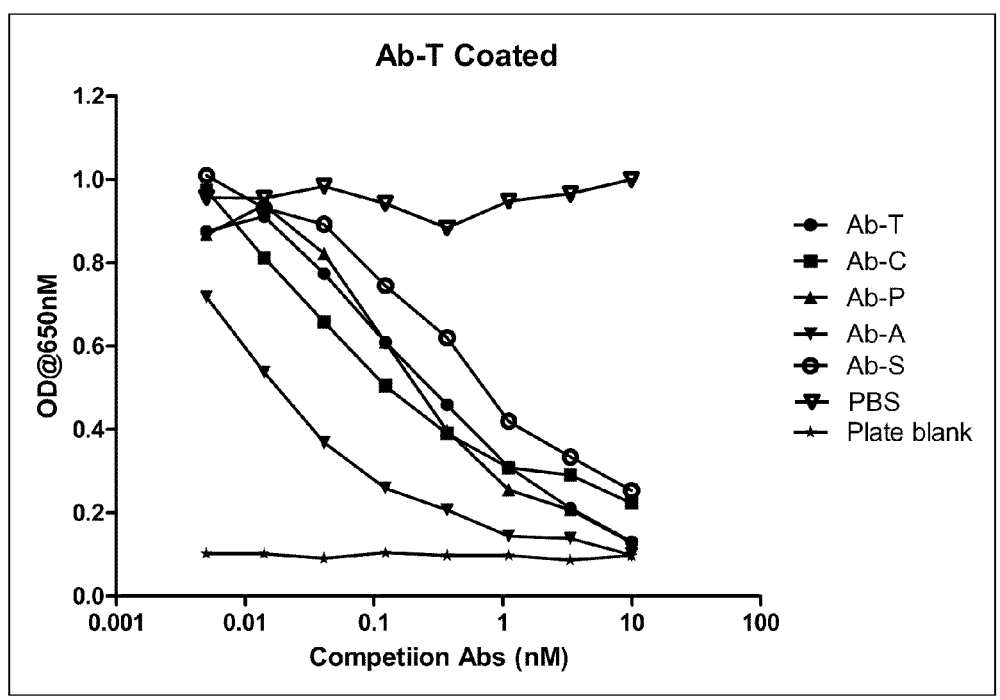
FIG. 25: Competition ELISA binding assay shows that the binding of Antibody T to human WISE can be cross-blocked completely by itself, Ab-A, Ab-C, Ab-P and Ab-S.
Figure 26:
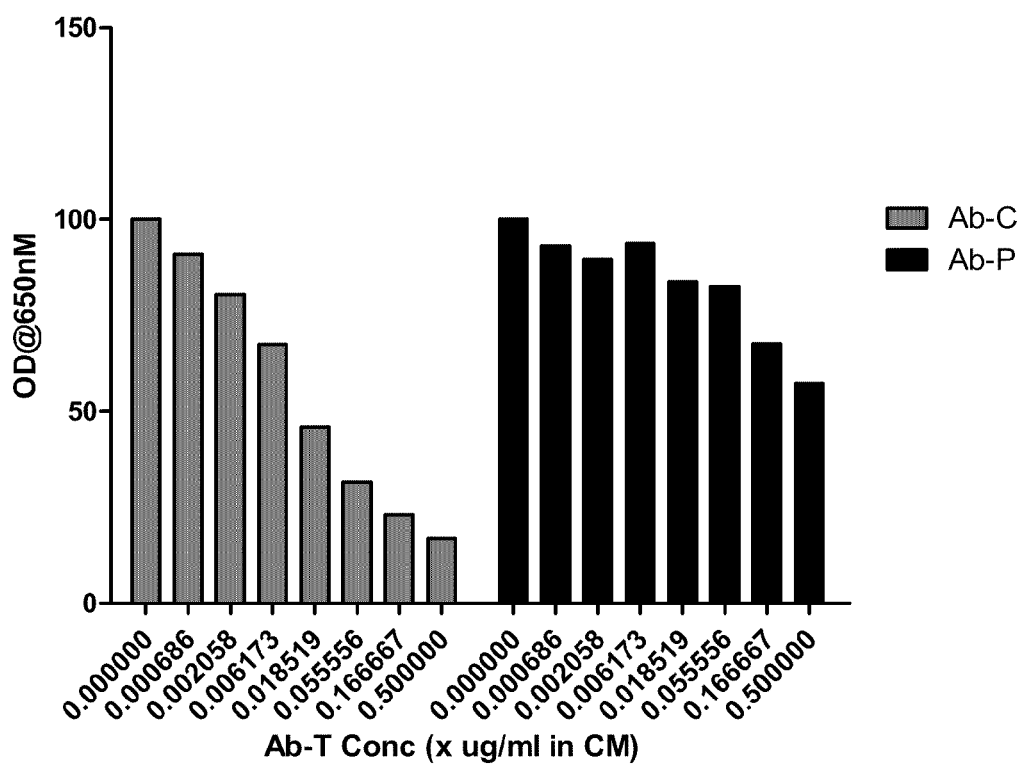
FIG. 26: Competition ELISA binding assay shows that the binding of Antibody P and C to human WISE can be cross-blocked by Ab-T completely or partially respectively.
Figure 27:
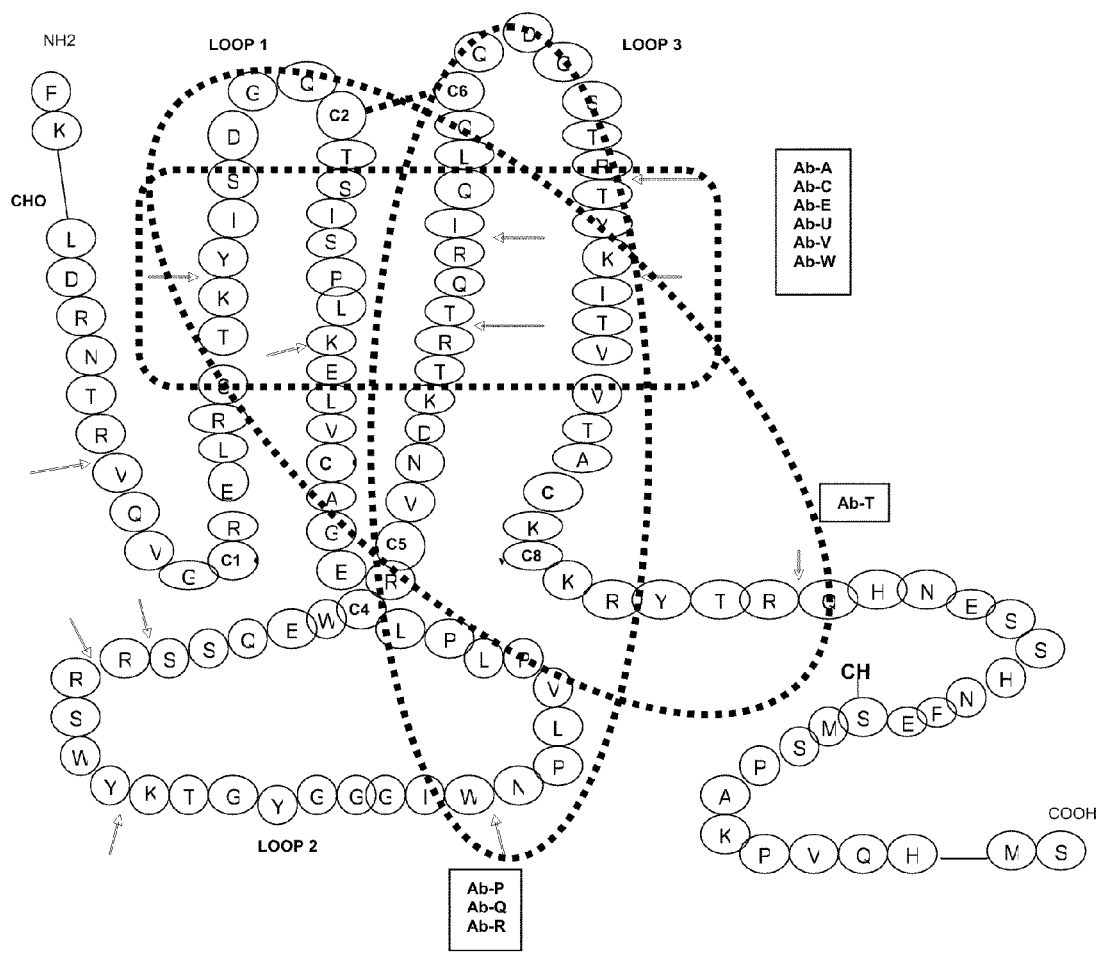
FIG. 27: The diagram shows the potential epitope areas covered by different antibodies based on competition binding assay and cell-based neutralizing assay. Arrows indicate the cleavage sites upon trypsin digestion.

To identify which peptides compete with WISE for binding to the antibodies of the invention, rhuWise was immobilized on a CM5 surface with high density. 3 nM of mature antibodies Ab-A, Ab-C and Ab-E were pre-incubated with and without 30 nM peptides and huWise (as control), then injected over the huWise surfaces. As shown in FIGS. 9A and B both T49 and T56.1 peptides blocked the binding of the antibodies to huWISE. As these antibodies bind to a conformational epitope as demonstrated by western blot, it is postulated that these antibodies' binding sites involve domains formed by loop 1 and/or loop 3 as well as residues from the cytine knot.

Affinity Measurement of Selected Antibodies

Binding of muAbs with rhuWise and rmuWise were tested on KinExA. Azlactone beads (Pierce) was pre-coated with rhuWise/rmuWise at pH9.0 and blocked with ethanolamine, then further washed with sample buffer (0.1 mg/mL Heparin in BSA/P20/PBS solution). 10 pM and 100 pM of Ab-A, Ab-C and Ab-E were incubated with various concentrations (0.1 pM-3 nM) of rhuWise/rmuWise at room temperature for at least 10 hours before run through the rhuWise/rmuWise coated beads.

The amount of the bead-bound muAbs were quantified by fluorescent (Cy5) labeled goat anti-mouse IgG (H+L) antibody (Jackson Immuno Research). The binding signal is proportional to the concentration of free muAbs at binding equilibrium. Equilibrium dissociation constant (Kd) was obtained from nonlinear regression of the competition curves using a two-curve one-site homogeneous binding model (KinExA™ Pro software). Mature antibodies Ab-A, Ab-C and Ab-E have similar affinity for mouse and human WISE, and the Kd measure for human WISE is approximately 2 pM for Ab-A, approximately 4 pM for Ab-C, and approximately 18 pM for Ab-E.

From the foregoing, although specific embodiments of the invention have been described herein for purposes of illustration, various modifications may be made without deviating from the spirit and scope of the invention. Accordingly, the invention is not limited except as by the appended claims. All publications, published patent applications, and patent documents disclosed herein are hereby incorporated by reference.

Humanization of Ab-A, Ab-C, Ab-E, Ab-P and Ab-T

Each of the variable domains of Ab-A and Ab-C were cloned onto a human IgG2 constant domain to make chimeric antibodies (Ab-I and Ab-J) and the appropriate CDR regions of SEQ ID NOs: 10, 12, 18 and 20 were grafted into either human kappa light chains (CDRs of SEQ ID NOs:10 and 18) or a human IgG2 framework (CDRs of SEQ ID NOs: 12 and 20) to give antibodies Ab-B, Ab-D, and Ab-G, Ab-H, Ab-K, Ab-L, Ab-N and Ab-O.

Each of the variable domains of Ab-P and Ab-T were cloned onto a human IgG2 constant domain to make chimeric antibodies (Ab-Q and Ab-X) and the appropriate CDR regions of SEQ ID NOs: 48, 50, 266, 268 were grafted into either human kappa light chain (CDRs of SEQ ID NO: 50) or lambda chain (CDRs of SEQ ID NO: 266) respectively; or a human IgG2 framework (CDRs of SEQ ID NOs: 48, 268) to give rise to humanized antibodies Ab-R and Ab-M.

The ability of the antibodies to bind human WISE was determined using the following binding assay. 96 well plates were coated with 50 µl/well of a 2 µg/ml solution of each testing antibody in coating buffer for two hours at room temperature. The plates were then washed once using PBS+ 0.05% Tween 20 (Sigma). Block solution was added to each well and incubated overnight at 4° c. A serial dilution of biotinylated human WISE protein starting at 30 ng/ml or 100 ng/ml in blocking solution that had been premixed with a 1:10,000 dilution of Nuetravidin-HRP (Pierce) was then added to each well of the plate and incubated overnight at 4° c. After incubation plates were washed. Finally, 50 µl/well of TMB (Pierce) was added to each well and the plates were read on an absorbance plate reader. Data were plotted PRISM software. Data is shown in FIGS. 3, 4 and 5, 6.

Figure 7:
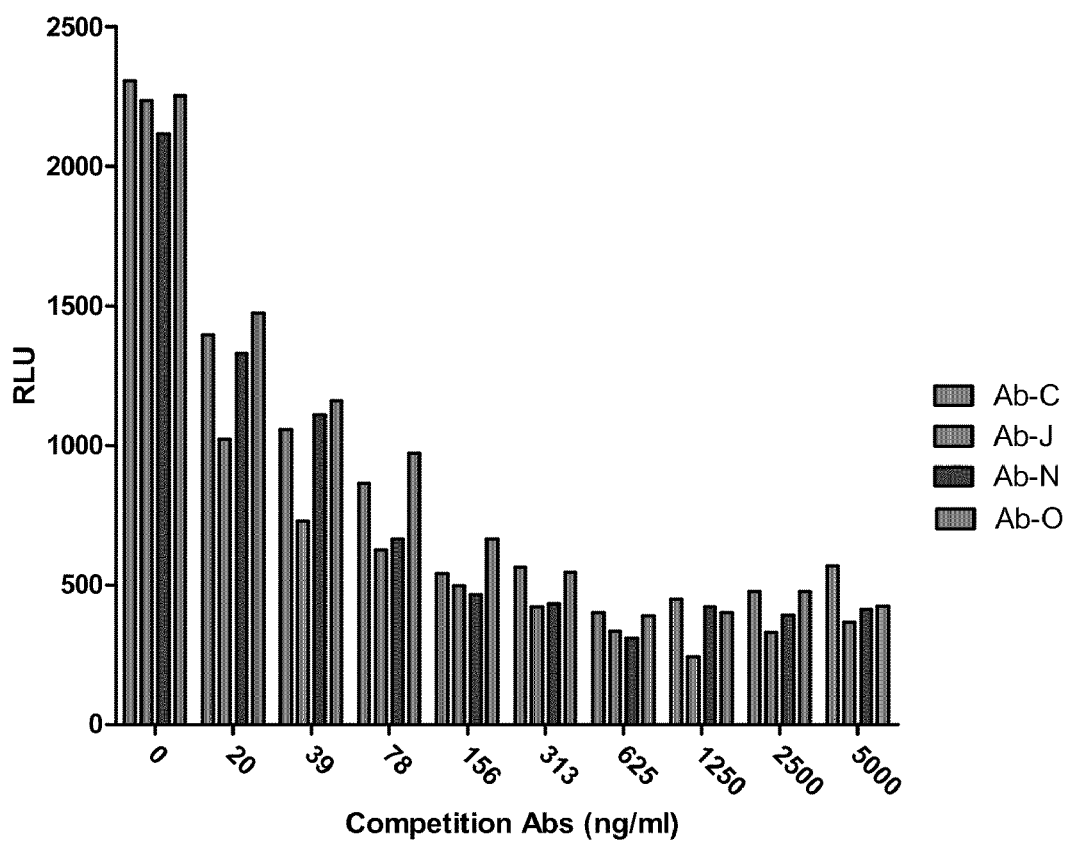
FIG. 7: Competition assay showing binding of Ab-C can be dose dependently cross-blocked by Ab-C, Ab-J, Ab-N and Ab-O.

The ability of the humanized antibodies to croos-block the binding of Ab-C to human WISE was determined using competition binding assay. 96 well plates were coated with 50 µl/well of a 1 µg/ml solution of antibody C (Ab-C) in coating buffer for two hours at room temperature. The plates were then washed once using PBS+0.05% Tween 20 (Sigma). Block solution was added to each well and incubated overnight at 4° c. A two fold serial dilution of testing antibodies Ab-C, Ab-J, Ab-N and Ab-O, were added to each well along with biotinylated human WISE protein at 1 ng/ml in blocking solution that had been premixed with a 1:10,000 dilution of Nuetravidin-HRP (Pierce) was then added to each well of the plate and incubated overnight at 4° c. After incubation plates were washed. Finally, 50 µl/well of TMB (Pierce) was added to each well and the plates were read on an absorbance plate reader. Data were plotted PRISM software. Data is shown in FIG. 7.

Figure 8:
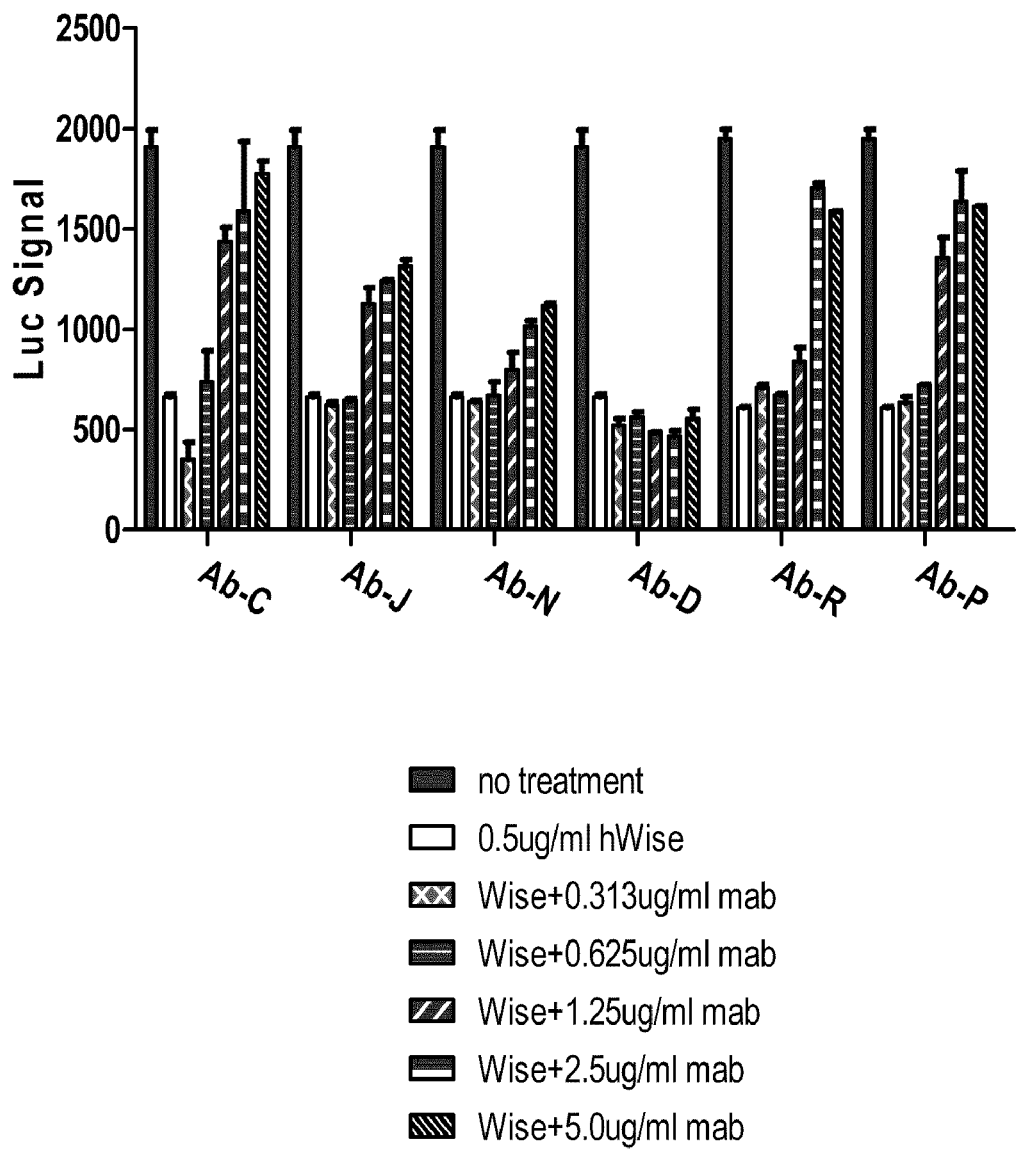
FIG. 8: Bioactivity of various antibodies (Ab-C, Ab-J, Ab-N, Ab-D, Ab-P, Ab-R) in neutralizing WISE activity in MC3T3-E1 SuperTopFlash (STF) cells. For each set of columns, the first column shows no treatment, the second is human WISE with no antibody, and for each of the six antibodies 0.5 ug/ml of human WISE is mixed with the antibody before being added to the testing well.

The ability of the chimeric or humanized antibodies to neutralize WISE activity relative to that of the original rodent antibodies were determined using a cell-based assay with MC3T3-E1 SuperTopFlash (STF) cells. The cells were differentiated first for five days according to the detailed procedures described in this invention and then they were either treated with PBS only or human WISE protein only at 0.5 ug/ml or 0.5 ug/ml human WISE proteins that has been premixed with a two fold serial dilution of the testing antibodies starting at 5 ug/ml, Twenty four hours later the luciferase signal was determined using Luminometer (LMAX, Molecular Device) according to manufacturer's instruction. Data were plotted PRISM software. Data is shown in FIG. 8.

Cloning of Anti-WISE Humanized Antibodies:

These anti-WISE antibodies are humanized antibodies that were generated by complementarity determining region (CDR) grafting of mouse or rat CDRs into human germline acceptor framework sequences.

Full-length rodent cDNAs encoding both antibody light and heavy chains were isolated from single cell cloned hybridoma cells using RACE followed by PCR. The cDNAs for the variable regions of the chosen lead candidate murine antibodies Ab-C, Ab-A, and rat antibody Ab-P and Ab-T, were used as design templates for CDR grafting.

Antibody C was humanized by CDR grafting and mutagenesis to generate several light chain and heavy chain variants. The light chain depicted in SEQ ID NO: 22, variant 1, was generated by grafting the Ab-C light chain CDRs into human germline acceptor frameworks VK1 O2 and JK2. Residue 22 (Kabat numbering) was maintained as the murine serine residue.

The light chain depicted in SEQ ID NO: 46, light chain variant 2, was generated by grafting the Ab-C light chain CDRs into human germline acceptor frameworks VK4 B3 and JK2. Residue 22 (Kabat numbering) was again maintained as in the murine serine residue.

The light chain depicted in SEQ ID NO: 122, light chain variant 3, was generated by making Y36F, Y87F mutations in SEQ ID NO: 22.

The heavy chain depicted in SEQ ID NO: 24, heavy chain variant 1, was generated by grafting the murine heavy chain CDRs into human germline acceptor frameworks VH1 1-69 and JH4. The heavy chain depicted in SEQ ID NO: 36, heavy chain variant 2, was generated by grafting the murine heavy chain CDRs into human germline acceptor frameworks VH1 1-69 and JH4 and back mutate the following select CDR2 residues into their original murine residues: M48I, G49A, R66K, V67A, .T68Q and I69L.

Antibody A (SEQ ID NO: 10 and 12) was humanized by CDR grafting and mutagenesis to generate a humanized light chain and several humanized heavy chain variants.

The humanized light chain variant 1 depicted in SEQ ID NO: 14 was generated by CDR grafting the light chain murine CDRs into human germline acceptor framework VK2 A17 for framework 1 and human germline acceptor frameworks VK2 A19 and JK4 for frameworks 2, 3 and 4 to maintain as much homology as possible between the murine and humanized versions. The amino acid at Kabat position 87 was maintained as the murine phenylalanine due to it's proximity to CDR3 and potential involvement in loop structure and antigen binding (SEQ ID NO:14).

Humanized heavy chain variant 1 depicted in SEQ ID NO: 16 was generated by grafting the murine heavy chain CDRs into human germline acceptor framework VH 1 1-02 for frameworks 1 and 2 and human germline acceptor sequence VH7 7-4.1 and JH4 for frameworks 3 and 4. The naturally occurring cysteine residue at position 82a was replaced with a serine to avoid heterogeneous disulfide bond formation (SEQ ID NO: 16).

Humanized heavy chain variant 2 depicted in SEQ ID NO: 34 was generated by reversion of CDR2 and CDR3 proximal residues: R38K, Y91F and A93V (SEQ ID NO: 34).

Antibody P was humanized by CDR grafting. The light chain depicted in SEQ ID NO: 54 was generated by grafting the rat light chain CDRs into human germline acceptor framework VK3 L2 and JK4 (SEQ ID NO: 54).

The heavy chain depicted in SEQ ID NO: 52 was generated by grafting the rat heavy chain CDRs into human germline acceptor framework VH3 3-33 and JH4. Murine residues that were kept in place due to proximity to CDRs 1 and 3 included proline 28 (P28), threonine 93 (T93) and serine 94 (S94) (SEQ ID NO: 52).

Antibody T was humanized by CDR grafting. The light chain depicted in SEQ ID NO: 271 was designed by grafting the rat light chain CDRs into human germline acceptor framework VL6 6a and JL2. Rat residues that were kept in place due to their importance as canonical or interface residues included glutamine 1 (Q1), valine 2 (V2), glutamic acid 40 (E40), arginine 42 (R42) and phenylalanine 87 (F87).

The heavy chain depicted in SEQ ID NO: 272 was designed by grafting the rat heavy chain CDRs into human germline acceptor framework VH4 4-59 and JH3. Rat residues that were kept in place due to proximity to CDRs 1 and 3 or their importance as interface and canonical residues included phenylalanine 27 (F27), leucine 29 (L29), threonine 30 (T30), valine 37 (V37), arginine 71 (R71) and valine 93 (V93).

Phage Derived Anti-Wise Ab-C Light Chain

Part 1. Construction of LC-Shuffling Library $3.5 \times 10^{11}$ pfu (ten times of library size) of 310Fab library (Dyax) and $4 \times 10^{11}$ pfu of TQ library (Target Quest) were used to infect 2 L of TG1 culture in log phase (OD600 at 0.6) at 37° C. for 30 minutes. Infected cells were spun down, re-suspended and plated on ten 2XYT-CG 245 mm square plates. After overnight incubation at 37° C., cells were scraped off and spun down. The cell pellets were used for megaprep of phagemid plasmids of libraries.

Phagemid plasmids of 310Fab library and TQ library were digested with SfiI and NotI. Digested samples were run on preparative 0.5% agarose gel to separate the VH-CH1 fragment pool and the pCES1-LC fragment pool. The large vector-LC fragment bands (5242 bp for TQ library and 4517 bp for 310Fab library) were excised and DNA eluted using QIAquick Gel Extraction kit (Qiagen).

Humanized anti-WISE Ab-C VH-CH1 fragment was amplified with primers 5104-91 (CCG TTC GTG GCC CAG CCG GCC TCT GCT CAG GTT CAG CTG GTG CAG TCT G; SEQ ID NO: 281) and 5104-93 (GTG ATG GTG ATG ATG ATG TGC GGC CGC ACA TTT GCG CTC AAC TGT CTT GTC; SEQ ID NO: 282) using humanized anti-WISE Ab-C IgG2 gamma chain (SEQ ID NO: 24) as the template. Amplified humanized Ab-C heavy chain VH-CH1 fragment (676 bp) was digested with SfiI and NotI and purified using PCR purification kit from Qiagen.

Humanized Ab-C VH-CH1 SfiI/NotI fragment was ligated to pCES1-LC SfiI/NotI fragment pool at 4:1 and 3:1 ratio, respectively. Ligated DNA was cleaned up by phenol chloroform extraction and ethanol precipitation. 20 ug of ligated DNA from TQ library and 93 ug of ligated DNA from 310Fab library were used to transform electro-competent TG1 cells (Stratagene, #200123) at 500 ng DNA per 100 ul cells and 300 ul/cuvette by electroporation in BioRad Gene Pulser using 0.22CM cuvettes (BioRad, Catalog #1652086) at 25 uF, 200 ohm, 2500V. Electroporated cells were diluted 3× with SOC and incubated at 37° C. for 1 hour. Transformed cells were titered and plated on 2XY-CG 245 mm square plates and incubated overnight at 37° C. Cells of transformant colonies were scraped off and used for phage rescue. The library size of the constructed TQ-LC shuffling library was 6.6×106 and the library size of the constructed 310 Fab-LC shuffling library was 2.1×109.

Phagemid phages were rescued from LC-shuffling libraries separately. 2XYT-CG media were inoculated with 10× library size inoculums from LC-shuffling libraries, respectively, to OD600 0.1. The cultures were grown to OD600 0.5, then infected with KO7 helper phage (Invitrogen) at MOI of 20. After 30 minutes of incubation at 37° C., cells were spun down, re-suspended into 2XY-CK, and incubated at 30° C. overnight. The cells were spun down by centrifugation. The phage supernatants were transferred into fresh tubes. ⅕th volume of 20% PEG/1.5M NaCl was added to the phage supernatant to precipitated the phage. The mixture was incubated on ice for 1-3 hour. Precipitated phage was spun down by centrifugation at 14K for 30 minutes. Phage pellet was re-suspended into 1 ml of PBS and centrifuged at 14 K for 10 minutes to remove cell debris. Phage precipitation was repeated as described above. Final phage pellet was re-suspended into 1 ml of PBS/1% BSA.

Part 2. LC-Shuffling Library Panning

1×1011 pfu of rescued phage from TQ-LC shuffling library and 1×1012 pfu of rescued phage from 310Fab-LC shuffling library were used for panning against bionitylated hu-WISE coated on Streptavidin M-280 Dynabeads (Dynal Biotech, #112.06). Panning procedures are: three 30-minutes Negative selections with biotinylated FGF23 coated streptavidin Dynabeads, followed by 60-minute Positive selection, then washing the beads 6× with 3% BSA/3% MPBT (0.1% Tween-20), 6× with PBST, and 2× with PBS, and finally elution of bound phages with 1 ml of 0.1M TEA followed by neutralization with 0.5 ml of 1M Tris HCl. For each round, panning was done at two antigen coating concentrations and a 10- or 20-fold reduction of coating concentrations in the subsequent rounds except for RD4 as shown below: RD1A (3.3 ug/ml); RD2B (0.33 ug/ml); RD3D (0.015 ug/ml); RD4D (0.015 ug/ml) and RD1B (0.33 ug/ml); RD2C (0.033 ug/ml); RD3E (0.0033 ug/ml); RD4E (0.0033 ug/ml). For RD3 panning, two washing protocols were implemented. Besides the regular washing, additional overnight washing steps were carried out for a separate set of RD3 panning.

Part 3: Phagemid Clonal Analysis and Clone Selection

Eluted RD2, RD3 and RD4 phagemid clones were screened in phage ELISA on Neutravidin plates coated with biotinylated human WISE at 3.3 ug/ml and 0.33 ug/ml. One 96-well plate of individual clones from each RD2, RD3 and RD4 eluted pool were screened. Clones that showed similar binding signals at both antigen concentrations were cherry-picked and sequenced. A total of 77 unique phagemid clones were identified. Two of them were dropped due to the presence of an amber codon in the framework. All of the remainders were converted to IgG2 into corresponding pTT5 vectors with VκⅠO12-O2 signal peptide sequence (MDMRV-PAQLLGLLLLWLRGARC; amino acids 1-22 of SEQ ID NO: 58) by inserting the variable region of HC and lambda LC as BssHII/BsMBI fragments and the variable region of kappa LC as BssHII/BwiI fragments.

Part 4: Transient Transfection of LC Mutant IgG2

Equal amount of humanized anti-WISE Ab-C IgG2 gamma chain vector and the light chain vector at final concentration of 0.5 ug/ml were used to transfect 50 ml of 293 6E cells at 1×10$^6$ cell/ml using PEI as the transfectant. Trypton was added on Day 2 of the transfection. Conditioned medium was collected on Day 7. The polypeptides of the light chains identified in this example are: L1 (SEQ ID NO: 76), L13 (SEQ ID NO: 78), L16 (SEQ ID NO: 80), L18 (SEQ ID NO: 82), L23 (SEQ ID NO: 84), L24 (SEQ ID NO: 86), L28 (SEQ ID NO: 88), L29, (SEQ ID NO: 90), L48 (SEQ ID NO: 92), L60 (SEQ ID NO: 94), L62 (SEQ ID NO: 96), L63 (SEQ ID NO: 98), L65 (SEQ ID NO: 100), L66 (SEQ ID NO: 102), L66 (SEQ ID NO: 104), L67 (SEQ ID NO: 106), L69 (SEQ ID NO: 108), L7 (SEQ ID NO: 110), L70 (SEQ ID NO: 112), L72 (SEQ ID NO: 114), L74 (SEQ ID NO: 116), L75 (SEQ ID NO: 118), L76 (SEQ ID NO: 120), and L9 (SEQ ID NO: 122) and when paired with the heavy chain depicted in SEQ ID NO: 24 are active in binding WISE protein and inhibiting WISE activity in various assays including MC3T3-E1 Super-TopFlash (STF) assay.

Fine Epitope Mapping by Site-Directed Mutagenesis

Alanine scanning was utilized to determine contact points of the antibodies with the WISE protein. Site directed single amino acid mutations in the first and third loops of the WISE protein were introduced using PCR with Stratagene's QuikChange site-directed mutagenesis kit. The DNA constructs were sequence confirmed and transfected into 293 cells for transient production of mutated proteins. The effect of single amino acid mutation was found to have no effect for protein expression. The supernatants and purified proteins were tested and all mutants retained their ability to inhibit Wnt signaling as the wild type protein in MC3T3-E1 STF reporter cell line.

Relative capture of individual WISE mutant proteins or wild type proteins by either neutralizing antibodies such as Ab-C, Ab-E, Ab-A or Ab-P or non-neutralizing antibody Ab-S were compared to assess whether any of these mutations affects binding of antibodies to WISE proteins. The bound WISE proteins were then detected using HRP-conjugated affinity-purified polyclonal antibodies against WISE.

Individual mutant proteins were tested for functional activity to assess whether any of the residues required for binding is also critical for WISE protein activity. The single mutants retained the activity of inhibiting TCF-Luc expression in the above described cell-based assay.

The relative neutralizing activity of individual antibodies was obtained by comparing the ability of the test antibody to reverse the inhibition of TCF-Luc activity either by wild type human WISE or mutant WISE proteins. The data are shown in FIGS. 11-18 for Ab-R, Ab-C, Ab-A, Ab-E, Ab-U, Ab-V, Ab-W, and Ab-T.

In vivo Activities of Anti-WISE Mab in Mouse Model of Bleomycin Induced Lung Fibrosis The effect of WISE inhibition on disease progression and fibrosis was evaluated using a mouse model of bleomycin induced lung fibrosis. Female C57Bl/6 mice of 8-10 weeks old (Jackson Lab) were pre-treated twice (Days -5 and -3) with injections of WISE Ab, sTGF-beta Receptor-muFc, and mIgG2b control isotype by intraperitoneal route. On Day 0, a single dose of intratracheal bleomycin (3.75 u/kg or saline control) was given to each mice followed by a M,W,F, dosing regimen of each treatment for 2 weeks. Two weeks (day 14) post-bleomycin, mice was anesthetized using Avertin and blood/tissues will be collected as follows: Right lungs were snap frozen for Sircol collagen assay, the left lung from each mouse was inflated with and then placed in 10% neutral-buffered formalin in preparation for light microscopy. Sections of lungs were stained with hematoxylin and eosin (H&E) and Sirius red (demonstration of collagen) stains and by immunohistochemical methods to demonstrate alpha smooth muscle actin (αSMA) and fibroblast specific protein 1 (FSP-1 or A100S4), and examined by routine light microscopy. In addition serum or bronchoalveolar lavage fluid from each mouse was collected for the measurement of osteopontin level using ELISA (R&D system).

H&E-stained tissue sections were scored for the amount of the lung tissue that was characterized as alveolar collapse/consolidation on a semi-quantitative scale where 0=not present, 1=≦10% of lung affected, 2=11%-33% of lung affected, 3=34%-67% of lung affected, and 4=>67% of lung affected. Additionally, the severity of the alveolar and interstitial changes in areas of lung not affected by alveolar collapse/consolidation was scored for severity according to a semi-quantitative scale where 0=not present, 1=minimal, 2=mild, 3=moderate, 4=severe. The total H&E score represented the sum of these 2 scores. All slides were examined without knowledge of treatment group on 2 separate occasions separated by at least 2 days. The final H&E score was taken as the average of the scores determined on these 2 days.

Lung sections stained by Sirius red and by immunohistochemical methods to demonstrate αSMA or FSP-1 were evaluated for the extent of specific staining and assigned scores according to a semi-quantitative scale where 0=not present, 1=minimal, 2=mild, 3=moderate, 4=severe. All slides were examined without knowledge of treatment group on 2 separate occasions separated by at least 2 days. The final score for each parameter was taken as the average of the scores determined on these 2 days.

Figure 28:
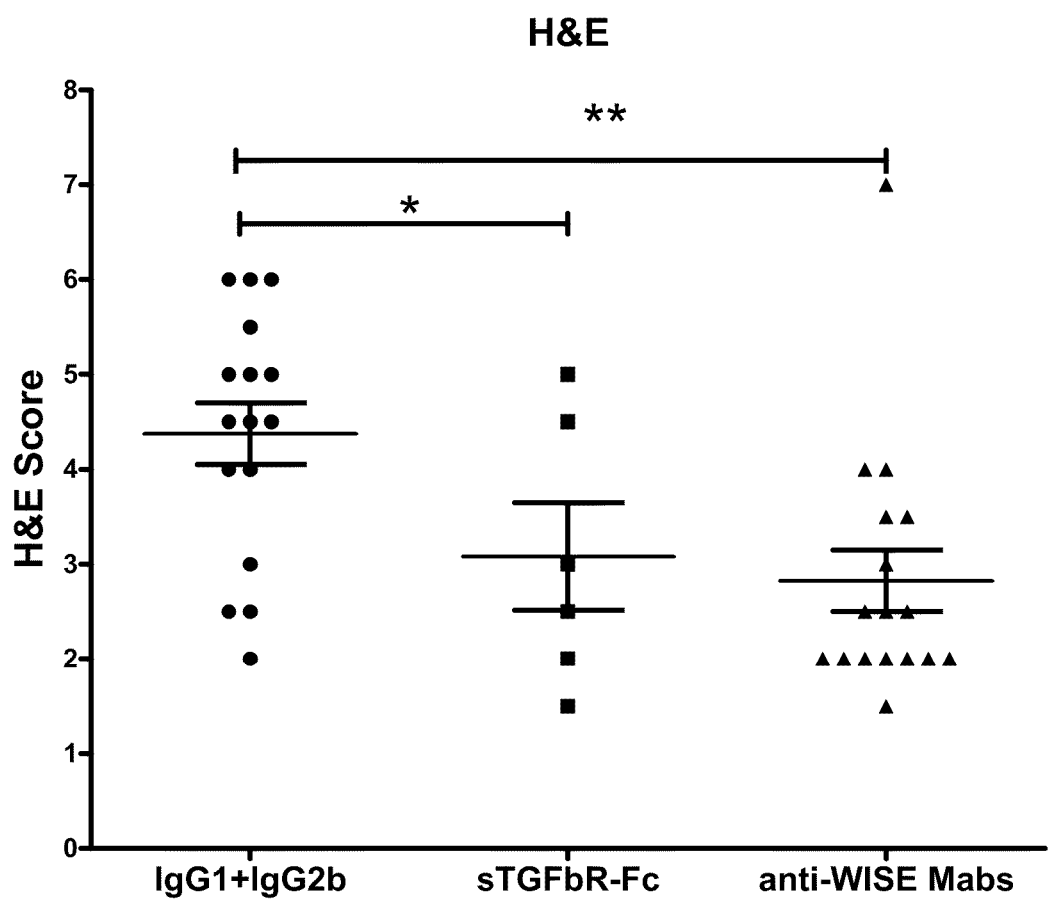
FIG. 28: Prophylactic anti-WISE Mab Treatment reduced lung injury in Bleomycin induced lung injury model.
Figure 29:
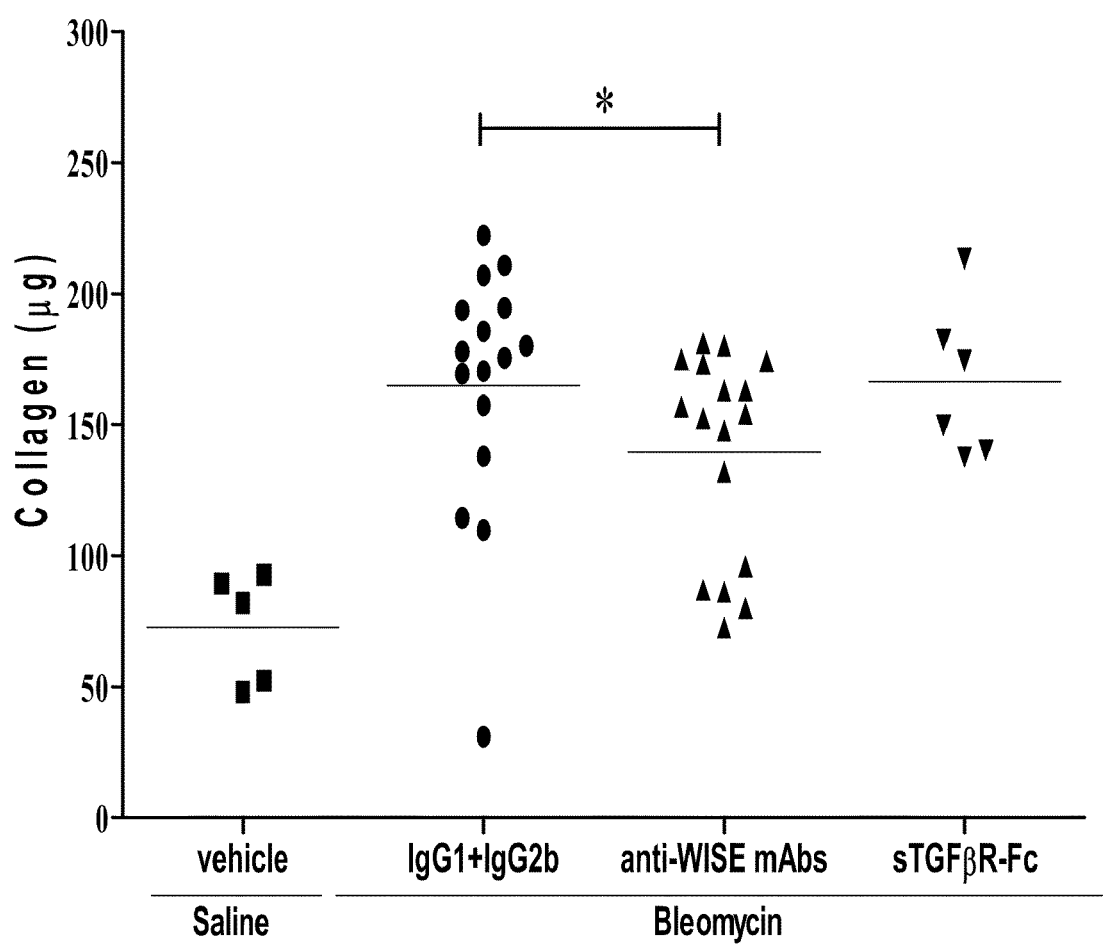
FIG. 29: Prophylactic anti-WISE Mab Treatment reduced collagen deposition in Bleomycin induced lung injury model.
Figure 30:
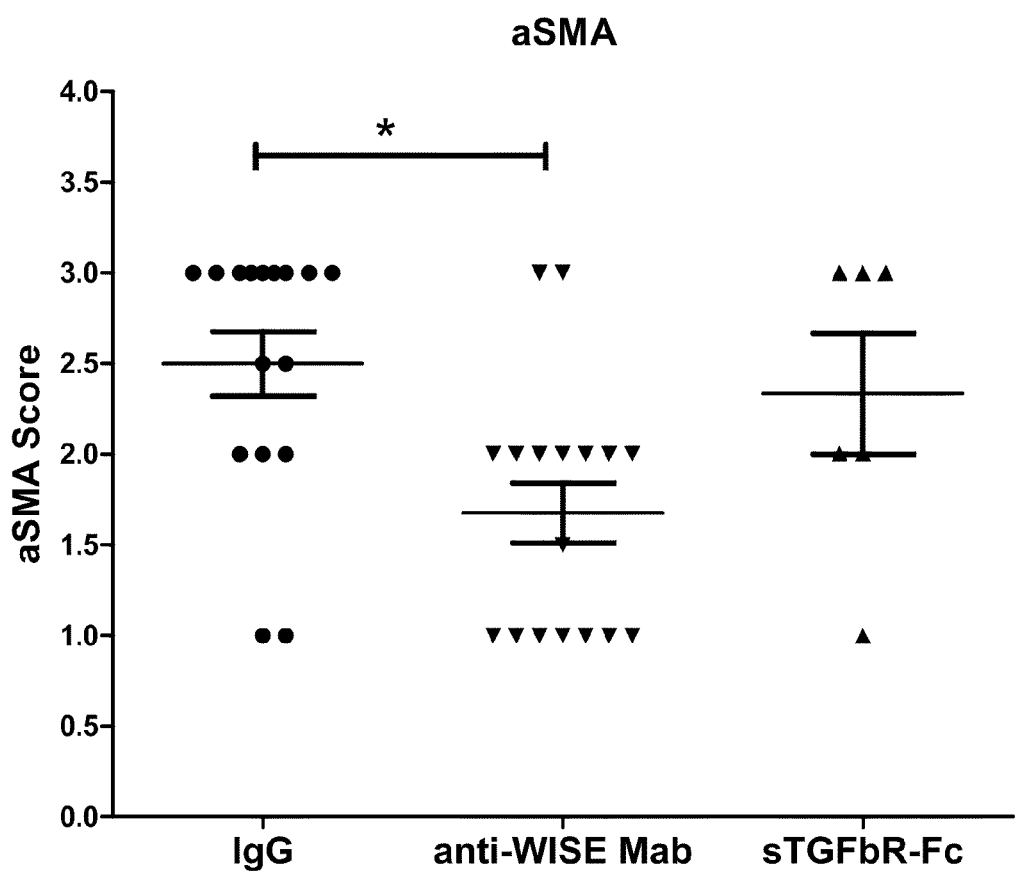
FIG. 30: Prophylactic anti-WISE Mab Treatment reduced aSMA expression in Bleomycin induced lung injury model.
Figure 31:
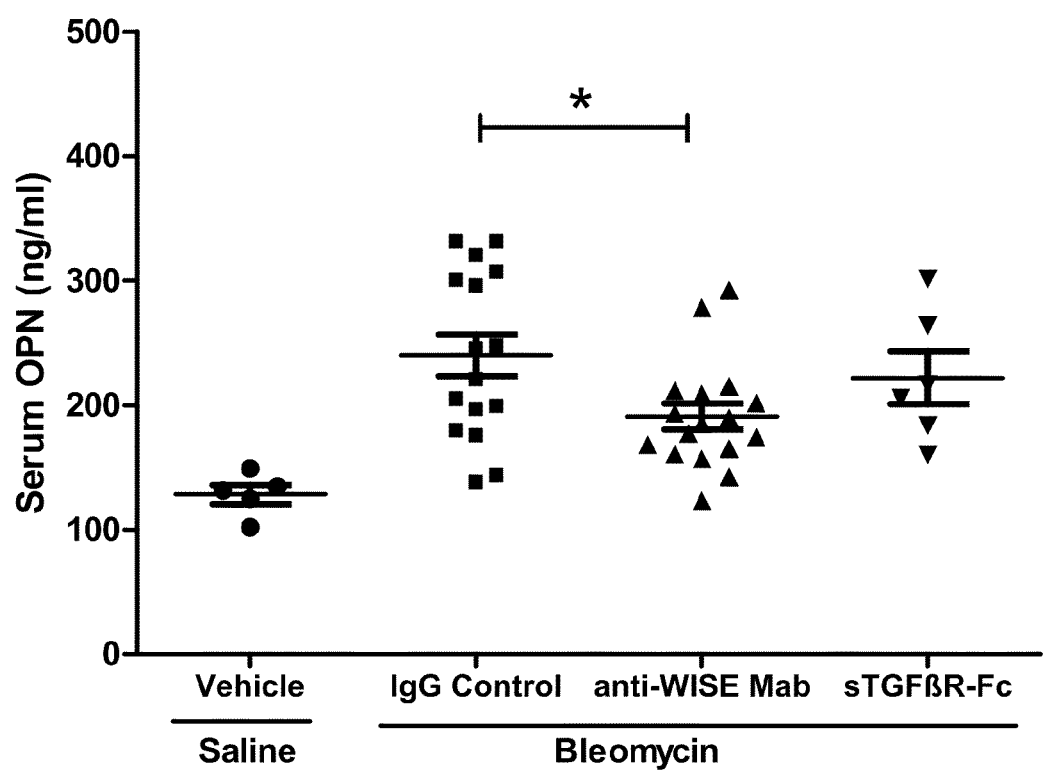
FIG. 31: Prophylactic anti-WISE Mab Treatment reduced serum OPN level in Bleomycin induced lung injury model.

In the first study, two anti-WISE antibodies Ab-C (20 mg/kg n=10) and Ab-E (20 mg/kg, n=10) were used and both mIgG1 (n=10) and IgG2b (n=10) control IgG were used. The results for Ab-C and Ab-E are similar and thus data were pooled as anti-WISE Mab; and the results for two IgG controls are similar and thus pooled as IgG control. The results are shown in FIG. 28, 29, 30 31. Prophylactic treatment of mice with anti-WISE antibody significantly reduced lung injury based on H&E score (FIG. 28), collagen deposition measured by Sircol collagen assay (FIG. 29), the expression of myofibroblast marker alpha smooth muscle actin (aSMA by immunohistochemistry, FIG. 30), and finally the level of osteopontin in serum measured by ELISA (FIG. 31). Similarly, Sirius red staining and the expression of FSP1 were also significantly reduced by WISE antibody treatment. These parameters were also reduced by sTGFbR_mFc at 5 mg/kg but the effect was less than what was observed with anti-WISE antibodies.

Figure 32:
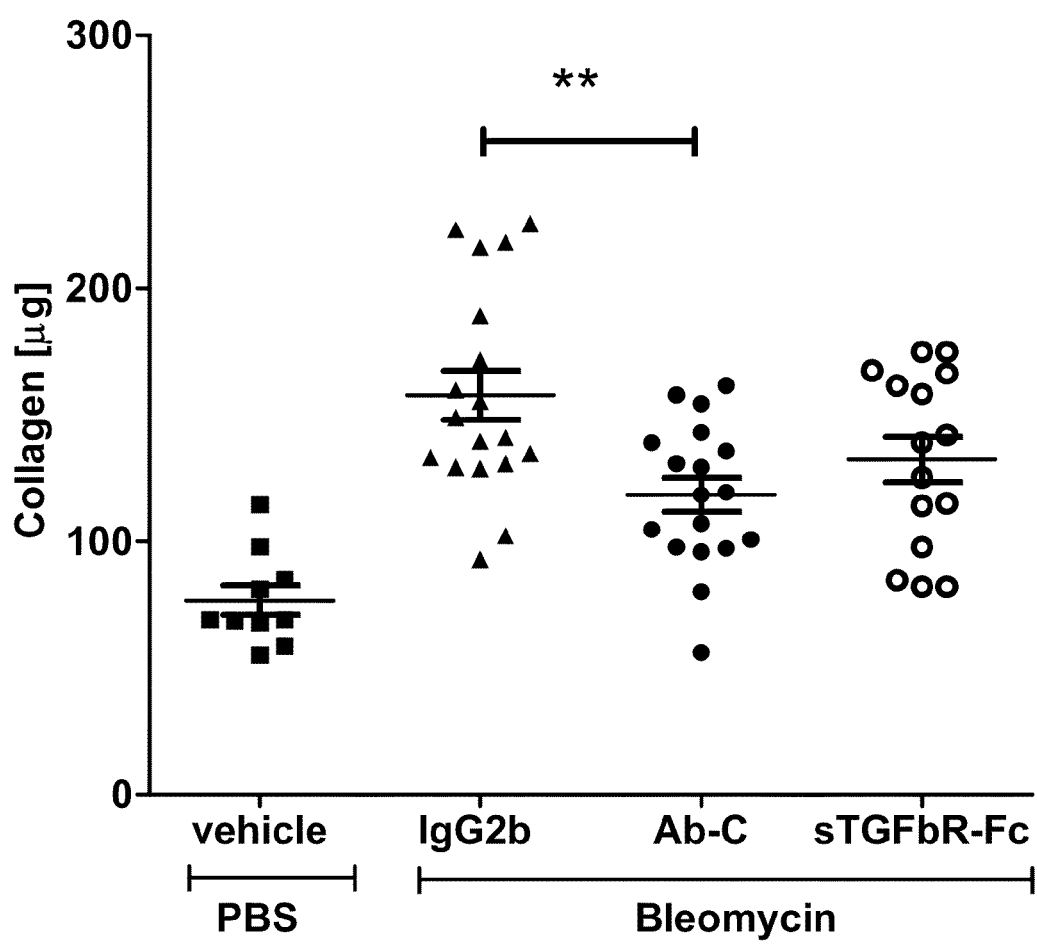
FIG. 32: Prophylactic Treatment with Anti-WISE Mab Reduced Collagen Production in a Mouse Model of Bleomycin-induced lung fibrosis.
Figure 33:
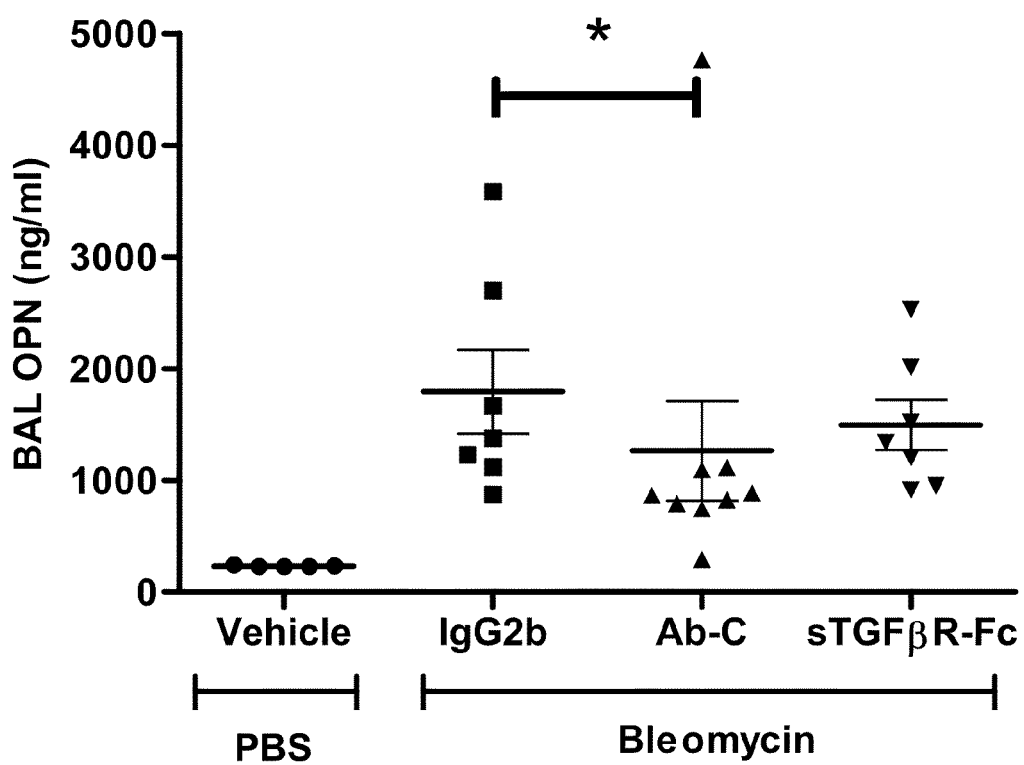
FIG. 33: Prophylactic Treatment with Anti-WISE Mab Reduced BAL OPN expression in a Mouse Model of Bleomycin-induced lung fibrosis.

In the 2nd study, anti-WISE Ab-C (20 mg/kg every two days, n=20) and mIgG2b (20 mg/kg every two days, n=20) control IgG were used. The soluble TGFbeta-Receptor mouse Fc protein (3 mg/kg every two days) was used as positive control. The results are shown in FIG. 32-33. The goal is to assess the impact on collagen deposition using a large number animals in light of the variation in collagen deposition observed during the first study. Prophylactic treatment of mice with anti-WISE antibody C significantly reduced collagen deposition (about 50% relative to IgG2b control) measured by Sircol collagen assay (FIG. 32). Brochoalveolar lavarge fluid from a subset of mice was also collected and as shown in FIG. 33, anti-WISE Ab-C significantly reduced the BAL OPN level. In addition, several souble markers of tissue injury or fibrosis were found elevated upon belomycin injection but were significantly reduced in BAL fluid from Ab-C treated mice versus those treated with IgG2b control, those include MMP9, VEGF, IP10, MIP-2, MIP-1 gamma and IgA. Because mice with BAL fluid harvest don't have good morphological preservation, not all lung samples were collected for histological study and thus a third study was conducted to evaluate that.

Figure 34:
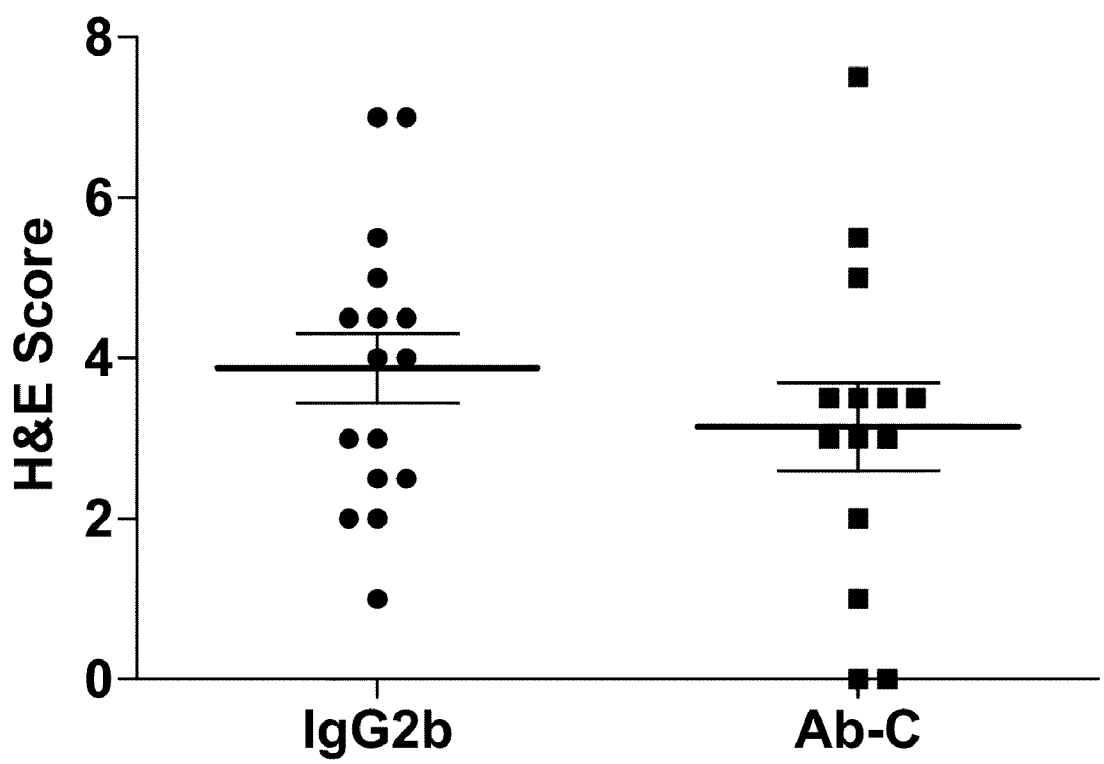
FIG. 34: Histological analysis trends towards a moderate reduction in lung injury with WISE Ab.
Figure 35:
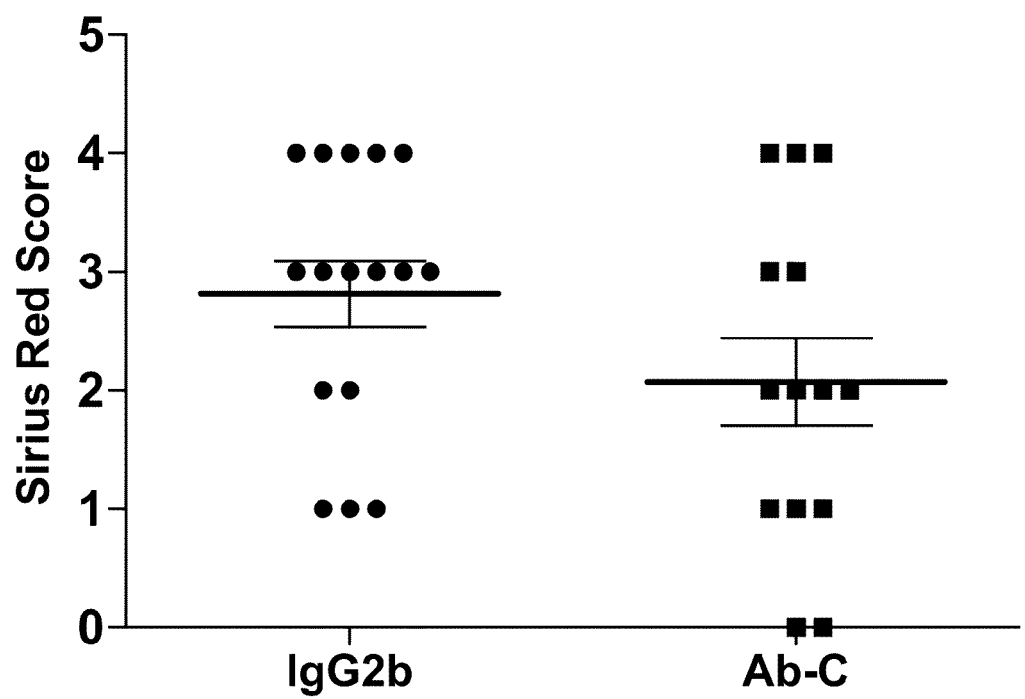
FIG. 35: Histological analysis trends towards a moderate reduction in Sirius Red score with WISE Ab.
Figure 36:
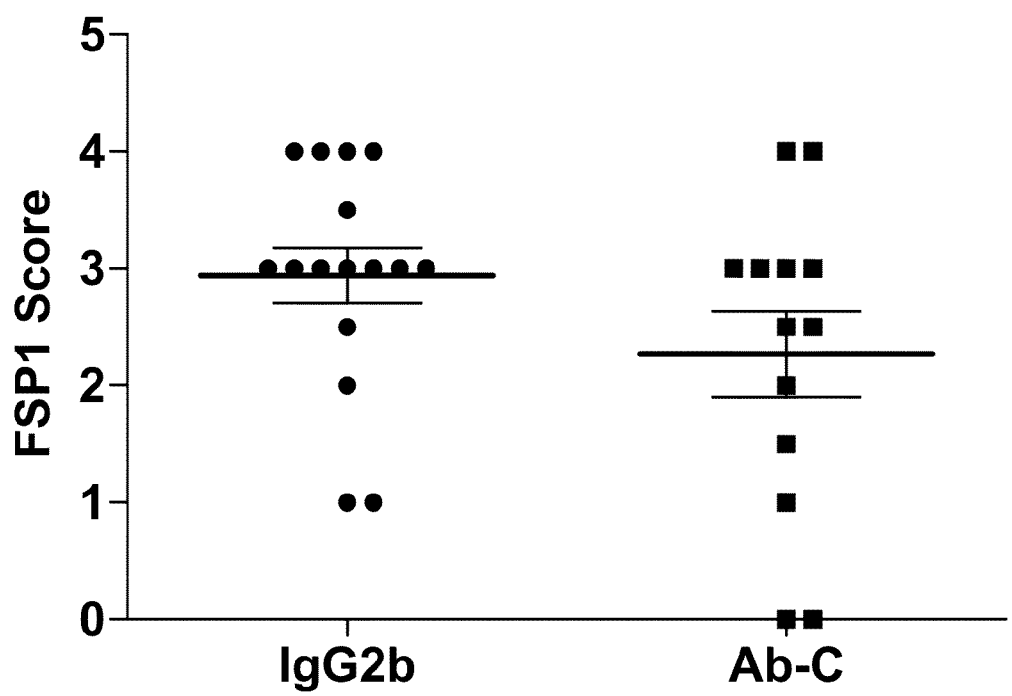
FIG. 36: Histological analysis trends towards a moderate reduction in fibrotic marker FSP1 expression with WISE Ab.
Figure 37:
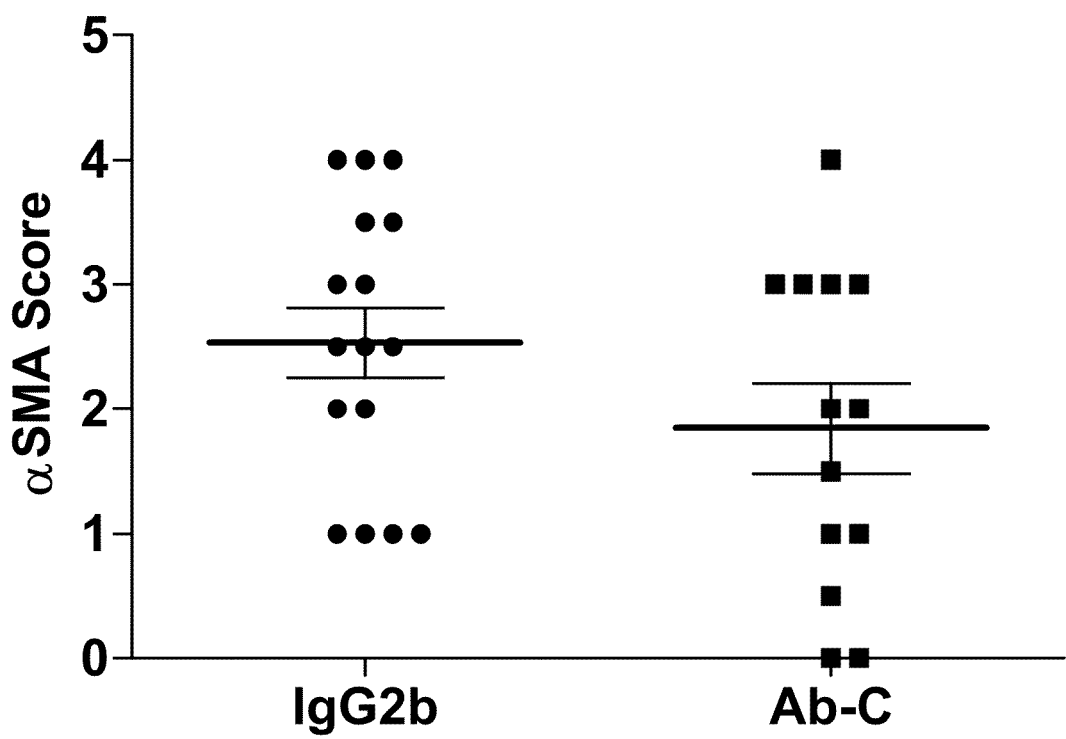
FIG. 37: Histological analysis trends towards a moderate reduction in fibrotic markeraSMA expression with WISE Ab.
Figure 38:
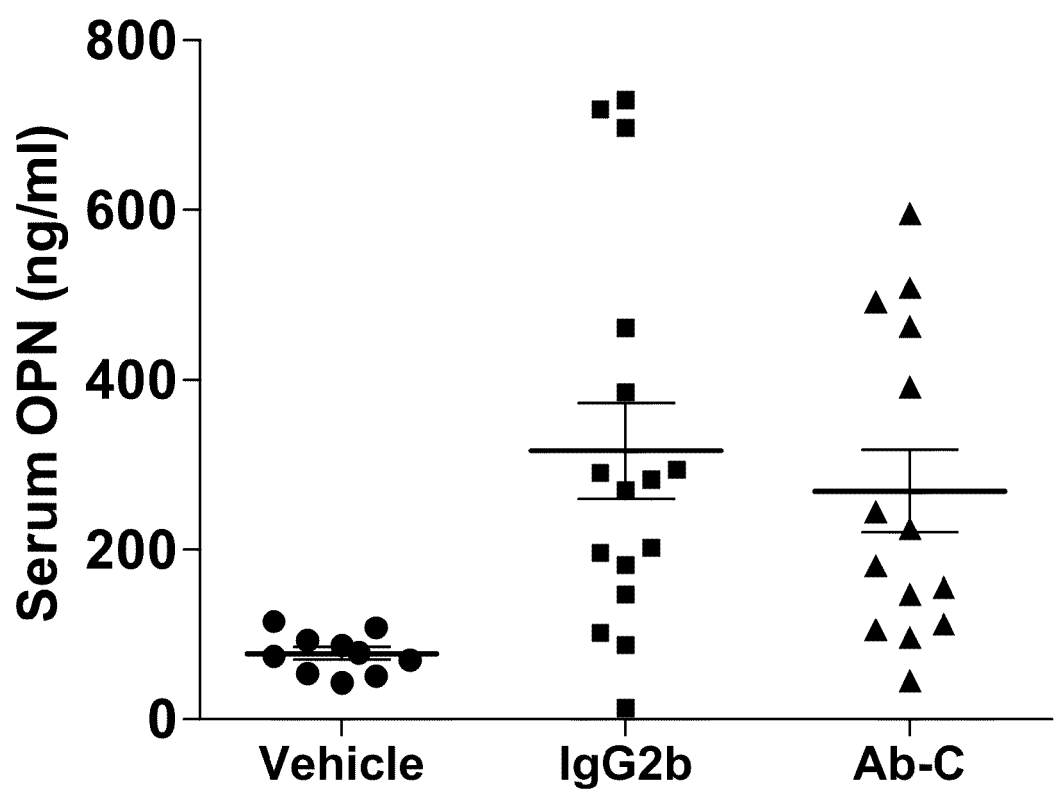
FIG. 38: WISE Ab treatment moderately decreased serum OPN levels.

In the 3rd study, anti-WISE antibody Ab-C (20 mg/kg, n=20) was used and mIgG2b (n=20) control IgG was used. Histological assessment using H&E, Sirius red staining and IHC of aSMA, FSP1 were performed. Prophylactic treatment of mice with anti-WISE antibody C resulted in lower lung injury based on H&E score (FIG. 34), collagen deposition measured by Sirius Red (FIG. 35), the expression of myofibroblast marker FSP1 (FIG. 36) and alpha smooth muscle actin (aSMA by immunohistochemistry, FIG. 37), and lower serum osteopontin level measured by ELISA (FIG. 38). It is noted that the collagen deposited in the IgG control group measured by sircol collagen assay was twice as much as what was reported in the $1^{st}$ and $2^{nd}$ study and thus these mice have more server disease than those in the previous two studies (a new batch bleomycin was used).

These data showed that anti-WISE antibody treatment prophylactically can reduce lung injury, collagen deposition and myofibroblast markers, and osteopontin level in both BAL fluid and serum in the bleomycin induced lung fibrosis model. It is interesting to note that OPN is highly upregulated in human IPF samples (Pardo et al PLOS Medicine 2005 Volume 2, Page 0891-0903; Kadota et al. Respiratory Medicine Volume 99 Issue 1, January 2005, Pages 111-117) and knockout of OPN itself resulted in reduced fibrosis in several fibrosis models including bleomycin model and unilateral ureteral obstruction (UUO) induced renal fibrosis model, cyclosporine induced renal toxicity model. In addition, Opn knockout mice did not develop albuminuria in response to LPS injection, and Opn knockout mice were protected from diabetes-induced albuminuria and mesangial expansion. (Takahashi et al. Am. J. Respir. Cell Mol. Biol, Volume 24, Number 3, March, 2001 264-271; Berman et al *Am J Physiol Lung Cell Mol Physiol* 286: L1311-L1318, 2004; Mazzali et al *Kidney International* (2002) 62, 78-85; Yoo et al. *Kidney International* (2006) 70, 1735-1741; Lorenzen *JASN*, Vol. 19, No. 5. (May 2008), pp. 884-890) Thus WISE Ab treatment may have utility in treating a variety of disorders involving kidney and lung injury and related fibrosis.

In addition, elevated osteopontin (OPN) plasma levels are highly prognostic in advanced non-small cell lung cancer (NSCLC) (2006 ASCO Annual Meeting, Abstract 7198) and it has been shown that OPN can promote integrin activation and cancer cell survival (Lee et al Cancer Research Mar. 1, 2007; 67(5):2089-97). OPN can also promote tumor metastasis and elevated osteopontin levels in various cancer types are associated with poor prognosis (reviewed by El-Tanani M K Front Biosci. May 1, 2008; 13:4276-84; Johnston et al Front Bioscience. May 1, 2008: 13: 4361-4372). Thus, WISE binding agents may also reduce cancer cell survival and metastasis through its ability to decrease osteopontin expression in tumor.

The Effect of Anti-WISE Antibody Treatment on Proteinuria in Col4a3 KO Mice

Figure 39:
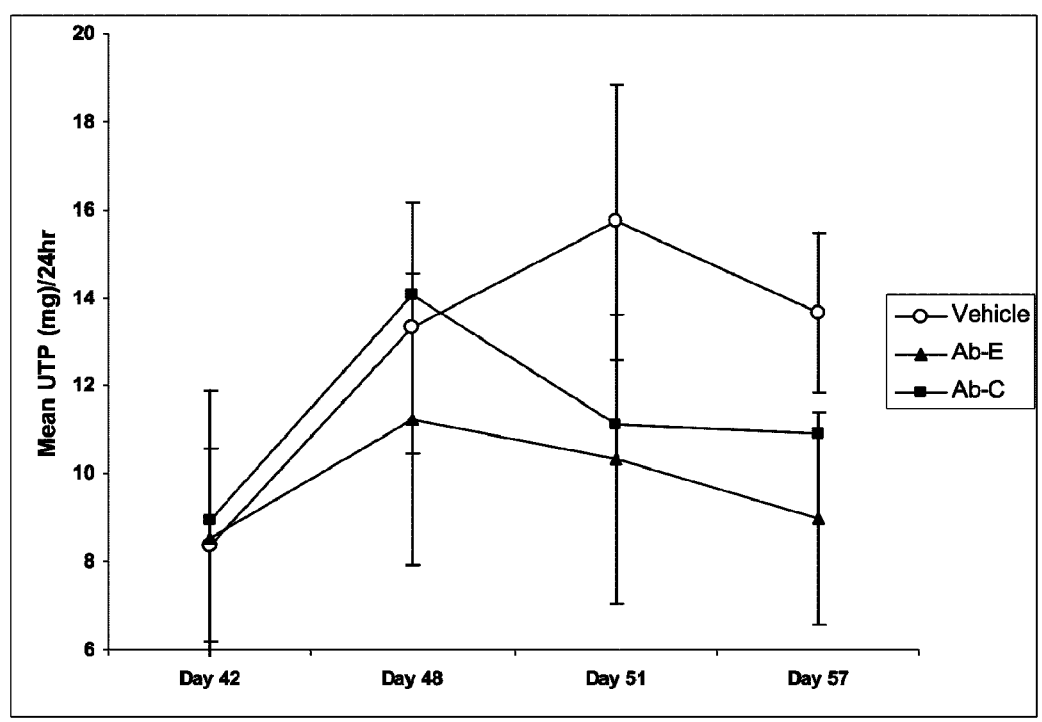
FIG. 39: WISE Antibody treatment reduced 24 hr Urinary Total Protein (UTP) in Col4a3 KO mice.

Col4a3 KO mice (129-Col4a3<tm1Dec>/J) were obtained from the Jackson Laboratory. Col4a3 mice develop server proteinuria starting age of week 5 and gradually develop end stage renal disease at week 10 or later. To evaluate the impact of anti-WISE treatment after proteinuria has been developed, treatments were started at age of day 43 (week 6) with 20 mg/kg of anti-WISE antibody Ab-C or Ab-E or vehicle every other day (IP). Treatments were continued for 14 days. Each group (n=12) received six injections during the study period. Urinary samples were collected in metabolic cages on day 42 (1 day before treatment), day 48, day 52 and day 57. Twenty four hour total urinary protein (UTP) excretion were measured using Albuwell M (Exocell Inc.) according to manufacturer's instruction and adjusted for urine volume. FIG. 39 shows that 24 hr total urinary protein (UTP) was statistically significantly lower in anti-WISE treated groups compared to vehicle treated groups. Along with the observation reported for WISE KO mice, this data suggests potential utility of anti-WISE agents in reducing proteinuria which is a common manifestation in various kidney diseases such as glomerulonephritis, membranous nephropathy, diabetic nephropathy and transplantation related nephropathy.

The invention claimed is:

1. An isolated antibody or fragment thereof that binds WISE, wherein the heavy chain of said antibody comprises SEQ ID NO: 24.

2. An antibody or fragment thereof according to claim 1 in combination with one or more of a pharmaceutically acceptable excipient, diluent or carrier.

3. An antibody or fragment thereof according to claim 1 conjugated to at least one of Fc, PEG, albumin, and transferrin.

4. An antibody or fragment thereof of claim 1 comprising a light chain selected from the group consisting of SEQ ID NOs: 22, 46, 76, 78, 80, 82, 84, 86, 88, 90, 92, 94, 96, 98, 100, 102, 104, 106, 108, 110, 112, 114, 116, 118, 120, and 122.

5. An antibody or fragment thereof of claim 1 that inhibits WISE activity.

* * * * *

SEQUENCE LISTING

```
<160> NUMBER OF SEQ ID NOS: 282

<210> SEQ ID NO 1
<211> LENGTH: 673
<212> TYPE: DNA
<213> ORGANISM: Homo sapiens

<400> SEQUENCE: 1
atgcttcctc ctgccattca tttctatctc cttccccttg catgcatcct aatgaaaagc      60
tgtttggctt ttaaaaatga tgccacagaa atcctttatt cacatgtggt taaacctgtt     120
ccagcacacc ccagcagcaa cagcacgttg aatcaagcca gaaatggagg caggcatttc     180
agtaacactg gactggatcg gaacactcgg gttcaagtgg gttgccggga actgcgttcc     240
accaaataca tctctgatgg ccagtgcacc agcatcagcc ctctgaagga gctggtgtgt     300
gctggcgagt gcttgcccct gccagtgctc cctaactgga ttggaggagg ctatggaaca     360
aagtactgga gcaggaggag ctcccaggag tggcggtgtg tcaatgacaa acccgtacc      420 cagagaatcc agctgcagtg ccaagatggc agcacacgca cctacaaaat cacagtagtc     480
actgcctgca agtgcaagag gtacacccgg cagcacaacg agtccagtca caactttgag    540
agcatgtcac ctgccaagcc agtccagcat cacagagagc ggaaaagagc cagcaaatcc    600
agcaagcaca gcatgagtta gctcgagggg cggatccccc gggctgcagg aattcgatat    660
caagcttgct agc                                                       673

<210> SEQ ID NO 2
<211> LENGTH: 206
<212> TYPE: PRT
<213> ORGANISM: Homo sapiens

<400> SEQUENCE: 2

Met Leu Pro Pro Ala Ile His Phe Tyr Leu Leu Pro Leu Ala Cys Ile
1               5                   10                  15

Leu Met Lys Ser Cys Leu Ala Phe Lys Asn Asp Ala Thr Glu Ile Leu
            20                  25                  30

Tyr Ser His Val Val Lys Pro Val Pro Ala His Pro Ser Ser Asn Ser
        35                  40                  45

Thr Leu Asn Gln Ala Arg Asn Gly Gly Arg His Phe Ser Asn Thr Gly
    50                  55                  60

Leu Asp Arg Asn Thr Arg Val Gln Val Gly Cys Arg Glu Leu Arg Ser
65                  70                  75                  80
```

```
Thr Lys Tyr Ile Ser Asp Gly Gln Cys Thr Ser Ile Ser Pro Leu Lys
                85                  90                  95

Glu Leu Val Cys Ala Gly Glu Cys Leu Pro Leu Pro Val Leu Pro Asn
            100                 105                 110

Trp Ile Gly Gly Tyr Gly Thr Lys Tyr Trp Ser Arg Arg Ser Ser
            115                 120                 125

Gln Glu Trp Arg Cys Val Asn Asp Lys Thr Arg Thr Gln Arg Ile Gln
        130                 135                 140

Leu Gln Cys Gln Asp Gly Ser Thr Arg Thr Tyr Lys Ile Thr Val Val
145                 150                 155                 160

Thr Ala Cys Lys Cys Lys Arg Tyr Thr Arg Gln His Asn Glu Ser Ser
                165                 170                 175

His Asn Phe Glu Ser Met Ser Pro Ala Lys Pro Val Gln His His Arg
            180                 185                 190

Glu Arg Lys Arg Ala Ser Lys Ser Ser Lys His Ser Met Ser
        195                 200                 205
```

<210> SEQ ID NO 3
<211> LENGTH: 627
<212> TYPE: DNA
<213> ORGANISM: Mus musculus

<400> SEQUENCE: 3

```
atgcttcctc ctgccattca tctctctctc attcccctgc tctgcatcct gatgagaaac    60
tgtttggctt ttaaaaatga tgccacagaa atcctttatt cacatgtggt taaacctgtc   120
ccggcacacc ccagcagcaa cagcaccctg aatcaagcca ggaatggagg caggcatttc   180
agtagcactg gactggatcg aaacagtcga gttcaagtgg gctgcaggga actgcggtcc   240
accaaataca tttcggacgg ccagtgcacc agcatcagcc ctctgaagga gctggtgtgc   300
gcgggcgagt gcttgcccct gccggtgctt cccaactgga tcggaggagg ctatggaaca   360
aagtactgga gccggaggag ctctcaggag tggcggtgtg tcaacgacaa gacgcgcacc   420
cagaggatcc agctgcagtg tcaggacggc agcacgcgca cctacaaaat caccgtggtc   480
acggcgtgca gtgcaagag gtacacccgt cagcacaacg agtccagcca caactttgaa   540
agcgtgtcgc ccgccaagcc cgcccagcac cacagagagc ggaagagagc cagcaaatcc   600
agcaagcaca gtctgagcta gctcgag                                       627
```

<210> SEQ ID NO 4
<211> LENGTH: 206
<212> TYPE: PRT
<213> ORGANISM: Mus musculus

<400> SEQUENCE: 4

```
Met Leu Pro Pro Ala Ile His Leu Ser Leu Ile Pro Leu Leu Cys Ile
1               5                   10                  15

Leu Met Arg Asn Cys Leu Ala Phe Lys Asn Asp Ala Thr Glu Ile Leu
            20                  25                  30

Tyr Ser His Val Val Lys Pro Val Pro Ala His Pro Ser Ser Asn Ser
        35                  40                  45

Thr Leu Asn Gln Ala Arg Asn Gly Gly Arg His Phe Ser Ser Thr Gly
    50                  55                  60

Leu Asp Arg Asn Ser Arg Val Gln Val Gly Cys Arg Glu Leu Arg Ser
65                  70                  75                  80

Thr Lys Tyr Ile Ser Asp Gly Gln Cys Thr Ser Ile Ser Pro Leu Lys
                85                  90                  95
```

Glu Leu Val Cys Ala Gly Glu Cys Leu Pro Leu Pro Val Leu Pro Asn
              100                 105                 110

Trp Ile Gly Gly Tyr Gly Thr Lys Tyr Trp Ser Arg Arg Ser Ser
         115                 120                 125

Gln Glu Trp Arg Cys Val Asn Asp Lys Thr Arg Thr Gln Arg Ile Gln
        130                 135                 140

Leu Gln Cys Gln Asp Gly Ser Thr Arg Thr Tyr Lys Ile Thr Val Val
145                 150                 155                 160

Thr Ala Cys Lys Cys Lys Arg Tyr Thr Arg Gln His Asn Glu Ser Ser
                165                 170                 175

His Asn Phe Glu Ser Val Ser Pro Ala Lys Pro Ala Gln His His Arg
            180                 185                 190

Glu Arg Lys Arg Ala Ser Lys Ser Ser Lys His Ser Leu Ser
        195                 200                 205

<210> SEQ ID NO 5
<211> LENGTH: 629
<212> TYPE: DNA
<213> ORGANISM: Rattus norvegicus

<400> SEQUENCE: 5
atgcttcctc ctgccattca tctctctctc attcccctgc tctgcatcct gatgaaaaac       60
tgtttggctt ttaaaaatga tgccacagaa atcctttatt cacatgtggt taaacctgtt      120
tcagcacacc ccagcagcaa cagcaccttg aatcaagcca ggaatggagg caggcacttc      180
agtagcacgg gactggatcg aaatagtcga gttcaagtgg gctgcaggga actgcggtcc      240
accaaataca tctcggatgg ccagtgcacc agcatcagcc ctctgaagga gctggtgtgc      300
gcgggtgagt gcttgcccct gccagtgctt cccaactgga tcggaggagg ctacggaaca      360
aagtactgga gccggaggag ctcccaggag tggcggtgtg tcaacgacaa gacgcgcacc      420
cagagaatcc agctgcagtg tcaggacggc agcacacgcc cctacaaaat caccgtggtc      480
acagcgtgca gtgcaagag gtacacccgg cagcacaacg agtccagcca caactttgaa      540
agcgtgtctc ccgccaagcc cgcccagcac acagagagc ggaagagagc cagcaaatcc      600
agcaagcaca gtctgagcta ggcggccgc                                       629

<210> SEQ ID NO 6
<211> LENGTH: 206
<212> TYPE: PRT
<213> ORGANISM: Rattus norvegicus

<400> SEQUENCE: 6

Met Leu Pro Pro Ala Ile His Phe Tyr Leu Leu Pro Leu Ala Cys Ile
1               5                   10                  15

Leu Met Lys Ser Cys Leu Ala Phe Lys Asn Asp Ala Thr Glu Ile Leu
            20                  25                  30

Tyr Ser His Val Val Lys Pro Val Pro Ala His Pro Ser Ser Asn Ser
        35                  40                  45

Thr Met Asn Gln Ala Arg Asn Gly Gly Arg His Phe Ser Asn Thr Gly
    50                  55                  60

Leu Asp Arg Asn Thr Arg Val Gln Val Gly Cys Arg Glu Leu Arg Ser
65                  70                  75                  80

Thr Lys Tyr Ile Ser Asp Gly Gln Cys Thr Ser Ile Ser Pro Leu Lys
                85                  90                  95

Glu Leu Val Cys Ala Gly Glu Cys Leu Pro Leu Pro Val Leu Pro Asn
            100                 105                 110

Trp Ile Gly Gly Gly Tyr Gly Thr Lys Tyr Trp Ser Arg Arg Ser Ser
            115                 120                 125

Gln Glu Trp Arg Cys Val Asn Asp Lys Thr Arg Thr Gln Arg Ile Gln
        130                 135                 140

Leu Gln Cys Gln Asp Gly Ser Thr Arg Thr Tyr Lys Ile Thr Val Val
145                 150                 155                 160

Thr Ala Cys Lys Cys Lys Arg Tyr Thr Arg Gln His Asn Glu Ser Ser
                165                 170                 175

His Asn Phe Glu Ser Met Ser Pro Ala Lys Pro Val Gln His His Arg
            180                 185                 190

Glu Arg Lys Arg Ala Ser Lys Ser Ser Lys His Ser Met Ser
        195                 200                 205

<210> SEQ ID NO 7
<211> LENGTH: 629
<212> TYPE: DNA
<213> ORGANISM: Macaca fascicularis

<400> SEQUENCE: 7
atgcttcctc ctgccattca tctctctctc attcccctgc tctgcatcct gatgaaaaac      60
tgtttggctt ttaaaaatga tgccacagaa atcctttatt cacatgtggt taaacctgtt     120
tcagcacacc ccagcagcaa cagcaccttg aatcaagcca ggaatggagg caggcacttc     180
agtagcacgg gactggatcg aaatagtcga gttcaagtgg gctgcaggga actgcggtcc     240
accaaataca tctcggatgg ccagtgcacc agcatcagcc ctctgaagga gctggtgtgc     300
gcgggtgagt gcttgcccct tccagtgctt cccaactgga tcggaggagg ctacggaaca     360
aagtactgga gccggaggag ctcccaggag tggcggtgtg tcaacgacaa gacgcgcacc     420
cagagaatcc agctgcagtg tcaggacggc agcacacgca cctacaaaat caccgtggtc     480
acagcgtgca gtgcaagag gtacacccgg cagcacaacg agtccagcca caactttgaa     540
agcgtgtctc ccgccaagcc cgcccagcac acagagagc ggaagagagc cagcaaatcc     600
agcaagcaca gtctgagcta ggcggccgc                                      629

<210> SEQ ID NO 8
<211> LENGTH: 206
<212> TYPE: PRT
<213> ORGANISM: Macaca fascicularis

<400> SEQUENCE: 8

Met Leu Pro Pro Ala Ile His Leu Ser Leu Ile Pro Leu Leu Cys Ile
1               5                   10                  15

Leu Met Lys Asn Cys Leu Ala Phe Lys Asn Asp Ala Thr Glu Ile Leu
            20                  25                  30

Tyr Ser His Val Val Lys Pro Val Ser Ala His Pro Ser Ser Asn Ser
        35                  40                  45

Thr Leu Asn Gln Ala Arg Asn Gly Gly Arg His Phe Ser Ser Thr Gly
    50                  55                  60

Leu Asp Arg Asn Ser Arg Val Gln Val Gly Cys Arg Glu Leu Arg Ser
65                  70                  75                  80

Thr Lys Tyr Ile Ser Asp Gly Gln Cys Thr Ser Ile Ser Pro Leu Lys
                85                  90                  95

Glu Leu Val Cys Ala Gly Glu Cys Leu Pro Leu Pro Val Leu Pro Asn
            100                 105                 110

Trp Ile Gly Gly Gly Tyr Gly Thr Lys Tyr Trp Ser Arg Arg Ser Ser
            115                 120                 125

```
Gln Glu Trp Arg Cys Val Asn Asp Lys Thr Arg Thr Gln Arg Ile Gln
        130                 135                 140

Leu Gln Cys Gln Asp Gly Ser Thr Arg Thr Tyr Lys Ile Thr Val Val
145                 150                 155                 160

Thr Ala Cys Lys Cys Lys Arg Tyr Thr Arg Gln His Asn Glu Ser Ser
                165                 170                 175

His Asn Phe Glu Ser Val Ser Pro Ala Lys Pro Ala Gln His His Arg
            180                 185                 190

Glu Arg Lys Arg Ala Ser Lys Ser Ser Lys His Ser Leu Ser
        195                 200                 205
```

<210> SEQ ID NO 9
<211> LENGTH: 714
<212> TYPE: DNA
<213> ORGANISM: Homo sapiens

<400> SEQUENCE: 9

```
atgaagttgc ctgttaggct gttggtgctg atgttctgga ttcctgcttc cagcagtgat    60
gttgtgatga cccaaactcc actctccctg cctgtcagtc ttggagatca agcctccatc   120
tcttgcagat ctagtcagag ccttgaacac agtaatggaa acacctattt acattggtac   180
ctgcagaagc caggccagtc tccaaagctc ctgatctaca agtttccaa ccgattttct    240
ggggtcccag acaggttcag tggcagtgga tcagggacag atttcacact caagatcagc   300
agagtggagg ctgaggatct gggagtttat ttctgctctc aaagtacaca tgttccgctc   360
acgttcggtg ctgggaccaa ggtggagctg aaacgggctg atgctgcacc aactgtatcc   420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat gaacgacata cagctatac ctgtgaggcc    660
actcacaaga catcaacttc acccattgtc aagagcttca caggaatga gtgt          714
```

<210> SEQ ID NO 10
<211> LENGTH: 238
<212> TYPE: PRT
<213> ORGANISM: Homo sapiens

<400> SEQUENCE: 10

```
Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Glu His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Leu Thr Phe Gly Ala Gly Thr Lys Val
        115                 120                 125
```

```
Glu Leu Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
210                 215                 220

Ser Thr Ser Pro Ile Val Lys Ser Phe Asn Arg Asn Glu Cys
225                 230                 235

<210> SEQ ID NO 11
<211> LENGTH: 1428
<212> TYPE: DNA
<213> ORGANISM: Mus musculus

<400> SEQUENCE: 11
atgggttggc tgtggaactt gctattcctg atggcagctg cccaaagtgc ccaagcacag      60
atccacttgg tacagtctgg acctgagctg aagaagcctg agagactgt caagatctcc     120
tgcaaggcgt ctgggttttc cttcacaacc tatggaatga gctgggtgaa acaggctcca    180
ggaaagggtt taaagtggat gggctggata aataccact ctggagtgcc acatatgct     240
gatgacttca agggacggtt tgccttctct ttggaaacct ctgccagcac tgcctatttg    300
cagatcaaca acctcaaaaa tgaggacacg gctacatatt tctgtgtaag ggggagggaa    360
tattactacg gtagtggcat tgctttctgg ggccaaggga ctctggtcac tgtctctgca    420
gccaaaacaa cacccccatc agtctatcca ctggcccctg gtgtggaga tacaactggt    480
tcctctgtga ctctgggatg cctggtcaag ggctacttcc ctgagtcagt gactgtgact    540
tggaactctg gatccctgtc cagcagtgtg cacaccttcc cagctctcct gcagtctgga    600
ctctacacta tgagcagctc agtgactgtc ccctccagca cctggccaag tcagaccgtc    660
acctgcagcg ttgctcaccc agccagcagc accacgtggg acaaaaaact tgagcccagc    720
gggcccattt caacaatcaa cccctgtcct ccatgcaagg agtgtcacaa atgcccagct    780
cctaacctcg agggtggacc atccgtcttc atcttccctc aaatatcaa ggatgtactc     840
atgatctccc tgacacccaa ggtcacgtgt gtggtggtgg atgtgagcga ggatgaccca    900
gacgtccgga tcagctggtt tgtgaacaac gtggaagtac acacagctca gacacaaacc    960
catagagagg attacaacag tactatccgg gtggtcagtg ccctccccat ccagcaccag   1020
gactggatga gtggcaagga gttcaaatgc aaggtcaaca acaaagacct cccatcaccc   1080
atcgagagaa ccatctcaaa aattaaaggg ctagtcagag ctccacaagt atacatcttg   1140
ccgccaccag cagagcagtt gtccaggaaa gatgtcagtc tcacttgcct ggtcgtgggc   1200
ttcaaccctg agacatcag tgtggagtgg accagcaatg ggcatacaga ggagaactac   1260
aaggacaccg caccagtcct ggactctgac ggttcttact tcatatacag caagctcgat   1320
ataaaaacaa gcaagtggga gaaaacagat tccttctcat gcaacgtgag aacgagggt   1380
ctgaaaatt actacctgaa gaagaccatc tcccggtctc cgggtaaa                 1428

<210> SEQ ID NO 12
<211> LENGTH: 476
```

<212> TYPE: PRT
<213> ORGANISM: Mus musculus

<400> SEQUENCE: 12

```
Met Gly Trp Leu Trp Asn Leu Leu Phe Leu Met Ala Ala Ala Gln Ser
1               5                   10                  15

Ala Gln Ala Gln Ile His Leu Val Gln Ser Gly Pro Glu Leu Lys Lys
            20                  25                  30

Pro Gly Glu Thr Val Lys Ile Ser Cys Lys Ala Ser Gly Phe Ser Phe
        35                  40                  45

Thr Thr Tyr Gly Met Ser Trp Val Lys Gln Ala Pro Gly Lys Gly Leu
    50                  55                  60

Lys Trp Met Gly Trp Ile Asn Thr Tyr Ser Gly Val Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Val Arg Gly Arg Glu Tyr Tyr Gly Ser Gly Ile Ala
        115                 120                 125

Phe Trp Gly Gln Gly Thr Leu Val Thr Val Ser Ala Ala Lys Thr Thr
    130                 135                 140

Pro Pro Ser Val Tyr Pro Leu Ala Pro Gly Cys Gly Asp Thr Thr Gly
145                 150                 155                 160

Ser Ser Val Thr Leu Gly Cys Leu Val Lys Gly Tyr Phe Pro Glu Ser
                165                 170                 175

Val Thr Val Thr Trp Asn Ser Gly Ser Leu Ser Ser Val His Thr
            180                 185                 190

Phe Pro Ala Leu Leu Gln Ser Gly Leu Tyr Thr Met Ser Ser Ser Val
    195                 200                 205

Thr Val Pro Ser Ser Thr Trp Pro Ser Gln Thr Val Thr Cys Ser Val
210                 215                 220

Ala His Pro Ala Ser Ser Thr Thr Val Asp Lys Lys Leu Glu Pro Ser
225                 230                 235                 240

Gly Pro Ile Ser Thr Ile Asn Pro Cys Pro Pro Cys Lys Glu Cys His
                245                 250                 255

Lys Cys Pro Ala Pro Asn Leu Glu Gly Gly Pro Ser Val Phe Ile Phe
            260                 265                 270

Pro Pro Asn Ile Lys Asp Val Leu Met Ile Ser Leu Thr Pro Lys Val
        275                 280                 285

Thr Cys Val Val Val Asp Val Ser Glu Asp Asp Pro Asp Val Arg Ile
    290                 295                 300

Ser Trp Phe Val Asn Asn Val Glu Val His Thr Ala Gln Thr Gln Thr
305                 310                 315                 320

His Arg Glu Asp Tyr Asn Ser Thr Ile Arg Val Val Ser Ala Leu Pro
                325                 330                 335

Ile Gln His Gln Asp Trp Met Ser Gly Lys Glu Phe Lys Cys Lys Val
            340                 345                 350

Asn Asn Lys Asp Leu Pro Ser Pro Ile Glu Arg Thr Ile Ser Lys Ile
        355                 360                 365

Lys Gly Leu Val Arg Ala Pro Gln Val Tyr Ile Leu Pro Pro Pro Ala
    370                 375                 380

Glu Gln Leu Ser Arg Lys Asp Val Ser Leu Thr Cys Leu Val Val Gly
385                 390                 395                 400
```

```
Phe Asn Pro Gly Asp Ile Ser Val Glu Trp Thr Ser Asn Gly His Thr
                405                 410                 415
Glu Glu Asn Tyr Lys Asp Thr Ala Pro Val Leu Asp Ser Asp Gly Ser
            420                 425                 430
Tyr Phe Ile Tyr Ser Lys Leu Asp Ile Lys Thr Ser Lys Trp Glu Lys
        435                 440                 445
Thr Asp Ser Phe Ser Cys Asn Val Arg His Glu Gly Leu Lys Asn Tyr
450                 455                 460
Tyr Leu Lys Lys Thr Ile Ser Arg Ser Pro Gly Lys
465                 470                 475
```

<210> SEQ ID NO 13
<211> LENGTH: 1044
<212> TYPE: DNA
<213> ORGANISM: Homo sapiens

<400> SEQUENCE: 13

```
atggacatga gggtgcccgc tcagctcctg gggctcctgc tgctgtggct gagaggtgcg    60
cgctgcgatg tagttatgac acagtctccc ctgtctttgc cagtcacatt gggtcagccc   120
gcctctatta gctgccgaag ttctcagtct ttggagcatt ccaacggcaa tacttacttg   180
cactggtatc tgcagaagcc cggacaaagc cccaacttc tcatctataa agtcagcaat    240
aggttcagcg gggtgcctga taggttctcc ggctccggca gcggcactga ttttaccctt   300
aaaatcagtc gggtcgaagc tgaagatgta ggcgtgtact tttgctcaca gtccacacac   360
gtacccctga cttttggagg tggaacgaaa gtggagatca acgtacggt ggctgcacca    420
tctgtcttca tcttcccgcc atctgatgag cagttgaaat ctggaactgc tctgttgtg    480
tgcctgctga taacttcta tcccagagag gccaaagtac agtggaaggt ggataacgcc    540
ctccaatcgg gtaactccca ggagagtgtc acagagcagg acagcaagga cagcacctac   600
agcctcagca gcaccctgac gctgagcaaa gcagactacg agaaacacaa agtctacgcc   660
tgcgaagtca cccatcaggg cctgagctcg cccgtcacaa agagcttcaa caggggagag   720
tgtcgtacgg tggctgcacc atctgtcttc atcttcccgc catctgatga gcagttgaaa   780
tctggaactg cctctgttgt gtgcctgctg ataacttct atcccagaga ggccaaagta    840
cagtggaagg tggataacgc cctccaatcg gtaactccc aggagagtgt cacagagcag    900
gacagcaagg acagcaccta cagcctcagc agcaccctga cgctgagcaa agcagactac   960
gagaaacaca agtctacgc ctgcgaagtc acccatcagg gcctgagctc gcccgtcaca   1020
aagagcttca caggggaga gtgt                                          1044
```

<210> SEQ ID NO 14
<211> LENGTH: 241
<212> TYPE: PRT
<213> ORGANISM: Homo sapiens

<400> SEQUENCE: 14

```
Met Asp Met Arg Val Pro Ala Gln Leu Leu Gly Leu Leu Leu Leu Trp
1               5                   10                  15
Leu Arg Gly Ala Arg Cys Asp Val Val Met Thr Gln Ser Pro Leu Ser
            20                  25                  30
Leu Pro Val Thr Leu Gly Gln Pro Ala Ser Ile Ser Cys Arg Ser Ser
        35                  40                  45
Gln Ser Leu Glu His Ser Asn Gly Asn Thr Tyr Leu His Trp Tyr Leu
    50                  55                  60
Gln Lys Pro Gly Gln Ser Pro Gln Leu Leu Ile Tyr Lys Val Ser Asn
```

```
            65                  70                  75                  80
Arg Phe Ser Gly Val Pro Asp Arg Phe Ser Gly Ser Gly Ser Gly Thr
                    85                  90                  95

Asp Phe Thr Leu Lys Ile Ser Arg Val Glu Ala Glu Asp Val Gly Val
            100                 105                 110

Tyr Phe Cys Ser Gln Ser Thr His Val Pro Leu Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 15
<211> LENGTH: 1407
<212> TYPE: DNA
<213> ORGANISM: Homo sapiens

<400> SEQUENCE: 15
atggacatga gggtgcccgc tcagctcctg gggctcctgc tgctgtggct gagaggtgcg        60
cgctgccagg tgcagctcgt gcaaagtggg gccgaagtga aaaaacctgg agcaagcgtt      120
aaagtgtcct gcaaagcgtc tggctacacc tttactacct atggaatgtc atgggtgaaa      180
caagcacccg gccaaggtct ggagtggatg ggttggataa acacatattc cggcgtcccc      240
acctatgcag acgactttaa aggccgcttc gtgttctccc ttgacacctc tgtaagtacc      300
gcgtatctgc aaatcaattc cctgaaagcc gaggacactg ccgtgtactt tgcgtgcggg      360
ggccgagaat actactatgg cagcggcata gccttttggg gtcaggggac cctggtgacc      420
gtctctagtg cctccaccaa gggcccatcg gtcttccccc tggcgccctg ctccaggagc      480
acctccgaga gcacagcggc cctgggctgc ctggtcaagg actacttccc cgaaccggtg      540
acggtgtcgt ggaactcagg cgctctgacc agcggcgtgc acaccttccc agctgtccta      600
cagtcctcag gactctactc cctcagcagc gtggtgaccg tgccctccag caacttcggc      660
acccagacct acacctgcaa cgtagatcac aagcccagca acaccaaggt ggacaagaca      720
gttgagcgca atgttgtgtc gagtgcccca cgtgcccagc accacctgt ggcaggaccg      780 tcagtcttcc tcttcccccc aaaacccaag gacaccctca tgatctcccg gacccctgag      840
gtcacgtgcg tggtggtgga cgtgagccac gaagaccccg aggtccagtt caactggtac      900
gtggacggcg tggaggtgca taatgccaag acaaagccac gggaggagca gttcaacagc      960
acgttccgtg tggtcagcgt cctcaccgtt gtgcaccagg actggctgaa cggcaaggag     1020
tacaagtgca aggtctccaa caaaggcctc cagccccca tcgagaaaac catctccaaa     1080
accaaagggc agccccgaga accacaggtg tacaccctgc ccccatcccg ggaggagatg     1140
```

-continued

```
accaagaacc aggtcagcct gacctgcctg gtcaaaggct tctacccccag cgacatcgcc    1200 gtggagtggg agagcaatgg gcagccggag aacaactaca agaccacacc tcccatgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaa                                        1407
```

<210> SEQ ID NO 16
<211> LENGTH: 469
<212> TYPE: PRT
<213> ORGANISM: Homo sapiens

<400> SEQUENCE: 16

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Thr Tyr Gly Met Ser Trp Val Arg Gln Ala Pro Gly
    50                  55                  60

Gln Gly Leu Glu Trp Met Gly Trp Ile Asn Thr Tyr Ser Gly Val Pro
65                  70                  75                  80

Thr Tyr Ala Asp Asp Phe Lys Gly Arg Phe Val Phe Ser Leu Asp Thr
                85                  90                  95

Ser Val Ser Thr Ala Tyr Leu Gln Ile Asn Ser Leu Lys Ala Glu Asp
            100                 105                 110

Thr Ala Val Tyr Tyr Cys Ala Arg Gly Arg Glu Tyr Tyr Tyr Gly Ser
        115                 120                 125

Gly Ile Ala Phe Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335
```

```
Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Met Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
    450                 455                 460

Leu Ser Pro Gly Lys
465

<210> SEQ ID NO 17
<211> LENGTH: 714
<212> TYPE: DNA
<213> ORGANISM: Homo sapiens

<400> SEQUENCE: 17
atggagaaag acacactcct gctatgggtc ctgcttctct gggttccagg gtccacaggt      60
gacattgtgc tgacccaatc tccaccttct ttggctgtgt ctctagggca gagggccacc     120
atctcctgca gagccagcga aagtgttgat aattatggct ctagttttat gaactggttc     180
caacagaaac caggacagcc acccaaactc ctcatctttg ctgcatccaa ccaaggatcc     240
ggggtccctg ccaggtttag tggcagtggg tctgggacag acttcagcct caacatccat     300
cctatggagg aggatgatgc tgcaatgtat ttctgtcagc aaagtaagga ggttccgtac     360
acgttcggag gggggaccaa actggaaata aaacgggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600
agcacccttc gcttgaccaa ggacgagtat gaacgacata acagctatac ctgtgaggcc     660
actcacaaga catcaacttc acccattgtc aagagcttca caggaatga gtgt            714

<210> SEQ ID NO 18
<211> LENGTH: 238
<212> TYPE: PRT
<213> ORGANISM: Homo sapiens

<400> SEQUENCE: 18

Met Glu Lys Asp Thr Leu Leu Leu Trp Val Leu Leu Leu Trp Val Pro
1               5                   10                  15

Gly Ser Thr Gly Asp Ile Val Leu Thr Gln Ser Pro Pro Ser Leu Ala
            20                  25                  30

Val Ser Leu Gly Gln Arg Ala Thr Ile Ser Cys Arg Ala Ser Glu Ser
        35                  40                  45

Val Asp Asn Tyr Gly Ser Ser Phe Met Asn Trp Phe Gln Gln Lys Pro
50                  55                  60
```

```
Gly Gln Pro Pro Lys Leu Leu Ile Phe Ala Ala Ser Asn Gln Gly Ser
 65                  70                  75                  80

Gly Val Pro Ala Arg Phe Ser Gly Ser Gly Ser Gly Thr Asp Phe Ser
                 85                  90                  95

Leu Asn Ile His Pro Met Glu Glu Asp Asp Ala Ala Met Tyr Phe Cys
            100                 105                 110

Gln Gln Ser Lys Glu Val Pro Tyr Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 19
<211> LENGTH: 1419
<212> TYPE: DNA
<213> ORGANISM: Mus musculus

<400> SEQUENCE: 19
atggaatgga actgggtcgt tctcttcctc ctgtcattaa ctgcaggtgt ctatgcccag     60
ggtcagatgc agcagtctgg agctgagctg gtgaagcctg ggcttcagt gcaactgtcc    120 tgcaagactt ctggcttcac cttcagcagt acctatataa gttggttgaa gcagaagcct    180
ggacagagtc ttgagtggat tgcatggatt tatgctggca ctggtggtac cagatataat    240
cggaagttca caggcaaggc ccaactgact gtagacacat cctccagcac agcctacatg    300
caattcagca gcctgacaac tgaggactct gccatctatt actgtgcaag agaggggtc    360 gacgggtggt ttacttactg gggccagggg actctggtca ctgtctctgc agccaaaaca    420
acacccccat cagtctatcc actggcccct gggtgtggag atacaactgg ttcctccgtg    480
actctgggat gcctggtcaa gggctacttc cctgagtcag tgactgtgac ttggaactct    540
ggatccctgt ccagcagtgt gcacaccttc ccagctctcc tgcagtctgg actctacact    600
atgagcagct cagtgactgt cccctccagc acctggccaa gtcagaccgt cacctgcagc    660
gttgctcacc cagccagcag caccacggtg gacaaaaaac ttgagcccag cgggcccatt    720
tcaacaatca cccctgtcc tccatgcaag gagtgtcaca atgcccagc tcctaacctc    780 gagggtggac catccgtctt catcttccct ccaaatatca aggatgtact catgatctcc    840
ctgacaccca aggtcacgtg tgtggtggtg gatgtgagcg aggatgaccc agacgtccag    900
atcagctggt ttgtgaacaa cgtggaagta cacacagctc agacacaaac ccatagagag    960
gattacaaca gtactatccg ggtggtcagc accctcccca tccagcacca ggactggatg   1020
agtggcaagg agttcaaatg caaggtcaac aacaaagacc tcccatcacc catcgagaga   1080
accatctcaa aacccaaagg gctagtcaga gctccacaag tatacacttt gccgccacca   1140
gcagagcagt tgtccaggaa agatgtcagt ctcacttgcc tggtcgtggg cttcaaccct   1200
```

-continued

```
ggagacatca gtgtggagtg gaccagcaat gggcatacag aggagaacta caaggacacc    1260
gcaccagttc ttgactctga cggttcttac ttcatatata gcaagctcaa tatgaaaaca    1320
agcaagtggg agaaaacaga ttccttctca tgcaacgtga cacgagggg tctgaaaaat     1380 tactacctga agaagaccat ctcccggtct ccgggtaaa                           1419

<210> SEQ ID NO 20
<211> LENGTH: 473
<212> TYPE: PRT
<213> ORGANISM: Mus musculus

<400> SEQUENCE: 20

Met Glu Trp Asn Trp Val Val Leu Phe Leu Leu Ser Leu Thr Ala Gly
1               5                   10                  15

Val Tyr Ala Gln Gly Gln Met Gln Gln Ser Gly Ala Glu Leu Val Lys
                20                  25                  30

Pro Gly Ala Ser Val Gln Leu Ser Cys Lys Thr Ser Gly Phe Thr Phe
            35                  40                  45

Ser Ser Thr Tyr Ile Ser Trp Leu Lys Gln Lys Pro Gly Gln Ser Leu
        50                  55                  60

Glu Trp Ile Ala Trp Ile Tyr Ala Gly Thr Gly Thr Arg Tyr Asn
65                  70                  75                  80

Arg Lys Phe Thr Gly Lys Ala Gln Leu Thr Val Asp Thr Ser Ser Ser
                85                  90                  95

Thr Ala Tyr Met Gln Phe Ser Ser Leu Thr Thr Glu Asp Ser Ala Ile
            100                 105                 110

Tyr Tyr Cys Ala Arg Glu Gly Val Asp Gly Trp Phe Thr Tyr Trp Gly
        115                 120                 125

Gln Gly Thr Leu Val Thr Val Ser Ala Ala Lys Thr Thr Pro Pro Ser
    130                 135                 140

Val Tyr Pro Leu Ala Pro Gly Cys Gly Asp Thr Thr Gly Ser Ser Val
145                 150                 155                 160

Thr Leu Gly Cys Leu Val Lys Gly Tyr Phe Pro Glu Ser Val Thr Val
                165                 170                 175

Thr Trp Asn Ser Gly Ser Leu Ser Ser Ser Val His Thr Phe Pro Ala
            180                 185                 190

Leu Leu Gln Ser Gly Leu Tyr Thr Met Ser Ser Ser Val Thr Val Pro
        195                 200                 205

Ser Ser Thr Trp Pro Ser Gln Thr Val Thr Cys Ser Val Ala His Pro
    210                 215                 220

Ala Ser Ser Thr Thr Val Asp Lys Lys Leu Glu Pro Ser Gly Pro Ile
225                 230                 235                 240

Ser Thr Ile Asn Pro Cys Pro Pro Cys Lys Glu Cys His Lys Cys Pro
                245                 250                 255

Ala Pro Asn Leu Glu Gly Gly Pro Ser Val Phe Ile Phe Pro Pro Asn
            260                 265                 270

Ile Lys Asp Val Leu Met Ile Ser Leu Thr Pro Lys Val Thr Cys Val
        275                 280                 285

Val Val Asp Val Ser Glu Asp Asp Pro Asp Val Gln Ile Ser Trp Phe
    290                 295                 300

Val Asn Asn Val Glu Val His Thr Ala Gln Thr Gln Thr His Arg Glu
305                 310                 315                 320

Asp Tyr Asn Ser Thr Ile Arg Val Val Ser Thr Leu Pro Ile Gln His
                325                 330                 335
```

```
Gln Asp Trp Met Ser Gly Lys Glu Phe Lys Cys Lys Val Asn Asn Lys
                 340                 345                 350
Asp Leu Pro Ser Pro Ile Glu Arg Thr Ile Ser Lys Pro Lys Gly Leu
             355                 360                 365
Val Arg Ala Pro Gln Val Tyr Thr Leu Pro Pro Ala Glu Gln Leu
    370                 375                 380
Ser Arg Lys Asp Val Ser Leu Thr Cys Leu Val Val Gly Phe Asn Pro
385                 390                 395                 400
Gly Asp Ile Ser Val Glu Trp Thr Ser Asn Gly His Thr Glu Glu Asn
                405                 410                 415
Tyr Lys Asp Thr Ala Pro Val Leu Asp Ser Asp Gly Ser Tyr Phe Ile
             420                 425                 430
Tyr Ser Lys Leu Asn Met Lys Thr Ser Lys Trp Glu Lys Thr Asp Ser
            435                 440                 445
Phe Ser Cys Asn Val Arg His Glu Gly Leu Lys Asn Tyr Tyr Leu Lys
    450                 455                 460
Lys Thr Ile Ser Arg Ser Pro Gly Lys
465                 470
```

<210> SEQ ID NO 21
<211> LENGTH: 720
<212> TYPE: DNA
<213> ORGANISM: Homo sapiens

<400> SEQUENCE: 21

```
atggacatga gggtgcccgc tcagctcctg gggctcctgc tgctgtggct gagaggtgcg      60
cgctgtgaca ttcagatgac tcagtccccc tcctctctct ccgcttcagt cggggacaga     120
gtgactatca gctgccgagc cagtgagtca gtcgataatt atggctcatc cttcatgaat     180
tggtatcagc agaagccggg aaaagcccca aagctcctca tttacgccgc ttcaaaccag     240
ggttcagggg ttccctcccg cttctccggc tctgggtctg gcactgattt tacactgact     300
attagctccc tccagcctga agactttgct acctattatt gccagcagag caaagaggtc     360
ccctatacct tcggacaggg tactaaactg gagattaaac gtacggtggc tgcaccatct     420
gtcttcatct tcccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga acacaaaagt ctacgcctgc     660
gaagtcaccc atcagggcct gagctcgccc gtcacaaaga gcttcaacag gggagagtgt     720
```

<210> SEQ ID NO 22
<211> LENGTH: 240
<212> TYPE: PRT
<213> ORGANISM: Homo sapiens

<400> SEQUENCE: 22

```
Met Asp Met Arg Val Pro Ala Gln Leu Leu Gly Leu Leu Leu Leu Trp
1               5                   10                  15
Leu Arg Gly Ala Arg Cys Asp Ile Gln Met Thr Gln Ser Pro Ser Ser
                20                  25                  30
Leu Ser Ala Ser Val Gly Asp Arg Val Thr Ile Ser Cys Arg Ala Ser
            35                  40                  45
Glu Ser Val Asp Asn Tyr Gly Ser Ser Phe Met Asn Trp Tyr Gln Gln
        50                  55                  60
Lys Pro Gly Lys Ala Pro Lys Leu Leu Ile Tyr Ala Ala Ser Asn Gln
```

```
                65                  70                  75                  80
Gly Ser Gly Val Pro Ser Arg Phe Ser Gly Ser Gly Ser Gly Thr Asp
                    85                  90                  95
Phe Thr Leu Thr Ile Ser Ser Leu Gln Pro Glu Asp Phe Ala Thr Tyr
                100                 105                 110
Tyr Cys Gln Gln Ser Lys Glu Val Pro Tyr Thr Phe Gly Gln Gly Thr
            115                 120                 125
Lys Leu Glu Ile Lys Arg Thr Val Ala Ala Pro Ser Val Phe Ile Phe
        130                 135                 140
Pro Pro Ser Asp Glu Gln Leu Lys Ser Gly Thr Ala Ser Val Val Cys
145                 150                 155                 160
Leu Leu Asn Asn Phe Tyr Pro Arg Glu Ala Lys Val Gln Trp Lys Val
                165                 170                 175
Asp Asn Ala Leu Gln Ser Gly Asn Ser Gln Glu Ser Val Thr Glu Gln
                180                 185                 190
Asp Ser Lys Asp Ser Thr Tyr Ser Leu Ser Ser Thr Leu Thr Leu Ser
            195                 200                 205
Lys Ala Asp Tyr Glu Lys His Lys Val Tyr Ala Cys Glu Val Thr His
        210                 215                 220
Gln Gly Leu Ser Ser Pro Val Thr Lys Ser Phe Asn Arg Gly Glu Cys
225                 230                 235                 240

<210> SEQ ID NO 23
<211> LENGTH: 1398
<212> TYPE: DNA
<213> ORGANISM: Homo sapiens

<400> SEQUENCE: 23
atggacatga gggtgcccgc tcagctcctg gggctcctgc tgctgtggct gagaggtgcg    60
cgctgtcagg ttcagctggt gcagtctgga gccgaggtca agaagcctgg aagctctgta   120
aaggtgtcat gcaaggctag cggcggcacg ttctcttcaa catacatctc ttgggttcgg   180
caggctccag gcaagggct ggagtggatg gggtggattt acgccggaac aggaggtacg    240
cgctacaata ggaagttcac gggaagggtg acaatcactg ctgacgaatc cacttctacc   300
gcctatatgg aactgtcctc tttgcggtcc gaggacacag ccgtgtacta ttgtgctcgg   360
gagggagtcg atggttggtt tacttattgg ggccagggta ctctcgtaac cgtctctagt   420
gcctccacca agggcccatc ggtcttcccc ctggcgccct gctccaggag cacctccgag   480
agcacagcgg ccctgggctg cctggtcaag gactacttcc ccgaaccggt gacggtgtcg   540
tggaactcag gcgctctgac cagcggcgtg cacaccttcc cagctgtcct acagtcctca   600
ggactctact ccctcagcag cgtggtgacc gtgccctcca gcaacttcgg cacccagacc   660
tacacctgca acgtagatca caagcccagc aacaccaagg tggacaagac agttgagcgc   720
aaatgttgtg tcgagtgccc accgtgccca gcaccacctg tggcaggacc gtcagtcttc   780
ctcttccccc caaaacccaa ggacaccctc atgatctccc ggacccctga ggtcacgtgc   840
gtggtggtgg acgtgagcca cgaagacccc gaggtccagt tcaactggta cgtggacggc   900
gtggaggtgc ataatgccaa gacaaagcca cgggaggagc agttcaacag cacgttccgt   960
gtggtcagcg tcctcaccgt tgtgcaccag gactggctga acggcaagga gtacaagtgc  1020
aaggtctcca acaaaggcct cccagccccc atcgagaaaa ccatctccaa aaccaaaggg  1080
cagccccgag aaccacaggt gtacaccctg cccccatccc gggaggagat gaccaagaac  1140
caggtcagcc tgacctgcct ggtcaaaggc ttctacccca gcgacatcgc cgtggagtgg  1200
```

```
gagagcaatg ggcagccgga gaacaactac aagaccacac ctcccatgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaa                                                  1398

<210> SEQ ID NO 24
<211> LENGTH: 466
<212> TYPE: PRT
<213> ORGANISM: Homo sapiens

<400> SEQUENCE: 24

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Thr Tyr Ile Ser Trp Val Arg Gln Ala Pro Gly
    50                  55                  60

Gln Gly Leu Glu Trp Met Gly Trp Ile Tyr Ala Gly Thr Gly Gly Thr
65                  70                  75                  80

Arg Tyr Asn Arg Lys Phe Thr Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg Glu Gly Val Asp Gly Trp Phe Thr
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
```

```
                340             345             350
Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 25
<211> LENGTH: 714
<212> TYPE: DNA
<213> ORGANISM: Mus musculus

<400> SEQUENCE: 25
atggagaaag acacactcct gctatgggtc ctgcttctct gggttccagg ttccacaggt    60
gacattgtgc tgacccaatc tccagcttct ttggctgtgt ctctagggca gagggccacc   120
atctcctgca gagccagcga aagtgttgat aattatggca ttagttttat gaactggttc   180
caacagaaac aggacagcc acccaaactc ctcatctatg atgcatccaa ccaaggatac    240
ggggtccctg ccaggtttag tgccagtggg tctgggacag acttcagcct caacatccat   300
cctatggagg aggatgatat tgcaatgtat ttctgtcagc aaagtaagga ggttccgtac   360
acgttcggag gggggaccaa actggaaata aaacgggctg atgctgcacc aactgtatcc   420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat gaacgacata cagctatac ctgtgaggcc    660 actcacaaga catcaacttc acccattgtc aagagcttca caggaatga gtgt          714

<210> SEQ ID NO 26
<211> LENGTH: 240
<212> TYPE: PRT
<213> ORGANISM: Mus musculus

<400> SEQUENCE: 26

Met Asp Met Arg Val Pro Ala Gln Leu Leu Gly Leu Leu Leu Leu Trp
1               5                   10                  15

Leu Arg Gly Ala Arg Cys Asp Ile Val Leu Thr Gln Ser Pro Ala Ser
            20                  25                  30

Leu Ala Val Ser Leu Gly Gln Arg Ala Thr Ile Ser Cys Arg Ala Ser
        35                  40                  45

Glu Ser Val Asp Asn Tyr Gly Ile Ser Phe Met Asn Trp Phe Gln Gln
    50                  55                  60

Lys Pro Gly Gln Pro Pro Lys Leu Leu Ile Tyr Asp Ala Ser Asn Gln
65                  70                  75                  80
```

```
Gly Tyr Gly Val Pro Ala Arg Phe Ser Ala Ser Gly Ser Gly Thr Asp
                85                  90                  95
Phe Ser Leu Asn Ile His Pro Met Glu Glu Asp Ile Ala Met Tyr
            100                 105                 110
Phe Cys Gln Gln Ser Lys Glu Val Pro Tyr Thr Phe Gly Gly Gly Thr
            115                 120                 125
Lys Leu Glu Ile Lys Arg Ala Asp Ala Ala Pro Thr Val Ser Ile Phe
130                 135                 140
Pro Pro Ser Ser Glu Gln Leu Thr Ser Gly Gly Ala Ser Val Val Cys
145                 150                 155                 160
Phe Leu Asn Asn Phe Tyr Pro Lys Asp Ile Asn Val Lys Trp Lys Ile
                165                 170                 175
Asp Gly Ser Glu Arg Gln Asn Gly Val Leu Asn Ser Trp Thr Asp Gln
            180                 185                 190
Asp Ser Lys Asp Ser Thr Tyr Ser Met Ser Ser Thr Leu Thr Leu Thr
            195                 200                 205
Lys Asp Glu Tyr Glu Arg His Asn Ser Tyr Thr Cys Glu Ala Thr His
210                 215                 220
Lys Thr Ser Thr Ser Pro Ile Val Lys Ser Phe Asn Arg Asn Glu Cys
225                 230                 235                 240

<210> SEQ ID NO 27
<211> LENGTH: 1383
<212> TYPE: DNA
<213> ORGANISM: Mus musculus

<400> SEQUENCE: 27
atggaatgga actgggtcgt tctcttcctc ctgtcattaa ctgcaggtgt ctatgcccag      60
ggtcagatgc agcagtctgg agctgagctg gtgaagcctg ggcttcagt gaagctgtcc     120
tgcaagactt ctggcttcac cttcaacagt cactatataa gttggttgaa gcaaaagcct     180
ggacagactc ttgagtggat tgcatggatt tatgctggaa ctggtggtac taggtataat     240
cagaagttca caggcaaggc ccaactgact gtagacacat cctccagcac agcctacatg     300
caattcagca gcctgacaac tgaggactct gccatctatt actgtgcaag agaggggtc     360
gacgggtggt ttacttactg gggccaaggg actctggtca ctgtctctgc agccaaaacg     420
acaccccat ctgtctatcc actggcccct ggatctgctg cccaaactaa ctccatggtg     480
accctgggat gcctggtcaa gggctatttc cctgagccag tgacagtgac ctggaactct     540
ggatccctgt ccagcggtgt gcacaccttc ccagctgtcc tgcagtctga cctctacact     600
ctgagcagct cagtgactgt cccctccagc acctggccca gcgagaccgt cacctgcaac     660
gttgcccacc cggccagcag caccaaggtg gacaagaaaa ttgtgcccag ggattgtggt     720
tgtaagcctt gcatatgtac agtcccagaa gtatcatctg tcttcatctt cccccccaag     780
cccaaggatg tgctcaccat tactctgact cctaaggtca cgtgtgttgt ggtagacatc     840
agcaaggatg atcccgaggt ccagttcagc tggtttgtag atgatgtgga ggtgcacaca     900
gctcagacgc aaccccggga ggagcagttc aacagcactt tccgctcagt cagtgaactt     960
cccatcatgc accaggactg gctcaatggc aaggagttca atgcagggt caacagtgca    1020
gctttccctg cccccatcga gaaaaccatc tccaaaacca aggcagacc gaaggctcca    1080
caggtgtaca ccattccacc tcccaaggag cagatggcca aggataaagt cagtctgacc    1140
tgcatgataa cagacttctt ccctgaagac attactgtgg agtggcagtg gaatgggcag    1200
ccagcggaga actacaagaa cactcagccc atcatggaca cagatggctc ttacttcgtc    1260
```

```
tacagcaagc tcaatgtgca gaagagcaac tgggaggcag gaaatacttt cacctgctct   1320
gtgttacatg agggcctgca caaccaccat actgagaaga gcctctccca ctctcctggt   1380
aaa                                                                 1383
```

<210> SEQ ID NO 28
<211> LENGTH: 442
<212> TYPE: PRT
<213> ORGANISM: Mus musculus

<400> SEQUENCE: 28

```
Gln Gly Gln Met Gln Gln Ser Gly Ala Glu Leu Val Lys Pro Gly Ala
1               5                  10                  15

Ser Val Lys Leu Ser Cys Lys Thr Ser Gly Phe Thr Phe Asn Ser His
            20                  25                  30

Tyr Ile Ser Trp Leu Lys Gln Lys Pro Gly Gln Thr Leu Glu Trp Ile
        35                  40                  45

Ala Trp Ile Tyr Ala Gly Thr Gly Gly Thr Arg Tyr Asn Gln Lys Phe
    50                  55                  60

Thr Gly Lys Ala Gln Leu Thr Val Asp Thr Ser Ser Ser Thr Ala Tyr
65                  70                  75                  80

Met Gln Phe Ser Ser Leu Thr Thr Glu Asp Ser Ala Ile Tyr Tyr Cys
                85                  90                  95

Ala Arg Glu Gly Val Asp Gly Trp Phe Thr Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350
```

Met Ala Lys Asp Lys Val Ser Leu Thr Cys Met Ile Thr Asp Phe Phe
                355                 360                 365

Pro Glu Asp Ile Thr Val Glu Trp Gln Trp Asn Gly Gln Pro Ala Glu
        370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440

<210> SEQ ID NO 29
<211> LENGTH: 720
<212> TYPE: DNA
<213> ORGANISM: Homo sapiens

<400> SEQUENCE: 29
atggacatga gggtgcccgc tcagctcctg gggctcctgc tgctgtggct gagaggtgcg      60
cgctgtgaca ttgtgctgac ccaatctcca gcttctttgg ctgtgtctct agggcagagg     120
gccaccatct cctgcagagc cagcgaaagt gttgataatt atggcattag ttttatgaac     180
tggttccaac agaaaccagg acagccaccc aaactcctca tctatgatgc atccaaccaa     240
ggatacgggg tccctgccag gtttagtgcc agtgggtctg gacagacttc agcctcaac     300 atccatccta tggaggagga tgatattgca atgtatttct gtcagcaaag taaggaggtt     360
ccgtacacgt tcggagggggg gaccaaactg gaaataaaac gtacggtggc tgcaccatct     420
gtcttcatct tcccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga aacacaaagt ctacgcctgc     660
gaagtcaccc atcagggcct gagctcgccc gtcacaaaga gcttcaacag gggagagtgt     720

<210> SEQ ID NO 30
<211> LENGTH: 240
<212> TYPE: PRT
<213> ORGANISM: Homo sapiens

<400> SEQUENCE: 30

Met Asp Met Arg Val Pro Ala Gln Leu Leu Gly Leu Leu Leu Leu Trp
1               5                   10                  15

Leu Arg Gly Ala Arg Cys Asp Ile Val Leu Thr Gln Ser Pro Ala Ser
            20                  25                  30

Leu Ala Val Ser Leu Gly Gln Arg Ala Thr Ile Ser Cys Arg Ala Ser
        35                  40                  45

Glu Ser Val Asp Asn Tyr Gly Ile Ser Phe Met Asn Trp Phe Gln Gln
    50                  55                  60

Lys Pro Gly Gln Pro Pro Lys Leu Leu Ile Tyr Asp Ala Ser Asn Gln
65                  70                  75                  80

Gly Tyr Gly Val Pro Ala Arg Phe Ser Ala Ser Gly Ser Gly Thr Asp
                85                  90                  95

Phe Ser Leu Asn Ile His Pro Met Glu Glu Asp Asp Ile Ala Met Tyr
            100                 105                 110

```
Phe Cys Gln Gln Ser Lys Glu Val Pro Tyr Thr Phe Gly Gly Gly Thr
        115                 120                 125
Lys Leu Glu Ile Lys Arg Thr Val Ala Ala Pro Ser Val Phe Ile Phe
    130                 135                 140
Pro Pro Ser Asp Glu Gln Leu Lys Ser Gly Thr Ala Ser Val Val Cys
145                 150                 155                 160
Leu Leu Asn Asn Phe Tyr Pro Arg Glu Ala Lys Val Gln Trp Lys Val
                165                 170                 175
Asp Asn Ala Leu Gln Ser Gly Asn Ser Gln Glu Ser Val Thr Glu Gln
            180                 185                 190
Asp Ser Lys Asp Ser Thr Tyr Ser Leu Ser Ser Thr Leu Thr Leu Ser
        195                 200                 205
Lys Ala Asp Tyr Glu Lys His Lys Val Tyr Ala Cys Glu Val Thr His
    210                 215                 220
Gln Gly Leu Ser Ser Pro Val Thr Lys Ser Phe Asn Arg Gly Glu Cys
225                 230                 235                 240
```

<210> SEQ ID NO 31
<211> LENGTH: 1389
<212> TYPE: DNA
<213> ORGANISM: Homo sapiens

<400> SEQUENCE: 31

| | | | | | |
|---|---|---|---|---|---|
| atggaatgga | actgggtcgt | tctcttcctc | ctgtcattaa | ctgcaggtgt | ctatgcccag | 60 |
| ggtcagatgc | agcagtctgg | agctgagctg | gtgaagcctg | gggcttcagt | gaagctgtcc | 120 |
| tgcaagactt | ctggcttcac | cttcaacagt | cactatataa | gttggttgaa | gcaaaagcct | 180 |
| ggacagactc | ttgagtggat | tgcatggatt | tatgctggaa | ctggtggtac | taggtataat | 240 |
| cagaagttca | caggcaaggc | caactgact | gtagacacat | cctccagcac | agcctacatg | 300 |
| caattcagca | gcctgacaac | tgaggactct | gccatctatt | actgtgcaag | agaggggtc | 360 |
| gacgggtggt | ttacttactg | gggccaaggg | actctggtca | ctgtctctgc | agcctccacc | 420 |
| aagggcccat | cggtcttccc | cctggcgccc | tgctccagga | gcacctccga | gagcacagcg | 480 |
| gccctgggct | gcctggtcaa | ggactacttc | cccgaaccgg | tgacggtgtc | gtggaactca | 540 |
| ggcgctctga | ccagcggcgt | gcacaccttc | ccagctgtcc | tacagtcctc | aggactctac | 600 |
| tccctcagca | gcgtggtgac | cgtgccctcc | agcaacttcg | gcacccagac | ctacacctgc | 660 |
| aacgtagatc | acaagcccag | caacaccaag | gtggacaaga | cagttgagcg | caaatgttgt | 720 |
| gtcgagtgcc | caccgtgccc | agcaccacct | gtggcaggac | cgtcagtctt | cctcttcccc | 780 |
| ccaaaaccca | aggacaccct | catgatctcc | cggacccctg | aggtcacgtg | cgtggtggtg | 840 |
| gacgtgagcc | acgaagaccc | cgaggtccag | ttcaactggt | acgtggacgg | cgtggaggtg | 900 |
| cataatgcca | agacaaagcc | acgggaggag | cagttcaaca | gcacgttccg | tgtggtcagc | 960 |
| gtcctcaccg | ttgtgcacca | ggactggctg | aacggcaagg | agtacaagtg | caaggtctcc | 1020 |
| aacaaaggcc | tcccagcccc | catcgagaaa | accatctcca | aaccaaagg | gcagccccga | 1080 |
| gaaccacagg | tgtacaccct | gcccccatcc | cgggaggaga | tgaccaagaa | ccaggtcagc | 1140 |
| ctgacctgcc | tggtcaaagg | cttctacccc | agcgacatcg | ccgtggagtg | ggagagcaat | 1200 |
| gggcagccgg | agaacaacta | caagaccaca | cctcccatgc | tggactccga | cggctccttc | 1260 |
| ttcctctaca | gcaagctcac | cgtggacaag | agcaggtggc | agcaggggaa | cgtcttctca | 1320 |
| tgctccgtga | tgcatgaggc | tctgcacaac | cactacacgc | agaagagcct | ctccctgtct | 1380 |
| ccgggtaaa | | | | | | 1389 |

<210> SEQ ID NO 32
<211> LENGTH: 463
<212> TYPE: PRT
<213> ORGANISM: Homo sapiens

<400> SEQUENCE: 32

```
Met Glu Trp Asn Trp Val Val Leu Phe Leu Ser Leu Thr Ala Gly
1               5                   10                  15

Val Tyr Ala Gln Gly Gln Met Gln Gln Ser Gly Ala Glu Leu Val Lys
            20                  25                  30

Pro Gly Ala Ser Val Lys Leu Ser Cys Lys Thr Ser Gly Phe Thr Phe
            35                  40                  45

Asn Ser His Tyr Ile Ser Trp Leu Lys Gln Lys Pro Gly Gln Thr Leu
            50                  55                  60

Glu Trp Ile Ala Trp Ile Tyr Ala Gly Thr Gly Thr Arg Tyr Asn
65                  70                  75                  80

Gln Lys Phe Thr Gly Lys Ala Gln Leu Thr Val Asp Thr Ser Ser Ser
                85                  90                  95

Thr Ala Tyr Met Gln Phe Ser Ser Leu Thr Thr Glu Asp Ser Ala Ile
            100                 105                 110

Tyr Tyr Cys Ala Arg Glu Gly Val Asp Gly Trp Phe Thr Tyr Trp Gly
            115                 120                 125

Gln Gly Thr Leu Val Thr Val Ser Ala Ala Ser Thr Lys Gly Pro Ser
        130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Asn Phe Gly Thr Gln Thr Tyr Thr Cys Asn Val Asp His
        210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380
```

```
Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
            405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
        450                 455                 460
```

<210> SEQ ID NO 33
<211> LENGTH: 1407
<212> TYPE: DNA
<213> ORGANISM: Homo sapiens

<400> SEQUENCE: 33

```
atggacatga gggtgcccgc tcagctcctg gggctcctgc tgctgtggtt gagaggtgcc      60
agatgtcagg tgcaattggt tcagagtggg gcggaggtca agaagcctgg agccagtgtc     120
aaagtcagct gcaaggcctc cggctacaca tttactactt acggaatgtc ttgggtgcgc     180
caagccccag gcaagggct tgaatggatg ggttggatca acacttatag cggagttcca     240
acctacgccg atgactttaa aggccggttt gtcttttccc tggacacaag cgtttcaacc     300
gcctatctgc agattaattc cctgaaggcg gaggacacag ccgtttacta ttgtgcaaga     360
ggaagagagt actactacgg cagtggcatc gcatttgggg ccagggcac tctggtcacc     420
gtctctagtg cctccaccaa gggcccatcg gtcttccccc tggcgccctg ctccaggagc     480
acctccgaga gcacagcggc cctgggctgc ctggtcaagg actacttccc cgaaccggtg     540
acggtgtcgt ggaactcagg cgctctgacc agcggcgtgc acaccttccc agctgtccta     600
cagtcctcag gactctactc cctcagcagc gtggtgaccg tgccctccag caacttcggc     660
acccagacct acacctgcaa cgtagatcac aagcccagca acaccaaggt ggacaagaca     720
gttgagcgca aatgttgtgt cgagtgccca ccgtgcccag caccacctgt ggcaggaccg     780
tcagtcttcc tcttcccccc aaaacccaag gacaccctca tgatctcccg gacccctgag     840
gtcacgtgcg tggtggtgga cgtgagccac gaagaccccg aggtccagtt caactggtac     900
gtggacggcg tggaggtgca taatgccaag acaaagccac gggaggagca gttcaacagc     960
acgttccgtg tggtcagcgt cctcaccgtt gtgcaccagg actggctgaa cggcaaggag    1020
tacaagtgca aggtctccaa caaaggcctc ccagccccca tcgagaaaac catctccaaa    1080
accaaagggc agccccgaga accacaggtg tacaccctgc ccccatcccg ggaggagatg    1140
accaagaacc aggtcagcct gacctgcctg gtcaaaggct tctaccccag cgacatcgcc    1200
gtggagtggg agagcaatgg gcagccggag aacaactaca agaccacacc tcccatgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaa                                        1407
```

<210> SEQ ID NO 34
<211> LENGTH: 469
<212> TYPE: PRT
<213> ORGANISM: Homo sapiens

<400> SEQUENCE: 34

Met Asp Met Arg Val Pro Ala Gln Leu Leu Gly Leu Leu Leu Leu Trp

-continued

```
1               5                   10                  15
Leu Arg Gly Ala Arg Cys Gln Val Gln Leu Val Gln Ser Gly Ala Glu
                20                  25                  30

Val Lys Lys Pro Gly Ala Ser Val Lys Val Ser Cys Lys Ala Ser Gly
                35                  40                  45

Tyr Thr Phe Thr Thr Tyr Gly Met Ser Trp Val Lys Gln Ala Pro Gly
                50                  55                  60

Gln Gly Leu Glu Trp Met Gly Trp Ile Asn Thr Tyr Ser Gly Val Pro
65                  70                  75                  80

Thr Tyr Ala Asp Asp Phe Lys Gly Arg Phe Val Phe Ser Leu Asp Thr
                85                  90                  95

Ser Val Ser Thr Ala Tyr Leu Gln Ile Asn Ser Leu Lys Ala Glu Asp
                100                 105                 110

Thr Ala Val Tyr Phe Cys Val Arg Gly Arg Glu Tyr Tyr Tyr Gly Ser
                115                 120                 125

Gly Ile Ala Phe Trp Gly Gln Gly Thr Leu Val Thr Val Ser Ser Ala
                130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
                195                 200                 205

Ser Ser Val Val Thr Val Pro Ser Ser Asn Phe Gly Thr Gln Thr Tyr
                210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Gln Phe Asn Trp Tyr Val Asp Gly Val
                290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
                340                 345                 350

Pro Ile Glu Lys Thr Ile Ser Lys Thr Lys Gly Gln Pro Arg Glu Pro
                355                 360                 365

Gln Val Tyr Thr Leu Pro Pro Ser Arg Glu Glu Met Thr Lys Asn Gln
                370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
                420                 425                 430
```

```
Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 35
<211> LENGTH: 1398
<212> TYPE: DNA
<213> ORGANISM: Homo sapiens

<400> SEQUENCE: 35
atggacatga gggtgcccgc tcagctcctg gggctcctgc tgctgtggct gagaggtgcg      60
cgctgtcagg tgcagcttgt gcaatccggg gctgaggtta aaaaaccagg gtccagcgtg     120
aaagtttcct gcaaggcctc tggaggaacg tttagctcca cgtacattag ctgggtgaga     180
caagcccctg gacagggctt ggaatggatc gcctggatct acgcaggtac cggggggtacc     240 agatacaatc agaaatttac aggtaaggcc aacttactg ctgacgagag tacaagcact     300
gcctatatgg aattgtctag cctgcgctcc gaggatacag ctgtctacta ctgtgcccga     360
gagggcgtgg acgggtggtt tacctactgg ggacagggaa cccttgtgac cgtctctagt     420
gcctccacca agggcccatc ggtcttcccc ctggcgccct gctccaggag cacctccgag     480
agcacagcgg ccctgggctg cctggtcaag gactacttcc ccgaaccggt gacggtgtcg     540
tggaactcag cgctctgac cagcggcgtg cacaccttcc cagctgtcct acagtcctca     600
ggactctact ccctcagcag cgtggtgacc gtgccctcca gcaacttcgg cacccagacc     660
tacacctgca acgtagatca caagcccagc aacaccaagg tggacaagac agttgagcgc     720
aaatgttgtg tcgagtgccc accgtgccca gcaccacctg tggcaggacc gtcagtcttc     780
ctcttccccc caaaacccaa ggacaccctc atgatctccc ggacccctga ggtcacgtgc     840
gtggtggtgg acgtgagcca cgaagacccc gaggtccagt tcaactggta cgtggacggc     900
gtggaggtgc ataatgccaa gacaaagcca cgggaggagc agttcaacag cacgttccgt     960
gtggtcagcg tcctcaccgt tgtgcaccag gactggctga acggcaagga gtacaagtgc    1020
aaggtctcca acaaaggcct cccagccccc atcgagaaaa ccatctccaa accaaaaggg    1080
cagccccgag aaccacaggt gtacaccctg cccccatccc gggaggagat gaccaagaac    1140
caggtcagcc tgacctgcct ggtcaaaggc ttctacccca gcgacatcgc cgtggagtgg    1200
gagagcaatg ggcagccgga gaacaactac aagaccacac tcccatgct ggactccgac    1260 ggctccttct cctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaa                                                 1398

<210> SEQ ID NO 36
<211> LENGTH: 466
<212> TYPE: PRT
<213> ORGANISM: Homo sapiens

<400> SEQUENCE: 36

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ser Ser Val Lys Val Ser Cys Lys Ala Ser Gly
```

-continued

```
             35                  40                  45
Gly Thr Phe Ser Ser Thr Tyr Ile Ser Trp Val Arg Gln Ala Pro Gly
 50                  55                  60
Gln Gly Leu Glu Trp Ile Ala Trp Ile Tyr Ala Gly Thr Gly Gly Thr
 65                  70                  75                  80
Arg Tyr Asn Arg Lys Phe Thr Gly Lys Ala Gln Leu Thr Ala Asp Glu
                     85                  90                  95
Ser Thr Ser Thr Ala Tyr Met Glu Leu Ser Ser Leu Arg Ser Glu Asp
                    100                 105                 110
Thr Ala Val Tyr Tyr Cys Ala Arg Glu Gly Val Asp Gly Trp Phe Thr
                    115                 120                 125
Tyr Trp Gly Gln Gly Thr Leu Val Thr Val Ser Ser Ala Ser Thr Lys
130                 135                 140
Gly Pro Ser Val Phe Pro Leu Ala Pro Cys Ser Arg Ser Thr Ser Glu
145                 150                 155                 160
Ser Thr Ala Ala Leu Gly Cys Leu Val Lys Asp Tyr Phe Pro Glu Pro
                    165                 170                 175
Val Thr Val Ser Trp Asn Ser Gly Ala Leu Thr Ser Gly Val His Thr
                    180                 185                 190
Phe Pro Ala Val Leu Gln Ser Ser Gly Leu Tyr Ser Leu Ser Ser Val
                    195                 200                 205
Val Thr Val Pro Ser Ser Asn Phe Gly Thr Gln Thr Tyr Thr Cys Asn
                    210                 215                 220
Val Asp His Lys Pro Ser Asn Thr Lys Val Asp Lys Thr Val Glu Arg
225                 230                 235                 240
Lys Cys Cys Val Glu Cys Pro Pro Cys Pro Ala Pro Pro Val Ala Gly
                    245                 250                 255
Pro Ser Val Phe Leu Phe Pro Pro Lys Pro Lys Asp Thr Leu Met Ile
                    260                 265                 270
Ser Arg Thr Pro Glu Val Thr Cys Val Val Val Asp Val Ser His Glu
                    275                 280                 285
Asp Pro Glu Val Gln Phe Asn Trp Tyr Val Asp Gly Val Glu Val His
                    290                 295                 300
Asn Ala Lys Thr Lys Pro Arg Glu Glu Gln Phe Asn Ser Thr Phe Arg
305                 310                 315                 320
Val Val Ser Val Leu Thr Val Val His Gln Asp Trp Leu Asn Gly Lys
                    325                 330                 335
Glu Tyr Lys Cys Lys Val Ser Asn Lys Gly Leu Pro Ala Pro Ile Glu
                    340                 345                 350
Lys Thr Ile Ser Lys Thr Lys Gly Gln Pro Arg Glu Pro Gln Val Tyr
                    355                 360                 365
Thr Leu Pro Pro Ser Arg Glu Glu Met Thr Lys Asn Gln Val Ser Leu
                    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Met
                    405                 410                 415
Leu Asp Ser Asp Gly Ser Phe Phe Leu Tyr Ser Lys Leu Thr Val Asp
                    420                 425                 430
Lys Ser Arg Trp Gln Gln Gly Asn Val Phe Ser Cys Ser Val Met His
                    435                 440                 445
Glu Ala Leu His Asn His Tyr Thr Gln Lys Ser Leu Ser Leu Ser Pro
450                 455                 460
```

Gly Lys
465

<210> SEQ ID NO 37
<211> LENGTH: 714
<212> TYPE: DNA
<213> ORGANISM: Homo sapiens

<400> SEQUENCE: 37

```
atgaagttgc ctgttaggct gttggtgctg atgttctgga ttcctgcttc cagcagtgat      60
gttgtgatga cccaaactcc actctccctg cctgtcagtc ttggagatca agcctccatc     120
tcttgcagat ctagtcagag ccttgaacac agtaatggaa acacctattt acattggtac     180
ctgcagaagc caggccagtc tccaaagctc ctgatctaca agtttccaa ccgattttct      240
ggggtcccag acaggttcag tggcagtgga tcagggacag atttcacact caagatcagc     300
agagtggagg ctgaggatct gggagtttat ttctgctctc aaagtacaca tgttccgctc     360
acgttcggtg ctgggaccaa ggtggagctg aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc      660
acccatcagg gcctgagctc gcccgtcaca aagagcttca caggggaga gtgt            714
```

<210> SEQ ID NO 38
<211> LENGTH: 238
<212> TYPE: PRT
<213> ORGANISM: Homo sapiens

<400> SEQUENCE: 38

```
Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Glu His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Leu Thr Phe Gly Ala Gly Thr Lys Val
        115                 120                 125

Glu Leu Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
```

```
                195                 200                 205
Asp Tyr Glu Lys His Lys Val Tyr Ala Cys Glu Val Thr His Gln Gly
            210                 215                 220

Leu Ser Ser Pro Val Thr Lys Ser Phe Asn Arg Gly Glu Cys
225                 230                 235

<210> SEQ ID NO 39
<211> LENGTH: 1398
<212> TYPE: DNA
<213> ORGANISM: Homo sapiens

<400> SEQUENCE: 39
atgggttggc tgtggaactt gctattcctg atggcagctg cccaaagtgc ccaagcacag      60
atccacttgg tacagtctgg acctgagctg aagaagcctg agagactgt caagatctcc     120 tgcaaggcgt ctgggttttc cttcacaacc tatggaatga gctgggtgaa acaggctcca     180
ggaaagggtt taaagtggat gggctggata aataccctact ctggagtgcc tacatatgct     240
gatgacttca agggacggtt tgccttctct ttggaaacct ctgccagcac tgcctatttg     300
cagatcaaca acctcaaaaa tgaggacacg gctacatatt tctgtgtaag ggggagggaa     360
tattactacg gtagtggcat tgctttctgg ggccaaggga ctctggtcac tgtctctgca     420
gcctccacca agggcccatc ggtcttcccc ctggcgccct gctccaggag cacctccgag     480
agcacagcgg ccctgggctg cctggtcaag gactacttcc ccgaaccggt gacggtgtcg     540
tggaactcag cgctctgac cagcggcgtg cacaccttcc cagctgtcct acagtcctca     600
ggactctact ccctcagcag cgtggtgacc gtgccctcca gcaacttcgg cacccagacc     660
tacacctgca acgtagatca caagcccagc aacaccaagg tggacaagac agttgagcgc     720
aaatgttgtg tcgagtgccc accgtgccca gcaccacctg tggcaggacc gtcagtcttc     780
ctcttccccc caaaacccaa ggacaccctc atgatctccc ggaccctga ggtcacgtgc     840 gtggtggtgg acgtgagcca cgaagacccc gaggtccagt tcaactggta cgtggacggc     900
gtggaggtgc ataatgccaa gacaaagcca cgggaggagc agttcaacag cacgttccgt     960
gtggtcagcg tcctcaccgt tgtgcaccag gactggctga acggcaagga gtacaagtgc    1020
aaggtctcca acaaaggcct cccagccccc atcgagaaaa ccatctccaa aaccaaaggg    1080
cagccccgag aaccacaggt gtacaccctg cccccatccc gggaggagat gaccaagaac    1140
caggtcagcc tgacctgcct ggtcaaaggc ttctacccca gcgacatcgc cgtggagtgg    1200
gagagcaatg ggcagccgga gaacaactac aagaccacac tcccatgct ggactccgac    1260 ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaa                                                 1398

<210> SEQ ID NO 40
<211> LENGTH: 466
<212> TYPE: PRT
<213> ORGANISM: Homo sapiens

<400> SEQUENCE: 40

Met Gly Trp Leu Trp Asn Leu Leu Phe Leu Met Ala Ala Ala Gln Ser
1               5                   10                  15

Ala Gln Ala Gln Ile His Leu Val Gln Ser Gly Pro Glu Leu Lys Lys
            20                  25                  30

Pro Gly Glu Thr Val Lys Ile Ser Cys Lys Ala Ser Gly Phe Ser Phe
        35                  40                  45
```

```
Thr Thr Tyr Gly Met Ser Trp Val Lys Gln Ala Pro Gly Lys Gly Leu
         50              55                  60
Lys Trp Met Gly Trp Ile Asn Thr Tyr Ser Gly Val Pro Thr Tyr Ala
 65              70                  75                  80
Asp Asp Phe Lys Gly Arg Phe Ala Phe Ser Leu Glu Thr Ser Ala Ser
             85                  90                  95
Thr Ala Tyr Leu Gln Ile Asn Asn Leu Lys Asn Glu Asp Thr Ala Thr
             100                 105                 110
Tyr Phe Cys Val Arg Gly Arg Glu Tyr Tyr Gly Ser Gly Ile Ala
             115                 120                 125
Phe Trp Gly Gln Gly Thr Leu Val Thr Val Ser Ala Ala Ser Thr Lys
 130                 135                 140
Gly Pro Ser Val Phe Pro Leu Ala Pro Cys Ser Arg Ser Thr Ser Glu
 145                 150                 155                 160
Ser Thr Ala Ala Leu Gly Cys Leu Val Lys Asp Tyr Phe Pro Glu Pro
                 165                 170                 175
Val Thr Val Ser Trp Asn Ser Gly Ala Leu Thr Ser Gly Val His Thr
                 180                 185                 190
Phe Pro Ala Val Leu Gln Ser Ser Gly Leu Tyr Ser Leu Ser Ser Val
                 195                 200                 205
Val Thr Val Pro Ser Ser Asn Phe Gly Thr Gln Thr Tyr Thr Cys Asn
 210                 215                 220
Val Asp His Lys Pro Ser Asn Thr Lys Val Asp Lys Thr Val Glu Arg
 225                 230                 235                 240
Lys Cys Cys Val Glu Cys Pro Pro Cys Pro Ala Pro Pro Val Ala Gly
                 245                 250                 255
Pro Ser Val Phe Leu Phe Pro Pro Lys Pro Lys Asp Thr Leu Met Ile
                 260                 265                 270
Ser Arg Thr Pro Glu Val Thr Cys Val Val Val Asp Val Ser His Glu
                 275                 280                 285
Asp Pro Glu Val Gln Phe Asn Trp Tyr Val Asp Gly Val Glu Val His
                 290                 295                 300
Asn Ala Lys Thr Lys Pro Arg Glu Glu Gln Phe Asn Ser Thr Phe Arg
 305                 310                 315                 320
Val Val Ser Val Leu Thr Val Val His Gln Asp Trp Leu Asn Gly Lys
                 325                 330                 335
Glu Tyr Lys Cys Lys Val Ser Asn Lys Gly Leu Pro Ala Pro Ile Glu
                 340                 345                 350
Lys Thr Ile Ser Lys Thr Lys Gly Gln Pro Arg Glu Pro Gln Val Tyr
                 355                 360                 365
Thr Leu Pro Pro Ser Arg Glu Glu Met Thr Lys Asn Gln Val Ser Leu
 370                 375                 380
Thr Cys Leu Val Lys Gly Phe Tyr Pro Ser Asp Ile Ala Val Glu Trp
 385                 390                 395                 400
Glu Ser Asn Gly Gln Pro Glu Asn Asn Tyr Lys Thr Thr Pro Pro Met
                 405                 410                 415
Leu Asp Ser Asp Gly Ser Phe Phe Leu Tyr Ser Lys Leu Thr Val Asp
                 420                 425                 430
Lys Ser Arg Trp Gln Gln Gly Asn Val Phe Ser Cys Ser Val Met His
                 435                 440                 445
Glu Ala Leu His Asn His Tyr Thr Gln Lys Ser Leu Ser Leu Ser Pro
 450                 455                 460
Gly Lys
```

<210> SEQ ID NO 41
<211> LENGTH: 714
<212> TYPE: DNA
<213> ORGANISM: Homo sapiens

<400> SEQUENCE: 41

```
atggagaaag acacactcct gctatgggtc ctgcttctct gggttccagg gtccacaggt    60
gacattgtgc tgacccaatc tccaccttct ttggctgtgt ctctagggca gagggccacc   120
atctcctgca gagccagcga aagtgttgat aattatggct ctagttttat gaactggttc   180
caacagaaac caggacagcc acccaaactc ctcatctttg ctgcatccaa ccaaggatcc   240
ggggtccctg ccaggtttag tggcagtggg tctgggacag acttcagcct caacatccat   300
cctatggagg aggatgatgc tgcaatgtat ttctgtcagc aaagtaagga ggttccgtac   360
acgttcggag gggggaccaa actggaaata aaacgaactg tggctgcacc atctgtcttc   420
atcttcccgc catctgatga gcagttgaaa tctggaactg cctctgttgt gtgcctgctg   480
aataacttct atcccagaga ggccaaagta cagtggaagg tggataacgc cctccaatcg   540
ggtaactccc aggagagtgt cacagagcag gacagcaagg acagcaccta cagcctcagc   600
agcaccctga cgctgagcaa agcagactac gagaaacaca agtctacgc ctgcgaagtc   660
acccatcagg gcctgagctc gcccgtcaca aagagcttca caggggagag tgt           714
```

<210> SEQ ID NO 42
<211> LENGTH: 238
<212> TYPE: PRT
<213> ORGANISM: Homo sapiens

<400> SEQUENCE: 42

Met Glu Lys Asp Thr Leu Leu Trp Val Leu Leu Trp Val Pro
1               5                   10                  15

Gly Ser Thr Gly Asp Ile Val Leu Thr Gln Ser Pro Pro Ser Leu Ala
            20                  25                  30

Val Ser Leu Gly Gln Arg Ala Thr Ile Ser Cys Arg Ala Ser Glu Ser
        35                  40                  45

Val Asp Asn Tyr Gly Ser Ser Phe Met Asn Trp Phe Gln Gln Lys Pro
    50                  55                  60

Gly Gln Pro Pro Lys Leu Leu Ile Phe Ala Ala Ser Asn Gln Gly Ser
65                  70                  75                  80

Gly Val Pro Ala Arg Phe Ser Gly Ser Gly Ser Gly Thr Asp Phe Ser
                85                  90                  95

Leu Asn Ile His Pro Met Glu Glu Asp Asp Ala Ala Met Tyr Phe Cys
            100                 105                 110

Gln Gln Ser Lys Glu Val Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
     210                 215                 220

Leu Ser Ser Pro Val Thr Lys Ser Phe Asn Arg Gly Glu Cys
225                 230                 235

<210> SEQ ID NO 43
<211> LENGTH: 1389
<212> TYPE: DNA
<213> ORGANISM: Homo sapiens

<400> SEQUENCE: 43

| | | | | | |
|---|---|---|---|---|---|
| atggaatgga | actgggtcgt | tctcttcctc | ctgtcattaa | ctgcaggtgt | ctatgcccag | 60 |
| ggtcagatgc | agcagtctgg | agctgagctg | gtgaagcctg | ggcttcagt | gcaactgtcc | 120 |
| tgcaagactt | ctggcttcac | cttcagcagt | acctatataa | gttggttgaa | gcagaagcct | 180 |
| ggacagagtc | ttgagtggat | tgcatggatt | tatgctggca | ctggtggtac | cagatataat | 240 |
| cggaagttca | caggcaaggc | ccaactgact | gtagacacat | cctccagcac | agcctacatg | 300 |
| caattcagca | gcctgacaac | tgaggactct | gccatctatt | actgtgcaag | agaggggtc | 360 |
| gacggggtgg | ttacttactg | gggccagggg | actctggtca | ctgtctctgc | agcctccacc | 420 |
| aagggcccat | cggtcttccc | cctggcgccc | tgctccagga | gcacctccga | gagcacagcg | 480 |
| gccctgggct | gcctggtcaa | ggactacttc | cccgaaccgg | tgacggtgtc | gtggaactca | 540 |
| ggcgctctga | ccagcggcgt | gcacaccttc | ccagctgtcc | tacagtcctc | aggactctac | 600 |
| tccctcagca | gcgtggtgac | cgtgccctcc | agcaacttcg | gcacccagac | ctacacctgc | 660 |
| aacgtagatc | acaagcccag | caacaccaag | gtggacaaga | cagttgagcg | caaatgttgt | 720 |
| gtcgagtgcc | caccgtgccc | agcaccacct | gtggcaggac | cgtcagtctt | cctcttcccc | 780 |
| ccaaaaccca | aggacaccct | catgatctcc | cggacccctg | aggtcacgtg | cgtggtggtg | 840 |
| gacgtgagcc | acgaagaccc | cgaggtccag | ttcaactggt | acgtggacgg | cgtggaggtg | 900 |
| cataatgcca | agacaaagcc | acgggaggag | cagttcaaca | gcacgttccg | tgtggtcagc | 960 |
| gtcctcaccg | ttgtgcacca | ggactggctg | aacggcaagg | agtacaagtg | caaggtctcc | 1020 |
| aacaaaggcc | tcccagcccc | catcgagaaa | accatctcca | aaaccaaagg | gcagccccga | 1080 |
| gaaccacagg | tgtacaccct | gcccccatcc | cgggaggaga | tgaccaagaa | ccaggtcagc | 1140 |
| ctgacctgcc | tggtcaaagg | cttctacccc | agcgacatcg | ccgtggagtg | ggagagcaat | 1200 |
| gggcagccgg | agaacaacta | caagaccaca | cctcccatgc | tggactccga | cggctccttc | 1260 |
| ttcctctaca | gcaagctcac | cgtggacaag | agcaggtggc | agcaggggaa | cgtcttctca | 1320 |
| tgctccgtga | tgcatgaggc | tctgcacaac | cactacacgc | agaagagcct | ctccctgtct | 1380 |
| ccgggtaaa | | | | | | 1389 |

<210> SEQ ID NO 44
<211> LENGTH: 463
<212> TYPE: PRT
<213> ORGANISM: Homo sapiens

<400> SEQUENCE: 44

Met Glu Trp Asn Trp Val Val Leu Phe Leu Leu Ser Leu Thr Ala Gly
1               5                   10                  15

Val Tyr Ala Gln Gly Gln Met Gln Gln Ser Gly Ala Glu Leu Val Lys
            20                  25                  30

Pro Gly Ala Ser Val Gln Leu Ser Cys Lys Thr Ser Gly Phe Thr Phe
        35                  40                  45

```
Ser Ser Thr Tyr Ile Ser Trp Leu Lys Gln Lys Pro Gly Gln Ser Leu
    50                  55                  60

Glu Trp Ile Ala Trp Ile Tyr Ala Gly Thr Gly Thr Arg Tyr Asn
65                  70                  75                  80

Arg Lys Phe Thr Gly Lys Ala Gln Leu Thr Val Asp Thr Ser Ser
                85                  90                  95

Thr Ala Tyr Met Gln Phe Ser Ser Leu Thr Thr Glu Asp Ser Ala Ile
                100                 105                 110

Tyr Tyr Cys Ala Arg Glu Gly Val Asp Gly Trp Phe Thr Tyr Trp Gly
            115                 120                 125

Gln Gly Thr Leu Val Thr Val Ser Ala Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 45
```

<211> LENGTH: 720
<212> TYPE: DNA
<213> ORGANISM: Homo sapiens

<400> SEQUENCE: 45

```
atggacatga gggtgcccgc tcagctcctg gggctcctgc tgctgtggtt gagaggtgcc    60
agatgtgata tcgtgatgac ccaatctccg gatagcctgg ccgtgagtct tggggagcga   120
gctacaataa gctgtagagc gtccgaatct gttgataatt acggatcctc tttcatgaac   180
tggtatcaac agaaaccagg ccaacctcca aagctgctca tctacgcagc cagcaaccag   240
gggtccgggg tgccggatcg gttcagcggt agcggatccg gcaccgattt tacgctcacg   300
atcagttccc tgcaggccga ggacgtagcc gtatactatt gcaacagag caaagaagtg   360
ccctacacat tcggtcaggg caccaagctc gagatcaaac gtacggtggc tgcaccatct   420
gtcttcatct tcccgccatc tgatgagcag ttgaaatctg gaactgcctc tgttgtgtgc   480
ctgctgaata acttctatcc cagagaggcc aaagtacagt ggaaggtgga taacgccctc   540
caatcgggta actcccagga gagtgtcaca gagcaggaca gcaaggacag cacctacagc   600
ctcagcagca ccctgacgct gagcaaagca gactacgaga acacaaaagt ctacgcctgc   660
gaagtcaccc atcagggcct gagctcgccc gtcacaaaga gcttcaacag gggagagtgt   720
```

<210> SEQ ID NO 46
<211> LENGTH: 240
<212> TYPE: PRT
<213> ORGANISM: Homo sapiens

<400> SEQUENCE: 46

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Asp Ser
            20                  25                  30

Leu Ala Val Ser Leu Gly Glu Arg Ala Thr Ile Ser Cys Arg Ala Ser
        35                  40                  45

Glu Ser Val Asp Asn Tyr Gly Ser Ser Phe Met Asn Trp Tyr Gln Gln
    50                  55                  60

Lys Pro Gly Gln Pro Pro Lys Leu Leu Ile Tyr Ala Ala Ser Asn Gln
65                  70                  75                  80

Gly Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Ser Lys Glu Val Pro Tyr Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 47
<211> LENGTH: 1407
<212> TYPE: DNA
<213> ORGANISM: Rattus norvegicus

<400> SEQUENCE: 47

```
atggacatca ggctcagctt ggttttcctt gtcctttcca taaaaggtgt ccactgtgag     60
gtgcgactgg tggagtctgg tggaggctta gtgcagcctg gaaggtctct gaaactctcc    120
tgtgcagcct ccggattccc tttcagtaat tatggcatgg cctgggtccg ccaggctcca    180
acgaggggc tggagtgggt cgcaagtatt acttatgatg gtagtattac tttttatcga    240
gattccgtga agggccgatt cactatctcc agagataatg caaaaagtac cctgtacctg    300
caaatggaca gtctgaggtc tgaggacaca gccacttatt attgtacaag ttccgatact    360
acggattatt accacggagg ttttggtttt gcttactggg gccaaggcac tctggtcact    420
gtctcttcag ctgaaacaac agccccatct gtctatccac tggctcctgg aactgctctc    480
aaaagtaact ccatggtgac cctgggatgc ctggtcaagg gctatttccc tgagccagtc    540
accgtgacct ggaactctgg agccctgtcc agcggtgtgc acaccttccc agctgtcctg    600
cagtctgggc tctacactct caccagctca gtgactgtac cctccagcac ctggcccagc    660
cagaccgtca cctgcaacgt agcccacccg ccagcagca ccaaggtgga caagaaaatt    720
gtgcccagaa actgtggagg tgattgcaag ccttgtatat gtacaggctc agaagtatca    780
tctgtcttca tcttcccccc aaagcccaaa gatgtgctca ccatcactct gactcctaag    840
gtcacgtgtg ttgtggtaga cattagccag gacgatcccg aggtccattt cagctggttt    900
gtagatgacg tggaagtcca cacagctcag actcgaccac cagaggagca gttcaacagc    960
actttccgct cagtcagtga actccccatc ctgcaccagg actggctcaa tggcaggacg   1020
ttcagatgca aggtcaccag tgcagctttc ccatccccca tcgagaaaac catctccaaa   1080
cccgaaggca gaacacaagt tccgcatgta tacaccatgt cacctaccaa ggaagagatg   1140
acccagaatg aagtcagtat cacctgcatg gtaaaaggct ctatccccc agacatttat   1200
gtggagtggc agatgaacgg gcagccacag aaaactaca agaacactcc acctacgatg   1260
gacacagatg ggagttactt cctctacagc aagctcaatg tgaagaagga aaaatggcag   1320
cagggaaaca cgttcacgtg ttctgtgctg catgaaggcc tgcacaacca ccatactgag   1380
aagagtctct cccactctcc gggtaaa                                        1407
```

<210> SEQ ID NO 48
<211> LENGTH: 469
<212> TYPE: PRT
<213> ORGANISM: Rattus norvegicus

<400> SEQUENCE: 48

Met Asp Ile Arg Leu Ser Leu Val Phe Leu Val Leu Ser Ile Lys Gly
1               5                   10                  15

Val His Cys Glu Val Arg Leu Val Glu Ser Gly Gly Gly Leu Val Gln
                20                  25                  30

Pro Gly Arg Ser Leu Lys Leu Ser Cys Ala Ala Ser Gly Phe Pro Phe
            35                  40                  45

Ser Asn Tyr Gly Met Ala Trp Val Arg Gln Ala Pro Thr Arg Gly Leu
        50                  55                  60

Glu Trp Val Ala Ser Ile Thr Tyr Asp Gly Ser Ile Thr Phe Tyr Arg

```
                65                  70                  75                  80
Asp Ser Val Lys Gly Arg Phe Thr Ile Ser Arg Asp Asn Ala Lys Ser
                            85                  90                  95

Thr Leu Tyr Leu Gln Met Asp Ser Leu Arg Ser Glu Asp Thr Ala Thr
                100                 105                 110

Tyr Tyr Cys Thr Ser Ser Asp Thr Asp Tyr Tyr His Gly Gly Phe
            115                 120                 125

Trp Phe Ala Tyr Trp Gly Gln Gly Thr Leu Val Thr Val Ser Ser Ala
    130                 135                 140

Glu Thr Thr Ala Pro Ser Val Tyr Pro Leu Ala Pro Gly Thr Ala Leu
145                 150                 155                 160

Lys Ser Asn Ser Met Val Thr Leu Gly Cys Leu Val Lys Gly Tyr Phe
                165                 170                 175

Pro Glu Pro Val Thr Val Thr Trp Asn Ser Gly Ala Leu Ser Ser Gly
            180                 185                 190

Val His Thr Phe Pro Ala Val Leu Gln Ser Gly Leu Tyr Thr Leu Thr
        195                 200                 205

Ser Ser Val Thr Val Pro Ser Ser Thr Trp Pro Ser Gln Thr Val Thr
210                 215                 220

Cys Asn Val Ala His Pro Ala Ser Ser Thr Lys Val Asp Lys Lys Ile
225                 230                 235                 240

Val Pro Arg Asn Cys Gly Gly Asp Cys Lys Pro Cys Ile Cys Thr Gly
                245                 250                 255

Ser Glu Val Ser Ser Val Phe Ile Phe Pro Pro Lys Pro Lys Asp Val
            260                 265                 270

Leu Thr Ile Thr Leu Thr Pro Lys Val Thr Cys Val Val Val Asp Ile
        275                 280                 285

Ser Gln Asp Asp Pro Glu Val His Phe Ser Trp Phe Val Asp Asp Val
290                 295                 300

Glu Val His Thr Ala Gln Thr Arg Pro Pro Glu Glu Gln Phe Asn Ser
305                 310                 315                 320

Thr Phe Arg Ser Val Ser Glu Leu Pro Ile Leu His Gln Asp Trp Leu
                325                 330                 335

Asn Gly Arg Thr Phe Arg Cys Lys Val Thr Ser Ala Ala Phe Pro Ser
            340                 345                 350

Pro Ile Glu Lys Thr Ile Ser Lys Pro Glu Gly Arg Thr Gln Val Pro
        355                 360                 365

His Val Tyr Thr Met Ser Pro Thr Lys Glu Glu Met Thr Gln Asn Glu
370                 375                 380

Val Ser Ile Thr Cys Met Val Lys Gly Phe Tyr Pro Pro Asp Ile Tyr
385                 390                 395                 400

Val Glu Trp Gln Met Asn Gly Gln Pro Gln Glu Asn Tyr Lys Asn Thr
                405                 410                 415

Pro Pro Thr Met Asp Thr Asp Gly Ser Tyr Phe Leu Tyr Ser Lys Leu
            420                 425                 430

Asn Val Lys Lys Glu Lys Trp Gln Gln Gly Asn Thr Phe Thr Cys Ser
        435                 440                 445

Val Leu His Glu Gly Leu His Asn His His Thr Glu Lys Ser Leu Ser
450                 455                 460

His Ser Pro Gly Lys
465

<210> SEQ ID NO 49
<211> LENGTH: 711
```

```
<212> TYPE: DNA
<213> ORGANISM: Rattus norvegicus

<400> SEQUENCE: 49
atggagacag acagactcct gctatgggca ctgctgctct gggttccagg ctccactggt      60
gacattgtct tgacccagtc tcctgctttg gctgtgtctc tagggcagag ggccacactc     120
tcctgtaggg ccagccaaag tgtcagtata tctggacata atcttatgca ctggtaccaa     180
cagaaaccag gacagcaacc caaactcctc atctatcgtg catccaacct accatctggg     240
atccctgcca ggttcagtgg cagtgggtct gggacaggct tcaccctcac catcaatcct     300
gtgcaggctg atgacattgc aacctattac tgtcagcaga gtagggagtc tccgtggacg     360
ttcggtggag gcaccacgtt ggaattgaaa cgggctgatg ctgcaccaac tgtatctatc     420
ttcccaccat ccacggaaca gttagcaact ggaggtgcct cagtcgtgtg cctcatgaac     480
aacttctatc ccagagacat cagtgtcaag tggaagattg atggcactga acgacgagat     540
ggtgtcctgg acagtgttac tgatcaggac agcaaagaca gcacgtacag catgagcagc     600
accctctcgt tgaccaaggc tgactatgaa agtcataacc tctatacctg tgaggttgtt     660
cataagacat catcctcacc cgtcgtcaag agcttcaaca ggaatgagtg t              711

<210> SEQ ID NO 50
<211> LENGTH: 237
<212> TYPE: PRT
<213> ORGANISM: Rattus norvegicus

<400> SEQUENCE: 50
```

Met Glu Thr Asp Arg Leu Leu Trp Ala Leu Leu Leu Trp Val Pro
1               5                   10                  15

Gly Ser Thr Gly Asp Ile Val Leu Thr Gln Ser Pro Ala Leu Ala Val
                20                  25                  30

Ser Leu Gly Gln Arg Ala Thr Leu Ser Cys Arg Ala Ser Gln Ser Val
            35                  40                  45

Ser Ile Ser Gly His Asn Leu Met His Trp Tyr Gln Gln Lys Pro Gly
        50                  55                  60

Gln Gln Pro Lys Leu Leu Ile Tyr Arg Ala Ser Asn Leu Pro Ser Gly
65                  70                  75                  80

Ile Pro Ala Arg Phe Ser Gly Ser Gly Ser Gly Thr Gly Phe Thr Leu
                85                  90                  95

Thr Ile Asn Pro Val Gln Ala Asp Asp Ile Ala Thr Tyr Tyr Cys Gln
            100                 105                 110

Gln Ser Arg Glu Ser Pro Trp Thr Phe Gly Gly Gly Thr Thr Leu Glu
        115                 120                 125

Leu Lys Arg Ala Asp Ala Ala Pro Thr Val Ser Ile Phe Pro Pro Ser
    130                 135                 140

Thr Glu Gln Leu Ala Thr Gly Gly Ala Ser Val Val Cys Leu Met Asn
145                 150                 155                 160

Asn Phe Tyr Pro Arg Asp Ile Ser Val Lys Trp Lys Ile Asp Gly Thr
                165                 170                 175

Glu Arg Arg Asp Gly Val Leu Asp Ser Val Thr Asp Gln Asp Ser Lys
            180                 185                 190

Asp Ser Thr Tyr Ser Met Ser Ser Thr Leu Ser Leu Thr Lys Ala Asp
        195                 200                 205

Tyr Glu Ser His Asn Leu Tyr Thr Cys Glu Val Val His Lys Thr Ser
210                 215                 220

Ser Ser Pro Val Val Lys Ser Phe Asn Arg Asn Glu Cys

<210> SEQ ID NO 51
<211> LENGTH: 1416
<212> TYPE: DNA
<213> ORGANISM: Homo sapiens

<400> SEQUENCE: 51

```
atggacatga gggtgcccgc tcagctcctg gggctcctgc tgctgtggct gagaggtgcc      60
agatgtcagg tccaactggt tgagtcaggc ggaggtgtcg tacagcctgg aagaagtttg     120
cgcctgtctt gtgcggcgtc cggattccca ttcagcaact acggcatggc ctgggttcgg     180
caagcgcccg aaagggact ggaatgggtt gcctccatta catacgacgg agcatcacc      240
ttttaccggg atagtgttaa gggccggttt accatctccc gcgacaactc taagaacacc     300
ctctatctcc aaatgaattc cctccgggcc gaggacaccg cagtgtatta ctgcaccagc     360
tctgacacaa ccgattatta ccacggcgga ttctggttcg cttattgggg ccaaggcaca     420
ttggtcaccg tctctagtgc ctccaccaag ggcccatcgg tcttcccct ggcgccctgc      480
tccaggagca cctccgagag cacagcggcc ctgggctgcc tggtcaagga ctacttcccc     540
gaaccggtga cggtgtcgtg aactcaggc gctctgacca gcggcgtgca caccttccca      600
gctgtcctac agtcctcagg actctactcc ctcagcagcg tggtgaccgt gccctccagc     660
aacttcggca cccagaccta cacctgcaac gtagatcaca agcccagcaa caccaaggtg     720
gacaagacag ttgagcgcaa atgttgtgtc gagtgcccac cgtgcccagc accacctgtg     780
gcaggaccgt cagtcttcct cttcccccca aaacccaagg acaccctcat gatctcccgg     840
acccctgagg tcacgtgcgt ggtggtggac gtgagccacg aagaccccga ggtccagttc     900
aactggtacg tggacggcgt ggaggtgcat aatgccaaga caaagccacg ggaggagcag     960
ttcaacagca cgttccgtgt ggtcagcgtc ctcaccgttg tgcaccagga ctggctgaac    1020
ggcaaggagt acaagtgcaa ggtctccaac aaaggcctcc cagcccccat cgagaaaacc    1080
atctccaaaa ccaaagggca gccccgagaa ccacaggtgt acaccctgcc cccatcccgg    1140
gaggagatga ccaagaacca ggtcagcctg acctgcctgg tcaaaggctt ctaccccagc    1200
gacatcgccg tggagtggga gagcaatggg cagccggaga caactacaa gaccacacct     1260
cccatgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga agagcctctc cctgtctccg ggtaaa                               1416
```

<210> SEQ ID NO 52
<211> LENGTH: 472
<212> TYPE: PRT
<213> ORGANISM: Homo sapiens

<400> SEQUENCE: 52

```
Met Asp Met Arg Val Pro Ala Gln Leu Leu Gly Leu Leu Leu Leu Trp
 1               5                  10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Pro Phe Ser Asn Tyr Gly Met Ala Trp Val Arg Gln Ala Pro Gly
    50                  55                  60

Lys Gly Leu Glu Trp Val Ala Ser Ile Thr Tyr Asp Gly Ser Ile Thr
65                  70                  75                  80
```

Phe Tyr Arg Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Thr Ser Asp Thr Thr Asp Tyr Tyr His
        115                 120                 125

Gly Gly Phe Trp Phe Ala Tyr Trp Gly Gln Gly Thr Leu Val Thr Val
    130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
    210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Asn Ser Thr Phe Arg Val Val Ser Val Leu Thr Val Val His Gln
                325                 330                 335

Asp Trp Leu Asn Gly Lys Glu Tyr Lys Cys Lys Val Ser Asn Lys Gly
            340                 345                 350

Leu Pro Ala Pro Ile Glu Lys Thr Ile Ser Lys Thr Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Met Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 53
<211> LENGTH: 720
<212> TYPE: DNA

<213> ORGANISM: Homo sapiens

<400> SEQUENCE: 53

```
atggacatga gggtgcccgc tcagctcctg gggctcctgc tgctgtggct gagaggtgcc    60
agatgtgaaa ttgtgatgac acagagccct gctaccttga gtgtttctcc gggcgagcgg   120
gccacactgt catgtagggc atcacaaagc gtgtcaatca gtgggcacaa tctcatgcat   180
tggtatcaac agaagcccgg ccaggcaccc cgccttctca tctatcgagc atccaatctg   240
ccttctggta ttccagctag attttccggc agcggctccg gcacagagtt cactctgacc   300
atcagctcct tgcaatctga ggactttgca gtgtactatt gccagcagag cagggaatca   360
ccctggacct tcggggggtgg aaccaaggtg gaaataaaac gtacggtggc tgcaccatct   420
gtcttcatct cccgccatc tgatgagcag ttgaaatctg gaactgcctc tgttgtgtgc   480
ctgctgaata acttctatcc cagagaggcc aaagtacagt ggaaggtgga taacgccctc   540
caatcgggta actcccagga gagtgtcaca gagcaggaca gcaaggacag cacctacagc   600
ctcagcagca ccctgacgct gagcaaagca gactacgaga acacaaaagt ctacgcctgc   660
gaagtcaccc atcagggcct gagctcgccc gtcacaaaga gcttcaacag gggagagtgt   720
```

<210> SEQ ID NO 54
<211> LENGTH: 240
<212> TYPE: PRT
<213> ORGANISM: Homo sapiens

<400> SEQUENCE: 54

```
Met Asp Met Arg Val Pro Ala Gln Leu Leu Gly Leu Leu Leu Leu Trp
1               5                   10                  15

Leu Arg Gly Ala Arg Cys Glu Ile Val Met Thr Gln Ser Pro Ala Thr
            20                  25                  30

Leu Ser Val Ser Pro Gly Glu Arg Ala Thr Leu Ser Cys Arg Ala Ser
        35                  40                  45

Gln Ser Val Ser Ile Ser Gly His Asn Leu Met His Trp Tyr Gln Gln
    50                  55                  60

Lys Pro Gly Gln Ala Pro Arg Leu Leu Ile Tyr Arg Ala Ser Asn Leu
65                  70                  75                  80

Pro Ser Gly Ile Pro Ala Arg Phe Ser Gly Ser Gly Ser Gly Thr Glu
                85                  90                  95

Phe Thr Leu Thr Ile Ser Ser Leu Gln Ser Glu Asp Phe Ala Val Tyr
            100                 105                 110

Tyr Cys Gln Gln Ser Arg Glu Ser Pro Trp Thr Phe Gly Gly Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 55
<211> LENGTH: 711
<212> TYPE: DNA
<213> ORGANISM: Homo sapiens

<400> SEQUENCE: 55

```
atggagacag acagactcct gctatgggca ctgctgctct gggttccagg ctccactggt      60
gacattgtct tgacccagtc tcctgctttg gctgtgtctc tagggcagag ggccacactc     120
tcctgtaggg ccagccaaag tgtcagtata tctggacata atcttatgca ctggtaccaa     180
cagaaaccag gacagcaacc caaactcctc atctatcgtg catccaacct accatctggg     240
atccctgcca ggttcagtgg cagtgggtct gggacaggct tcaccctcac catcaatcct     300
gtgcaggctg atgacattgc aacctattac tgtcagcaga gtagggagtc tccgtggacg     360
ttcggtggag gcaccacgtt ggaattgaaa cgaactgtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg t              711
```

<210> SEQ ID NO 56
<211> LENGTH: 237
<212> TYPE: PRT
<213> ORGANISM: Homo sapiens

<400> SEQUENCE: 56

```
Met Glu Thr Asp Arg Leu Leu Leu Trp Ala Leu Leu Leu Trp Val Pro
 1               5                  10                  15

Gly Ser Thr Gly Asp Ile Val Leu Thr Gln Ser Pro Ala Leu Ala Val
            20                  25                  30

Ser Leu Gly Gln Arg Ala Thr Leu Ser Cys Arg Ala Ser Gln Ser Val
        35                  40                  45

Ser Ile Ser Gly His Asn Leu Met His Trp Tyr Gln Gln Lys Pro Gly
    50                  55                  60

Gln Gln Pro Lys Leu Leu Ile Tyr Arg Ala Ser Asn Leu Pro Ser Gly
65                  70                  75                  80

Ile Pro Ala Arg Phe Ser Gly Ser Gly Ser Gly Thr Gly Phe Thr Leu
                85                  90                  95

Thr Ile Asn Pro Val Gln Ala Asp Asp Ile Ala Thr Tyr Tyr Cys Gln
            100                 105                 110

Gln Ser Arg Glu Ser Pro Trp Thr Phe Gly Gly Gly Thr Thr Leu Glu
        115                 120                 125

Leu Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205
```

```
Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235

<210> SEQ ID NO 57
<211> LENGTH: 1407
<212> TYPE: DNA
<213> ORGANISM: Homo sapiens

<400> SEQUENCE: 57
atggacatca ggctcagctt ggttttcctt gtcctttcca taaaaggtgt ccactgtgag     60
gtgcgactgg tggagtctgg tggaggctta gtgcagcctg aaggtctctg aaactctcc    120 tgtgcagcct ccggattccc tttcagtaat tatggcatgg cctgggtccg ccaggctcca    180
acgagggggc tggagtgggt cgcaagtatt acttatgatg gtagtattac ttttatcga    240 gattccgtga agggccgatt cactatctcc agagataatg caaaaagtac cctgtacctg    300
caaatggaca gtctgaggtc tgaggacaca gccacttatt attgtacaag ttccgatact    360
acggattatt accacggagg ttttggtttt gcttactggg gccaaggcac tctggtcact    420
gtctcttcag cctccaccaa gggcccatcg gtcttccccc tggcgccctg ctccaggagc    480
acctccgaga gcacagcggc cctgggctgc ctggtcaagg actacttccc cgaaccggtg    540
acggtgtcgt ggaactcagg cgctctgacc agcggcgtgc acaccttccc agctgtccta    600
cagtcctcag gactctactc cctcagcagc gtggtgaccg tgccctccag caacttcggc    660
acccagacct acacctgcaa cgtagatcac aagcccagca caccaaggt ggacaagaca    720 gttgagcgca aatgttgtgt cgagtgccca ccgtgcccag caccacctgt ggcaggaccg    780
tcagtcttcc tcttcccccc aaaacccaag gacaccctca tgatctcccg gacccctgag    840
gtcacgtgcg tggtggtgga cgtgagccac gaagaccccg aggtccagtt caactggtac    900
gtggacggcg tggaggtgca taatgccaag acaaagccac gggaggagca gttcaacagc    960
acgttccgtg tggtcagcgt cctcaccgtt gtgcaccagg actggctgaa cggcaaggag   1020
tacaagtgca aggtctccaa caaaggcctc ccagccccca tcgagaaaac catctccaaa   1080
accaaagggc agccccgaga accacaggtg tacaccctgc ccccatcccg ggaggagatg   1140
accaagaacc aggtcagcct gacctgcctg gtcaaaggct tctacccag cgacatcgcc   1200 gtggagtggg agagcaatgg gcagccggag aacaactaca agaccacacc tcccatgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaa                                      1407

<210> SEQ ID NO 58
<211> LENGTH: 469
<212> TYPE: PRT
<213> ORGANISM: Homo sapiens

<400> SEQUENCE: 58

Met Asp Ile Arg Leu Ser Leu Val Phe Leu Val Leu Ser Ile Lys Gly
1               5                   10                  15

Val His Cys Glu Val Arg Leu Val Glu Ser Gly Gly Gly Leu Val Gln
                20                  25                  30

Pro Gly Arg Ser Leu Lys Leu Ser Cys Ala Ala Ser Gly Phe Pro Phe
            35                  40                  45

Ser Asn Tyr Gly Met Ala Trp Val Arg Gln Ala Pro Thr Arg Gly Leu
```

-continued

```
            50                  55                  60
Glu Trp Val Ala Ser Ile Thr Tyr Asp Gly Ser Ile Thr Phe Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
                100                 105                 110

Tyr Tyr Cys Thr Ser Ser Asp Thr Asp Tyr Tyr His Gly Gly Phe
                115                 120                 125

Trp Phe Ala Tyr Trp Gly Gln Gly Thr Leu Val Thr Val Ser Ser Ala
            130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
                195                 200                 205

Ser Ser Val Val Thr Val Pro Ser Ser Asn Phe Gly Thr Gln Thr Tyr
210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Gln Phe Asn Trp Tyr Val Asp Gly Val
                290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
                340                 345                 350

Pro Ile Glu Lys Thr Ile Ser Lys Thr Lys Gly Gln Pro Arg Glu Pro
                355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Tyr Lys Thr Thr
                405                 410                 415

Pro Pro Met Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
                450                 455                 460

Leu Ser Pro Gly Lys
465
```

-continued

<210> SEQ ID NO 59
<211> LENGTH: 444
<212> TYPE: DNA
<213> ORGANISM: Mus musculus

<400> SEQUENCE: 59

| | | | | | |
|---|---|---|---|---|---|
| atgacattga | acatgctgtt | ggggctgaag | tgggttttct | ttgttgtttt | ttatcaaggt | 60 |
| gtgcattgtg | aggtgcagct | tgttgagtct | ggtggaggat | tggtgcagcc | taaagggtca | 120 |
| ttgaaactct | catgtgcagc | ctctggattc | agcttcaata | cctacgccat | gaactgggtc | 180 |
| cgccaggctc | caggaaaggg | tttggaatgg | gttgctcgca | taagaagtaa | aagtaataat | 240 |
| tatgcaacat | attatgccga | ttcagtgaaa | gacagattca | ccatctccag | agatgattca | 300 |
| gaaagcatgc | tctatctgca | aatgaacaac | ttgaaaactg | aggacacagc | catgtgttac | 360 |
| tgtgtgagac | ataggagcaa | tgattttac | ttcggagtg | ctatggacta | ctggggtcaa | 420 |
| ggaacctcag | tcaccgtctc | ctca | | | | 444 |

<210> SEQ ID NO 60
<211> LENGTH: 484
<212> TYPE: PRT
<213> ORGANISM: Mus musculus

<400> SEQUENCE: 60

Met Thr Leu Asn Met Leu Leu Gly Leu Lys Trp Val Phe Val Val
1               5                   10                  15

Phe Tyr Gln Gly Val His Cys Glu Val Gln Leu Val Glu Ser Gly Gly
            20                  25                  30

Gly Leu Val Gln Pro Lys Gly Ser Leu Lys Leu Ser Cys Ala Ala Ser
        35                  40                  45

Gly Phe Ser Phe Asn Thr Tyr Ala Met Asn Trp Val Arg Gln Ala Pro
    50                  55                  60

Gly Lys Gly Leu Glu Trp Val Ala Arg Ile Arg Ser Lys Ser Asn Asn
65                  70                  75                  80

Tyr Ala Thr Tyr Tyr Ala Asp Ser Val Lys Asp Arg Phe Thr Ile Ser
                85                  90                  95

Arg Asp Asp Ser Glu Ser Met Leu Tyr Leu Gln Met Asn Asn Leu Lys
            100                 105                 110

Thr Glu Asp Thr Ala Met Cys Tyr Cys Val Arg His Arg Ser Asn Asp
        115                 120                 125

Phe Tyr Phe Gly Ser Ala Met Asp Tyr Trp Gly Gln Gly Thr Ser Val
    130                 135                 140

Thr Val Ser Ser Ala Lys Thr Thr Pro Pro Ser Val Tyr Pro Leu Ala
145                 150                 155                 160

Pro Gly Cys Gly Asp Thr Thr Gly Ser Ser Val Thr Leu Gly Cys Leu
                165                 170                 175

Val Lys Gly Tyr Phe Pro Glu Ser Val Thr Val Thr Trp Asn Ser Gly
            180                 185                 190

Ser Leu Ser Ser Ser Val His Thr Phe Pro Ala Leu Leu Gln Ser Gly
        195                 200                 205

Leu Tyr Thr Met Ser Ser Ser Val Thr Val Pro Ser Ser Thr Trp Pro
    210                 215                 220

Ser Gln Thr Val Thr Cys Ser Val Ala His Pro Ala Ser Ser Thr Thr
225                 230                 235                 240

Val Asp Lys Lys Leu Glu Pro Ser Gly Pro Ile Ser Thr Ile Asn Pro
                245                 250                 255

-continued

```
Cys Pro Pro Cys Lys Glu Cys His Lys Cys Pro Ala Pro Asn Leu Glu
            260                 265                 270
Gly Gly Pro Ser Val Phe Ile Phe Pro Pro Asn Ile Lys Asp Val Leu
        275                 280                 285
Met Ile Ser Leu Thr Pro Lys Val Thr Cys Val Val Val Asp Val Ser
290                 295                 300
Glu Asp Asp Pro Asp Val Arg Ile Ser Trp Phe Val Asn Asn Val Glu
305                 310                 315                 320
Val His Thr Ala Gln Thr Gln Thr His Arg Glu Asp Tyr Asn Ser Thr
                325                 330                 335
Ile Arg Val Val Ser Ala Leu Pro Ile Gln His Gln Asp Trp Met Ser
            340                 345                 350
Gly Lys Glu Phe Lys Cys Lys Val Asn Asn Lys Asp Leu Pro Ser Pro
        355                 360                 365
Ile Glu Arg Thr Ile Ser Lys Pro Lys Gly Leu Val Arg Ala Pro Gln
370                 375                 380
Val Tyr Thr Leu Pro Pro Pro Ala Glu Gln Leu Ser Arg Lys Asp Val
385                 390                 395                 400
Ser Leu Thr Cys Leu Val Val Gly Phe Asn Pro Gly Asp Ile Ser Val
                405                 410                 415
Glu Trp Thr Ser Asn Gly His Thr Glu Glu Asn Tyr Lys Asp Thr Ala
            420                 425                 430
Pro Val Leu Asp Ser Asp Gly Ser Tyr Phe Ile Tyr Ser Lys Leu Asn
        435                 440                 445
Met Lys Thr Ser Lys Trp Glu Lys Thr Asp Ser Phe Ser Cys Asn Val
450                 455                 460
Arg His Glu Gly Leu Lys Asn Tyr Tyr Leu Lys Lys Thr Ile Ser Arg
465                 470                 475                 480
Ser Pro Gly Lys

<210> SEQ ID NO 61
<211> LENGTH: 702
<212> TYPE: DNA
<213> ORGANISM: Mus musculus

<400> SEQUENCE: 61
atgagtgtgc ccactcaggt cctggggttg ctgctgctgt ggcttacaga tgccagatgt      60
gacatccaga tgactcagtc tccagcctcc ctatctgtat ctgtgggaga aactgtcacc     120
atcacatgtc gagcaagtga gaatatttac agtaatttag catggtatca gcagaaacag     180
ggagaatctc ctcagctcct ggtctatgct gcaactaact tagcagatgg tgtgccatca     240
aggttcagtg gcagtggatc agccacacag tattcccctca agatcaacag cctgcagtct     300
gaagattttg ggaattatta ctgtcaacat ttttgggta ctcctccgac gttcggtgga     360
ggcaccaagc tggaaatcaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaagg acgagtatga acgacataac agctatacct gtgaggccac tcacaagaca     660
tcaacttcac ccattgtcaa gagcttcaac aggaatgagt gt                       702

<210> SEQ ID NO 62
<211> LENGTH: 234
<212> TYPE: PRT
```

<213> ORGANISM: Mus musculus

<400> SEQUENCE: 62

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
        35                  40                  45

Ile Tyr Ser Asn Leu Ala Trp Tyr Gln Gln Lys Gln Gly Glu Ser Pro
    50                  55                  60

Gln Leu Leu Val Tyr Ala Ala Thr Asn Leu Ala Asp Gly Val Pro Ser
65                  70                  75                  80

Arg Phe Ser Gly Ser Gly Ser Ala Thr Gln Tyr Ser Leu Lys Ile Asn
                85                  90                  95

Ser Leu Gln Ser Glu Asp Phe Gly Asn Tyr Tyr Cys Gln His Phe Trp
            100                 105                 110

Gly Thr Pro Pro Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
210                 215                 220

Ile Val Lys Ser Phe Asn Arg Asn Glu Cys
                225                 230

<210> SEQ ID NO 63
<211> LENGTH: 411
<212> TYPE: PRT
<213> ORGANISM: Mus musculus

<400> SEQUENCE: 63

Ala Thr Gly Gly Ala Ala Thr Gly Gly Ala Ala Cys Thr Gly Gly
1               5                   10                  15

Thr Cys Gly Thr Thr Cys Thr Cys Thr Thr Cys Cys Thr Cys Cys Thr
            20                  25                  30

Gly Thr Cys Ala Thr Ala Ala Cys Thr Gly Cys Ala Gly Gly Thr
        35                  40                  45

Gly Thr Cys Thr Ala Thr Gly Cys Cys Cys Ala Gly Gly Thr Cys
    50                  55                  60

Ala Gly Ala Thr Gly Cys Ala Gly Cys Ala Gly Thr Cys Thr Gly Gly
65                  70                  75                  80

Ala Gly Cys Thr Gly Ala Gly Cys Thr Gly Gly Thr Gly Ala Ala Gly
                85                  90                  95

Cys Cys Thr Gly Gly Gly Gly Cys Thr Thr Cys Ala Gly Thr Gly Ala
            100                 105                 110

Ala Gly Cys Thr Gly Thr Cys Cys Thr Gly Cys Ala Ala Gly Ala Cys
        115                 120                 125

```
Thr Thr Cys Thr Gly Gly Cys Thr Cys Ala Cys Thr Thr Cys
    130                 135                 140
Ala Gly Cys Ala Gly Thr Ala Gly Cys Thr Ala Cys Ala Thr Ala Ala
145                 150                 155                 160
Gly Thr Thr Gly Gly Thr Thr Gly Ala Ala Gly Cys Ala Ala Ala
                165                 170                 175
Gly Cys Cys Thr Gly Gly Ala Cys Ala Gly Ala Gly Thr Cys Thr Thr
                180                 185                 190
Gly Ala Gly Thr Gly Gly Ala Thr Thr Gly Cys Ala Thr Gly Gly Ala
                195                 200                 205
Thr Thr Thr Ala Thr Gly Cys Thr Gly Gly Ala Ala Cys Thr Gly Gly
210                 215                 220
Thr Gly Cys Thr Ala Cys Thr Ala Gly Gly Thr Ala Thr Thr Ala Thr
225                 230                 235                 240
Cys Ala Gly Ala Gly Gly Thr Thr Cys Ala Cys Ala Gly Gly Cys Ala
                245                 250                 255
Ala Gly Gly Cys Cys Cys Ala Ala Thr Thr Gly Ala Cys Thr Gly Thr
                260                 265                 270
Thr Gly Ala Cys Ala Cys Ala Thr Cys Cys Thr Cys Cys Ala Gly Cys
                275                 280                 285
Ala Cys Ala Gly Cys Cys Thr Ala Cys Ala Thr Gly Cys Ala Ala Cys
                290                 295                 300
Thr Cys Ala Gly Cys Ala Gly Cys Cys Thr Gly Ala Cys Ala Ala Cys
305                 310                 315                 320
Thr Gly Ala Gly Gly Ala Cys Thr Cys Thr Gly Cys Cys Gly Thr Cys
                325                 330                 335
Thr Ala Thr Thr Ala Cys Thr Gly Thr Gly Cys Ala Ala Gly Ala Gly
                340                 345                 350
Ala Gly Gly Gly Gly Thr Cys Gly Ala Cys Gly Gly Ala Thr Gly
                355                 360                 365
Gly Thr Thr Thr Ala Cys Thr Ala Cys Thr Gly Gly Gly Gly Cys
370                 375                 380
Cys Ala Ala Gly Gly Ala Cys Thr Cys Thr Gly Gly Thr Cys Ala
385                 390                 395                 400
Cys Thr Gly Thr Cys Thr Cys Thr Gly Cys Ala
                405                 410

<210> SEQ ID NO 64
<211> LENGTH: 137
<212> TYPE: PRT
<213> ORGANISM: Mus musculus

<400> SEQUENCE: 64

Met Glu Trp Asn Trp Val Val Leu Phe Leu Leu Ser Leu Thr Ala Gly
1               5                   10                  15
Val Tyr Ala Gln Gly Gln Met Gln Gln Ser Gly Ala Glu Leu Val Lys
                20                  25                  30
Pro Gly Ala Ser Val Lys Leu Ser Cys Lys Thr Ser Gly Phe Thr Phe
            35                  40                  45
Ser Ser Ser Tyr Ile Ser Trp Leu Lys Gln Lys Pro Gly Gln Ser Leu
        50                  55                  60
Glu Trp Ile Ala Trp Ile Tyr Ala Gly Thr Gly Ala Thr Arg Tyr Tyr
65                  70                  75                  80
Gln Arg Phe Thr Gly Lys Ala Gln Leu Thr Val Asp Thr Ser Ser Ser
                85                  90                  95
```

```
Thr Ala Tyr Met Gln Leu Ser Ser Leu Thr Thr Glu Asp Ser Ala Val
            100                 105                 110
Tyr Tyr Cys Ala Arg Glu Gly Val Asp Gly Trp Phe Thr Tyr Trp Gly
            115                 120                 125
Gln Gly Thr Leu Val Thr Val Ser Ala
        130                 135
```

<210> SEQ ID NO 65
<211> LENGTH: 714
<212> TYPE: DNA
<213> ORGANISM: Mus musculus

<400> SEQUENCE: 65

```
atggagaaag acacactcct gctatgggtc ctgcttctct gggttccagg ttccacaggt    60
gacattgtgc tgacccaatc tccagcttct ttggctgtgt ctctagggca gagggccacc   120
atctcctgca gagccagcga aagtgttgat aattatggca ttagttttat gaactggttc   180
caacagaaac caggacagcc acccaaactc ctcatctatg atgcatccaa ccaaggatac   240
ggggtccctg ccaggtttag tggcagtggg tctgggacag acttcagcct caacatccat   300
cctatggagg aggatgatat tgcaatgtat ttctgtcagc aaagtaagga ggttccgtac   360
acgttcggag gggggaccaa gctggaaatc aaacgggctg atgctgcacc aactgtatcc   420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat gaacgacata cagctatac ctgtgaggcc   660
actcacaaga gatcaacttc acccattgtc aagagcttca caggaatga gtgt          714
```

<210> SEQ ID NO 66
<211> LENGTH: 238
<212> TYPE: PRT
<213> ORGANISM: Mus musculus

<400> SEQUENCE: 66

```
Met Glu Lys Asp Thr Leu Leu Trp Val Leu Leu Leu Trp Val Pro
1               5                   10                  15
Gly Ser Thr Gly Asp Ile Val Leu Thr Gln Ser Pro Ala Ser Leu Ala
            20                  25                  30
Val Ser Leu Gly Gln Arg Ala Thr Ile Ser Cys Arg Ala Ser Glu Ser
        35                  40                  45
Val Asp Asn Tyr Gly Ile Ser Phe Met Asn Trp Phe Gln Gln Lys Pro
    50                  55                  60
Gly Gln Pro Pro Lys Leu Leu Ile Tyr Asp Ala Ser Asn Gln Gly Tyr
65                  70                  75                  80
Gly Val Pro Ala Arg Phe Ser Gly Ser Gly Ser Gly Thr Asp Phe Ser
                85                  90                  95
Leu Asn Ile His Pro Met Glu Glu Asp Asp Ile Ala Met Tyr Phe Cys
            100                 105                 110
Gln Gln Ser Lys Glu Val Pro Tyr Thr Phe Gly Gly Gly Thr Lys Leu
        115                 120                 125
Glu Ile Lys Arg Ala Asp Ala Ala Pro Thr Val Ser Ile Phe Pro Pro
    130                 135                 140
Ser Ser Glu Gln Leu Thr Ser Gly Gly Ala Ser Val Val Cys Phe Leu
145                 150                 155                 160
```

```
Asn Asn Phe Tyr Pro Lys Asp Ile Asn Val Lys Trp Lys Ile Asp Gly
            165                 170                 175

Ser Glu Arg Gln Asn Gly Val Leu Asn Ser Trp Thr Asp Gln Asp Ser
        180                 185                 190

Lys Asp Ser Thr Tyr Ser Met Ser Ser Thr Leu Thr Leu Thr Lys Asp
            195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 67
<211> LENGTH: 411
<212> TYPE: DNA
<213> ORGANISM: Mus musculus

<400> SEQUENCE: 67
atggaatgga actgggtcgt tctcttcctc ctgtcattaa ctgcaggtgt ctatgcccag      60
ggtcagatgc agcagtctgg agctgagctg gtgaagcctg gggcttcagt gaagctgtcc     120
tgcaagactt ctggcttcac cttcagcagt agctacataa gttggttgaa gcaaaagcct     180
ggacagagtc ttgagtggat tgcatggatt tatgctggaa ctggtgctac taggtattat     240
cagaggttca caggcaaggc ccaattgact gtagacacat cctccagcac agcctacatg     300
caactcagca gcctgacaac tgaggactct gccgtctatt actgtgcaag agaggggtc      360 gacgggtggt ttacttactg gggccaaggg actctggtca ctgtctctgc a              411

<210> SEQ ID NO 68
<211> LENGTH: 137
<212> TYPE: PRT
<213> ORGANISM: Mus musculus

<400> SEQUENCE: 68

Met Glu Trp Asn Trp Val Val Leu Phe Leu Leu Ser Leu Thr Ala Gly
1               5                   10                  15

Val Tyr Ala Gln Gly Gln Met Gln Gln Ser Gly Ala Glu Leu Val Lys
            20                  25                  30

Pro Gly Ala Ser Val Lys Leu Ser Cys Lys Thr Ser Gly Phe Thr Phe
        35                  40                  45

Ser Ser Ser Tyr Ile Ser Trp Leu Lys Gln Lys Pro Gly Gln Ser Leu
    50                  55                  60

Glu Trp Ile Ala Trp Ile Tyr Ala Gly Thr Gly Ala Thr Arg Tyr Tyr
65                  70                  75                  80

Gln Arg Phe Thr Gly Lys Ala Gln Leu Thr Val Asp Thr Ser Ser Ser
                85                  90                  95

Thr Ala Tyr Met Gln Leu Ser Ser Leu Thr Thr Glu Asp Ser Ala Val
            100                 105                 110

Tyr Tyr Cys Ala Arg Glu Gly Val Asp Gly Trp Phe Thr Tyr Trp Gly
        115                 120                 125

Gln Gly Thr Leu Val Thr Val Ser Ala
    130                 135

<210> SEQ ID NO 69
<211> LENGTH: 714
<212> TYPE: DNA
<213> ORGANISM: Mus musculus

<400> SEQUENCE: 69
```

-continued

```
atggagaaag acacactcct gctatgggtc ctgcttctct gggttccagg ttccacaggt    60
gacattgtgc tgacccaatc tccagcttct ttggctgtgt ctctagggca gagggccacc   120
atctcctgca gagccagcga aagtgttgat aattctggca tttgtttttat gaactggttc   180 caacagaaac caggacagcc acccaaactc ctcatctatg atgcatccaa ccaaggatac   240
ggggtccctg ccaggtttag tggcagtggg tctgggacag acttcagcct caacatccat   300
cctatggagg aggatgatat tgcaatgtat ttctgtcagc aaagtaagga ggttccgtac   360
acgttcggag gggggaccaa gctggaaatc aaacgggctg atgctgcacc aactgtatcc   420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat gaacgacata cagctatac ctgtgaggcc   660 actcacaaga catcaacttc acccattgtc aagagcttca caggaatga gtgt          714
```

<210> SEQ ID NO 70
<211> LENGTH: 238
<212> TYPE: PRT
<213> ORGANISM: Mus musculus

<400> SEQUENCE: 70

```
Met Glu Lys Asp Thr Leu Leu Leu Trp Val Leu Leu Leu Trp Val Pro
1               5                   10                  15
Gly Ser Thr Gly Asp Ile Val Leu Thr Gln Ser Pro Ala Ser Leu Ala
            20                  25                  30
Val Ser Leu Gly Gln Arg Ala Thr Ile Ser Cys Arg Ala Ser Glu Ser
        35                  40                  45
Val Asp Asn Ser Gly Ile Cys Phe Met Asn Trp Phe Gln Gln Lys Pro
    50                  55                  60
Gly Gln Pro Pro Lys Leu Leu Ile Tyr Asp Ala Ser Asn Gln Gly Tyr
65                  70                  75                  80
Gly Val Pro Ala Arg Phe Ser Gly Ser Gly Ser Gly Thr Asp Phe Ser
                85                  90                  95
Leu Asn Ile His Pro Met Glu Glu Asp Asp Ile Ala Met Tyr Phe Cys
            100                 105                 110
Gln Gln Ser Lys Glu Val Pro Tyr Thr Phe Gly Gly Gly Thr Lys Leu
        115                 120                 125
Glu Ile Lys Arg Ala Asp Ala Ala Pro Thr Val Ser Ile Phe Pro Pro
    130                 135                 140
Ser Ser Glu Gln Leu Thr Ser Gly Gly Ala Ser Val Val Cys Phe Leu
145                 150                 155                 160
Asn Asn Phe Tyr Pro Lys Asp Ile Asn Val Lys Trp Lys Ile Asp Gly
                165                 170                 175
Ser Glu Arg Gln Asn Gly Val Leu Asn Ser Trp Thr Asp Gln Asp Ser
            180                 185                 190
Lys Asp Ser Thr Tyr Ser Met Ser Ser Thr Leu Thr Leu Thr Lys Asp
        195                 200                 205
Glu Tyr Glu Arg His Asn Ser Tyr Thr Cys Glu Ala Thr His Lys Thr
    210                 215                 220
Ser Thr Ser Pro Ile Val Lys Ser Phe Asn Arg Asn Glu Cys
225                 230                 235
```

<210> SEQ ID NO 71
<211> LENGTH: 411

<212> TYPE: DNA
<213> ORGANISM: Mus musculus

<400> SEQUENCE: 71

| | | | | |
|---|---|---|---|---|
| atggaatgga actgggtcgt tctcttcctc ctgtcattaa ctgcaggtgt ctatgcccag | | | | 60 |
| ggtcagatgc agcagtctgg agctgagctg gtgaagcctg ggcttcagt gcaactgtcc | | | | 120 |
| tgcaagactt ctggcttcac cttcagcagt acctatataa gttggttgaa gcaaaagcct | | | | 180 |
| ggacagagtc ttgagtggat tgcatggatt tatgctggaa ctggtggtac cagatataat | | | | 240 |
| cggaagttca caggcaaggc ccaactgact gtagacacat cctccagcac agcctacatg | | | | 300 |
| caattcagca gcctgacaac tgaggactct gccatctatt actgtgcaag agaggggtc | | | | 360 |
| gacgggtggt ttacttactg gggccagggg actctggtca ctgtctctgc a | | | | 411 |

<210> SEQ ID NO 72
<211> LENGTH: 137
<212> TYPE: PRT
<213> ORGANISM: Mus musculus

<400> SEQUENCE: 72

Met Glu Trp Asn Trp Val Val Leu Phe Leu Leu Ser Leu Thr Ala Gly
1               5                   10                  15

Val Tyr Ala Gln Gly Gln Met Gln Gln Ser Gly Ala Glu Leu Val Lys
            20                  25                  30

Pro Gly Ala Ser Val Gln Leu Ser Cys Lys Thr Ser Gly Phe Thr Phe
        35                  40                  45

Ser Ser Thr Tyr Ile Ser Trp Leu Lys Gln Lys Pro Gly Gln Ser Leu
    50                  55                  60

Glu Trp Ile Ala Trp Ile Tyr Ala Gly Thr Gly Gly Thr Arg Tyr Asn
65                  70                  75                  80

Arg Lys Phe Thr Gly Lys Ala Gln Leu Thr Val Asp Thr Ser Ser Ser
                85                  90                  95

Thr Ala Tyr Met Gln Phe Ser Ser Leu Thr Thr Glu Asp Ser Ala Ile
            100                 105                 110

Tyr Tyr Cys Ala Arg Glu Gly Val Asp Gly Trp Phe Thr Tyr Trp Gly
        115                 120                 125

Gln Gly Thr Leu Val Thr Val Ser Ala
    130                 135

<210> SEQ ID NO 73
<211> LENGTH: 714
<212> TYPE: DNA
<213> ORGANISM: Mus musculus

<400> SEQUENCE: 73

| | | | | |
|---|---|---|---|---|
| atggagaaag acacactcct gctatgggtc ctgcttctct gggttccagg ttccacaggt | | | | 60 |
| gacattgtgc tgacccaatc tccaccttct ttggctgtgt ctctaggca gagggccacc | | | | 120 |
| atctcctgca gagccagcga aagtgttgat aattatggca ctagttttat gaactggttc | | | | 180 |
| caacagaaac caggacagcc acccaaactc ctcatctttg ctgcatccaa ccaaggatcc | | | | 240 |
| ggggtccctg ccaggtttag tggcagtggg tctgggacag acttcagcct caacatccat | | | | 300 |
| cctatggagg aggatgatac tgcaatgtat ttctgtcagc aaagtaagga ggttccgtac | | | | 360 |
| acgttcggag gggggaccaa gctggaaata aaacggctg atgctgcacc aactgtatcc | | | | 420 |
| atcttcccac catccagtga gcagttaaca tctggaggtg cctcagtcgt gtgcttcttg | | | | 480 |
| aacaacttct accccaaaga catcaatgtc aagtggaaga ttgatggcag tgaacgacaa | | | | 540 |

```
aatggcgtcc tgaacagttg gactgatcag gacagcaaag acagcaccta cagcatgagc      600
agcaccctca cgttgaccaa ggacgagtat gaacgacata cagctatac ctgtgaggcc       660 actcacaaga catcaacttc acccattgtc aagagcttca acaggaatga gtgt            714
```

<210> SEQ ID NO 74
<211> LENGTH: 238
<212> TYPE: PRT
<213> ORGANISM: Mus musculus

<400> SEQUENCE: 74

```
Met Glu Lys Asp Thr Leu Leu Leu Trp Val Leu Leu Leu Trp Val Pro
1               5                   10                  15

Gly Ser Thr Gly Asp Ile Val Leu Thr Gln Ser Pro Ser Leu Ala
            20                  25                  30

Val Ser Leu Gly Gln Arg Ala Thr Ile Ser Cys Arg Ala Ser Glu Ser
        35                  40                  45

Val Asp Asn Tyr Gly Thr Ser Phe Met Asn Trp Phe Gln Gln Lys Pro
    50                  55                  60

Gly Gln Pro Pro Lys Leu Leu Ile Phe Ala Ala Ser Asn Gln Gly Ser
65                  70                  75                  80

Gly Val Pro Ala Arg Phe Ser Gly Ser Gly Ser Gly Thr Asp Phe Ser
                85                  90                  95

Leu Asn Ile His Pro Met Glu Glu Asp Asp Thr Ala Met Tyr Phe Cys
            100                 105                 110

Gln Gln Ser Lys Glu Val Pro Tyr Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

<210> SEQ ID NO 75
<211> LENGTH: 658
<212> TYPE: DNA
<213> ORGANISM: Mus musculus

<400> SEQUENCE: 75

```
gcgctgtcag tctgtcgtga cgcagccgcc ctcagtgtct ggggcccag ggcagagggt       60 caccatgtcc tgcactggga gcagctccaa cctcggggca ggttatgatg taaactggta    120
ccagcagctt ccaggaaaag cccccaaagt cctcatctat ggtaacgaaa ttcggccctc    180 agggtccct gaccgattct ctggctccaa gtctgacacc tcagccaccc tggacatcac    240
cggactccag actggggacg aggccgacta ttactgcgaa acgtgggata gcagtctgag    300
tactgtggtc ttcggcggag ggaccaagtt gaccgtccta ggtcagccca aggctgcccc    360
ctcggtcacg ctcttcccac cctcctctga ggagcttcaa gccaacaagg ccacactggt    420
```

```
gtgtctcata agtgacttct acccgggagc cgtgacagtg gcctggaagg cagatagcag    480
ccccgtcaag gcgggagtgg agaccaccac accctccaaa caaagcaaca acaagtacgc    540
ggccagcagc tacctgagcc tgacgcctga gcagtggaag tcccacaaaa gctacagctg    600
ccaggtcacg catgaaggga gcaccgtgga agacagtg gcccctgcag aatgctct        658
```

<210> SEQ ID NO 76
<211> LENGTH: 239
<212> TYPE: PRT
<213> ORGANISM: Mus musculus

<400> SEQUENCE: 76

```
Met Asp Met Arg Val Pro Ala Gln Leu Leu Gly Leu Leu Leu Leu Trp
1               5                   10                  15

Leu Arg Gly Ala Arg Cys Gln Ser Val Val Thr Gln Pro Pro Ser Val
            20                  25                  30

Ser Gly Ala Pro Gly Gln Arg Val Thr Met Ser Cys Thr Gly Ser Ser
        35                  40                  45

Ser Asn Leu Gly Ala Gly Tyr Asp Val Asn Trp Tyr Gln Gln Leu Pro
    50                  55                  60

Gly Lys Ala Pro Lys Val Leu Ile Tyr Gly Asn Glu Ile Arg Pro Ser
65                  70                  75                  80

Gly Val Pro Asp Arg Phe Ser Gly Ser Lys Ser Asp Thr Ser Ala Thr
                85                  90                  95

Leu Asp Ile Thr Gly Leu Gln Thr Gly Asp Glu Ala Asp Tyr Tyr Cys
            100                 105                 110

Glu Thr Trp Asp Ser Ser Leu Ser Thr Val Val Phe Gly Gly Gly Thr
        115                 120                 125

Lys Leu Thr Val Leu Gly Gln Pro Lys Ala Ala Pro Ser Val Thr Leu
    130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Ser Ser Pro Val Lys Ala Gly Val Glu Thr Thr Thr Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Lys Ser Tyr Ser Cys Gln Val Thr His
    210                 215                 220

Glu Gly Ser Thr Val Glu Lys Thr Val Ala Pro Ala Glu Cys Ser
225                 230                 235
```

<210> SEQ ID NO 77
<211> LENGTH: 708
<212> TYPE: DNA
<213> ORGANISM: Mus musculus

<400> SEQUENCE: 77

```
atggacatga gggtgcccgc tcagctcctg ggctcctgc tgctgtggct gagaggtgcg    60
cgctgtgaca tccagatgac ccagtctcca tcctccctgt ctgcttctgt aggagacaga    120
gtcaccatca cttgccgggc aagtcagagc attagcgagt acttaaattg gtaccagcag    180
aaacctgggc aggctcccag gctcctcatc tatggtgtat ccaccagggc cactggcatc    240
gcagccaggt tcagtggcag tgggtctggg acagacttca ctctcaccat cagcagcctg    300
```

```
cagcctgaag attctgcagt ttattactgt cagcaggatt ataacgttcc gtacactttt      360
ggccagggga ccaagctgga gatcaaacgt acggtggctg caccatctgt cttcatcttc      420
ccgccatctg atgagcagtt gaaatctgga actgcctctg ttgtgtgcct gctgaataac      480
ttctatccca gagaggccaa agtacagtgg aaggtggata acgccctcca atcgggtaac      540
tcccaggaga gtgtcacaga gcaggacagc aaggacagca cctacagcct cagcagcacc      600
ctgacgctga gcaaagcaga ctacgagaaa cacaaagtct acgcctgcga agtcacccat      660
cagggcctga gctcgcccgt cacaaagagc ttcaacaggg gagagtgt                   708
```

```
<210> SEQ ID NO 78
<211> LENGTH: 236
<212> TYPE: PRT
<213> ORGANISM: Mus musculus

<400> SEQUENCE: 78
```

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Glu Tyr Leu Asn Trp Tyr Gln Gln Lys Pro Gly Gln
    50                  55                  60

Ala Pro Arg Leu Leu Ile Tyr Gly Val Ser Thr Arg Ala Thr Gly Ile
65                  70                  75                  80

Ala Ala Arg Phe Ser Gly Ser Gly Ser Gly Thr Asp Phe Thr Leu Thr
                85                  90                  95

Ile Ser Ser Leu Gln Pro Glu Asp Ser Ala Val Tyr Tyr Cys Gln Gln
            100                 105                 110

Asp Tyr Asn Val Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

```
<210> SEQ ID NO 79
<211> LENGTH: 708
<212> TYPE: DNA
<213> ORGANISM: Mus musculus

<400> SEQUENCE: 79
atggacatga gggtgcccgc tcagctcctg gggctcctgc tgctgtggct gagaggtgcg       60
cgctgtgaca tccagttgac ccagtctcca ttctccctgt ctgcatctgt tggagacaga      120
gtcaccatca cttgccgggc aagtcagagt attaatgata cttaaattg gtatctccag       180
```

```
aaaccgggga agcccctaa actcctgatc tttgctgcat ccacttcgca aagtggtgtc    240
ccatcgcggt tcagcggcaa tggatttggg acagatttct ctctcatcat cagcggcctt    300
cagcctgagg atgttggcac ttattattgc aacagaatg acagcatgcc tttcaccttc    360
ggccagggga ctcgactgga cattaaacgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata cgccctcca atcgggtaac     540 tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgt                 708
```

<210> SEQ ID NO 80
<211> LENGTH: 236
<212> TYPE: PRT
<213> ORGANISM: Mus musculus

<400> SEQUENCE: 80

```
Met Asp Met Arg Val Pro Ala Gln Leu Leu Gly Leu Leu Leu Leu Trp
1               5                   10                  15

Leu Arg Gly Ala Arg Cys Asp Ile Gln Leu Thr Gln Ser Pro Phe Ser
            20                  25                  30

Leu Ser Ala Ser Val Gly Asp Arg Val Thr Ile Thr Cys Arg Ala Ser
        35                  40                  45

Gln Ser Ile Asn Asp Asn Leu Asn Trp Tyr Leu Gln Lys Pro Gly Lys
    50                  55                  60

Ala Pro Lys Leu Leu Ile Phe Ala Ala Ser Thr Ser Gln Ser Gly Val
65                  70                  75                  80

Pro Ser Arg Phe Ser Gly Asn Gly Phe Gly Thr Asp Phe Ser Leu Ile
                85                  90                  95

Ile Ser Gly Leu Gln Pro Glu Asp Val Gly Thr Tyr Tyr Cys Gln Gln
            100                 105                 110

Asn Asp Ser Met Pro Phe Thr Phe Gly Gln Gly Thr Arg Leu Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 81
<211> LENGTH: 708
<212> TYPE: DNA
<213> ORGANISM: Mus musculus

<400> SEQUENCE: 81

-continued

```
atggacatga gggtgcccgc tcagctcctg gggctcctgc tgctgtggct gagaggtgcg      60
cgctgtgaca tccagttgac ccagtctcca tcctccctgt ctgcttctgt tggagacaga    120
gtcaccatca cttgccaggc gagtcaagac attaacaatt atttaagttg gtatcaacag    180
aaaccaggaa aagcccctaa ggtcctgatt tacgatacat ccaatttgga aacaggggtc    240
ccatcaaggt tcagtggaag tggatctggg acagacttca ctttcaccat cagcagcctg    300
cagcctgaag atattgcaac atattactgt caacagtctg ataatctccc gtacaccttt    360
ggccagggga ccaagttgga gatcaaacgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgt              708
```

<210> SEQ ID NO 82
<211> LENGTH: 236
<212> TYPE: PRT
<213> ORGANISM: Mus musculus

<400> SEQUENCE: 82

```
Met Asp Met Arg Val Pro Ala Gln Leu Leu Gly Leu Leu Leu Leu Trp
  1               5                  10                  15
Leu Arg Gly Ala Arg Cys Asp Ile Gln Leu Thr Gln Ser Pro Ser Ser
             20                  25                  30
Leu Ser Ala Ser Val Gly Asp Arg Val Thr Ile Thr Cys Gln Ala Ser
         35                  40                  45
Gln Asp Ile Asn Asn Tyr Leu Ser Trp Tyr Gln Gln Lys Pro Gly Lys
     50                  55                  60
Ala Pro Lys Val Leu Ile Tyr Asp Thr Ser Asn Leu Glu Thr Gly Val
 65                  70                  75                  80
Pro Ser Arg Phe Ser Gly Ser Gly Ser Gly Thr Asp Phe Thr Phe Thr
                 85                  90                  95
Ile Ser Ser Leu Gln Pro Glu Asp Ile Ala Thr Tyr Tyr Cys Gln Gln
            100                 105                 110
Ser Asp Asn Leu Pro Tyr Thr Phe Gly Gln Gly Thr Lys Leu Glu Ile
        115                 120                 125
Lys Arg Thr Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235
```

<210> SEQ ID NO 83
<211> LENGTH: 711

```
<212> TYPE: DNA
<213> ORGANISM: Mus musculus

<400> SEQUENCE: 83
atggacatga gggtgcccgc tcagctcctg gggctcctgc tgctgtggct gagaggtgcg      60
cgctgtgaca tccagatgac ccagtctcca ggcaccctgt ctttgtctcc aggggaaaga     120
gccaccctct ctgtagggc cagtcagaga gttagcagca gctacttagc ctggtaccag     180
cagagacctg gccaggctcc caggctcctc atgtatggta catctagttg gccactggc     240 atcccagaca ggttcagtgg cagtggatct gggacagatt tcactctcac catcagcagt     300
ctgcaacctg aagattttgc aacttactat tgtcaacaaa gttccagtat cccgtacact     360
tttggccagg ggaccaagct ggagatcaaa cgtacggtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg t              711

<210> SEQ ID NO 84
<211> LENGTH: 237
<212> TYPE: PRT
<213> ORGANISM: Mus musculus

<400> SEQUENCE: 84
```

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Gly Thr
            20                  25                  30

Leu Ser Leu Ser Pro Gly Glu Arg Ala Thr Leu Phe Cys Arg Ala Ser
        35                  40                  45

Gln Arg Val Ser Ser Ser Tyr Leu Ala Trp Tyr Gln Gln Arg Pro Gly
    50                  55                  60

Gln Ala Pro Arg Leu Leu Met Tyr Gly Thr Ser Ser Trp Ala Thr Gly
65                  70                  75                  80

Ile Pro Asp Arg Phe Ser Gly Ser Gly Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Ser Ser Ser Ile Pro Tyr Thr Phe Gly Gln Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

225              230                 235

<210> SEQ ID NO 85
<211> LENGTH: 711
<212> TYPE: DNA
<213> ORGANISM: Mus musculus

<400> SEQUENCE: 85

| | | | | | |
|---|---|---|---|---|---|
| atggacatga | gggtgcccgc | tcagctcctg | gggctcctgc | tgctgtggct | gagaggtgcg | 60 |
| cgctgtgaaa | cgacactcac | gcagtctcca | gctctcttgt | ctttgtctcc | aggggagaga | 120 |
| gccaccctct | cctgcagggc | cagccagact | cttagcttcg | acttcttcgc | ctggtatcaa | 180 |
| cagaagcctg | gccaggctcc | cagtctcctc | atctctggta | tttccacccg | gccgctggc | 240 |
| gtcccagaca | ggttcagtgg | cagtgggtct | gggacagact | tcactctcac | tatcgacaga | 300 |
| ctggaacctg | aagattttgc | agtgtatttc | tgtcagcagt | ccagcagttt | accgctcacc | 360 |
| ttcggcggag | ggaccaaggt | ggagatcaga | cgtacggtgg | ctgccaccatc | tgtcttcatc | 420 |
| ttcccgccat | ctgatgagca | gttgaaatct | ggaactgcct | ctgttgtgtg | cctgctgaat | 480 |
| aacttctatc | ccagagaggc | caaagtacag | tggaaggtgg | ataacgccct | ccaatcgggt | 540 |
| aactcccagg | agagtgtcac | agagcaggac | agcaaggaca | gcacctacag | cctcagcagc | 600 |
| accctgacgc | tgagcaaagc | agactacgag | aaacacaaag | tctacgcctg | cgaagtcacc | 660 |
| catcagggcc | tgagctcgcc | cgtcacaaag | agcttcaaca | ggggagagtg | t | 711 |

<210> SEQ ID NO 86
<211> LENGTH: 237
<212> TYPE: PRT
<213> ORGANISM: Mus musculus

<400> SEQUENCE: 86

Met Asp Met Arg Val Pro Ala Gln Leu Leu Gly Leu Leu Leu Trp
1               5                   10                  15

Leu Arg Gly Ala Arg Cys Glu Thr Thr Leu Thr Gln Ser Pro Ala Leu
            20                  25                  30

Leu Ser Leu Ser Pro Gly Glu Arg Ala Thr Leu Ser Cys Arg Ala Ser
        35                  40                  45

Gln Thr Leu Ser Phe Asp Phe Phe Ala Trp Tyr Gln Gln Lys Pro Gly
    50                  55                  60

Gln Ala Pro Ser Leu Leu Ile Ser Gly Ile Ser Thr Arg Ala Ala Gly
65                  70                  75                  80

Val Pro Asp Arg Phe Ser Gly Ser Gly Ser Gly Thr Asp Phe Thr Leu
                85                  90                  95

Thr Ile Asp Arg Leu Glu Pro Glu Asp Phe Ala Val Tyr Phe Cys Gln
            100                 105                 110

Gln Ser Ser Ser Leu Pro Leu Thr Phe Gly Gly Gly Thr Lys Val Glu
        115                 120                 125

Ile Arg Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 87
<211> LENGTH: 708
<212> TYPE: DNA
<213> ORGANISM: Mus musculus

<400> SEQUENCE: 87
atggacatga gggtgcccgc tcagctcctg gggctcctgc tgctgtggct gagaggtgcg    60
cgctgtgaca tccagatgac ccagtctcca tcctccctgt ctgcatctgt agggacaga   120 gtcaccatca cttgccgggc aagtcagagc attagcgact atttaaattg gtatcagcag   180
agaccaggga aagcccctaa cctcctgatc tttgcttcaa acactttgca aggtggggtc   240
ccatcaaggt tcagaggcag tggatctggg acagatttca ctctcaccat taacagtctg   300
caacatgaag attttggaac ttactactgt caacagagtt acagaacccc tctcactttc   360
ggcggaggga ccaaggtgga gatcaagcgt acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata cgccctcca atcgggtaac   540 tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt              708

<210> SEQ ID NO 88
<211> LENGTH: 236
<212> TYPE: PRT
<213> ORGANISM: Mus musculus

<400> SEQUENCE: 88

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Asp Tyr Leu Asn Trp Tyr Gln Gln Arg Pro Gly Lys
    50                  55                  60

Ala Pro Asn Leu Leu Ile Phe Ala Ser Asn Thr Leu Gln Gly Gly Val
65                  70                  75                  80

Pro Ser Arg Phe Arg Gly Ser Gly Ser Gly Thr Asp Phe Thr Leu Thr
                85                  90                  95

Ile Asn Ser Leu Gln His Glu Asp Phe Gly Thr Tyr Tyr Cys Gln Gln
            100                 105                 110

Ser Tyr Arg Thr Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

```
Gln Ser Gly Asn Ser Gln Glu Ser Val Thr Glu Gln Asp Ser Lys Asp
                180                 185                 190
Ser Thr Tyr Ser Leu Ser Ser Thr Leu Thr Leu Ser Lys Ala Asp Tyr
            195                 200                 205
Glu Lys His Lys Val Tyr Ala Cys Glu Val Thr His Gln Gly Leu Ser
        210                 215                 220
Ser Pro Val Thr Lys Ser Phe Asn Arg Gly Glu Cys
225                 230                 235

<210> SEQ ID NO 89
<211> LENGTH: 708
<212> TYPE: DNA
<213> ORGANISM: Mus musculus

<400> SEQUENCE: 89
atggacatga gggtgcccgc tcagctcctg gggctcctgc tgctgtggct gagaggtgcg    60
cgctgtgaca tccagatgac ccagtctcca ctctccctgt ctgcatctgt aggagacaga   120
gtcgccatca cttgtcgggc aagtcagagc attagcgact ctttaaattg gtatcagcag   180
aaaccgggaa aacctcctaa gatcgtgatc tatgctgcat ccggtttgcc gagtggggtc   240
ccatcaaggt tcagtggcgg tggctctggg acagatttca ctctcgtcat cagtactcta   300
caacctgaag attttgcaac ttactactgt caacagagtt acagtgcccc gctcactttc   360
ggcggaggga ccaaggtgga gatcagtcgt acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt               708

<210> SEQ ID NO 90
<211> LENGTH: 236
<212> TYPE: PRT
<213> ORGANISM: Mus musculus

<400> SEQUENCE: 90

Met Asp Met Arg Val Pro Ala Gln Leu Leu Gly Leu Leu Leu Leu Trp
1               5                   10                  15
Leu Arg Gly Ala Arg Cys Asp Ile Gln Met Thr Gln Ser Pro Leu Ser
            20                  25                  30
Leu Ser Ala Ser Val Gly Asp Arg Val Ala Ile Thr Cys Arg Ala Ser
        35                  40                  45
Gln Ser Ile Ser Asp Ser Leu Asn Trp Tyr Gln Gln Lys Pro Gly Lys
    50                  55                  60
Pro Pro Lys Ile Val Ile Tyr Ala Ala Ser Gly Leu Pro Ser Gly Val
65                  70                  75                  80
Pro Ser Arg Phe Ser Gly Gly Gly Ser Gly Thr Asp Phe Thr Leu Val
                85                  90                  95
Ile Ser Thr Leu Gln Pro Glu Asp Phe Ala Thr Tyr Tyr Cys Gln Gln
            100                 105                 110
Ser Tyr Ser Ala Pro Leu Thr Phe Gly Gly Gly Thr Lys Val Glu Ile
        115                 120                 125
Ser Arg Thr Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
```

```
                 145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
                180                 185                 190
Ser Thr Tyr Ser Leu Ser Ser Thr Leu Thr Leu Ser Lys Ala Asp Tyr
                195                 200                 205
Glu Lys His Lys Val Tyr Ala Cys Glu Val Thr His Gln Gly Leu Ser
                210                 215                 220
Ser Pro Val Thr Lys Ser Phe Asn Arg Gly Glu Cys
225                 230                 235

<210> SEQ ID NO 91
<211> LENGTH: 708
<212> TYPE: DNA
<213> ORGANISM: Mus musculus

<400> SEQUENCE: 91
atggacatga gggtgcccgc tcagctcctg gggctcctgc tgctgtggct gagaggtgcg      60
cgctgtgaca tccagatgac ccagtctcca tcctccctgt ctgcgtctat aggagacaga     120
gtcaccatca cttgccaggc gagtcaggac attaacaact atttaaattg gtatcagcag     180
aaacaaggga aagcccctaa ggtcctgatc ttcgatgcgt ccaatttggc agcaggcgtc     240
ccatcaaggt tcagtggcag tggatctggg acagatttta ctttaaccat cagcagccta     300
cagcctgaag atattgcaac atattactgt caacaatatg acaatctccc tctgacattc     360
ggccaaggga ccaaggtgga caataaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgcctccaa atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgt                  708

<210> SEQ ID NO 92
<211> LENGTH: 236
<212> TYPE: PRT
<213> ORGANISM: Mus musculus

<400> SEQUENCE: 92

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
                20                  25                  30

Leu Ser Ala Ser Ile Gly Asp Arg Val Thr Ile Thr Cys Gln Ala Ser
                35                  40                  45

Gln Asp Ile Asn Asn Tyr Leu Asn Trp Tyr Gln Gln Lys Gln Gly Lys
            50                  55                  60

Ala Pro Lys Val Leu Ile Phe Asp Ala Ser Asn Leu Ala Ala Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Ile Ala Thr Tyr Tyr Cys Gln Gln
                100                 105                 110

Tyr Asp Asn Leu Pro Leu Thr Phe Gly Gln Gly Thr Lys Val Asp Asn
                115                 120                 125
```

```
Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 93
<211> LENGTH: 717
<212> TYPE: DNA
<213> ORGANISM: Mus musculus

<400> SEQUENCE: 93
atggacatga gggtgcccgc tcagctcctg gggctcctgc tgctgtggct gagaggtgcg     60
cgctgtcagt ctgtcgtgac gcagccgccc gcagtgtctg ggccccagg  acagaggatc    120 accatctcct gcactgggag cagctccaac atcggggcag gttatgatgt acactggtac    180
cagcagtttc caggaacagc ccccaaagtc ctcatctttg ctaacgacta tcggccctca    240
ggggtccctg accgattctc tgcctccaag tctgccacct cagcctccct ggccatccgt    300
gggctccagt ctgaggatga ggctgattac tactgccagt cctatgacaa ccgcctgagt    360
ggttatgtct tcggaactgg gaccaaggtc accgtcctag gtcagcccaa ggctgccccc    420
tcggtcacgc tcttcccacc ctcctctgag gagcttcaag ccaacaaggc cacactggtg    480
tgtctcataa gtgacttcta cccgggagcc gtgacagtgg cctggaaggc agatagcagc    540
cccgtcaagg cgggagtgga gaccaccaca ccctccaaac aaagcaacaa caagtacgcg    600
gccagcagct acctgagcct gacgcctgag cagtggaagt cccacaaaag ctacagctgc    660
caggtcacgc atgaagggag caccgtggag aagacagtgg cccctgcaga atgctct      717

<210> SEQ ID NO 94
<211> LENGTH: 239
<212> TYPE: PRT
<213> ORGANISM: Mus musculus

<400> SEQUENCE: 94

Met Asp Met Arg Val Pro Ala Gln Leu Leu Gly Leu Leu Leu Leu Trp
1               5                   10                  15

Leu Arg Gly Ala Arg Cys Gln Ser Val Val Thr Gln Pro Pro Ala Val
                20                  25                  30

Ser Gly Ala Pro Gly Gln Arg Ile Thr Ile Ser Cys Thr Gly Ser Ser
            35                  40                  45

Ser Asn Ile Gly Ala Gly Tyr Asp Val His Trp Tyr Gln Gln Phe Pro
        50                  55                  60

Gly Thr Ala Pro Lys Val Leu Ile Phe Ala Asn Asp Tyr Arg Pro Ser
65                  70                  75                  80

Gly Val Pro Asp Arg Phe Ser Ala Ser Lys Ser Ala Thr Ser Ala Ser
                85                  90                  95
```

```
Leu Ala Ile Arg Gly Leu Gln Ser Glu Asp Glu Ala Asp Tyr Tyr Cys
                100                 105                 110

Gln Ser Tyr Asp Asn Arg Leu Ser Gly Tyr Val Phe Gly Thr Gly Thr
            115                 120                 125

Lys Val Thr Val Leu Gly Gln Pro Lys Ala Ala Pro Ser Val Thr Leu
130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Ser Ser Pro Val Lys Ala Gly Val Glu Thr Thr Thr Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Lys Ser Tyr Ser Cys Gln Val Thr His
210                 215                 220

Glu Gly Ser Thr Val Glu Lys Thr Val Ala Pro Ala Glu Cys Ser
225                 230                 235

<210> SEQ ID NO 95
<211> LENGTH: 717
<212> TYPE: DNA
<213> ORGANISM: Mus musculus

<400> SEQUENCE: 95
atggacatga gggtgcccgc tcagctcctg gggctcctgc tgctgtggct gagaggtgcg     60
cgctgtcagg ctgtgctgac tcagccgtcc tcagtgtctg ggccccagg gcggagggtc     120 accatctcct gcactgggag cagttccaac atcggggcag gttatgatgt acactggtat    180
caacaacttc caggaaaagc ccccaaactc gtcatctctg ctaacaccaa tcggccctca    240
ggggtccctg accgattctc aggctccaag tctggcacct cagcctccct ggccatcact    300
gggctccagg ctgaggatga ggctgattat tactgccagt cgtatgacaa cagcgtgagt    360
gcttatgtct tcggaactgg gaccaaggtc accgtcctag gtcagcccaa ggctgccccc    420
tcggtcacgc tcttcccacc ctcctctgag gagcttcaag ccaacaaggc cacactggtg    480
tgtctcataa gtgacttcta cccgggagcc gtgacagtgg cctggaaggc agatagcagc    540
cccgtcaagg cgggagtgga gaccaccaca ccctccaaac aaagcaacaa caagtacgcg    600
gccagcagct acctgagcct gacgcctgag cagtggaagt cccacaaaag ctacagctgc    660
caggtcacgc atgaagggag caccgtggag aagacagtgg cccctgcaga atgctct      717

<210> SEQ ID NO 96
<211> LENGTH: 239
<212> TYPE: PRT
<213> ORGANISM: Mus musculus

<400> SEQUENCE: 96

Met Asp Met Arg Val Pro Ala Gln Leu Leu Gly Leu Leu Leu Leu Trp
1               5                   10                  15

Leu Arg Gly Ala Arg Cys Gln Ala Val Leu Thr Gln Pro Ser Ser Val
            20                  25                  30

Ser Gly Ala Pro Gly Arg Arg Val Thr Ile Ser Cys Thr Gly Ser Ser
        35                  40                  45

Ser Asn Ile Gly Ala Gly Tyr Asp Val His Trp Tyr Gln Gln Leu Pro
    50                  55                  60

Gly Lys Ala Pro Lys Leu Val Ile Ser Ala Asn Thr Asn Arg Pro Ser
```

```
                65                  70                  75                  80
Gly Val Pro Asp Arg Phe Ser Gly Ser Lys Ser Gly Thr Ser Ala Ser
                    85                  90                  95

Leu Ala Ile Thr Gly Leu Gln Ala Glu Asp Glu Ala Asp Tyr Tyr Cys
                100                 105                 110

Gln Ser Tyr Asp Asn Ser Val Ser Ala Tyr Val Phe Gly Thr Gly Thr
                115                 120                 125

Lys Val Thr Val Leu Gly Gln Pro Lys Ala Ala Pro Ser Val Thr Leu
            130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Ser Ser Pro Val Lys Ala Gly Val Glu Thr Thr Pro Ser
                180                 185                 190

Lys Gln Ser Asn Asn Lys Tyr Ala Ala Ser Ser Tyr Leu Ser Leu Thr
                195                 200                 205

Pro Glu Gln Trp Lys Ser His Lys Ser Tyr Ser Cys Gln Val Thr His
            210                 215                 220

Glu Gly Ser Thr Val Glu Lys Thr Val Ala Pro Ala Glu Cys Ser
225                 230                 235

<210> SEQ ID NO 97
<211> LENGTH: 717
<212> TYPE: DNA
<213> ORGANISM: Mus musculus

<400> SEQUENCE: 97
atggacatga gggtgcccgc tcagctcctg gggctcctgc tgctgtggct gagaggtgcg      60
cgctgtcaga gcgctttgac tcagacaccc tcagtgtctg gaccccccgg gcagagggtc     120
accatctcct gcactgggag cagatccaac atcggggcag gatatgatgt acagtggtac     180
cagcagtttc ctggaacagc ccccgactc ctcatctatg ctaataacat tcgatcctca     240
ggggtccctg accgattctc tggctccaag tctggcacct cagcctccct ggccatcact     300
ggactccagg ctgaggatga ggctacttat tactgccagt cctatgacag aagtctcagt     360
ggttatgtct tcggaactgg gaccgaggtc accgtcgtag gtcagcccaa ggctgccccc     420
tcggtcacgc tcttcccacc ctcctctgag gagcttcaag ccaacaaggc cacactggtg     480
tgtctcataa gtgacttcta cccgggagcc gtgacagtgg cctggaaggc agatagcagc     540
cccgtcaagg cgggagtgga gaccaccaca ccctccaaac aaagcaacaa caagtacgcg     600
gccagcagct acctgagcct gacgcctgag cagtggaagt cccacaaaag ctacagctgc     660
caggtcacgc atgaagggag caccgtggag aagacagtgg cccctgcaga atgctct      717

<210> SEQ ID NO 98
<211> LENGTH: 239
<212> TYPE: PRT
<213> ORGANISM: Mus musculus

<400> SEQUENCE: 98

Met Asp Met Arg Val Pro Ala Gln Leu Leu Gly Leu Leu Leu Leu Trp
1               5                   10                  15

Leu Arg Gly Ala Arg Cys Gln Ser Ala Leu Thr Gln Thr Pro Ser Val
                20                  25                  30

Ser Gly Thr Pro Gly Gln Arg Val Thr Ile Ser Cys Thr Gly Ser Arg
                35                  40                  45
```

Ser Asn Ile Gly Ala Gly Tyr Asp Val Gln Trp Tyr Gln Gln Phe Pro
         50                  55                  60

Gly Thr Ala Pro Arg Leu Leu Ile Tyr Ala Asn Asn Ile Arg Ser Ser
 65                  70                  75                  80

Gly Val Pro Asp Arg Phe Ser Gly Ser Lys Ser Gly Thr Ser Ala Ser
                 85                  90                  95

Leu Ala Ile Thr Gly Leu Gln Ala Glu Asp Glu Ala Thr Tyr Tyr Cys
            100                 105                 110

Gln Ser Tyr Asp Arg Ser Leu Ser Gly Tyr Val Phe Gly Thr Gly Thr
        115                 120                 125

Glu Val Thr Val Val Gly Gln Pro Lys Ala Ala Pro Ser Val Thr Leu
    130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Ser Ser Pro Val Lys Ala Gly Val Glu Thr Thr Thr Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Lys Ser Tyr Ser Cys Gln Val Thr His
    210                 215                 220

Glu Gly Ser Thr Val Glu Lys Thr Val Ala Pro Ala Glu Cys Ser
225                 230                 235

<210> SEQ ID NO 99
<211> LENGTH: 717
<212> TYPE: DNA
<213> ORGANISM: Mus musculus

<400> SEQUENCE: 99
atggacatga gggtgcccgc tcagctcctg gggctcctgc tgctgtggct gagaggtgcg      60
cgctgtcagt ctgtgttgac gcagccgccc tcagtgtctg ggccccagg gcagagggtc     120 accatctcct gcactgggag cagctccaac atcggggcag gttatgatgt cactggtac     180 cagcagcttc caagaacagc ccccaaactc ctcatctatg gtgacaccaa tcggccctca     240
ggggtccctg accgattctc tggctccaag tctggcacct cagcctccct ggccatcact     300
gggctccaga ctgaggatga ggctgattat tattgccagt cctatgacag cagcctgagg     360
gcttatgtct tcggaactgg gaccaaggtc accgtcctag gtcagcccaa ggctgccccc     420
tcggtcacgc tcttcccacc ctcctctgag gagcttcaag ccaacaaggc cacactggtg     480
tgtctcataa gtgacttcta cccgggagcc gtgacagtgg cctggaaggc agatagcagc     540
cccgtcaagg cgggagtgga gaccaccaca ccctccaaac aaagcaacaa caagtacgcg     600
gccagcagct acctgagcct gacgcctgag cagtggaagt cccacaaaag ctacagctgc     660
caggtcacgc atgaagggag caccgtggag aagacagtgg cccctgcaga atgctct       717

<210> SEQ ID NO 100
<211> LENGTH: 239
<212> TYPE: PRT
<213> ORGANISM: Mus musculus

<400> SEQUENCE: 100

Met Asp Met Arg Val Pro Ala Gln Leu Leu Gly Leu Leu Leu Leu Trp
 1               5                  10                  15

-continued

Leu Arg Gly Ala Arg Cys Gln Ser Val Leu Thr Gln Pro Pro Ser Val
              20                  25                  30

Ser Gly Ala Pro Gly Gln Arg Val Thr Ile Ser Cys Thr Gly Ser Ser
         35                  40                  45

Ser Asn Ile Gly Ala Gly Tyr Asp Val His Trp Tyr Gln Gln Leu Pro
     50                  55                  60

Arg Thr Ala Pro Lys Leu Leu Ile Tyr Gly Asp Thr Asn Arg Pro Ser
65                  70                  75                  80

Gly Val Pro Asp Arg Phe Ser Gly Ser Lys Ser Gly Thr Ser Ala Ser
                 85                  90                  95

Leu Ala Ile Thr Gly Leu Gln Thr Glu Asp Glu Ala Asp Tyr Tyr Cys
             100                 105                 110

Gln Ser Tyr Asp Ser Ser Leu Arg Ala Tyr Val Phe Gly Thr Gly Thr
         115                 120                 125

Lys Val Thr Val Leu Gly Gln Pro Lys Ala Ala Pro Ser Val Thr Leu
130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Ser Ser Pro Val Lys Ala Gly Val Glu Thr Thr Thr Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Lys Ser Tyr Ser Cys Gln Val Thr His
    210                 215                 220

Glu Gly Ser Thr Val Glu Lys Thr Val Ala Pro Ala Glu Cys Ser
225                 230                 235

<210> SEQ ID NO 101
<211> LENGTH: 717
<212> TYPE: DNA
<213> ORGANISM: Mus musculus

<400> SEQUENCE: 101
atggacatga gggtgcccgc tcagctcctg gggctcctgc tgctgtggct gagaggtgcg      60
cgctgtcagt ctgtcgtgac gcagccgccc tcagtgtctg ggccccagg cagagggtc      120
accatctcct gcactgggag cagctccaac atcggggcag gttatgatgt tcactggtac     180
cagcagcttc caggagcagc ccccaaagtc ctcatctttg gtaacaacaa tcggccctca     240
ggaatccctg accgagtctc tggctccaag tctggcacct cagcctccct ggccatcagt     300
ggcctccaga ctgaggatga ggctgtttat tactgccagt cctatgacag cagcctgagt     360
gcttatgtct tcggaggtgg gacccaggtc accgtccttg gtcagcccaa ggctgccccc     420
tcggtcacgc tcttcccacc ctcctctgag gagcttcaag ccaacaaggc cacactggtg     480
tgtctcataa gtgacttcta cccgggagcc gtgacagtgg cctggaaggc agatagcagc     540
cccgtcaagg cgggagtgga gaccaccaca ccctccaaac aaagcaacaa caagtacgcg     600
gccagcagct acctgagcct gacgcctgag cagtggaagt cccacaaaag ctacagctgc     660
caggtcacgc atgaagggag caccgtggag aagacagtgg cccctgcaga atgctct       717

<210> SEQ ID NO 102
<211> LENGTH: 239
<212> TYPE: PRT
<213> ORGANISM: Mus musculus

<400> SEQUENCE: 102

```
Met Asp Met Arg Val Pro Ala Gln Leu Leu Gly Leu Leu Leu Trp
1               5                   10                  15
Leu Arg Gly Ala Arg Cys Gln Ser Val Val Thr Gln Pro Pro Ser Val
            20                  25                  30
Ser Gly Ala Pro Gly Gln Arg Val Thr Ile Ser Cys Thr Gly Ser Ser
        35                  40                  45
Ser Asn Ile Gly Ala Gly Tyr Asp Val His Trp Tyr Gln Gln Leu Pro
    50                  55                  60
Gly Ala Ala Pro Lys Val Leu Ile Phe Gly Asn Asn Asn Arg Pro Ser
65                  70                  75                  80
Gly Ile Pro Asp Arg Val Ser Gly Ser Lys Ser Gly Thr Ser Ala Ser
                85                  90                  95
Leu Ala Ile Ser Gly Leu Gln Thr Glu Asp Glu Ala Val Tyr Tyr Cys
            100                 105                 110
Gln Ser Tyr Asp Ser Ser Leu Ser Ala Tyr Val Phe Gly Gly Gly Thr
        115                 120                 125
Gln Val Thr Val Leu Gly Gln Pro Lys Ala Ala Pro Ser Val Thr Leu
    130                 135                 140
Phe Pro Pro Ser Ser Glu Glu Leu Gln Ala Asn Lys Ala Thr Leu Val
145                 150                 155                 160
Cys Leu Ile Ser Asp Phe Tyr Pro Gly Ala Val Thr Val Ala Trp Lys
                165                 170                 175
Ala Asp Ser Ser Pro Val Lys Ala Gly Val Glu Thr Thr Thr Pro Ser
            180                 185                 190
Lys Gln Ser Asn Asn Lys Tyr Ala Ala Ser Ser Tyr Leu Ser Leu Thr
        195                 200                 205
Pro Glu Gln Trp Lys Ser His Lys Ser Tyr Ser Cys Gln Val Thr His
    210                 215                 220
Glu Gly Ser Thr Val Glu Lys Thr Val Ala Pro Ala Glu Cys Ser
225                 230                 235
```

<210> SEQ ID NO 103
<211> LENGTH: 720
<212> TYPE: DNA
<213> ORGANISM: Mus musculus

<400> SEQUENCE: 103

```
atggacatga gggtgcccgc tcagctcctg gggctcctgc tgctgtggct gagaggtgcg    60
cgctgtaatt ttatgctgac tcagccccac tctgtgtcgg agtctccggg gaagacggtt   120
accatctcct gcacccgcaa cagtggcagc attgccagca actatgtgca gtggtaccag   180
cagcgcccgg gcagttcccc cgccactgtg atctatgagg ataatcaaag accctctggg   240
gtccctgatc ggttctctgg ctccatcgac atctcctcca actctgcctc cctcaccatc   300
tctggcctga gactgaggga cgaggctgac tactactgtc agtcttatga tagcagcaat   360
cccttttatg tcttcggaac tgggaccaag gtcaccgtcc tcggtcagcc caaggctgcc   420
ccctcggtca cgctcttccc accctcctct gaggagcttc aagccaacaa ggccacactg   480
gtgtgtctca taagtgactt ctacccggga gccgtgacag tggcctggaa ggcagatagc   540
agccccgtca aggcgggagt ggagaccacc acacctccaa acaaagcaa caacaagtac   600
gcggccagca gctacctgag cctgacgcct gagcagtgga gtcccacaa aagctacagc   660
tgccaggtca cgcatgaagg gagcaccgtg gagaagacag tggcccctgc agaatgctct   720
```

<210> SEQ ID NO 104
<211> LENGTH: 240
<212> TYPE: PRT
<213> ORGANISM: Mus musculus

<400> SEQUENCE: 104

Met Asp Met Arg Val Pro Ala Gln Leu Leu Gly Leu Leu Leu Leu Trp
1               5                   10                  15

Leu Arg Gly Ala Arg Cys Asn Phe Met Leu Thr Gln Pro His Ser Val
            20                  25                  30

Ser Glu Ser Pro Gly Lys Thr Val Thr Ile Ser Cys Thr Arg Asn Ser
        35                  40                  45

Gly Ser Ile Ala Ser Asn Tyr Val Gln Trp Tyr Gln Gln Arg Pro Gly
    50                  55                  60

Ser Ser Pro Ala Thr Val Ile Tyr Glu Asp Asn Gln Arg Pro Ser Gly
65                  70                  75                  80

Val Pro Asp Arg Phe Ser Gly Ser Ile Asp Ile Ser Ser Asn Ser Ala
                85                  90                  95

Ser Leu Thr Ile Ser Gly Leu Lys Thr Glu Asp Glu Ala Asp Tyr Tyr
            100                 105                 110

Cys Gln Ser Tyr Asp Ser Ser Asn Pro Phe Tyr Val Phe Gly Thr Gly
        115                 120                 125

Thr Lys Val Thr Val Leu Gly Gln Pro Lys Ala Ala Pro Ser Val Thr
    130                 135                 140

Leu Phe Pro Pro Ser Ser Glu Glu Leu Gln Ala Asn Lys Ala Thr Leu
145                 150                 155                 160

Val Cys Leu Ile Ser Asp Phe Tyr Pro Gly Ala Val Thr Val Ala Trp
                165                 170                 175

Lys Ala Asp Ser Ser Pro Val Lys Ala Gly Val Glu Thr Thr Thr Pro
            180                 185                 190

Ser Lys Gln Ser Asn Asn Lys Tyr Ala Ala Ser Ser Tyr Leu Ser Leu
        195                 200                 205

Thr Pro Glu Gln Trp Lys Ser His Lys Ser Tyr Ser Cys Gln Val Thr
    210                 215                 220

His Glu Gly Ser Thr Val Glu Lys Thr Val Ala Pro Ala Glu Cys Ser
225                 230                 235                 240

<210> SEQ ID NO 105
<211> LENGTH: 717
<212> TYPE: DNA
<213> ORGANISM: Mus musculus

<400> SEQUENCE: 105
atggacatga gggtgcccgc tcagctcctg gggctcctgc tgctgtggct gagaggtgcg      60
cgctgtaatt ttatgctgac tcagccccac tctgtgtcgg agtctccggg aagacgatt     120 accatctcct gcacccgcag cagtggcagc atttccagca actatgtgca gtggtaccaa    180
cagcgcccgg gcagctcccc caggatcgta atgtctgagg atgaccaaag accctctggg    240
gtctctgatc gattctctgg ctccatcgac atatcctcca actctgcctt cctcaccatc    300
tctggactga agcctgagga cgagggtgat tactactgtc agtcttatga taccgacatc    360
ccttatgtct tcggaactgg gaccaaggtc accgtcctag gtcagcccaa ggctgccccc    420
tcggtcacgc tcttcccacc ctcctctgag gagcttcaag ccaacaaggc cacactggtg    480
tgtctcataa gtgacttcta cccgggagcc gtgacagtgg cctggaaggc agatagcagc    540
cccgtcaagg cgggagtgga gaccaccaca ccctccaaac aaagcaacaa caagtacgcg    600

```
gccagcagct acctgagcct gacgcctgag cagtggaagt cccacaaaag ctacagctgc    660
caggtcacgc atgaagggag caccgtggag aagacagtgg cccctgcaga atgctct       717

<210> SEQ ID NO 106
<211> LENGTH: 239
<212> TYPE: PRT
<213> ORGANISM: Mus musculus

<400> SEQUENCE: 106

Met Asp Met Arg Val Pro Ala Gln Leu Leu Gly Leu Leu Leu Leu Trp
1               5                   10                  15

Leu Arg Gly Ala Arg Cys Asn Phe Met Leu Thr Gln Pro His Ser Val
            20                  25                  30

Ser Glu Ser Pro Gly Lys Thr Ile Thr Ile Ser Cys Thr Arg Ser Ser
        35                  40                  45

Gly Ser Ile Ser Ser Asn Tyr Val Gln Trp Tyr Gln Gln Arg Pro Gly
    50                  55                  60

Ser Ser Pro Arg Ile Val Met Ser Glu Asp Asp Gln Arg Pro Ser Gly
65                  70                  75                  80

Val Ser Asp Arg Phe Ser Gly Ser Ile Asp Ile Ser Ser Asn Ser Ala
                85                  90                  95

Phe Leu Thr Ile Ser Gly Leu Lys Pro Glu Asp Glu Gly Asp Tyr Tyr
            100                 105                 110

Cys Gln Ser Tyr Asp Thr Asp Ile Pro Tyr Val Phe Gly Thr Gly Thr
        115                 120                 125

Lys Val Thr Val Leu Gly Gln Pro Lys Ala Ala Pro Ser Val Thr Leu
    130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Ser Ser Pro Val Lys Ala Gly Val Glu Thr Thr Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Lys Ser Tyr Ser Cys Gln Val Thr His
    210                 215                 220

Glu Gly Ser Thr Val Glu Lys Thr Val Ala Pro Ala Glu Cys Ser
225                 230                 235

<210> SEQ ID NO 107
<211> LENGTH: 708
<212> TYPE: DNA
<213> ORGANISM: Mus musculus

<400> SEQUENCE: 107
atggacatga gggtgcccgc tcagctcctg ggctcctgc tgctgtggct gagaggtgcg    60
cgctgtgaca tccagatgac ccagtctcca tcttccctgt ctgcatctgt aggagacaga   120
atcaccataa gttgccaggc gagtcaagac attgacaact atttaaattg gtatcagcag   180
aaatcaggga agcccctaa actcctgatc tacgatgcat acaatttgaa ggcaggggtc    240
ccctcaagat tccgtggaag tagatctggg acagattttt ttttgactat cagcagcctg   300
cagcctgaag attttgcaac ctattactgt ctacagcaat atagatatcc cctcactttc   360 ggcgaggga ctaaggtgga gatcaaacgt acgtggctg caccatctgt cttcatcttc    420
ccgccatctg atgagcagtt gaaatctgga actgcctctg ttgtgtgcct gctgaataac   480
```

```
ttctatccca gagaggccaa agtacagtgg aaggtggata acgccctcca atcgggtaac      540
tcccaggaga gtgtcacaga gcaggacagc aaggacagca cctacagcct cagcagcacc      600
ctgacgctga gcaaagcaga ctacgagaaa cacaaagtct acgcctgcga agtcacccat      660
cagggcctga gctcgcccgt cacaaagagc ttcaacaggg gagagtgt                   708
```

<210> SEQ ID NO 108
<211> LENGTH: 236
<212> TYPE: PRT
<213> ORGANISM: Mus musculus

<400> SEQUENCE: 108

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
                20                  25                  30

Leu Ser Ala Ser Val Gly Asp Arg Ile Thr Ile Ser Cys Gln Ala Ser
            35                  40                  45

Gln Asp Ile Asp Asn Tyr Leu Asn Trp Tyr Gln Gln Lys Ser Gly Lys
        50                  55                  60

Ala Pro Lys Leu Leu Ile Tyr Asp Ala Tyr Asn Leu Lys Ala Gly Val
65                  70                  75                  80

Pro Ser Arg Phe Arg Gly Ser Arg Ser Gly Thr Asp Phe Phe Leu Thr
                85                  90                  95

Ile Ser Ser Leu Gln Pro Glu Asp Phe Ala Thr Tyr Tyr Cys Leu Gln
                100                 105                 110

Gln Tyr Arg Tyr Pro Leu Thr Phe Gly Gly Gly Thr Lys Val Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235
```

<210> SEQ ID NO 109
<211> LENGTH: 717
<212> TYPE: DNA
<213> ORGANISM: Mus musculus

<400> SEQUENCE: 109

```
atggacatga gggtgcccgc tcagctcctg gggctcctgc tgctgtggct gagaggtgcg      60
cgctgtcagt ctgtgttgac gcagccgccc tcagtgtctg ggccccaggc agagggtc       120 accatctcct gcactggggg cagctccaac atcggggcag gttatgaagt ccactggtac     180
cagttggtcc caggaagagc ccccagattc ctcattcatg gtgacaacga tcggccctca     240
ggggtccctg accgattctc ggcctccgag tctggctcct catccttcct ggccatcagt     300
```

```
gggctccagg atgatgatga ggctgattat tactgccagt cctatgacac cagcctgagt    360
gcttgggtgt tcggcggcgg gaccaagctg accgtcctag gtcagcccaa ggctgccccc    420
tcggtcacgc tcttcccacc ctcctctgag gagcttcaag ccaacaaggc cacactggtg    480
tgtctcataa gtgacttcta cccgggagcc gtgacagtgg cctggaaggc agatagcagc    540
cccgtcaagg cgggagtgga gaccaccaca ccctccaaac aaagcaacaa caagtacgcg    600
gccagcagct acctgagcct gacgcctgag cagtggaagt cccacaaaag ctacagctgc    660
caggtcacgc atgaagggag caccgtggag aagacagtgg cccctgcaga atgctct      717
```

```
<210> SEQ ID NO 110
<211> LENGTH: 239
<212> TYPE: PRT
<213> ORGANISM: Mus musculus

<400> SEQUENCE: 110
```

```
Met Asp Met Arg Val Pro Ala Gln Leu Leu Gly Leu Leu Leu Leu Trp
1               5                   10                  15

Leu Arg Gly Ala Arg Cys Gln Ser Val Leu Thr Gln Pro Pro Ser Val
                20                  25                  30

Ser Gly Ala Pro Gly Gln Arg Val Thr Ile Ser Cys Thr Gly Gly Ser
            35                  40                  45

Ser Asn Ile Gly Ala Gly Tyr Glu Val His Trp Tyr Gln Leu Val Pro
        50                  55                  60

Gly Arg Ala Pro Arg Phe Leu Ile His Gly Asp Asn Asp Arg Pro Ser
65                  70                  75                  80

Gly Val Pro Asp Arg Phe Ser Ala Ser Glu Ser Gly Ser Ser Ser Phe
                85                  90                  95

Leu Ala Ile Ser Gly Leu Gln Asp Asp Glu Ala Asp Tyr Tyr Cys
            100                 105                 110

Gln Ser Tyr Asp Thr Ser Leu Ser Ala Trp Val Phe Gly Gly Gly Thr
        115                 120                 125

Lys Leu Thr Val Leu Gly Gln Pro Lys Ala Ala Pro Ser Val Thr Leu
    130                 135                 140

Phe Pro Pro Ser Ser Glu Glu Leu Gln Ala Asn Lys Ala Thr Leu Val
145                 150                 155                 160

Cys Leu Ile Ser Asp Phe Tyr Pro Gly Ala Val Thr Val Ala Trp Lys
                165                 170                 175

Ala Asp Ser Ser Pro Val Lys Ala Gly Val Glu Thr Thr Thr Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Lys Ser Tyr Ser Cys Gln Val Thr His
    210                 215                 220

Glu Gly Ser Thr Val Glu Lys Thr Val Ala Pro Ala Glu Cys Ser
225                 230                 235
```

```
<210> SEQ ID NO 111
<211> LENGTH: 711
<212> TYPE: DNA
<213> ORGANISM: Mus musculus

<400> SEQUENCE: 111
```

```
atggacatga gggtgcccgc tcagctcctg gggctcctgc tgctgtggct gagaggtgcg    60
cgctgtgaca tccagatgac ccagtctcca ggcaccctgt ctttgtctcc agggaaaga    120 gccaccctct cctgcaggac cagtcagagt gttagcagta cctccgtagc ctggtaccag    180
```

```
cagaaacctg gccaggctcc caggctcctc atgtatgatg catccagtag ggccgctggc    240
atcccagaca ggttcagtgg cagtgggtct gtgacagact tcactctcac catcagcaga    300
ctggagcctg aagattttgc aacttactac tgtcaacaga gttacagtct tccgtacact    360
tttggccagg ggaccaaggt ggagatcaaa cgtacggtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg t             711
```

<210> SEQ ID NO 112
<211> LENGTH: 237
<212> TYPE: PRT
<213> ORGANISM: Mus musculus

<400> SEQUENCE: 112

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Gly Thr
            20                  25                  30

Leu Ser Leu Ser Pro Gly Glu Arg Ala Thr Leu Ser Cys Arg Thr Ser
        35                  40                  45

Gln Ser Val Ser Ser Thr Ser Val Ala Trp Tyr Gln Gln Lys Pro Gly
    50                  55                  60

Gln Ala Pro Arg Leu Leu Met Tyr Asp Ala Ser Ser Arg Ala Ala Gly
65                  70                  75                  80

Ile Pro Asp Arg Phe Ser Gly Ser Gly Ser Val Thr Asp Phe Thr Leu
                85                  90                  95

Thr Ile Ser Arg Leu Glu Pro Glu Asp Phe Ala Thr Tyr Tyr Cys Gln
            100                 105                 110

Gln Ser Tyr Ser Leu Pro Tyr Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 113
<211> LENGTH: 711
<212> TYPE: DNA
<213> ORGANISM: Mus musculus

<400> SEQUENCE: 113

```
atggacatga gggtgcccgc tcagctcctg gggctcctgc tgctgtggct gagaggtgcg    60
cgctgtaaca tccagatgac ccagtctcca ggcaccctgt ctttgtctcc aggggaaaga   120
gccaccctct cctgcagggc cagtcagagt gttaccggca accacttagc ctggtaccag   180
cagaagcctg gccaggctcc cagggtcctc atgtatgata catccagtag gccactggc   240 atcccagaca ggttcagtgg cagtgggtct gggacagatt tcactctcac catcagcagc   300
ctgcagcctg aagatattgc aacatattac tgtcaacagt ttgataatct cccgtacact   360
tttggccagg ggaccaagct ggagatcaaa cgtacggtgg ctgcaccatc tgtcttcatc   420
ttcccgccat ctgatgagca gttgaaatct ggaactgcct ctgttgtgtg cctgctgaat   480
aacttctatc ccagagaggc caaagtacag tggaaggtgg ataacgccct ccaatcgggt   540
aactcccagg agagtgtcac agagcaggac agcaaggaca gcacctacag cctcagcagc   600
accctgacgc tgagcaaagc agactacgag aaacacaaag tctacgcctg cgaagtcacc   660
catcagggcc tgagctcgcc cgtcacaaag agcttcaaca ggggagagtg t            711
```

<210> SEQ ID NO 114
<211> LENGTH: 237
<212> TYPE: PRT
<213> ORGANISM: Mus musculus

<400> SEQUENCE: 114

```
Met Asp Met Arg Val Pro Ala Gln Leu Leu Gly Leu Leu Leu Leu Trp
1               5                   10                  15

Leu Arg Gly Ala Arg Cys Asn Ile Gln Met Thr Gln Ser Pro Gly Thr
            20                  25                  30

Leu Ser Leu Ser Pro Gly Glu Arg Ala Thr Leu Ser Cys Arg Ala Ser
        35                  40                  45

Gln Ser Val Thr Gly Asn His Leu Ala Trp Tyr Gln Gln Lys Pro Gly
    50                  55                  60

Gln Ala Pro Arg Val Leu Met Tyr Asp Thr Ser Ser Arg Ala Thr Gly
65                  70                  75                  80

Ile Pro Asp Arg Phe Ser Gly Ser Gly Ser Gly Thr Asp Phe Thr Leu
                85                  90                  95

Thr Ile Ser Ser Leu Gln Pro Glu Asp Ile Ala Thr Tyr Tyr Cys Gln
            100                 105                 110

Gln Phe Asp Asn Leu Pro Tyr Thr Phe Gly Gln Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 115
<211> LENGTH: 708

```
<212> TYPE: DNA
<213> ORGANISM: Mus musculus

<400> SEQUENCE: 115
atggacatga gggtgcccgc tcagctcctg gggctcctgc tgctgtggct gagaggtgcg      60
cgctgtgaca tccagatgac ccagtctcca tcctccctgt cagcatctgt aggagacaga     120
gtcaccatta cttgtcgggc aagtcgagac attagtgtct atgtaaattg gtatcaactg     180
aaaccagggc aggcccctag actcctcatc tatggtgcat ccaatttggg gtttggtgtc     240
ccatcccgtt tcagcggcag tggatatggg acagatttcg ctctcaccat cagcggtctg     300
cagcctgaag attttgcaac ttactcctgt caacagagtt atagtatccc tctgacgttc     360
ggccaaggga ccagggtaga caccaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgt                  708

<210> SEQ ID NO 116
<211> LENGTH: 236
<212> TYPE: PRT
<213> ORGANISM: Mus musculus

<400> SEQUENCE: 116

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Arg Asp Ile Ser Val Tyr Val Asn Trp Tyr Gln Leu Lys Pro Gly Gln
    50                  55                  60

Ala Pro Arg Leu Leu Ile Tyr Gly Ala Ser Asn Leu Gly Phe Gly Val
65                  70                  75                  80

Pro Ser Arg Phe Ser Gly Ser Gly Tyr Gly Thr Asp Phe Ala Leu Thr
                85                  90                  95

Ile Ser Gly Leu Gln Pro Glu Asp Phe Ala Thr Tyr Ser Cys Gln Gln
            100                 105                 110

Ser Tyr Ser Ile Pro Leu Thr Phe Gly Gln Gly Thr Arg Val Asp Thr
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
```

<210> SEQ ID NO 117
<211> LENGTH: 708
<212> TYPE: DNA
<213> ORGANISM: Mus musculus

<400> SEQUENCE: 117

```
atggacatga gggtgcccgc tcagctcctg gggctcctgc tgctgtggct gagaggtgcg    60
cgctgtgaca tccagatgac ccagtctcca gactccctgt ctgcatctgt aggagacaga   120
atcaccataa gttgccaggc gagtcaagac attgacaact atttaaattg gtatcagcag   180
agatcaggga aagcccctaa actcctgatc tacgatgcat acaatttgaa ggcaggggtc   240
ccctcaagat ccgtggaagt agatctgggg acagattttt ttttgaccat cagcagcctg   300
cagcctgaag attttggaac ttattactgt ctacagcaga gtagttaccc cctcacgttc   360
ggccaaggga ccaaggtgga aatcaaacgt acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt             708
```

<210> SEQ ID NO 118
<211> LENGTH: 236
<212> TYPE: PRT
<213> ORGANISM: Mus musculus

<400> SEQUENCE: 118

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Asp Ser
            20                  25                  30

Leu Ser Ala Ser Val Gly Asp Arg Ile Thr Ile Ser Cys Gln Ala Ser
        35                  40                  45

Gln Asp Ile Asp Asn Tyr Leu Asn Trp Tyr Gln Gln Arg Ser Gly Lys
    50                  55                  60

Ala Pro Lys Leu Leu Ile Tyr Asp Ala Tyr Asn Leu Lys Ala Gly Val
65                  70                  75                  80

Pro Ser Arg Phe Arg Gly Ser Arg Ser Gly Thr Asp Phe Phe Leu Thr
                85                  90                  95

Ile Ser Ser Leu Gln Pro Glu Asp Phe Gly Thr Tyr Tyr Cys Leu Gln
            100                 105                 110

Gln Ser Ser Tyr Pro Leu Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205
```

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 119
<211> LENGTH: 708
<212> TYPE: DNA
<213> ORGANISM: Mus musculus

<400> SEQUENCE: 119
atggacatga gggtgcccgc tcagctcctg gggctcctgc tgctgtggct gagaggtgcg       60
cgctgtgaca tccagatgac ccagtctcca gctaccctgt ctctgtctcc aggggaaaga     120
gccaccctct cctgcagggc cagtcggagt gttagcagca acttagcctg gtaccagcag     180
aaacctggcc gggcccccag gctcctcatg tttggtgcat ccaccagggc cactggtgtc     240
ccagcccggt tcagtggcag tgggtctggg acagagttca ctctcaccat cagcagcctg     300
cagtctgagg atgttgcaac ttattactgt cagcacgaca tgagttgcc gctcactttc       360 ggcggaggga caaaggtgga gctcaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgt               708

<210> SEQ ID NO 120
<211> LENGTH: 236
<212> TYPE: PRT
<213> ORGANISM: Mus musculus

<400> SEQUENCE: 120

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ala Thr
            20                  25                  30

Leu Ser Leu Ser Pro Gly Glu Arg Ala Thr Leu Ser Cys Arg Ala Ser
        35                  40                  45

Arg Ser Val Ser Ser Asn Leu Ala Trp Tyr Gln Gln Lys Pro Gly Arg
    50                  55                  60

Ala Pro Arg Leu Leu Met Phe Gly Ala Ser Thr Arg Ala Thr Gly Val
65                  70                  75                  80

Pro Ala Arg Phe Ser Gly Ser Gly Ser Gly Thr Glu Phe Thr Leu Thr
                85                  90                  95

Ile Ser Ser Leu Gln Ser Glu Asp Val Ala Thr Tyr Tyr Cys Gln His
            100                 105                 110

Asp Asn Glu Leu Pro Leu Thr Phe Gly Gly Gly Thr Lys Val Glu Leu
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

```
Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235
```

<210> SEQ ID NO 121
<211> LENGTH: 720
<212> TYPE: DNA
<213> ORGANISM: Homo sapiens

<400> SEQUENCE: 121

```
atggacatga gggtgcccgc tcagctcctg gggctcctgc tgctgtggct gagaggtgcg      60
cgctgtgaca ttcagatgac tcagtccccc tcctctctct ccgcttcagt cggggacaga     120
gtgactatca gctgccgagc cagtgagtca gtcgataatt atggctcatc cttcatgaat     180
tggtttcagc agaagccggg aaaagcccca aagctcctca tttacgccgc ttcaaaccag     240
ggttcagggg ttccctcccg cttctccggc tctgggtctg gcactgattt tacactgact     300
attagctccc tccagcctga agactttgct acctattttt gccagcagag caaagaggtc     360
ccctatacct tcggacaggg tactaaactg gagattaaac gtacggtggc tgcaccatct     420
gtcttcatct tcccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga aacacaaagt ctacgcctgc     660
gaagtcaccc atcagggcct gagctcgccc gtcacaaaga gcttcaacag gggagagtgt     720
```

<210> SEQ ID NO 122
<211> LENGTH: 240
<212> TYPE: PRT
<213> ORGANISM: Homo sapiens

<400> SEQUENCE: 122

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Ser Cys Arg Ala Ser
        35                  40                  45

Glu Ser Val Asp Asn Tyr Gly Ser Ser Phe Met Asn Trp Phe Gln Gln
    50                  55                  60

Lys Pro Gly Lys Ala Pro Lys Leu Leu Ile Tyr Ala Ala Ser Asn Gln
65                  70                  75                  80

Gly Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Phe Cys Gln Gln Ser Lys Glu Val Pro Tyr Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
```

```
            145                 150                 155                 160
Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

<210> SEQ ID NO 123
<211> LENGTH: 16
<212> TYPE: PRT
<213> ORGANISM: Mus musculus

<400> SEQUENCE: 123

Arg Ser Ser Gln Ser Leu Glu His Ser Asn Gly Asn Thr Tyr Leu His
1               5                   10                  15

<210> SEQ ID NO 124
<211> LENGTH: 7
<212> TYPE: PRT
<213> ORGANISM: Mus musculus

<400> SEQUENCE: 124

Lys Val Ser Asn Arg Phe Ser
1               5

<210> SEQ ID NO 125
<211> LENGTH: 9
<212> TYPE: PRT
<213> ORGANISM: Mus musculus

<400> SEQUENCE: 125

Ser Gln Ser Thr His Val Pro Leu Thr
1               5

<210> SEQ ID NO 126
<211> LENGTH: 112
<212> TYPE: PRT
<213> ORGANISM: Mus musculus

<400> SEQUENCE: 126

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Val Glu Leu Lys
            100                 105                 110
```

```
<210> SEQ ID NO 127
<211> LENGTH: 5
<212> TYPE: PRT
<213> ORGANISM: Mus musculus

<400> SEQUENCE: 127

Thr Tyr Gly Met Ser
1               5

<210> SEQ ID NO 128
<211> LENGTH: 17
<212> TYPE: PRT
<213> ORGANISM: Mus musculus

<400> SEQUENCE: 128

Trp Ile Asn Thr Tyr Ser Gly Val Pro Thr Tyr Ala Asp Asp Phe Lys
1               5                   10                  15

Gly

<210> SEQ ID NO 129
<211> LENGTH: 12
<212> TYPE: PRT
<213> ORGANISM: Mus musculus

<400> SEQUENCE: 129

Gly Arg Glu Tyr Tyr Tyr Gly Ser Gly Ile Ala Phe
1               5                   10

<210> SEQ ID NO 130
<211> LENGTH: 121
<212> TYPE: PRT
<213> ORGANISM: Mus musculus

<400> SEQUENCE: 130

Gln Ile His Leu Val Gln Ser Gly Pro Glu Leu Lys Lys Pro Gly Glu
1               5                   10                  15

Thr Val Lys Ile Ser Cys Lys Ala Ser Gly Phe Ser Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Val Arg Gly Arg Glu Tyr Tyr Tyr Gly Ser Gly Ile Ala Phe Trp Gly
            100                 105                 110

Gln Gly Thr Leu Val Thr Val Ser Ala
        115                 120

<210> SEQ ID NO 131
<211> LENGTH: 15
<212> TYPE: PRT
<213> ORGANISM: Mus musculus

<400> SEQUENCE: 131

Arg Ala Ser Glu Ser Val Asp Asn Tyr Gly Ser Ser Phe Met Asn
1               5                   10                  15

<210> SEQ ID NO 132
<211> LENGTH: 7
```

```
<212> TYPE: PRT
<213> ORGANISM: Mus musculus

<400> SEQUENCE: 132

Ala Ala Ser Asn Gln Gly Ser
1               5

<210> SEQ ID NO 133
<211> LENGTH: 9
<212> TYPE: PRT
<213> ORGANISM: Mus musculus

<400> SEQUENCE: 133

Gln Gln Ser Lys Glu Val Pro Tyr Thr
1               5

<210> SEQ ID NO 134
<211> LENGTH: 111
<212> TYPE: PRT
<213> ORGANISM: Mus musculus

<400> SEQUENCE: 134

Asp Ile Val Leu Thr Gln Ser Pro Pro Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ser Ser Phe Met Asn Trp Phe Gln Gln Lys Pro Gly Gln Pro Pro
        35                  40                  45

Lys Leu Leu Ile Phe Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Ala Ala Met Tyr Phe Cys Gln Gln Ser Lys
                85                  90                  95

Glu Val Pro Tyr Thr Phe Gly Gly Gly Thr Lys Leu Glu Ile Lys
            100                 105                 110

<210> SEQ ID NO 135
<211> LENGTH: 5
<212> TYPE: PRT
<213> ORGANISM: Mus musculus

<400> SEQUENCE: 135

Ser Thr Tyr Ile Ser
1               5

<210> SEQ ID NO 136
<211> LENGTH: 17
<212> TYPE: PRT
<213> ORGANISM: Mus musculus

<400> SEQUENCE: 136

Trp Ile Tyr Ala Gly Thr Gly Gly Thr Arg Tyr Asn Arg Lys Phe Thr
1               5                   10                  15

Gly

<210> SEQ ID NO 137
<211> LENGTH: 9
<212> TYPE: PRT
<213> ORGANISM: Mus musculus

<400> SEQUENCE: 137
```

```
Glu Gly Val Asp Gly Trp Phe Thr Tyr
1               5
```

\<210\> SEQ ID NO 138
\<211\> LENGTH: 118
\<212\> TYPE: PRT
\<213\> ORGANISM: Mus musculus

\<400\> SEQUENCE: 138

```
Gln Gly Gln Met Gln Gln Ser Gly Ala Glu Leu Val Lys Pro Gly Ala
1               5                   10                  15

Ser Val Gln Leu Ser Cys Lys Thr Ser Gly Phe Thr Phe Ser Ser Thr
            20                  25                  30

Tyr Ile Ser Trp Leu Lys Gln Lys Pro Gly Gln Ser Leu Glu Trp Ile
        35                  40                  45

Ala Trp Ile Tyr Ala Gly Thr Gly Thr Arg Tyr Asn Arg Lys Phe
    50                  55                  60

Thr Gly Lys Ala Gln Leu Thr Val Asp Thr Ser Ser Ser Thr Ala Tyr
65                  70                  75                  80

Met Gln Phe Ser Ser Leu Thr Thr Glu Asp Ser Ala Ile Tyr Tyr Cys
                85                  90                  95

Ala Arg Glu Gly Val Asp Gly Trp Phe Thr Tyr Trp Gly Gln Gly Thr
                100                 105                 110

Leu Val Thr Val Ser Ala
            115
```

\<210\> SEQ ID NO 139
\<211\> LENGTH: 15
\<212\> TYPE: PRT
\<213\> ORGANISM: Mus musculus

\<400\> SEQUENCE: 139

```
Arg Ala Ser Glu Ser Val Asp Asn Tyr Gly Ile Ser Phe Met Asn
1               5                   10                  15
```

\<210\> SEQ ID NO 140
\<211\> LENGTH: 7
\<212\> TYPE: PRT
\<213\> ORGANISM: Mus musculus

\<400\> SEQUENCE: 140

```
Asp Ala Ser Asn Gln Gly Tyr
1               5
```

\<210\> SEQ ID NO 141
\<211\> LENGTH: 9
\<212\> TYPE: PRT
\<213\> ORGANISM: Mus musculus

\<400\> SEQUENCE: 141

```
Gln Gln Ser Lys Glu Val Pro Tyr Thr
1               5
```

\<210\> SEQ ID NO 142
\<211\> LENGTH: 111
\<212\> TYPE: PRT
\<213\> ORGANISM: Mus musculus

\<400\> SEQUENCE: 142

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
```

```
                20                  25                  30
Gly Ile Ser Phe Met Asn Trp Phe Gln Gln Lys Pro Gly Gln Pro Pro
            35                  40                  45

Lys Leu Leu Ile Tyr Asp Ala Ser Asn Gln Gly Tyr Gly Val Pro Ala
 50                  55                  60

Arg Phe Ser Ala Ser Gly Ser Gly Thr Asp Phe Ser Leu Asn Ile His
 65                  70                  75                  80

Pro Met Glu Glu Asp Asp Ile Ala Met Tyr Phe Cys Gln Gln Ser Lys
                 85                  90                  95

Glu Val Pro Tyr Thr Phe Gly Gly Gly Thr Lys Leu Glu Ile Lys
                100                 105                 110

<210> SEQ ID NO 143
<211> LENGTH: 5
<212> TYPE: PRT
<213> ORGANISM: Mus musculus

<400> SEQUENCE: 143

Ser His Tyr Ile Ser
1               5

<210> SEQ ID NO 144
<211> LENGTH: 17
<212> TYPE: PRT
<213> ORGANISM: Mus musculus

<400> SEQUENCE: 144

Trp Ile Tyr Ala Gly Thr Gly Gly Thr Arg Tyr Asn Gln Lys Phe Thr
1               5                  10                  15

Gly

<210> SEQ ID NO 145
<211> LENGTH: 9
<212> TYPE: PRT
<213> ORGANISM: Mus musculus

<400> SEQUENCE: 145

Glu Gly Val Asp Gly Trp Phe Thr Tyr
1               5

<210> SEQ ID NO 146
<211> LENGTH: 118
<212> TYPE: PRT
<213> ORGANISM: Mus musculus

<400> SEQUENCE: 146

Gln Gly Gln Met Gln Gln Ser Gly Ala Glu Leu Val Lys Pro Gly Ala
1               5                  10                  15

Ser Val Lys Leu Ser Cys Lys Thr Ser Gly Phe Thr Phe Asn Ser His
                20                  25                  30

Tyr Ile Ser Trp Leu Lys Gln Lys Pro Gly Gln Thr Leu Glu Trp Ile
            35                  40                  45

Ala Trp Ile Tyr Ala Gly Thr Gly Gly Thr Arg Tyr Asn Gln Lys Phe
        50                  55                  60

Thr Gly Lys Ala Gln Leu Thr Val Asp Thr Ser Ser Ser Thr Ala Tyr
 65                 70                  75                  80

Met Gln Phe Ser Ser Leu Thr Thr Glu Asp Ser Ala Ile Tyr Tyr Cys
                85                  90                  95

Ala Arg Glu Gly Val Asp Gly Trp Phe Thr Tyr Trp Gly Gln Gly Thr
                100                 105                 110
```

Leu Val Thr Val Ser Ala
        115

<210> SEQ ID NO 147
<211> LENGTH: 15
<212> TYPE: PRT
<213> ORGANISM: Rattus norvegicus

<400> SEQUENCE: 147

Arg Ala Ser Gln Ser Val Ser Ile Ser Gly His Asn Leu Met His
1               5                   10                  15

<210> SEQ ID NO 148
<211> LENGTH: 7
<212> TYPE: PRT
<213> ORGANISM: Rattus norvegicus

<400> SEQUENCE: 148

Arg Ala Ser Asn Leu Pro Ser
1               5

<210> SEQ ID NO 149
<211> LENGTH: 9
<212> TYPE: PRT
<213> ORGANISM: Rattus norvegicus

<400> SEQUENCE: 149

Gln Gln Ser Arg Glu Ser Pro Trp Thr
1               5

<210> SEQ ID NO 150
<211> LENGTH: 110
<212> TYPE: PRT
<213> ORGANISM: Rattus norvegicus

<400> SEQUENCE: 150

Asp Ile Val Leu Thr Gln Ser Pro Ala Leu Ala Val Ser Leu Gly Gln
1               5                   10                  15

Arg Ala Thr Leu Ser Cys Arg Ala Ser Gln Ser Val Ser Ile Ser Gly
            20                  25                  30

His Asn Leu Met His Trp Tyr Gln Gln Lys Pro Gly Gln Gln Pro Lys
        35                  40                  45

Leu Leu Ile Tyr Arg Ala Ser Asn Leu Pro Ser Gly Ile Pro Ala Arg
    50                  55                  60

Phe Ser Gly Ser Gly Ser Gly Thr Gly Phe Thr Leu Thr Ile Asn Pro
65                  70                  75                  80

Val Gln Ala Asp Asp Ile Ala Thr Tyr Tyr Cys Gln Gln Ser Arg Glu
                85                  90                  95

Ser Pro Trp Thr Phe Gly Gly Gly Thr Thr Leu Glu Leu Lys
            100                 105                 110

<210> SEQ ID NO 151
<211> LENGTH: 10
<212> TYPE: PRT
<213> ORGANISM: Mus musculus

<400> SEQUENCE: 151

Gly Phe Pro Phe Ser Asn Tyr Gly Met Ala
1               5                   10

<210> SEQ ID NO 152
<211> LENGTH: 17

```
<212> TYPE: PRT
<213> ORGANISM: Mus musculus

<400> SEQUENCE: 152

Ser Ile Thr Tyr Asp Gly Ser Ile Thr Phe Tyr Arg Asp Ser Val Lys
1               5                   10                  15

Gly

<210> SEQ ID NO 153
<211> LENGTH: 15
<212> TYPE: PRT
<213> ORGANISM: Mus musculus

<400> SEQUENCE: 153

Ser Asp Thr Thr Asp Tyr Tyr His Gly Gly Phe Trp Phe Ala Tyr
1               5                   10                  15

<210> SEQ ID NO 154
<211> LENGTH: 124
<212> TYPE: PRT
<213> ORGANISM: Mus musculus

<400> SEQUENCE: 154

Glu Val Arg Leu Val Glu Ser Gly Gly Gly Leu Val Gln Pro Gly Arg
1               5                   10                  15

Ser Leu Lys Leu Ser Cys Ala Ala Ser Gly Phe Pro Phe Ser Asn Tyr
            20                  25                  30

Gly Met Ala Trp Val Arg Gln Ala Pro Thr Arg Gly Leu Glu Trp Val
        35                  40                  45

Ala Ser Ile Thr Tyr Asp Gly Ser Ile Thr Phe Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Ser Ser Asp Thr Thr Asp Tyr Tyr His Gly Gly Phe Trp Phe Ala
            100                 105                 110

Tyr Trp Gly Gln Gly Thr Leu Val Thr Val Ser Ser
        115                 120

<210> SEQ ID NO 155
<211> LENGTH: 5
<212> TYPE: PRT
<213> ORGANISM: Mus musculus

<400> SEQUENCE: 155

Ser Ser Tyr Ile Ser
1               5

<210> SEQ ID NO 156
<211> LENGTH: 17
<212> TYPE: PRT
<213> ORGANISM: Mus musculus

<400> SEQUENCE: 156

Trp Ile Tyr Ala Gly Thr Gly Ala Thr Arg Tyr Tyr Gln Arg Phe Thr
1               5                   10                  15

Gly

<210> SEQ ID NO 157
<211> LENGTH: 9
```

```
<212> TYPE: PRT
<213> ORGANISM: Mus musculus

<400> SEQUENCE: 157

Glu Gly Val Asp Gly Trp Phe Thr Tyr
1               5

<210> SEQ ID NO 158
<211> LENGTH: 15
<212> TYPE: PRT
<213> ORGANISM: Mus musculus

<400> SEQUENCE: 158

Arg Ala Ser Glu Ser Val Asp Asn Tyr Gly Ile Ser Phe Met Asn
1               5                   10                  15

<210> SEQ ID NO 159
<211> LENGTH: 7
<212> TYPE: PRT
<213> ORGANISM: Mus musculus

<400> SEQUENCE: 159

Asp Ala Ser Asn Gln Gly Tyr
1               5

<210> SEQ ID NO 160
<211> LENGTH: 9
<212> TYPE: PRT
<213> ORGANISM: Mus musculus

<400> SEQUENCE: 160

Gln Gln Ser Lys Glu Val Pro Tyr Thr
1               5

<210> SEQ ID NO 161
<211> LENGTH: 5
<212> TYPE: PRT
<213> ORGANISM: Mus musculus

<400> SEQUENCE: 161

Ser Ser Tyr Ile Ser
1               5

<210> SEQ ID NO 162
<211> LENGTH: 17
<212> TYPE: PRT
<213> ORGANISM: Mus musculus

<400> SEQUENCE: 162

Trp Ile Tyr Ala Gly Thr Gly Ala Thr Arg Tyr Tyr Gln Arg Phe Thr
1               5                   10                  15

Gly

<210> SEQ ID NO 163
<211> LENGTH: 9
<212> TYPE: PRT
<213> ORGANISM: Mus musculus

<400> SEQUENCE: 163

Glu Gly Val Asp Gly Trp Phe Thr Tyr
1               5

<210> SEQ ID NO 164
<211> LENGTH: 15
<212> TYPE: PRT
```

<213> ORGANISM: Mus musculus

<400> SEQUENCE: 164

Arg Ala Ser Glu Ser Val Asp Asn Ser Gly Ile Cys Phe Met Asn
1               5                   10                  15

<210> SEQ ID NO 165
<211> LENGTH: 7
<212> TYPE: PRT
<213> ORGANISM: Mus musculus

<400> SEQUENCE: 165

Asp Ala Ser Asn Gln Gly Tyr
1               5

<210> SEQ ID NO 166
<211> LENGTH: 9
<212> TYPE: PRT
<213> ORGANISM: Mus musculus

<400> SEQUENCE: 166

Gln Gln Ser Lys Glu Val Pro Tyr Thr
1               5

<210> SEQ ID NO 167
<211> LENGTH: 5
<212> TYPE: PRT
<213> ORGANISM: Mus musculus

<400> SEQUENCE: 167

Ser Thr Tyr Ile Ser
1               5

<210> SEQ ID NO 168
<211> LENGTH: 17
<212> TYPE: PRT
<213> ORGANISM: Mus musculus

<400> SEQUENCE: 168

Trp Ile Tyr Ala Gly Thr Gly Gly Thr Arg Tyr Asn Arg Lys Phe Thr
1               5                   10                  15

Gly

<210> SEQ ID NO 169
<211> LENGTH: 9
<212> TYPE: PRT
<213> ORGANISM: Mus musculus

<400> SEQUENCE: 169

Glu Gly Val Asp Gly Trp Phe Thr Tyr
1               5

<210> SEQ ID NO 170
<211> LENGTH: 15
<212> TYPE: PRT
<213> ORGANISM: Mus musculus

<400> SEQUENCE: 170

Arg Ala Ser Glu Ser Val Asp Asn Tyr Gly Thr Ser Phe Met Asn
1               5                   10                  15

<210> SEQ ID NO 171
<211> LENGTH: 7
<212> TYPE: PRT

<400> SEQUENCE: 171

Ala Ala Ser Asn Gln Gly Ser
1               5

<210> SEQ ID NO 172
<211> LENGTH: 9
<212> TYPE: PRT
<213> ORGANISM: Mus musculus

<400> SEQUENCE: 172

Gln Gln Ser Lys Glu Val Pro Tyr Thr
1               5

<210> SEQ ID NO 173
<211> LENGTH: 14
<212> TYPE: PRT
<213> ORGANISM: Mus musculus

<400> SEQUENCE: 173

Thr Gly Ser Ser Ser Asn Leu Gly Ala Gly Tyr Asp Val Asn
1               5                   10

<210> SEQ ID NO 174
<211> LENGTH: 7
<212> TYPE: PRT
<213> ORGANISM: Mus musculus

<400> SEQUENCE: 174

Gly Asn Glu Ile Arg Pro Ser
1               5

<210> SEQ ID NO 175
<211> LENGTH: 11
<212> TYPE: PRT
<213> ORGANISM: Mus musculus

<400> SEQUENCE: 175

Glu Thr Trp Asp Ser Ser Leu Ser Thr Val Val
1               5                   10

<210> SEQ ID NO 176
<211> LENGTH: 111
<212> TYPE: PRT
<213> ORGANISM: Mus musculus

<400> SEQUENCE: 176

Gln Ser Val Val Thr Gln Pro Pro Ser Val Ser Gly Ala Pro Gly Gln
1               5                   10                  15

Arg Val Thr Met Ser Cys Thr Gly Ser Ser Ser Asn Leu Gly Ala Gly
            20                  25                  30

Tyr Asp Val Asn Trp Tyr Gln Gln Leu Pro Gly Lys Ala Pro Lys Val
        35                  40                  45

Leu Ile Tyr Gly Asn Glu Ile Arg Pro Ser Gly Val Pro Asp Arg Phe
    50                  55                  60

Ser Gly Ser Lys Ser Asp Thr Ser Ala Thr Leu Asp Ile Thr Gly Leu
65                  70                  75                  80

Gln Thr Gly Asp Glu Ala Asp Tyr Tyr Cys Glu Thr Trp Asp Ser Ser
                85                  90                  95

Leu Ser Thr Val Val Phe Gly Gly Gly Thr Lys Leu Thr Val Leu
            100                 105                 110

<210> SEQ ID NO 177
<211> LENGTH: 11
<212> TYPE: PRT
<213> ORGANISM: Mus musculus

<400> SEQUENCE: 177

Arg Ala Ser Gln Ser Ile Ser Glu Tyr Leu Asn
1               5                   10

<210> SEQ ID NO 178
<211> LENGTH: 7
<212> TYPE: PRT
<213> ORGANISM: Mus musculus

<400> SEQUENCE: 178

Gly Val Ser Thr Arg Ala Thr
1               5

<210> SEQ ID NO 179
<211> LENGTH: 9
<212> TYPE: PRT
<213> ORGANISM: Mus musculus

<400> SEQUENCE: 179

Gln Gln Asp Tyr Asn Val Pro Tyr Thr
1               5

<210> SEQ ID NO 180
<211> LENGTH: 107
<212> TYPE: PRT
<213> ORGANISM: Mus musculus

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Glu Tyr
            20                  25                  30

Leu Asn Trp Tyr Gln Gln Lys Pro Gly Gln Ala Pro Arg Leu Leu Ile
        35                  40                  45

Tyr Gly Val Ser Thr Arg Ala Thr Gly Ile Ala Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Val Tyr Tyr Cys Gln Gln Asp Tyr Asn Val Pro Tyr
                85                  90                  95

Thr Phe Gly Gln Gly Thr Lys Leu Glu Ile Lys
            100                 105

<210> SEQ ID NO 181
<211> LENGTH: 11
<212> TYPE: PRT
<213> ORGANISM: Mus musculus

<400> SEQUENCE: 181

Arg Ala Ser Gln Ser Ile Asn Asp Asn Leu Asn
1               5                   10

<210> SEQ ID NO 182
<211> LENGTH: 7
<212> TYPE: PRT
<213> ORGANISM: Mus musculus

<400> SEQUENCE: 182

```
Ala Ala Ser Thr Ser Gln Ser
 1               5
```

<210> SEQ ID NO 183
<211> LENGTH: 9
<212> TYPE: PRT
<213> ORGANISM: Mus musculus

<400> SEQUENCE: 183

```
Gln Gln Asn Asp Ser Met Pro Phe Thr
 1               5
```

<210> SEQ ID NO 184
<211> LENGTH: 107
<212> TYPE: PRT
<213> ORGANISM: Mus musculus

<400> SEQUENCE: 184

```
Asp Ile Gln Leu Thr Gln Ser Pro Phe Ser Leu Ser Ala Ser Val Gly
 1               5                  10                  15

Asp Arg Val Thr Ile Thr Cys Arg Ala Ser Gln Ser Ile Asn Asp Asn
                20                  25                  30

Leu Asn Trp Tyr Leu Gln Lys Pro Gly Lys Ala Pro Lys Leu Leu Ile
            35                  40                  45

Phe Ala Ala Ser Thr Ser Gln Ser Gly Val Pro Ser Arg Phe Ser Gly
        50                  55                  60

Asn Gly Phe Gly Thr Asp Phe Ser Leu Ile Ile Ser Gly Leu Gln Pro
 65                  70                  75                  80

Glu Asp Val Gly Thr Tyr Tyr Cys Gln Gln Asn Asp Ser Met Pro Phe
                 85                  90                  95

Thr Phe Gly Gln Gly Thr Arg Leu Asp Ile Lys
            100                 105
```

<210> SEQ ID NO 185
<211> LENGTH: 11
<212> TYPE: PRT
<213> ORGANISM: Mus musculus

<400> SEQUENCE: 185

```
Gln Ala Ser Gln Asp Ile Asn Asn Tyr Leu Ser
 1               5                  10
```

<210> SEQ ID NO 186
<211> LENGTH: 7
<212> TYPE: PRT
<213> ORGANISM: Mus musculus

<400> SEQUENCE: 186

```
Asp Thr Ser Asn Leu Glu Thr
 1               5
```

<210> SEQ ID NO 187
<211> LENGTH: 9
<212> TYPE: PRT
<213> ORGANISM: Mus musculus

<400> SEQUENCE: 187

```
Gln Gln Ser Asp Asn Leu Pro Tyr Thr
 1               5
```

<210> SEQ ID NO 188
<211> LENGTH: 107
<212> TYPE: PRT

<213> ORGANISM: Mus musculus

<400> SEQUENCE: 188

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Ser Trp Tyr Gln Gln Lys Pro Gly Lys Ala Pro Lys Val Leu Ile
        35                  40                  45

Tyr Asp Thr Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Asn Leu Pro Tyr
                85                  90                  95

Thr Phe Gly Gln Gly Thr Lys Leu Glu Ile Lys
            100                 105

<210> SEQ ID NO 189
<211> LENGTH: 12
<212> TYPE: PRT
<213> ORGANISM: Mus musculus

<400> SEQUENCE: 189

Arg Ala Ser Gln Arg Val Ser Ser Ser Tyr Leu Ala
1               5                   10

<210> SEQ ID NO 190
<211> LENGTH: 7
<212> TYPE: PRT
<213> ORGANISM: Mus musculus

<400> SEQUENCE: 190

Gly Thr Ser Ser Trp Ala Thr
1               5

<210> SEQ ID NO 191
<211> LENGTH: 9
<212> TYPE: PRT
<213> ORGANISM: Mus musculus

<400> SEQUENCE: 191

Gln Gln Ser Ser Ser Ile Pro Tyr Thr
1               5

<210> SEQ ID NO 192
<211> LENGTH: 108
<212> TYPE: PRT
<213> ORGANISM: Mus musculus

<400> SEQUENCE: 192

Asp Ile Gln Met Thr Gln Ser Pro Gly Thr Leu Ser Leu Ser Pro Gly
1               5                   10                  15

Glu Arg Ala Thr Leu Phe Cys Arg Ala Ser Gln Arg Val Ser Ser Ser
            20                  25                  30

Tyr Leu Ala Trp Tyr Gln Gln Arg Pro Gly Gln Ala Pro Arg Leu Leu
        35                  40                  45

Met Tyr Gly Thr Ser Ser Trp Ala Thr Gly Ile Pro Asp Arg Phe Ser
    50                  55                  60

Gly Ser Gly Ser Gly Thr Asp Phe Thr Leu Thr Ile Ser Ser Leu Gln
65                  70                  75                  80

```
Pro Glu Asp Phe Ala Thr Tyr Tyr Cys Gln Gln Ser Ser Ser Ile Pro
                85                  90                  95
Tyr Thr Phe Gly Gln Gly Thr Lys Leu Glu Ile Lys
            100                 105
```

<210> SEQ ID NO 193
<211> LENGTH: 12
<212> TYPE: PRT
<213> ORGANISM: Mus musculus

<400> SEQUENCE: 193

```
Arg Ala Ser Gln Thr Leu Ser Phe Asp Phe Phe Ala
1               5                   10
```

<210> SEQ ID NO 194
<211> LENGTH: 7
<212> TYPE: PRT
<213> ORGANISM: Mus musculus

<400> SEQUENCE: 194

```
Gly Ile Ser Thr Arg Ala Ala
1               5
```

<210> SEQ ID NO 195
<211> LENGTH: 9
<212> TYPE: PRT
<213> ORGANISM: Mus musculus

<400> SEQUENCE: 195

```
Gln Gln Ser Ser Ser Leu Pro Leu Thr
1               5
```

<210> SEQ ID NO 196
<211> LENGTH: 108
<212> TYPE: PRT
<213> ORGANISM: Mus musculus

<400> SEQUENCE: 196

```
Glu Thr Thr Leu Thr Gln Ser Pro Ala Leu Leu Ser Leu Ser Pro Gly
1               5                   10                  15
Glu Arg Ala Thr Leu Ser Cys Arg Ala Ser Gln Thr Leu Ser Phe Asp
            20                  25                  30
Phe Phe Ala Trp Tyr Gln Gln Lys Pro Gly Gln Ala Pro Ser Leu Leu
        35                  40                  45
Ile Ser Gly Ile Ser Thr Arg Ala Ala Gly Val Pro Asp Arg Phe Ser
    50                  55                  60
Gly Ser Gly Ser Gly Thr Asp Phe Thr Leu Thr Ile Asp Arg Leu Glu
65                  70                  75                  80
Pro Glu Asp Phe Ala Val Tyr Phe Cys Gln Gln Ser Ser Ser Leu Pro
                85                  90                  95
Leu Thr Phe Gly Gly Gly Thr Lys Val Glu Ile Arg
            100                 105
```

<210> SEQ ID NO 197
<211> LENGTH: 11
<212> TYPE: PRT
<213> ORGANISM: Mus musculus

<400> SEQUENCE: 197

```
Arg Ala Ser Gln Ser Ile Ser Asp Tyr Leu Asn
1               5                   10
```

<210> SEQ ID NO 198
<211> LENGTH: 7
<212> TYPE: PRT
<213> ORGANISM: Mus musculus

<400> SEQUENCE: 198

Ala Ser Asn Thr Leu Gln Gly
1               5

<210> SEQ ID NO 199
<211> LENGTH: 9
<212> TYPE: PRT
<213> ORGANISM: Mus musculus

<400> SEQUENCE: 199

Gln Gln Ser Tyr Arg Thr Pro Leu Thr
1               5

<210> SEQ ID NO 200
<211> LENGTH: 107
<212> TYPE: PRT
<213> ORGANISM: Mus musculus

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
            20                  25                  30

Leu Asn Trp Tyr Gln Gln Arg Pro Gly Lys Ala Pro Asn Leu Leu Ile
        35                  40                  45

Phe Ala Ser Asn Thr Leu Gln Gly Gly Val Pro Ser Arg Phe Arg Gly
    50                  55                  60

Ser Gly Ser Gly Thr Asp Phe Thr Leu Thr Ile Asn Ser Leu Gln His
65                  70                  75                  80

Glu Asp Phe Gly Thr Tyr Tyr Cys Gln Gln Ser Tyr Arg Thr Pro Leu
                85                  90                  95

Thr Phe Gly Gly Gly Thr Lys Val Glu Ile Lys
            100                 105

<210> SEQ ID NO 201
<211> LENGTH: 11
<212> TYPE: PRT
<213> ORGANISM: Mus musculus

<400> SEQUENCE: 201

Arg Ala Ser Gln Ser Ile Ser Asp Ser Leu Asn
1               5                   10

<210> SEQ ID NO 202
<211> LENGTH: 7
<212> TYPE: PRT
<213> ORGANISM: Mus musculus

<400> SEQUENCE: 202

Ala Ala Ser Gly Leu Pro Ser
1               5

<210> SEQ ID NO 203
<211> LENGTH: 9
<212> TYPE: PRT
<213> ORGANISM: Mus musculus

<400> SEQUENCE: 203

Gln Gln Ser Tyr Ser Ala Pro Leu Thr
1               5

<210> SEQ ID NO 204
<211> LENGTH: 107
<212> TYPE: PRT
<213> ORGANISM: Mus musculus

<400> SEQUENCE: 204

Asp Ile Gln Met Thr Gln Ser Pro Leu Ser Leu Ser Ala Ser Val Gly
1               5                   10                  15

Asp Arg Val Ala Ile Thr Cys Arg Ala Ser Gln Ser Ile Ser Asp Ser
            20                  25                  30

Leu Asn Trp Tyr Gln Gln Lys Pro Gly Lys Pro Pro Lys Ile Val Ile
        35                  40                  45

Tyr Ala Ala Ser Gly Leu Pro Ser Gly Val Pro Ser Arg Phe Ser Gly
    50                  55                  60

Gly Gly Ser Gly Thr Asp Phe Thr Leu Val Ile Ser Thr Leu Gln Pro
65                  70                  75                  80

Glu Asp Phe Ala Thr Tyr Tyr Cys Gln Gln Ser Tyr Ser Ala Pro Leu
                85                  90                  95

Thr Phe Gly Gly Gly Thr Lys Val Glu Ile Ser
            100                 105

<210> SEQ ID NO 205
<211> LENGTH: 11
<212> TYPE: PRT
<213> ORGANISM: Mus musculus

<400> SEQUENCE: 205

Gln Ala Ser Gln Asp Ile Asn Asn Tyr Leu Asn
1               5                   10

<210> SEQ ID NO 206
<211> LENGTH: 7
<212> TYPE: PRT
<213> ORGANISM: Mus musculus

<400> SEQUENCE: 206

Asp Ala Ser Asn Leu Ala Ala
1               5

<210> SEQ ID NO 207
<211> LENGTH: 9
<212> TYPE: PRT
<213> ORGANISM: Mus musculus

<400> SEQUENCE: 207

Gln Gln Tyr Asp Asn Leu Pro Leu Thr
1               5

<210> SEQ ID NO 208
<211> LENGTH: 107
<212> TYPE: PRT
<213> ORGANISM: Mus musculus

<400> SEQUENCE: 208

Asp Ile Gln Met Thr Gln Ser Pro Ser Ser Leu Ser Ala Ser Ile Gly
1               5                   10                  15

Asp Arg Val Thr Ile Thr Cys Gln Ala Ser Gln Asp Ile Asn Asn Tyr
            20                  25                  30

```
Leu Asn Trp Tyr Gln Gln Lys Gln Gly Lys Ala Pro Lys Val Leu Ile
         35                  40                  45

Phe Asp Ala Ser Asn Leu Ala Ala Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln Gln Tyr Asp Asn Leu Pro Leu
                 85                  90                  95

Thr Phe Gly Gln Gly Thr Lys Val Asp Asn Lys
            100                 105
```

<210> SEQ ID NO 209
<211> LENGTH: 14
<212> TYPE: PRT
<213> ORGANISM: Mus musculus

<400> SEQUENCE: 209

```
Thr Gly Ser Ser Ser Asn Ile Gly Ala Gly Tyr Asp Val His
 1               5                  10
```

<210> SEQ ID NO 210
<211> LENGTH: 7
<212> TYPE: PRT
<213> ORGANISM: Mus musculus

<400> SEQUENCE: 210

```
Ala Asn Asp Tyr Arg Pro Ser
 1               5
```

<210> SEQ ID NO 211
<211> LENGTH: 11
<212> TYPE: PRT
<213> ORGANISM: Mus musculus

<400> SEQUENCE: 211

```
Gln Ser Tyr Asp Asn Arg Leu Ser Gly Tyr Val
 1               5                  10
```

<210> SEQ ID NO 212
<211> LENGTH: 111
<212> TYPE: PRT
<213> ORGANISM: Mus musculus

<400> SEQUENCE: 212

```
Gln Ser Val Val Thr Gln Pro Pro Ala Val Ser Gly Ala Pro Gly Gln
 1               5                  10                  15

Arg Ile Thr Ile Ser Cys Thr Gly Ser Ser Ser Asn Ile Gly Ala Gly
             20                  25                  30

Tyr Asp Val His Trp Tyr Gln Gln Phe Pro Gly Thr Ala Pro Lys Val
         35                  40                  45

Leu Ile Phe Ala Asn Asp Tyr Arg Pro Ser Gly Val Pro Asp Arg Phe
 50                  55                  60

Ser Ala Ser Lys Ser Ala Thr Ser Ala Ser Leu Ala Ile Arg Gly Leu
 65                  70                  75                  80

Gln Ser Glu Asp Glu Ala Asp Tyr Tyr Cys Gln Ser Tyr Asp Asn Arg
                 85                  90                  95

Leu Ser Gly Tyr Val Phe Gly Thr Gly Thr Lys Val Thr Val Leu
            100                 105                 110
```

<210> SEQ ID NO 213
<211> LENGTH: 14

```
<212> TYPE: PRT
<213> ORGANISM: Mus musculus

<400> SEQUENCE: 213

Thr Gly Ser Ser Asn Ile Gly Ala Gly Tyr Asp Val His
1               5                   10

<210> SEQ ID NO 214
<211> LENGTH: 7
<212> TYPE: PRT
<213> ORGANISM: Mus musculus

<400> SEQUENCE: 214

Ala Asn Thr Asn Arg Pro Ser
1               5

<210> SEQ ID NO 215
<211> LENGTH: 11
<212> TYPE: PRT
<213> ORGANISM: Mus musculus

<400> SEQUENCE: 215

Gln Ser Tyr Asp Asn Ser Val Ser Ala Tyr Val
1               5                   10

<210> SEQ ID NO 216
<211> LENGTH: 111
<212> TYPE: PRT
<213> ORGANISM: Mus musculus

<400> SEQUENCE: 216

Gln Ala Val Leu Thr Gln Pro Ser Ser Val Ser Gly Ala Pro Gly Arg
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Lys Ala Pro Lys Leu
                35                  40                  45

Val Ile Ser Ala Asn Thr Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Val Ser Ala Tyr Val Phe Gly Thr Gly Thr Lys Val Thr Val Leu
                100                 105                 110

<210> SEQ ID NO 217
<211> LENGTH: 14
<212> TYPE: PRT
<213> ORGANISM: Mus musculus

<400> SEQUENCE: 217

Thr Gly Ser Arg Ser Asn Ile Gly Ala Gly Tyr Asp Val Gln
1               5                   10

<210> SEQ ID NO 218
<211> LENGTH: 7
<212> TYPE: PRT
<213> ORGANISM: Mus musculus

<400> SEQUENCE: 218

Ala Asn Asn Ile Arg Ser Ser
1               5
```

<210> SEQ ID NO 219
<211> LENGTH: 11
<212> TYPE: PRT
<213> ORGANISM: Mus musculus

<400> SEQUENCE: 219

Gln Ser Tyr Asp Arg Ser Leu Ser Gly Tyr Val
1               5                   10

<210> SEQ ID NO 220
<211> LENGTH: 111
<212> TYPE: PRT
<213> ORGANISM: Mus musculus

<400> SEQUENCE: 220

Gln Ser Ala Leu Thr Gln Thr Pro Ser Val Ser Gly Thr Pro Gly Gln
1               5                   10                  15

Arg Val Thr Ile Ser Cys Thr Gly Ser Arg Ser Asn Ile Gly Ala Gly
            20                  25                  30

Tyr Asp Val Gln Trp Tyr Gln Gln Phe Pro Gly Thr Ala Pro Arg Leu
        35                  40                  45

Leu Ile Tyr Ala Asn Asn Ile Arg Ser Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Thr Tyr Tyr Cys Gln Ser Tyr Asp Arg Ser
                85                  90                  95

Leu Ser Gly Tyr Val Phe Gly Thr Gly Thr Glu Val Thr Val Val
            100                 105                 110

<210> SEQ ID NO 221
<211> LENGTH: 14
<212> TYPE: PRT
<213> ORGANISM: Mus musculus

<400> SEQUENCE: 221

Thr Gly Ser Ser Ser Asn Ile Gly Ala Gly Tyr Asp Val His
1               5                   10

<210> SEQ ID NO 222
<211> LENGTH: 7
<212> TYPE: PRT
<213> ORGANISM: Mus musculus

<400> SEQUENCE: 222

Gly Asp Thr Asn Arg Pro Ser
1               5

<210> SEQ ID NO 223
<211> LENGTH: 11
<212> TYPE: PRT
<213> ORGANISM: Mus musculus

<400> SEQUENCE: 223

Gln Ser Tyr Asp Ser Ser Leu Arg Ala Tyr Val
1               5                   10

<210> SEQ ID NO 224
<211> LENGTH: 111
<212> TYPE: PRT
<213> ORGANISM: Mus musculus

<400> SEQUENCE: 224

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Arg Thr Ala Pro Lys Leu
        35                  40                  45

Leu Ile Tyr Gly Asp Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Thr Glu Asp Glu Ala Asp Tyr Tyr Cys Gln Ser Tyr Asp Ser Ser
                85                  90                  95

Leu Arg Ala Tyr Val Phe Gly Thr Gly Thr Lys Val Thr Val Leu
            100                 105                 110

<210> SEQ ID NO 225
<211> LENGTH: 14
<212> TYPE: PRT
<213> ORGANISM: Mus musculus

<400> SEQUENCE: 225

Thr Gly Ser Ser Ser Asn Ile Gly Ala Gly Tyr Asp Val His
1               5                   10

<210> SEQ ID NO 226
<211> LENGTH: 7
<212> TYPE: PRT
<213> ORGANISM: Mus musculus

<400> SEQUENCE: 226

Gly Asn Asn Asn Arg Pro Ser
1               5

<210> SEQ ID NO 227
<211> LENGTH: 11
<212> TYPE: PRT
<213> ORGANISM: Mus musculus

<400> SEQUENCE: 227

Gln Ser Tyr Asp Ser Ser Leu Ser Ala Tyr Val
1               5                   10

<210> SEQ ID NO 228
<211> LENGTH: 111
<212> TYPE: PRT
<213> ORGANISM: Mus musculus

<400> SEQUENCE: 228

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Ala Ala Pro Lys Val
        35                  40                  45

Leu Ile Phe Gly Asn Asn Asn Arg Pro Ser Gly Ile Pro Asp Arg Val
    50                  55                  60

Ser Gly Ser Lys Ser Gly Thr Ser Ala Ser Leu Ala Ile Ser Gly Leu
65                  70                  75                  80

Gln Thr Glu Asp Glu Ala Val Tyr Tyr Cys Gln Ser Tyr Asp Ser Ser

```
                    85                  90                  95

Leu Ser Ala Tyr Val Phe Gly Gly Thr Gln Val Thr Val Leu
                100                 105                 110

<210> SEQ ID NO 229
<211> LENGTH: 13
<212> TYPE: PRT
<213> ORGANISM: Mus musculus

<400> SEQUENCE: 229

Thr Arg Asn Ser Gly Ser Ile Ala Ser Asn Tyr Val Gln
1               5                   10

<210> SEQ ID NO 230
<211> LENGTH: 7
<212> TYPE: PRT
<213> ORGANISM: Mus musculus

<400> SEQUENCE: 230

Glu Asp Asn Gln Arg Pro Ser
1               5

<210> SEQ ID NO 231
<211> LENGTH: 11
<212> TYPE: PRT
<213> ORGANISM: Mus musculus

<400> SEQUENCE: 231

Gln Ser Tyr Asp Ser Ser Asn Pro Phe Tyr Val
1               5                   10

<210> SEQ ID NO 232
<211> LENGTH: 112
<212> TYPE: PRT
<213> ORGANISM: Mus musculus

<400> SEQUENCE: 232

Asn Phe Met Leu Thr Gln Pro His Ser Val Ser Glu Ser Pro Gly Lys
1               5                   10                  15

Thr Val Thr Ile Ser Cys Thr Arg Asn Ser Gly Ser Ile Ala Ser Asn
                20                  25                  30

Tyr Val Gln Trp Tyr Gln Gln Arg Pro Gly Ser Ser Pro Ala Thr Val
            35                  40                  45

Ile Tyr Glu Asp Asn Gln Arg Pro Ser Gly Val Pro Asp Arg Phe Ser
        50                  55                  60

Gly Ser Ile Asp Ile Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Pro Phe Tyr Val Phe Gly Thr Gly Thr Lys Val Thr Val Leu
                100                 105                 110

<210> SEQ ID NO 233
<211> LENGTH: 13
<212> TYPE: PRT
<213> ORGANISM: Mus musculus

<400> SEQUENCE: 233

Thr Arg Ser Ser Gly Ser Ile Ser Ser Asn Tyr Val Gln
1               5                   10

<210> SEQ ID NO 234
```

<211> LENGTH: 7
<212> TYPE: PRT
<213> ORGANISM: Mus musculus

<400> SEQUENCE: 234

Glu Asp Asp Gln Arg Pro Ser
1               5

<210> SEQ ID NO 235
<211> LENGTH: 10
<212> TYPE: PRT
<213> ORGANISM: Mus musculus

<400> SEQUENCE: 235

Gln Ser Tyr Asp Thr Asp Ile Pro Tyr Val
1               5                   10

<210> SEQ ID NO 236
<211> LENGTH: 111
<212> TYPE: PRT
<213> ORGANISM: Mus musculus

<400> SEQUENCE: 236

Asn Phe Met Leu Thr Gln Pro His Ser Val Ser Glu Ser Pro Gly Lys
1               5                   10                  15

Thr Ile Thr Ile Ser Cys Thr Arg Ser Ser Gly Ser Ile Ser Ser Asn
            20                  25                  30

Tyr Val Gln Trp Tyr Gln Gln Arg Pro Gly Ser Ser Pro Arg Ile Val
        35                  40                  45

Met Ser Glu Asp Asp Gln Arg Pro Ser Gly Val Ser Asp Arg Phe Ser
    50                  55                  60

Gly Ser Ile Asp Ile Ser Ser Asn Ser Ala Phe Leu Thr Ile Ser Gly
65                  70                  75                  80

Leu Lys Pro Glu Asp Glu Gly Asp Tyr Tyr Cys Gln Ser Tyr Asp Thr
                85                  90                  95

Asp Ile Pro Tyr Val Phe Gly Thr Gly Thr Lys Val Thr Val Leu
            100                 105                 110

<210> SEQ ID NO 237
<211> LENGTH: 11
<212> TYPE: PRT
<213> ORGANISM: Mus musculus

<400> SEQUENCE: 237

Gln Ala Ser Gln Asp Ile Asp Asn Tyr Leu Asn
1               5                   10

<210> SEQ ID NO 238
<211> LENGTH: 7
<212> TYPE: PRT
<213> ORGANISM: Mus musculus

<400> SEQUENCE: 238

Asp Ala Tyr Asn Leu Lys Ala
1               5

<210> SEQ ID NO 239
<211> LENGTH: 9
<212> TYPE: PRT
<213> ORGANISM: Mus musculus

<400> SEQUENCE: 239

Leu Gln Gln Tyr Arg Tyr Pro Leu Thr

<210> SEQ ID NO 240
<211> LENGTH: 107
<212> TYPE: PRT
<213> ORGANISM: Mus musculus

<400> SEQUENCE: 240

Asp Ile Gln Met Thr Gln Ser Pro Ser Ser Leu Ser Ala Ser Val Gly
1               5                   10                  15

Asp Arg Ile Thr Ile Ser Cys Gln Ala Ser Gln Asp Ile Asp Asn Tyr
            20                  25                  30

Leu Asn Trp Tyr Gln Gln Lys Ser Gly Lys Ala Pro Lys Leu Leu Ile
        35                  40                  45

Tyr Asp Ala Tyr Asn Leu Lys Ala Gly Val Pro Ser Arg Phe Arg Gly
    50                  55                  60

Ser Arg Ser Gly Thr Asp Phe Phe Leu Thr Ile Ser Ser Leu Gln Pro
65                  70                  75                  80

Glu Asp Phe Ala Thr Tyr Tyr Cys Leu Gln Gln Tyr Arg Tyr Pro Leu
                85                  90                  95

Thr Phe Gly Gly Gly Thr Lys Val Glu Ile Lys
            100                 105

<210> SEQ ID NO 241
<211> LENGTH: 14
<212> TYPE: PRT
<213> ORGANISM: Mus musculus

<400> SEQUENCE: 241

Thr Gly Gly Ser Ser Asn Ile Gly Ala Gly Tyr Glu Val His
1               5                   10

<210> SEQ ID NO 242
<211> LENGTH: 7
<212> TYPE: PRT
<213> ORGANISM: Mus musculus

<400> SEQUENCE: 242

Gly Asp Asn Asp Arg Pro Ser
1               5

<210> SEQ ID NO 243
<211> LENGTH: 11
<212> TYPE: PRT
<213> ORGANISM: Mus musculus

<400> SEQUENCE: 243

Gln Ser Tyr Asp Thr Ser Leu Ser Ala Trp Val
1               5                   10

<210> SEQ ID NO 244
<211> LENGTH: 111
<212> TYPE: PRT
<213> ORGANISM: Mus musculus

<400> SEQUENCE: 244

Gln Ser Val Leu Thr Gln Pro Pro Ser Val Ser Gly Ala Pro Gly Gln
1               5                   10                  15

Arg Val Thr Ile Ser Cys Thr Gly Gly Ser Ser Asn Ile Gly Ala Gly
            20                  25                  30

Tyr Glu Val His Trp Tyr Gln Leu Val Pro Gly Arg Ala Pro Arg Phe
        35                  40                  45

Leu Ile His Gly Asp Asn Asp Arg Pro Ser Gly Val Pro Asp Arg Phe
            50                  55                  60

Ser Ala Ser Glu Ser Gly Ser Ser Phe Leu Ala Ile Ser Gly Leu
65                  70                  75                  80

Gln Asp Asp Asp Glu Ala Asp Tyr Tyr Cys Gln Ser Tyr Asp Thr Ser
                85                  90                  95

Leu Ser Ala Trp Val Phe Gly Gly Gly Thr Lys Leu Thr Val Leu
            100                 105                 110

<210> SEQ ID NO 245
<211> LENGTH: 12
<212> TYPE: PRT
<213> ORGANISM: Mus musculus

<400> SEQUENCE: 245

Arg Thr Ser Gln Ser Val Ser Ser Thr Ser Val Ala
1               5                   10

<210> SEQ ID NO 246
<211> LENGTH: 7
<212> TYPE: PRT
<213> ORGANISM: Mus musculus

<400> SEQUENCE: 246

Asp Ala Ser Ser Arg Ala Ala
1               5

<210> SEQ ID NO 247
<211> LENGTH: 9
<212> TYPE: PRT
<213> ORGANISM: Mus musculus

<400> SEQUENCE: 247

Gln Gln Ser Tyr Ser Leu Pro Tyr Thr
1               5

<210> SEQ ID NO 248
<211> LENGTH: 108
<212> TYPE: PRT
<213> ORGANISM: Mus musculus

<400> SEQUENCE: 248

Asp Ile Gln Met Thr Gln Ser Pro Gly Thr Leu Ser Leu Ser Pro Gly
1               5                   10                  15

Glu Arg Ala Thr Leu Ser Cys Arg Thr Ser Gln Ser Val Ser Ser Thr
            20                  25                  30

Ser Val Ala Trp Tyr Gln Gln Lys Pro Gly Gln Ala Pro Arg Leu Leu
        35                  40                  45

Met Tyr Asp Ala Ser Ser Arg Ala Ala Gly Ile Pro Asp Arg Phe Ser
    50                  55                  60

Gly Ser Gly Ser Val Thr Asp Phe Thr Leu Thr Ile Ser Arg Leu Glu
65                  70                  75                  80

Pro Glu Asp Phe Ala Thr Tyr Tyr Cys Gln Gln Ser Tyr Ser Leu Pro
                85                  90                  95

Tyr Thr Phe Gly Gln Gly Thr Lys Val Glu Ile Lys
            100                 105

<210> SEQ ID NO 249
<211> LENGTH: 12
<212> TYPE: PRT
<213> ORGANISM: Mus musculus

```
<400> SEQUENCE: 249

Arg Ala Ser Gln Ser Val Thr Gly Asn His Leu Ala
1               5                   10

<210> SEQ ID NO 250
<211> LENGTH: 7
<212> TYPE: PRT
<213> ORGANISM: Mus musculus

<400> SEQUENCE: 250

Asp Thr Ser Ser Arg Ala Thr
1               5

<210> SEQ ID NO 251
<211> LENGTH: 9
<212> TYPE: PRT
<213> ORGANISM: Mus musculus

<400> SEQUENCE: 251

Gln Gln Phe Asp Asn Leu Pro Tyr Thr
1               5

<210> SEQ ID NO 252
<211> LENGTH: 108
<212> TYPE: PRT
<213> ORGANISM: Mus musculus

<400> SEQUENCE: 252

Asn Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Thr Gly Asn
            20                  25                  30

His Leu Ala Trp Tyr Gln Gln Lys Pro Gly Gln Ala Pro Arg Val Leu
        35                  40                  45

Met Tyr Asp Thr Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Gln
65                  70                  75                  80

Pro Glu Asp Ile Ala Thr Tyr Tyr Cys Gln Gln Phe Asp Asn Leu Pro
                85                  90                  95

Tyr Thr Phe Gly Gln Gly Thr Lys Leu Glu Ile Lys
            100                 105

<210> SEQ ID NO 253
<211> LENGTH: 11
<212> TYPE: PRT
<213> ORGANISM: Mus musculus

<400> SEQUENCE: 253

Arg Ala Ser Arg Asp Ile Ser Val Tyr Val Asn
1               5                   10

<210> SEQ ID NO 254
<211> LENGTH: 7
<212> TYPE: PRT
<213> ORGANISM: Mus musculus

<400> SEQUENCE: 254

Gly Ala Ser Asn Leu Gly Phe
1               5
```

<210> SEQ ID NO 255
<211> LENGTH: 9
<212> TYPE: PRT
<213> ORGANISM: Mus musculus

<400> SEQUENCE: 255

Gln Gln Ser Tyr Ser Ile Pro Leu Thr
1               5

<210> SEQ ID NO 256
<211> LENGTH: 107
<212> TYPE: PRT
<213> ORGANISM: Mus musculus

<400> SEQUENCE: 256

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Ser Val Tyr
                20                  25                  30

Val Asn Trp Tyr Gln Leu Lys Pro Gly Gln Ala Pro Arg Leu Leu Ile
            35                  40                  45

Tyr Gly Ala Ser Asn Leu Gly Phe Gly Val Pro Ser Arg Phe Ser Gly
        50                  55                  60

Ser Gly Tyr Gly Thr Asp Phe Ala Leu Thr Ile Ser Gly Leu Gln Pro
65                  70                  75                  80

Glu Asp Phe Ala Thr Tyr Ser Cys Gln Gln Ser Tyr Ser Ile Pro Leu
                85                  90                  95

Thr Phe Gly Gln Gly Thr Arg Val Asp Thr Lys
            100                 105

<210> SEQ ID NO 257
<211> LENGTH: 11
<212> TYPE: PRT
<213> ORGANISM: Mus musculus

<400> SEQUENCE: 257

Gln Ala Ser Gln Asp Ile Asp Asn Tyr Leu Asn
1               5                   10

<210> SEQ ID NO 258
<211> LENGTH: 7
<212> TYPE: PRT
<213> ORGANISM: Mus musculus

<400> SEQUENCE: 258

Asp Ala Tyr Asn Leu Lys Ala
1               5

<210> SEQ ID NO 259
<211> LENGTH: 9
<212> TYPE: PRT
<213> ORGANISM: Mus musculus

<400> SEQUENCE: 259

Leu Gln Gln Ser Ser Tyr Pro Leu Thr
1               5

<210> SEQ ID NO 260
<211> LENGTH: 107
<212> TYPE: PRT
<213> ORGANISM: Mus musculus

<400> SEQUENCE: 260

```
Asp Ile Gln Met Thr Gln Ser Pro Asp Ser Leu Ser Ala Ser Val Gly
 1               5                  10                  15

Asp Arg Ile Thr Ile Ser Cys Gln Ala Ser Gln Asp Ile Asp Asn Tyr
             20                  25                  30

Leu Asn Trp Tyr Gln Gln Arg Ser Gly Lys Ala Pro Lys Leu Leu Ile
         35                  40                  45

Tyr Asp Ala Tyr Asn Leu Lys Ala Gly Val Pro Ser Arg Phe Arg Gly
 50                  55                  60

Ser Arg Ser Gly Thr Asp Phe Phe Leu Thr Ile Ser Ser Leu Gln Pro
 65                  70                  75                  80

Glu Asp Phe Gly Thr Tyr Tyr Cys Leu Gln Gly Ser Ser Tyr Pro Leu
             85                  90                  95

Thr Phe Gly Gln Gly Thr Lys Val Glu Ile Lys
            100                 105
```

```
<210> SEQ ID NO 261
<211> LENGTH: 11
<212> TYPE: PRT
<213> ORGANISM: Mus musculus

<400> SEQUENCE: 261

Arg Ala Ser Arg Ser Val Ser Ser Asn Leu Ala
 1               5                  10

<210> SEQ ID NO 262
<211> LENGTH: 7
<212> TYPE: PRT
<213> ORGANISM: Mus musculus

<400> SEQUENCE: 262

Gly Ala Ser Thr Arg Ala Thr
 1               5

<210> SEQ ID NO 263
<211> LENGTH: 9
<212> TYPE: PRT
<213> ORGANISM: Mus musculus

<400> SEQUENCE: 263

Gln His Asp Asn Glu Leu Pro Leu Thr
 1               5

<210> SEQ ID NO 264
<211> LENGTH: 107
<212> TYPE: PRT
<213> ORGANISM: Mus musculus

<400> SEQUENCE: 264

Asp Ile Gln Met Thr Gln Ser Pro Ala Thr Leu Ser Leu Ser Pro Gly
 1               5                  10                  15

Glu Arg Ala Thr Leu Ser Cys Arg Ala Ser Arg Ser Val Ser Ser Asn
             20                  25                  30

Leu Ala Trp Tyr Gln Gln Lys Pro Gly Arg Ala Pro Arg Leu Leu Met
         35                  40                  45

Phe Gly Ala Ser Thr Arg Ala Thr Gly Val Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Val Ala Thr Tyr Tyr Cys Gln His Asp Asn Glu Leu Pro Leu
             85                  90                  95
```

```
Thr Phe Gly Gly Gly Thr Lys Val Glu Leu Lys
            100                 105
```

<210> SEQ ID NO 265
<211> LENGTH: 711
<212> TYPE: DNA
<213> ORGANISM: Rattus norvegicus

<400> SEQUENCE: 265

```
atggagacag acagactcct gctatgggca ctgctgctct gggttccagg ctccactggt      60
gacattgtct tgacccagtc tcctgctttg ctgtgtctc tagggcagag ggccacactc     120
tcctgtaggg ccagccaaag tgtcagtata tctggacata atcttatgca ctggtaccaa     180
cagaaaccag acagcaacc caaactcctc atctatcgtg catccaacct accatctggg     240
atccctgcca ggttcagtgg cagtgggtct gggacaggct tcaccctcac catcaatcct     300
gtgcaggctg atgacattgc aacctattac tgtcagcaga gtagggagtc tccgtggacg     360
ttcggtggag gcaccacgtt ggaattgaaa cgaactgtgg ctgcaccatc tgtcttcatc     420
ttcccgccat ctgatgagca gttgaaatct ggaactgcct ctgttgtgtg cctgctgaat     480
aacttctatc ccagagaggc caagtacag tggaaggtgg ataacgccct caatcgggt      540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg t              711
```

<210> SEQ ID NO 266
<211> LENGTH: 234
<212> TYPE: PRT
<213> ORGANISM: Rattus norvegicus

<400> SEQUENCE: 266

```
Met Thr Trp Thr Leu Leu Phe Leu Ala Phe Leu Tyr His Leu Thr Gly
1               5                   10                  15

Ser Cys Ala Gln Val Met Leu Thr Gln Pro Lys Ser Val Ser Thr Ser
            20                  25                  30

Leu Glu Ser Thr Val Lys Leu Ser Cys Lys Leu Asn Ser Asp Asn Ile
        35                  40                  45

Gly Thr Tyr Tyr Ile His Trp Tyr Gln Gln His Glu Gly Arg Ser Pro
    50                  55                  60

Thr Thr Met Ile Tyr Gly Asp Asp Lys Arg Asp Gly Val Pro Asp
65                  70                  75                  80

Arg Phe Ser Gly Ser Ile Asp Ser Ser Asn Ser Ala Phe Leu Thr
                85                  90                  95

Ile Asn Asn Val Gln Thr Glu Asp Glu Ala Ile Tyr Phe Cys His Ser
            100                 105                 110

Tyr Asp Asp His Ile Pro Ile Phe Gly Gly Gly Thr Lys Leu Thr Val
            115                 120                 125

Leu Gly Gln Pro Lys Ser Thr Pro Thr Leu Thr Val Phe Pro Pro Ser
        130                 135                 140

Thr Glu Glu Leu Gln Gly Asn Lys Ala Thr Leu Val Cys Leu Ile Ser
145                 150                 155                 160

Asp Phe Tyr Pro Ser Asp Val Glu Val Ala Trp Lys Ala Asn Gly Ala
                165                 170                 175

Pro Ile Ser Gln Gly Val Asp Thr Ala Asn Pro Thr Lys Gln Gly Asn
            180                 185                 190

Lys Tyr Ile Ala Ser Ser Phe Leu Arg Leu Thr Ala Glu Gln Trp Arg
```

```
                    195                 200                 205
Ser Arg Asn Ser Phe Thr Cys Gln Val Thr His Glu Gly Asn Thr Val
        210                 215                 220

Glu Lys Ser Leu Ser Pro Ala Glu Cys Val
225                 230

<210> SEQ ID NO 267
<211> LENGTH: 1380
<212> TYPE: DNA
<213> ORGANISM: Rattus norvegicus

<400> SEQUENCE: 267
atggctgtcc tggtgctgtt gctctgcctg gtgacatttc caagctgtgt cctgtcccag      60
gtgcagctga tggagtcagg acctggcctg gtgcagccct cagagaccct gtccctcacc     120
tgcactgtct ctgggttctc actgaccagc tataacgtgc actgggttcg acagcctcca     180
ggaaaaggtc tggagtggat gggagtattg tggagtgatg agacacagag ttataattca     240
gctctcaaat cccgactgag catcagaagg gacacctcca gaaccaagtt tttcttaaaa     300
atgaacagtc tgcaaagtga agacacaaat acttactact gtgtcagagg ggggttatta     360 cccggggggct actttgatta ctggggccaa ggagtcatgg tcacagtctc ctcagctgaa     420
acaacagccc catctgtcta tccactggct cctggaactg ctctcaaaag taactccatg     480
gtgaccctgg gatgcctggt caagggctat ttccctgagc cagtcaccgt gacctggaac     540
tctggagccc tgtccagcgg tgtgcacacc ttcccagctg tcctgcagtc tggactctac     600
actctcacca gctcagtgac tgtaccctcc agcacctggt ccagccaggc cgtcacctgc     660
aacgtagccc accggccag cagcaccaag gtggacaaga aaattgtgcc aagggaatgc     720
aatccttgtg gatgtacagg ctcagaagta tcatctgtct tcatcttccc cccaaagacc     780
aaagatgtgc tcaccatcac tctgactcct aaggtcacgt gtgttgtggt agacattagc     840
cagaatgatc ccgaggtccg gttcagctgg tttatagatg acgtggaagt ccacacagct     900
cagactcatg ccccggagaa gcagtccaac agcactttac gctcagtcag tgaactcccc     960
atcgtgcacc gggactggct caatggcaag acgttcaaat gcaaagtcaa cagtggagca    1020
ttccctgccc ccatcgagaa aagcatctcc aaacccgaag gcacaccacg aggtccacag    1080
gtatacacca tggcgcctcc caaggaagag atgacccaga gtcaagtcag tatcacctgc    1140
atggtaaaag gcttctatcc cccagacatt tatacggagt ggaagatgaa cgggcagcca    1200
caggaaaact acaagaacac tccacctacg atggacacag atgggagtta cttcctctac    1260
agcaagctca atgtaaagaa agaaacatgg cagcagggaa acacttttca cgtgttctgtg   1320 ctgcatgagg gcctgcacaa ccaccatact gagaagagtc tctcccactc tccgggtaaa    1380

<210> SEQ ID NO 268
<211> LENGTH: 460
<212> TYPE: PRT
<213> ORGANISM: Rattus norvegicus

<400> SEQUENCE: 268

Met Ala Val Leu Val Leu Leu Leu Cys Leu Val Thr Phe Pro Ser Cys
1               5                   10                  15

Val Leu Ser Gln Val Gln Leu Met Glu Ser Gly Pro Gly Leu Val Gln
            20                  25                  30

Pro Ser Glu Thr Leu Ser Leu Thr Cys Thr Val Ser Gly Phe Ser Leu
        35                  40                  45

Thr Ser Tyr Asn Val His Trp Val Arg Gln Pro Pro Gly Lys Gly Leu
```

```
                50                  55                  60
Glu Trp Met Gly Val Leu Trp Ser Asp Gly Asp Thr Asp Tyr Asn Ser
 65                  70                  75                  80

Ala Leu Lys Ser Arg Leu Ser Ile Arg Arg Asp Thr Ser Lys Asn Gln
                 85                  90                  95

Val Phe Leu Lys Met Asn Ser Leu Gln Ser Glu Asp Thr Asn Thr Tyr
                100                 105                 110

Tyr Cys Val Arg Gly Gly Leu Leu Pro Gly Gly Tyr Phe Asp Tyr Trp
                115                 120                 125

Gly Gln Gly Val Met Val Thr Val Ser Ser Ala Glu Thr Thr Ala Pro
130                 135                 140

Ser Val Tyr Pro Leu Ala Pro Gly Thr Ala Leu Lys Ser Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ala Leu Ser Ser Gly Val His Thr Phe Pro
                180                 185                 190

Ala Val Leu Gln Ser Gly Leu Tyr Thr Leu Thr Ser Ser Val Thr Val
                195                 200                 205

Pro Ser Ser Thr Trp Ser Ser Gln Ala Val Thr Cys Asn Val Ala His
210                 215                 220

Pro Ala Ser Ser Thr Lys Val Asp Lys Lys Ile Val Pro Arg Glu Cys
225                 230                 235                 240

Asn Pro Cys Gly Cys Thr Gly Ser Glu Val Ser Ser Val Phe Ile Phe
                245                 250                 255

Pro Pro Lys Thr Lys Asp Val Leu Thr Ile Thr Leu Thr Pro Lys Val
                260                 265                 270

Thr Cys Val Val Val Asp Ile Ser Gln Asn Asp Pro Glu Val Arg Phe
                275                 280                 285

Ser Trp Phe Ile Asp Asp Val Glu Val His Thr Ala Gln Thr His Ala
                290                 295                 300

Pro Glu Lys Gln Ser Asn Ser Thr Leu Arg Ser Val Ser Glu Leu Pro
305                 310                 315                 320

Ile Val His Arg Asp Trp Leu Asn Gly Lys Thr Phe Lys Cys Lys Val
                325                 330                 335

Asn Ser Gly Ala Phe Pro Ala Pro Ile Glu Lys Ser Ile Ser Lys Pro
                340                 345                 350

Glu Gly Thr Pro Arg Gly Pro Gln Val Tyr Thr Met Ala Pro Pro Lys
                355                 360                 365

Glu Glu Met Thr Gln Ser Gln Val Ser Ile Thr Cys Met Val Lys Gly
                370                 375                 380

Phe Tyr Pro Pro Asp Ile Tyr Thr Glu Trp Lys Met Asn Gly Gln Pro
385                 390                 395                 400

Gln Glu Asn Tyr Lys Asn Thr Pro Pro Thr Met Asp Thr Asp Gly Ser
                405                 410                 415

Tyr Phe Leu Tyr Ser Lys Leu Asn Val Lys Lys Glu Thr Trp Gln Gln
                420                 425                 430

Gly Asn Thr Phe Thr Cys Ser Val Leu His Glu Gly Leu His Asn His
                435                 440                 445

His Thr Glu Lys Ser Leu Ser His Ser Pro Gly Lys
450                 455                 460

<210> SEQ ID NO 269
<211> LENGTH: 235
```

<212> TYPE: PRT
<213> ORGANISM: Rattus norvegicus

<400> SEQUENCE: 269

Met Thr Trp Thr Leu Leu Phe Leu Ala Phe Leu Tyr His Leu Thr Gly
1               5                   10                  15

Ser Cys Ala Gln Val Met Leu Thr Gln Pro Lys Ser Val Ser Thr Ser
            20                  25                  30

Leu Glu Ser Thr Val Lys Leu Ser Cys Lys Leu Asn Ser Asp Asn Ile
        35                  40                  45

Gly Thr Tyr Tyr Ile His Trp Tyr Gln His Glu Gly Arg Ser Pro
    50                  55                  60

Thr Thr Met Ile Tyr Gly Asp Asp Lys Arg Pro Asp Gly Val Pro Asp
65                  70                  75                  80

Arg Phe Ser Gly Ser Ile Asp Ser Ser Asn Ser Ala Phe Leu Thr
                85                  90                  95

Ile Asn Asn Val Gln Thr Glu Asp Glu Ala Ile Tyr Phe Cys His Ser
                100                 105                 110

Tyr Asp Asp His Ile Pro Ile Phe Gly Gly Gly Thr Lys Leu Thr Val
                115                 120                 125

Leu Gly Gln Pro Lys Ala Asn Pro Thr Val Thr Leu Phe Pro Pro Ser
130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Gly Ser
                165                 170                 175

Pro Val Lys Ala Gly Val Glu Thr Thr Lys Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 270
<211> LENGTH: 464
<212> TYPE: PRT
<213> ORGANISM: Rattus norvegicus

<400> SEQUENCE: 270

Met Ala Val Leu Val Leu Leu Cys Leu Val Thr Phe Pro Ser Cys
1               5                   10                  15

Val Leu Ser Gln Val Gln Leu Met Glu Ser Gly Pro Gly Leu Val Gln
            20                  25                  30

Pro Ser Glu Thr Leu Ser Leu Thr Cys Thr Val Ser Gly Phe Ser Leu
        35                  40                  45

Thr Ser Tyr Asn Val His Trp Val Arg Gln Pro Pro Gly Lys Gly Leu
    50                  55                  60

Glu Trp Met Gly Val Leu Trp Ser Asp Gly Asp Thr Asp Tyr Asn Ser
65                  70                  75                  80

Ala Leu Lys Ser Arg Leu Ser Ile Arg Arg Asp Thr Ser Lys Asn Gln
                85                  90                  95

Val Phe Leu Lys Met Asn Ser Leu Gln Ser Glu Asp Thr Asn Thr Tyr
                100                 105                 110

Tyr Cys Val Arg Gly Gly Leu Leu Pro Gly Gly Tyr Phe Asp Tyr Trp

```
              115                 120                 125
Gly Gln Gly Val Met Val Thr Val Ser Ser Ala Ser Thr Lys Gly Pro
130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 271
<211> LENGTH: 238
<212> TYPE: PRT
<213> ORGANISM: Rattus norvegicus

<400> SEQUENCE: 271

Met Asp Met Arg Val Pro Ala Gln Leu Leu Gly Leu Leu Leu Leu Trp
1               5                   10                  15

Leu Arg Gly Ala Arg Cys Gln Val Met Leu Thr Gln Pro His Ser Val
            20                  25                  30

Ser Glu Ser Pro Gly Lys Thr Val Thr Ile Ser Cys Lys Leu Asn Ser
```

-continued

```
                35                  40                  45
Asp Asn Ile Gly Thr Tyr Tyr Ile His Trp Tyr Gln Gln Arg Glu Gly
 50                  55                  60

Arg Ser Pro Thr Thr Val Ile Tyr Gly Asp Asp Lys Arg Pro Asp Gly
 65                  70                  75                  80

Val Pro Asp Arg Phe Ser Gly Ser Ile Asp Ser Ser Ser Asn Ser Ala
                 85                  90                  95

Ser Leu Thr Ile Ser Gly Leu Lys Thr Glu Asp Glu Ala Asp Tyr Phe
                100                 105                 110

Cys His Ser Tyr Asp Asp His Ile Pro Ile Phe Gly Gly Gly Thr Lys
            115                 120                 125

Leu Thr Val Leu Gly Gln Pro Lys Ala Asn Pro Thr Val Thr Leu Phe
130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Gly Ser Pro Val Lys Ala Gly Val Glu Thr Thr Lys Pro Ser Lys
            180                 185                 190

Gln Ser Asn Asn Lys Tyr Ala Ala Ser Ser Tyr Leu Ser Leu Thr Pro
        195                 200                 205

Glu Gln Trp Lys Ser His Arg Ser Tyr Ser Cys Gln Val Thr His Glu
210                 215                 220

Gly Ser Thr Val Glu Lys Thr Val Ala Pro Thr Glu Cys Ser
225                 230                 235

<210> SEQ ID NO 272
<211> LENGTH: 467
<212> TYPE: PRT
<213> ORGANISM: Rattus norvegicus

<400> SEQUENCE: 272

Met Asp Met Arg Val Pro Ala Gln Leu Leu Gly Leu Leu Leu Leu Trp
 1               5                  10                  15

Leu Arg Gly Ala Arg Cys Gln Val Gln Leu Gln Glu Ser Gly Pro Gly
                 20                  25                  30

Leu Val Lys Pro Ser Glu Thr Leu Ser Leu Thr Cys Thr Val Ser Gly
             35                  40                  45

Phe Ser Leu Thr Ser Tyr Asn Val His Trp Val Arg Gln Pro Pro Gly
 50                  55                  60

Lys Gly Leu Glu Trp Ile Gly Val Leu Trp Ser Asp Gly Asp Thr Asp
 65                  70                  75                  80

Tyr Asn Ser Ala Leu Lys Ser Arg Val Thr Ile Ser Arg Asp Thr Ser
                 85                  90                  95

Lys Asn Gln Phe Ser Leu Lys Leu Ser Ser Val Thr Ala Ala Asp Thr
                100                 105                 110

Ala Val Tyr Tyr Cys Val Arg Gly Gly Leu Leu Pro Gly Gly Tyr Phe
            115                 120                 125

Asp Tyr Trp Gly Gln Gly Thr Met Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
```

```
                    180                 185                 190
Thr Phe Pro Ala Val Leu Gln Ser Ser Gly Leu Tyr Ser Leu Ser Ser
            195                 200                 205

Val Val Thr Val Pro Ser Ser Asn Phe Gly Thr Gln Thr Tyr Thr Cys
        210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 273
<211> LENGTH: 13
<212> TYPE: PRT
<213> ORGANISM: Rattus norvegicus

<400> SEQUENCE: 273

Lys Leu Asn Ser Asp Asn Ile Gly Thr Tyr Tyr Ile His
1               5                   10

<210> SEQ ID NO 274
<211> LENGTH: 7
<212> TYPE: PRT
<213> ORGANISM: Rattus norvegicus

<400> SEQUENCE: 274

Gly Asp Asp Lys Arg Pro Asp
1               5

<210> SEQ ID NO 275
```

```
<211> LENGTH: 9
<212> TYPE: PRT
<213> ORGANISM: Rattus norvegicus

<400> SEQUENCE: 275

His Ser Tyr Asp Asp His Ile Pro Ile
1               5

<210> SEQ ID NO 276
<211> LENGTH: 129
<212> TYPE: PRT
<213> ORGANISM: Rattus norvegicus

<400> SEQUENCE: 276

Met Thr Trp Thr Leu Leu Phe Leu Ala Phe Leu Tyr His Leu Thr Gly
1               5                   10                  15

Ser Cys Ala Gln Val Met Leu Thr Gln Pro Lys Ser Val Ser Thr Ser
                20                  25                  30

Leu Glu Ser Thr Val Lys Leu Ser Cys Lys Leu Asn Ser Asp Asn Ile
            35                  40                  45

Gly Thr Tyr Tyr Ile His Trp Tyr Gln Gln His Glu Gly Arg Ser Pro
        50                  55                  60

Thr Thr Met Ile Tyr Gly Asp Asp Lys Arg Pro Asp Gly Val Pro Asp
65                  70                  75                  80

Arg Phe Ser Gly Ser Ile Asp Ser Ser Asn Ser Ala Phe Leu Thr
                85                  90                  95

Ile Asn Asn Val Gln Thr Glu Asp Glu Ala Ile Tyr Phe Cys His Ser
                100                 105                 110

Tyr Asp Asp His Ile Pro Ile Phe Gly Gly Gly Thr Lys Leu Thr Val
            115                 120                 125

Leu

<210> SEQ ID NO 277
<211> LENGTH: 5
<212> TYPE: PRT
<213> ORGANISM: Rattus norvegicus

<400> SEQUENCE: 277

Ser Tyr Asn Val His
1               5

<210> SEQ ID NO 278
<211> LENGTH: 16
<212> TYPE: PRT
<213> ORGANISM: Rattus norvegicus

<400> SEQUENCE: 278

Val Leu Trp Ser Asp Gly Asp Thr Asp Tyr Asn Ser Ala Leu Lys Ser
1               5                   10                  15

<210> SEQ ID NO 279
<211> LENGTH: 11
<212> TYPE: PRT
<213> ORGANISM: Rattus norvegicus

<400> SEQUENCE: 279

Gly Gly Leu Leu Pro Gly Gly Tyr Phe Asp Tyr
1               5                   10

<210> SEQ ID NO 280
<211> LENGTH: 138
<212> TYPE: PRT
```

-continued

<213> ORGANISM: Rattus norvegicus

<400> SEQUENCE: 280

```
Met Ala Val Leu Val Leu Leu Cys Leu Val Thr Phe Pro Ser Cys
1               5                   10                  15

Val Leu Ser Gln Val Gln Leu Met Glu Ser Gly Pro Gly Leu Val Gln
            20                  25                  30

Pro Ser Glu Thr Leu Ser Leu Thr Cys Thr Val Ser Gly Phe Ser Leu
        35                  40                  45

Thr Ser Tyr Asn Val His Trp Val Arg Gln Pro Pro Gly Lys Gly Leu
    50                  55                  60

Glu Trp Met Gly Val Leu Trp Ser Asp Gly Asp Thr Asp Tyr Asn Ser
65                  70                  75                  80

Ala Leu Lys Ser Arg Leu Ser Ile Arg Arg Asp Thr Ser Lys Asn Gln
            85                  90                  95

Val Phe Leu Lys Met Asn Ser Leu Gln Ser Glu Asp Thr Asn Thr Tyr
            100                 105                 110

Tyr Cys Val Arg Gly Gly Leu Leu Pro Gly Gly Tyr Phe Asp Tyr Trp
        115                 120                 125

Gly Gln Gly Val Met Val Thr Val Ser Ser
    130                 135
```

<210> SEQ ID NO 281
<211> LENGTH: 49
<212> TYPE: DNA
<213> ORGANISM: Mus musculus

<400> SEQUENCE: 281
ccgttcgtgg cccagccggc ctctgctcag gttcagctgg tgcagtctg       49

<210> SEQ ID NO 282
<211> LENGTH: 51
<212> TYPE: DNA
<213> ORGANISM: Mus musculus

<400> SEQUENCE: 282
gtgatggtga tgatgatgtg cggccgcaca tttgcgctca actgtcttgt c     51